US007875647B2

(12) United States Patent
Lee et al.

(10) Patent No.: US 7,875,647 B2
(45) Date of Patent: Jan. 25, 2011

(54) HETEROARYL-PYRAZOLE DERIVATIVES AS CANNABINOID CB1 RECEPTOR ANTAGONISTS

(75) Inventors: Jinhwa Lee, Yongin-si (KR); Jeong Min Kim, Seoul (KR); Chong-Hwan Jonathan Chang, Yongin-si (KR); Suk Ho Lee, Suwon-si (KR); Hee Jeong Seo, Seoul (KR); Suk Youn Kang, Yongin-si (KR); Kwang-Seop Song, Yongin-si (KR); Jong Yup Kim, Yongin-si (KR); Min-ah Kim, Seongnam-si (KR); Sung-han Lee, Seoul (KR); Kwang-Woo Ahn, Seoul (KR); Myung Eun Jung, Seongnam-si (KR); Ji-Hyun Park, Seongnam-si (KR)

(73) Assignee: Green Cross Corporation, Yongin-si (KR)

( * ) Notice: Subject to any disclaimer, the term of this patent is extended or adjusted under 35 U.S.C. 154(b) by 521 days.

(21) Appl. No.: 11/863,501

(22) Filed: Sep. 28, 2007

(65) Prior Publication Data

US 2008/0081812 A1    Apr. 3, 2008

Related U.S. Application Data

(63) Continuation-in-part of application No. 11/541,269, filed on Sep. 29, 2006, now abandoned.

(51) Int. Cl.
*A61K 31/415* (2006.01)
*A61K 31/4196* (2006.01)
*C07D 231/10* (2006.01)
*C07D 285/12* (2006.01)
*C07D 417/14* (2006.01)

(52) U.S. Cl. .................. 514/406; 548/125; 548/136; 548/250; 548/262.2; 548/364.1; 514/361; 514/363; 514/364; 514/403

(58) Field of Classification Search .............. 548/125, 548/136, 137, 143, 356.1, 373.1, 374.1, 364.1, 548/250, 262.2; 514/361, 363, 343, 403, 514/406
See application file for complete search history.

(56) References Cited

U.S. PATENT DOCUMENTS

| | | | |
|---|---|---|---|
| 5,925,768 | A | 7/1999 | Barth et al. |
| 6,509,367 | B1 | 1/2003 | Martin et al. |
| 6,825,209 | B2 | 11/2004 | Thomas et al. |
| 7,632,852 | B2 * | 12/2009 | Barth et al. ............... 514/364 |
| 2003/0199536 | A1 | 10/2003 | Thomas et al. |
| 2006/0030563 | A1 | 2/2006 | Makriyannis et al. |
| 2006/0100208 | A1 | 5/2006 | Makriyannis et al. |
| 2007/0021486 | A1 | 1/2007 | Barth et al. |

FOREIGN PATENT DOCUMENTS

| WO | WO 00/46209 | 8/2000 |
|---|---|---|
| WO | WO 2005/073197 A1 | 8/2005 |
| WO | WO 2005/084652 A2 | 9/2005 |
| WO | WO 2006/087480 A1 | 8/2006 |
| WO | WO 2006/133926 A1 | 12/2006 |
| WO | WO 2007/046550 A1 | 4/2007 |

OTHER PUBLICATIONS

Maslivets et al (1990): STN International HCAPLUS database, (Columbus, Ohio), Accession No.: 1990:55776.*
Barth et al (2006): STN International HCAPLUS database, (Columbus, Ohio), Accession No.: 2006:841713.*
Lan, R., et al., :Structure-Activity Relationships of Pyrazole Derivative as Cannabinoid Receptor Antagonists, J. Med. Chem. 1999, 42, 769-776.
Shim, J.Y., et al., "Molecular Interaction of the Antagonist N-(Piperidin-1-yl)-5-(4-chlorophenyl)-1-(2,4-dichlorophenyl)-4-methyl-1H-pyrazole-3-carboxamide with the $CB_1$ Cannabinoid Receptor," J. Med. Chem. 2002, 45, 1447-1459.
Francisco, M.E., et al., Synthesis and Structure—Activity Relationship of Amide and Hydrazide Analogues of the Cannabinoid $CB_1$ Receptor Antagonist N-(Piperidinyl)-5-(4-chlorophenyl)-1-(2,4-dicholorphenyl)-4-methyl-1H-pyrazole-3-carboxamide (SR141716), J. Med. Chem. 2002, 45, 2708-2719.
Katosh-Rouse, R., et al., "Synthesis, Structure-Activity Relationship, and Evaluation of SR141716 Analogues: Development of Central Cannabinoid Receptor Ligands with Lower Lipophilicity," J. Med. Chem. 2003, 46, 642-645.
Ruiu, S., et al., "Synthesis and Characterization of NESS 0327: A Novel Putative Antagonist of the $CB_1$ Cannabinoid Receptor," J. Pharmacology and Experimental Therapeutics, Mar. 2003, 306, 1, 363-370.
Rinaldi-Carmona, M., et al., "SR147778[5-(4-Bromophenyl)-1-(2,4-dichlorophenyl)-4-ethyl-N-(1-piperidinyl)-1H-pyrazole-3-carboxamide], a New potent and Selective Antagonist of the CB1 Cannabinoid Receptor: Biochemical and Pharmacological Characterization," J. Pharmacology And Experimental Therapeutics, May 3, 2004, 310, 3, 905-914.
Chen, J-Z., et al., "3D-QSAR Studies of Arylpyrazole Antagonists of Cannabinoid Receptor Subtypes CB1 and CB2. A Combined NMR an CoMFA Approach," J. Medicinal Chem., Depart. Of Pharmaceutical & Pharmacological Sciences, Univ. of Houston, Jul. 12, 2005.
Muccioli G.G., et al., "Current Knowledge on the Antagonists and Inverse Agonists of Cannabinoid Receptor," Current Medicial Chem., 2005, 12, 1361-1394.
Lange, J.H.M. et al., "Medicinal chemistry strategies to $CB_1$ cannabinoid receptor antagonists," DDT, 10, May 10, 2005, 693-702.
Alekseeva, O.O., "Synthesis of novel 5-substituted pyrazole derivatives as cannabinoid antagonists," Tetrahedron Letters, 2005, 46, 2159-2161.

* cited by examiner

*Primary Examiner*—Golam M Shameem
(74) *Attorney, Agent, or Firm*—Sughrue Mion, PLLC

(57) ABSTRACT

A heteroaryl-pyrazole compound of formula (I) or a pharmaceutically acceptable salt thereof is effective as a cannabinoid $CB_1$ receptor inverse agonist or antagonist, which is useful for preventing or treating obesity and obesity-related metabolic disorders. The present invention also provides a method for preparing the inventive heteroaryl-pyrasole compounds or a pharmaceutically acceptable salt thereof, a pharmaceutical composition containing same, and a method for preventing or treating obesity and obesity-related metabolic disorders.

6 Claims, 1 Drawing Sheet

HETEROARYL-PYRAZOLE DERIVATIVES AS CANNABINOID CB1 RECEPTOR ANTAGONISTS

CROSS-REFERENCE TO RELATED APPLICATION

This application is a continuation-in-part of U.S. Ser. No. 11/541,269 filed on Sep. 29, 2006, which is pending.

FIELD OF THE INVENTION

The present invention relates to a novel heteroaryl-pyrazole compound which is effective as a cannabinoid $CB_1$ receptor inverse agonist or antagonist.

BACKGROUND OF THE INVENTION

The World Health Organization (WHO) recently reported that obesity has become a global epidemic, posing a serious threat to public health because of the increased risk of associated health problems (See *Report of a WHO Consultation on Obesity: Obesity-Preventing and Managing a Global Epidemic*; World Health Organization: Geneva, 1997). Obesity is characterized by excess body fat, especially visceral fat, and constitutes a pro-inflammatory state eventually leading to serious health consequences. There are growing evidences that obesity as a chronic disease cannot be cured by short-term dieting or exercise alone, but additional pharmacological treatments would lead to higher success rates.

$CB_1$ cannabinoid receptor belongs to G-protein-coupled receptor (GPCR) type and is coupled to inhibitory G proteins (G(i/o)) to inhibit certain adenylyl cyclase isozymes, leading to decreased cAMP production, decreased $Ca^{2+}$ conductance, increased $K^+$ conductance, and increased mitogen-activated protein kinase activity (See Di Marzo et al., *Nat. Rev. Drug Discovery* 2004, 3, 771-784; Rhee, M. H. et al., *J. Neurochem.* 1998, 71, 1525-1534). The major physiological effect of cannabinoids (in the central nervous system (CNS) and neuronal tissues) is the modulation of neurotransmitter release via activation of presynaptic $CB_1$ receptors located on distinct types of axon terminals throughout the brain (See Howlett, A. C. et al., *Neuropharmacology* 2004, 47 (Suppl. 1), 345-358).

The $CB_1$ receptor is mainly expressed in several brain areas including the limbic system (amygdala, hippocampus), hypothalamus, cerebral cortex, cerebellum, and basal ganglia. In the cerebellum and basal ganglia cannabinoids modulate the locomotor activity. In the limbic system, cannabinoids influence learning, memory, emotion, and motivation, and through activation of $CB_1$ receptors in the limbic system-hypothalamus axis, cannabinoids have an important role in the control of appetite. Moreover, lower levels of $CB_1$ receptors can also be found in peripheral tissues including urinary bladder, testis, prostate, GI tract, heart, lung, adrenal gland, parotid gland, bone marrow, uterus, ovary, and adipose tissue (See Cota, D. et al., *J. Clin. Invest.* 2003, 112, 423-431; Ravinet Trillou, C. et al., *Int. J. Obes. Relat. Metab. Disord.* 2004, 28, 640-648; Galiegue, S. et al., *Eur. J. Biochem.* 1995, 232, 54-61; Howlett, A. C. et al., *Pharmacol. Rev.* 2002, 54, 161-202).

Many preclinical in vitro and in vivo experiments have shown that $CB_1$ receptor antagonists can influence energy homeostasis by central and peripheral mechanisms and may represent promising targets to treat diseases that are characterized by impaired energy balance. Already the first published studies with rimonabant (SR141716) in both rodents (See Amone, M. et al., *Psychopharmacology (Berlin)* 1997, 132, 104-106) and primates (See Simiand, J.; Keane, M.; Keane, P. E.; Soubrie, P. *Behav. Pharmacol.* 1998, 9, 179-181) showed clear differentiation, i.e., marked effects on sweet food intake versus marginal effects on regular chow intake or water drinking. Many other preclinical "proof of concept" studies have been performed in the meantime with several CB agonists and antagonists to further uncover the amount and mode of contribution of cannabinergic system modulators to energy homeostasis. Almost all of those studies have been recently reviewed (See Smith, R. A. et al., *IDrugs* 2005, 8, 53-66).

Considering the important impact of obesity on public health and the lack of any efficient and viable drug to cure it, it is no surprise that $CB_1$ antagonists are currently the subject of intense studies, which were published in several reviews (See Adam, J. et al., *Expert Opin. Ther. Patents,* 2002, 12(10), 1475-1489; Hertzog, D. L. *Expert Opin. Ther. Patents,* 2004, 14(10), 1435-1452; Lange, J. H. M. et al., *Drug Discov. Today,* 2005, 10, 693-702; Bishop, M. J. *J. Med. Chem.,* 2006, 49(14), 4008-4016).

SUMMARY OF THE INVENTION

It is a primary object of the present invention to provide a novel heteroaryl-pyrazole compound of formula (I) or a pharmaceutically acceptable salt thereof, which is effective as a cannabinoid $CB_1$ receptor inverse agonist or antagonist, useful for preventing or treating obesity and obesity-related metabolic disorders.

It is another object of the present invention to provide a method for preparing the inventive compound.

It is another object of the present invention to provide a pharmaceutical composition for preventing or treating obesity and obesity-related metabolic disorders, comprising the inventive compound as an active ingredient.

BRIEF DESCRIPTION OF DRAWINGS

The above and other objects and features of the present invention will become apparent from the following description of the invention, when taken in conjunction with the accompanying drawing, which show.

DETAILED DESCRIPTION OF THE INVENTION

Figure 1:
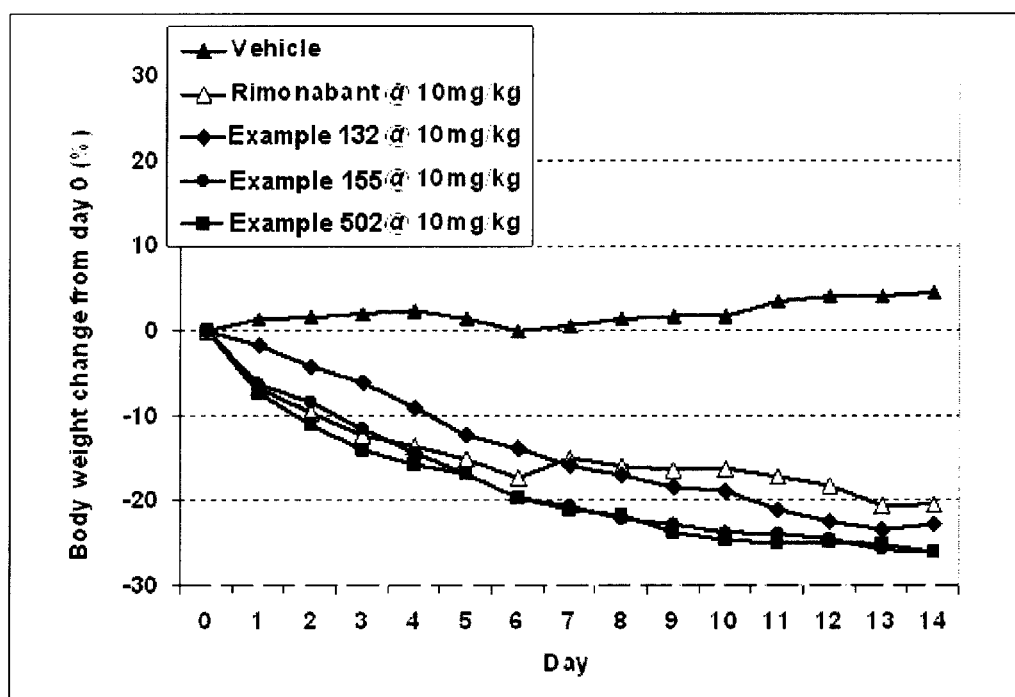
FIG. 1 shows chronic effects of compounds of Examples 132, 155 and 502, and rimonabant in DIO mice.

In accordance with one aspect of the present invention, there is provided a compound of formula (I) or a pharmaceutically acceptable salt thereof and a method for preparing same:

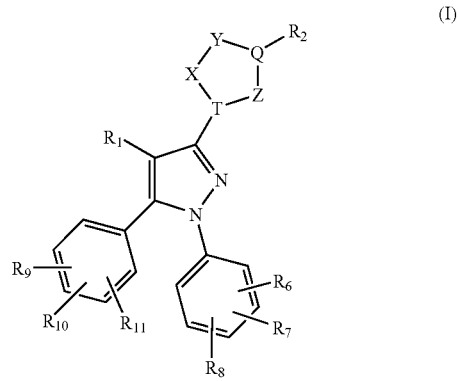

(I)

wherein:

R$_1$ is hydrogen, C$_{1-5}$ alkyl, substituted C$_{1-5}$ alkyl, C$_{2-4}$ alkenyl, substituted C$_{2-4}$ alkenyl, C$_{2-4}$ alkynyl, substituted C$_{2-4}$ alkynyl, halogen, or —(CH$_2$)$_n$—C$_{3-5}$ carbocycle, n being 0 or 1;

R$_2$ is hydrogen, NR$_3$R$_4$, carbocycle, substituted carbocycle, aryl, substituted aryl, heteroaryl, substituted heteroaryl, heterocycle, substituted heterocycle, C$_{1-8}$ alkyl optionally substituted with hydroxy, acyloxy, C$_{1-6}$ alkoxy, substituted C$_{1-6}$ alkoxy; C$_{3-5}$ alkenyloxy, substituted C$_{3-5}$ alkenyloxy; C$_{3-5}$ alkynyloxy, substituted C$_{3-5}$ alkynyloxy; aryloxy, substituted aryloxy; heteroaryloxy, substituted heteroaryloxy or halogen, C$_{2-6}$ alkenyl optionally substituted with alkoxy or halogen, C$_{2-6}$ alkynyl optionally substituted with alkoxy or halogen, —(CH$_2$)$_m$—C$_{3-6}$ carbocycle optionally substituted with alkoxy or halogen, or —(CH$_2$)$_m$—R$_5$, m being 1 or 2;

R$_3$ and R$_4$ are each independently hydrogen, C$_{1-6}$ alkyl, substituted C$_{1-6}$ alkyl, C$_{3-7}$ cycloalkyl, substituted C$_{3-7}$ cycloalkyl, aryl, substituted aryl, heteroaryl, substituted heteroaryl, heterocycloalkyl, substituted heterocycloalkyl; or R$_3$ and R$_4$, together with the nitrogen atom to which they are bonded, form a 4- to 10-membered saturated or unsaturated heterocyclic ring which is optionally substituted with one or more C$_{1-3}$ alkyl, benzyl, phenyl, C$_{1-3}$ alkoxy or halogen;

R$_5$ is phenyl, furanyl, benzofuranyl, thienyl, benzothienyl, pyridinyl, pyrimidinyl, pyrazinyl, pyridizinyl, tetrahydrofuranyl, tetrahydropyranyl, dioxanyl, 1,4-benzodioxanyl or benzo[1,3]dioxolyl, each being optionally substituted with one or more halogen, C$_{1-3}$ alkyl or C$_{1-2}$ alkoxy, each optionally having one to three fluorine substitutes;

R$_6$, R$_7$, R$_8$, R$_9$, R$_{10}$ and R$_{11}$, are each independently hydrogen, halogen, C$_{1-3}$ alkyl, C$_{1-3}$ alkoxy or trifluoromethyl;

X, Y and Z are each independently selected from the group consisting of —C(R$_{12}$)=, —O—, —N=, —N(R$_{13}$)— and —S— to form an aromatic heterocycle together with Q and T;

Q and T are each independently

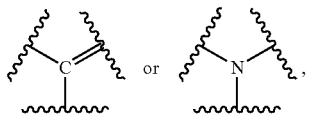

with the proviso that both Q and T can not be simultaneously

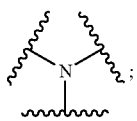

and

R$_{12}$ and R$_{13}$ are each independently hydrogen, NR$_3$R$_4$, carbocycle, substituted carbcycle, aryl, substituted aryl, heteroaryl, substituted heteroaryl, heterocycle, substituted heterocycle, C$_{1-8}$ alkyl optionally substituted with alkoxy or halogen, C$_{2-6}$ alkenyl optionally substituted with alkoxy or halogen, C$_{2-6}$ alkynyl optionally substituted with alkoxy or halogen, —(CH$_2$)$_m$—C$_{3-6}$ carbocycle optionally substituted with alkoxy or halogen, or —(CH$_2$)$_m$—R$_5$, m being 1 or 2, and R$_3$, R$_4$ and R$_5$ having the same meaning as defined above; or R$_2$ and R$_{12}$ are bonded together to form a 4- to 10-membered saturated or unsaturated carbocyclic or heterocyclic ring which is optionally substituted with one or more C$_{1-3}$ alkyl, benzyl, phenyl, C$_{1-3}$ alkoxy or halogen.

The aromatic heterocycles formed by X, Y, Z, Q and T encompass, for example, oxazole, isoxazole, thiazole, isothiazole, pyrazole, triazole, oxadiazole, thiadiazole and tetrazole.

It is to be understood that the present invention also includes a pharmaceutically acceptable salt and an addition salt of the inventive compound, such as a hydrochloride, hydrobromide or trifluoroacetate addition salt and a sodium, potassium and magnesium salt.

The compounds of the present invention may contain one or more asymmetric carbon atoms and may exist in racemic and optically active forms. All of these compounds and diastereomers are incorporated within the scope of the present invention.

One embodiment of the present invention is to provide a compound of formula (Ia) or a pharmaceutically acceptable salt thereof:

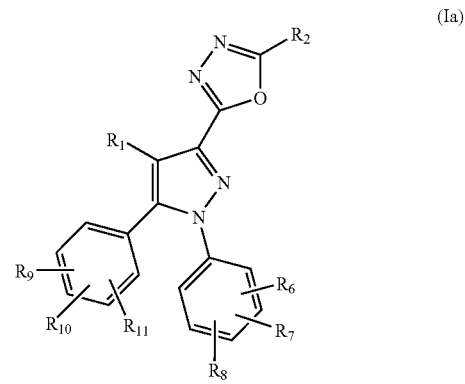

(Ia)

wherein R$_1$, R$_2$, R$_6$, R$_7$, R$_8$, R$_9$, R$_{10}$, and R$_{11}$ have the same meanings as defined in claim 1; with the proviso that when R$_1$ is C$_{1-5}$ alkyl, R$_2$ represents (i) or (ii):

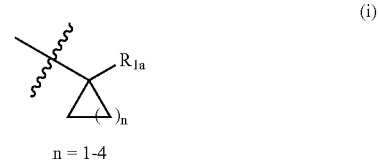

(i)

n = 1-4 wherein, R$_{1a}$ is C$_{1-6}$ alkyl, substituted C$_{1-6}$ alkyl; C$_{2-4}$ alkenyl, substituted C$_{2-4}$ alkenyl; C$_{2-4}$ alkynyl, substituted C$_{2-4}$ alkynyl; CN, carboxy, aminocarbonyl; aryl, substituted aryl; heteroaryl, substituted heteroaryl;

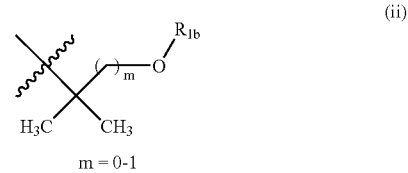

(ii)

m = 0-1 wherein R$_{1b}$ is hydrogen, acyl, C$_{1-6}$ alkyl, substituted C$_{1-6}$ alkyl; C$_{3-5}$ alkenyl, substituted C$_{3-5}$ alkenyl; C$_{3-5}$ alkynyl, substituted C$_{3-5}$ alkynyl; aryl, substituted aryl; heteroaryl, substituted heteroaryl.

Another embodiment of the present invention is to provide a compound of formula (Ib) or a pharmaceutically acceptable salt thereof:

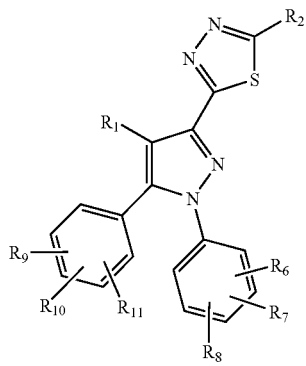

(Ib)

wherein $R_1$, $R_2$, $R_6$, $R_7$, $R_8$, $R_9$, $R_{10}$ and $R_{11}$ have the same meanings as defined above.

A further embodiment of the present invention is provide a compound of formula (Ic) or a pharmaceutically acceptable salt thereof:

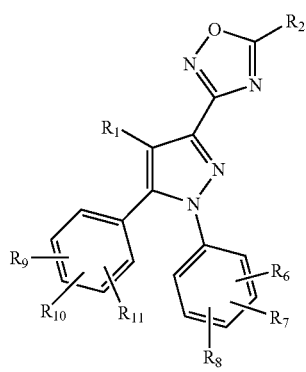

(Ic)

wherein $R_1$, $R_2$, $R_6$, $R_7$, $R_8$, $R_9$, $R_{10}$ and $R_{11}$ have the same meanings as defined above.

A still another embodiment of the present invention is to provide a compound of formula (Id) or a pharmaceutically acceptable salt thereof:

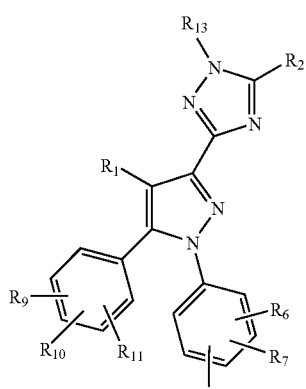

(Id)

wherein, $R_1$, $R_2$, $R_6$, $R_7$, $R_8$, $R_9$, $R_{10}$, $R_{11}$ and $R_{13}$ have the same meanings as defined above.

The present invention also provides a compound of formula (Ie) or (If) or a pharmaceutically acceptable salt thereof:

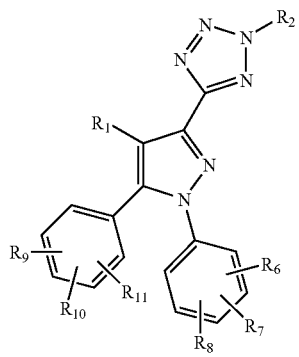

(Ie)

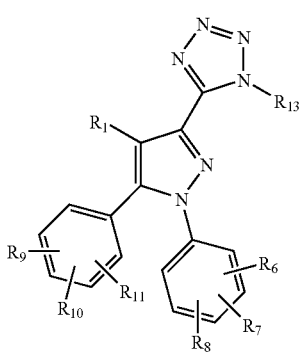

(If)

wherein $R_1$, $R_2$, $R_6$, $R_7$, $R_8$, $R_9$, $R_{10}$, $R_{11}$ and $R_{13}$ have the same meanings as defined above.

A further embodiment of the present invention is to provide a compound of formula (Ig) or a pharmaceutically acceptable salt thereof:

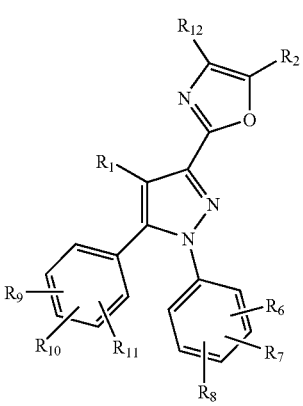

(Ig)

wherein $R_1$, $R_2$, $R_6$, $R_7$, $R_8$, $R_9$, $R_{10}$, $R_{11}$ and $R_{12}$ have the same meanings as defined above.

A still another embodiment of the present invention is to provide a compound of formula (Ih) or a pharmaceutically acceptable salt thereof:

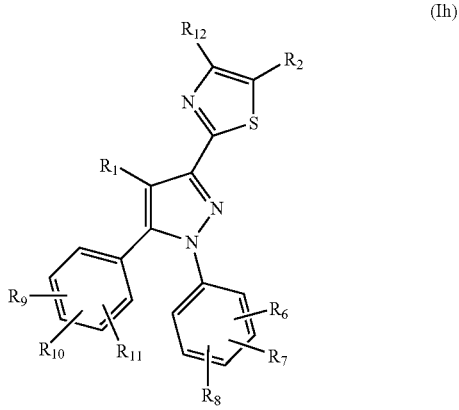

(Ih)

wherein $R_1$, $R_2$, $R_6$, $R_7$, $R_8$, $R_9$, $R_{10}$, $R_{11}$ and $R_{12}$ have the same meanings as defined above.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of $C_{1-3}$ alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of $C_{1-3}$ alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" refers to a non-aromatic cyclic hydrocarbon radical composed of three to seven carbon atoms. Five- to seven-membered rings may contain a double bond in the ring structure. Exemplary "carbocycle" groups include, but are not limited to, cyclopropyl, cyclobutyl, cyclopentyl, cyclopentenyl, cyclohexyl, and cycloheptyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, $SO_2$, O, N, or N-oxide, or refers to such an aromatic ring fused to one or more rings such as heteroaryl rings, aryl rings, heterocyclic rings, or carbocycle rings (e.g., a bicyclic or tricyclic ring system), each having optional substituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" refers to a three to seven-membered ring containing one or more heteroatomic moieties selected from S, SO, $SO_2$, O, N, or N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents.

Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein, the term "alkenyloxy" refers to the group —$OR_b$, where $R_b$ is alkenyl as defined above.

As used herein, the term "alkynyloxy" refers to the group —$OR_c$, where $R_c$ is alkynyl as defined above.

As used herein, the term "aralkoxy" refers to the group —$OR_aR_d$, wherein $R_a$ is alkyl and $R_d$ is aryl as defined above.

As used herein, the term "aryloxy" refers to the group —$OR_d$, wherein $R_d$ is aryl as defined above.

As used herein, the term "heteroaryloxy" refers to the group —$OR_e$, where $R_e$ is heteroaryl as defined above.

As used herein, the term "mercapto" refers to the group —SH.

As used herein, the term "sulfonyl" refers to the group —$SR_f$, wherein $R_f$ is substituted alkyl, substituted carbocycle, aryl, heteroaryl or heterocyclic, as defined above.

As used herein, the term "sulfonyl" refers to the group —S—(O)$R_f$, wherein $R_f$ is substituted alkyl, substituted carbocycle, aryl, heteroaryl or heterocyclic, as defined above.

As used herein, the term "sulfonyl" refers to the group —$S(O)_2R_f$, wherein $R_f$ is substituted alkyl, substituted carbocycle, aryl, heteroaryl or heterocyclic, as defined above.

As used herein, the term "oxo" refers to the group =O.

As used herein, the term "hydroxyl" refers to the group —OH.

As used herein, the term "amino" refers to the group —$NH_2$. The amino group is optionally substituted with substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted with substituted alkyl, substituted carbocycle, aryl, heteroaryl or heterocyclic, as defined above.

As used herein, the term "sulfonylamino" refers to the group —$NHS(O)_2R_f$ wherein $R_f$ is substituted alkyl, substituted carbocycle, aryl, heteroaryl or heterocyclic, as defined above.

As used herein, the term "carboxyamide" refers to the group —$NHC(O)R_f$ wherein $R_f$ is substituted alkyl, substituted carbocycle, aryl, heteroaryl or heterocyclic, as defined above.

As used herein, the term "carboxy" refers to the group —C(O)OH. The carboxy group is optionally substituted with substituted alkyl, substituted carbocycle, aryl, heteroaryl or heterocyclic, as defined above.

As used herein, the term "aminocarbonyl" refers to the group —$C(O)NH_2$. The aminocarbonyl group is optionally substituted with substituted alkyl, substituted carbocycle, aryl, heteroaryl or heterocyclic, as defined above.

As used herein, the term "ureido" refers to the group —$NHC(O)NHR_g$ wherein $R_g$ is hydrogen, alkyl, carbocycle or aryl as defined above.

As used herein, the term "guanidine" refers to the group —$NHC(=NH)NH_2$.

As used herein, the term "acyl" refers to the group —$C(O)R_h$, wherein $R_h$ is alkyl, carbocycle, or heterocyclic as defined herein.

As used herein, the term "aroyl" refers to the group —$C(O)R_d$, wherein $R_d$ is aryl as defined herein.

As used herein, the term "heteroaroyl" refers to the group —$C(O)R_e$, wherein $R_e$ is heteroaryl as defined herein.

As used herein, the term "acyloxy" refers to the group —$OC(O)R_h$, wherein $R_h$ is alkyl, carbocycle, or heterocyclic as defined herein.

As used herein, the term "aroyloxy" refers to the group —$OC(O)R_d$, wherein $R_d$ is aryl as defined herein.

As used herein, the term "heteroaroyloxy" refers to the group —$OC(O)R_e$, wherein $R_e$ is heteroaryl as defined herein.

Preferred compounds useful in the present invention are selected from the group consisting of:

2-(5-(4-chlorophenyl)-1-(2,4-dichlorophenyl)-4-methyl-1H-pyrazol-3-yl)-5-(pyridin-4-yl)-1,3,4-oxadiazole 2-(5-(4-chlorophenyl)-1-(2,4-dichlorophenyl)-4-methyl-1H-pyrazol-3-yl)-5-methyl-1,3,4-thiadiazole 2-(5-(4-chlorophenyl)-1-(2,4-dichlorophenyl)-4-methyl-1H-pyrazol-3-yl)-5-cyclopentyl-1,3,4-thiadiazole 2-(5-(4-chlorophenyl)-1-(2,4-dichlorophenyl)-4-methyl-1H-pyrazol-3-yl)-5-cyclohexyl-1,3,4-thiadiazole 5-(5-(4-chlorophenyl)-1-(2,4-dichlorophenyl)-4-methyl-1H-pyrazol-3-yl)-1-ethyl-1H-tetrazole 2-(5-(4-chlorophenyl)-1-(2,4-dichlorophenyl)-4-methyl-1H-pyrazol-3-yl)-5-(furan-2-yl)-1,3,4-oxadiazole 5-(5-(4-chlorophenyl)-1-(2,4-dichlorophenyl)-4-methyl-1H-pyrazol-3-yl)-1-cyclopentyl-1H-tetrazole 5-(5-(4-chlorophenyl)-1-(2,4-dichlorophenyl)-4-methyl-1H-pyrazol-3-yl)-2-cyclopentyl-2H-tetrazole 1-benzyl-5-(5-(4-chlorophenyl)-1-(2,4-dichlorophenyl)-4-methyl-1H-pyrazol-3-yl)-1H-tetrazole 2-benzyl-5-(5-(4-chlorophenyl)-1-(2,4-dichlorophenyl)-4-methyl-1H-pyrazol-3-yl)-2H-tetrazole 5-(5-(4-chlorophenyl)-1-(2,4-dichlorophenyl)-4-methyl-1H-pyrazol-3-yl)-2-cyclohexyl-2H-tetrazole 5-(5-(4-chlorophenyl)-1-(2,4-dichlorophenyl)-4-methyl-1H-pyrazol-3-yl)-1-cyclohexyl-1H-tetrazole 2-(5-(4-chlorophenyl)-1-(2,4-dichlorophenyl)-4-methyl-1H-pyrazol-3-yl)-5-cyclobutyl-1,3,4-thiadiazole 2-(5-(4-chlorophenyl)-1-(2,4-dichlorophenyl)-4-methyl-1H-pyrazol-3-yl)-5-(pyrazin-2-yl)-1,3,4-oxadiazole 2-(5-(4-chlorophenyl)-1-(2,4-dichlorophenyl)-4-methyl-1H-pyrazol-3-yl)-5-(pyrazin-2-yl)-1,3,4-thiadiazole 2-(5-(4-chlorophenyl)-1-(2,4-dichlorophenyl)-4-methyl-1H-pyrazol-3-yl)-5-(thiophen-2-yl)-1,3,4-oxadiazole 2-(5-(4-chlorophenyl)-1-(2,4-dichlorophenyl)-4-methyl-1H-pyrazol-3-yl)-5-(thiophen-2-yl)-1,3,4-thiadiazole
2-(5-(4-chlorophenyl)-1-(2,4-dichlorophenyl)-4-methyl-1H-pyrazol-3-yl)-5-(pyridin-2-ylmethyl)-1,3,4-thiadiazole
2-(5-(4-chlorophenyl)-1-(2,4-dichlorophenyl)-4-methyl-1H-pyrazol-3-yl)-5-isopropyl-1,3,4-thiadiazole
2-benzyl-5-(5-(4-chlorophenyl)-1-(2,4-dichlorophenyl)-4-methyl-1H-pyrazol-3-yl)-1,3,4-thiadiazole
5-(5-(4-chlorophenyl)-1-(2,4-dichlorophenyl)-4-methyl-1H-pyrazol-3-yl)-1-propyl-1H-tetrazole
5-(5-(4-chlorophenyl)-1-(2,4-dichlorophenyl)-4-methyl-1H-pyrazol-3-yl)-2-propyl-2H-tetrazole
3-((5-(5-(4-chlorophenyl)-1-(2,4-dichlorophenyl)-4-methyl-1H-pyrazol-3-yl)-1H-tetrazol-1-yl)methyl)pyridine
3-((5-(5-(4-chlorophenyl)-1-(2,4-dichlorophenyl)-4-methyl-1H-pyrazol-3-yl)-2H-tetrazol-2-yl)methyl)pyridine
2-((5-(5-(4-chlorophenyl)-1-(2,4-dichlorophenyl)-4-methyl-1H-pyrazol-3-yl)-1H-tetrazol-1-yl)methyl)pyridine
2-((5-(5-(4-chlorophenyl)-1-(2,4-dichlorophenyl)-4-methyl-1H-pyrazol-3-yl)-2H-tetrazol-2-yl)methyl)pyridine
4-((5-(5-(4-chlorophenyl)-1-(2,4-dichlorophenyl)-4-methyl-1H-pyrazol-3-yl)-1H-tetrazol-1-yl)methyl)pyridine
4-((5-(5-(4-chlorophenyl)-1-(2,4-dichlorophenyl)-4-methyl-1H-pyrazol-3-yl)-2H-tetrazol-2-yl)methyl)pyridine
5-(5-(4-chlorophenyl)-1-(2,4-dichlorophenyl)-4-methyl-1H-pyrazol-3-yl)-1-(furan-2-ylmethyl)-1H-tetrazole
5-(5-(4-chlorophenyl)-1-(2,4-dichlorophenyl)-4-methyl-1H-pyrazol-3-yl)-2-(furan-2-ylmethyl)-1H-tetrazole
2-butyl-5-(5-(4-chlorophenyl)-1-(2,4-dichlorophenyl)-4-methyl-1H-pyrazol-3-yl)-1,3,4-thiadiazole
5-(5-(4-chlorophenyl)-1-(2,4-dichlorophenyl)-4-methyl-1H-pyrazol-3-yl)-1-(furan-3-ylmethyl)-1H-tetrazole
5-(5-(4-chlorophenyl)-1-(2,4-dichlorophenyl)-4-methyl-1H-pyrazol-3-yl)-2-(furan-3-ylmethyl)-2H-tetrazole
5-(5-(4-chlorophenyl)-1-(2,4-dichlorophenyl)-4-methyl-1H-pyrazol-3-yl)-1-phenyl-1H-tetrazole
1-butyl-5-(5-(4-chlorophenyl)-1-(2,4-dichlorophenyl)-4-methyl-1H-pyrazol-3-yl)-1H-tetrazole
2-butyl-5-(5-(4-chlorophenyl)-1-(2,4-dichlorophenyl)-4-methyl-1H-pyrazol-3-yl)-2H-tetrazole
5-(5-(4-chlorophenyl)-1-(2,4-dichlorophenyl)-4-methyl-1H-pyrazol-3-yl)-1-pentyl-1H-tetrazole
5-(5-(4-chlorophenyl)-1-(2,4-dichlorophenyl)-4-methyl-1H-pyrazol-3-yl)-2-pentyl-2H-tetrazole
5-(5-(4-chlorophenyl)-1-(2,4-dichlorophenyl)-4-methyl-1H-pyrazol-3-yl)-1-isopropyl-1H-tetrazole
5-(5-(4-chlorophenyl)-1-(2,4-dichlorophenyl)-4-methyl-1H-pyrazol-3-yl)-2-isopropyl-2H-tetrazole
5-(5-(4-chlorophenyl)-1-(2,4-dichlorophenyl)-4-methyl-1H-pyrazol-3-yl)-1-(cyclohexylmethyl)-1H-tetrazole
5-(5-(4-chlorophenyl)-1-(2,4-dichlorophenyl)-4-methyl-1H-pyrazol-3-yl)-2-(cyclohexylmethyl)-2H-tetrazole
5-(5-(4-chlorophenyl)-1-(2,4-dichlorophenyl)-4-methyl-1H-pyrazol-3-yl)-1-(thiophen-3-ylmethyl)-1H-tetrazole
5-(5-(4-chlorophenyl)-1-(2,4-dichlorophenyl)-4-methyl-1H-pyrazol-3-yl)-2-(thiophen-3-ylmethyl)-2H-tetrazole
5-(5-(4-chlorophenyl)-1-(2,4-dichlorophenyl)-4-methyl-1H-pyrazol-3-yl)-1-cycloheptyl-1H-tetrazole
1-tert-butyl-5-(5-(4-chlorophenyl)-1-(2,4-dichlorophenyl)-4-methyl-1H-pyrazol-3-yl)-1H-tetrazole
5-(5-(4-chlorophenyl)-1-(2,4-dichlorophenyl)-4-methyl-1H-pyrazol-3-yl)-1-octyl-1H-tetrazole
2-(5-(4-chlorophenyl)-1-(2,4-dichlorophenyl)-4-methyl-1H-pyrazol-3-yl)-5-phenyl-1,3,4-thiadiazole
5-(5-(4-chlorophenyl)-1-(2,4-dichlorophenyl)-4-methyl-1H-pyrazol-3-yl)-1-hexyl-1H-tetrazole
1-Adamantyl-5-(5-(4-chlorophenyl)-1-(2,4-dichlorophenyl)-4-methyl-1H-pyrazol-3-yl)-1H-tetrazole
5-(5-(4-chlorophenyl)-1-(2,4-dichlorophenyl)-4-methyl-1H-pyrazol-3-yl)-1-cyclopropyl-1H-tetrazole
5-(5-(4-chlorophenyl)-1-(2,4-dichlorophenyl)-4-methyl-1H-pyrazol-3-yl)-1-phenethyl-1H-tetrazole
5-(5-(4-chlorophenyl)-1-(2,4-dichlorophenyl)-4-methyl-1H-pyrazol-3-yl)-2-phenethyl-2H-tetrazole
2-(5-(4-chlorophenyl)-1-(2,4-dichlorophenyl)-4-methyl-1H-pyrazol-3-yl)-5-(cyclopentylmethyl)-1,3,4-thiadiazole
5-(5-(4-chlorophenyl)-1-(2,4-dichlorophenyl)-4-methyl-1H-pyrazol-3-yl)-1-cyclobutyl-1H-tetrazole
3-(5-(4-chlorophenyl)-1-(2,4-dichlorophenyl)-4-methyl-1H-pyrazol-3-yl)-5-cyclopentyl-1H-1,2,4-triazole
2-(5-(4-chlorophenyl)-1-(2,4-dichlorophenyl)-4-methyl-1H-pyrazol-3-yl)-5-(tetrahydro-2H-pyran-4-yl)-1,3,4-thiadiazole
2-(5-(4-chlorophenyl)-1-(2,4-dichlorophenyl)-4-methyl-1H-pyrazol-3-yl)-5-(tetrahydrofuran-2-yl)-1,3,4-thiadiazole
3-(5-(4-chlorophenyl)-1-(2,4-dichlorophenyl)-4-methyl-1H-pyrazol-3-yl)-5-cyclohexyl-1H-1,2,4-triazole
3-(5-(4-chlorophenyl)-1-(2,4-dichlorophenyl)-4-methyl-1H-pyrazol-3-yl)-5-phenyl-1H-1,2,4-triazole
2-(benzofuran-2-yl)-5-(5-(4-chlorophenyl)-1-(2,4-dichlorophenyl)-4-methyl-1H-pyrazol-3-yl)-1,3,4-oxadiazole
2-(5-(4-chlorophenyl)-1-(2,4-dichlorophenyl)-4-methyl-1H-pyrazol-3-yl)-5-pentyl-1,3,4-thiadiazole
2-(5-(4-chlorophenyl)-1-(2,4-dichlorophenyl)-4-methyl-1H-pyrazol-3-yl)-5-cycloheptyl-1,3,4-thiadiazole
2-(5-(4-chlorophenyl)-1-(2,4-dichlorophenyl)-4-methyl-1H-pyrazol-3-yl)-5-(2,4-dichlorophenyl)-1,3,4-thiadiazole
3-(5-(4-chlorophenyl)-1-(2,4-dichlorophenyl)-4-methyl-1H-pyrazol-3-yl)-5-(thiophen-2-yl)-1H-1,2,4-triazole
3-(5-(4-chlorophenyl)-1-(2,4-dichlorophenyl)-4-methyl-1H-pyrazol-3-yl)-5-cycloheptyl-1H-1,2,4-triazole
3-(5-(4-chlorophenyl)-1-(2,4-dichlorophenyl)-4-methyl-1H-pyrazol-3-yl)-5-(furan-2-yl)-1H-1,2,4-triazole
3-(5-(4-chlorophenyl)-1-(2,4-dichlorophenyl)-4-methyl-1H-pyrazol-3-yl)-5-propyl-1H-1,2,4-triazole
3-(5-(4-chlorophenyl)-1-(2,4-dichlorophenyl)-4-methyl-1H-pyrazol-3-yl)-5-isopropyl-1H-1,2,4-triazole
3-(5-(4-chlorophenyl)-1-(2,4-dichlorophenyl)-4-methyl-1H-pyrazol-3-yl)-5-cyclopropyl-1H-1,2,4-triazole
3-(5-(4-chlorophenyl)-1-(2,4-dichlorophenyl)-4-methyl-1H-pyrazol-3-yl)-5-(cyclopropylmethyl)-1H-1,2,4-triazole
3-(5-(4-chlorophenyl)-1-(2,4-dichlorophenyl)-4-methyl-1H-pyrazol-3-yl)-5-cyclobutyl-1H-1,2,4-triazole
2-(5-(4-chlorophenyl)-1-(2,4-dichlorophenyl)-4-methyl-1H-pyrazol-3-yl)-5-(cyclopentylmethyl)-1,3,4-oxadiazole
2-(5-(4-chlorophenyl)-1-(2,4-dichlorophenyl)-4-methyl-1H-pyrazol-3-yl)-5-(tetrahydro-2H-pyran-4-yl)-1,3,4-oxadiazole
2-(5-(4-chlorophenyl)-1-(2,4-dichlorophenyl)-4-methyl-1H-pyrazol-3-yl)-5-(cyclohexylmethyl)-1,3,4-oxadiazole
2-(5-(4-bromophenyl)-1-(2,4-dichlorophenyl)-4-methyl-1H-pyrazol-3-yl)-5-cyclobutyl-1,3,4-thiadiazole
2-(5-(4-chlorophenyl)-1-(2,4-dichlorophenyl)-4-methyl-1H-pyrazol-3-yl)-5-(cyclohexylmethyl)-1,3,4-thiadiazole
2-(5-(4-chlorophenyl)-1-(2,4-dichlorophenyl)-4-methyl-1H-pyrazol-3-yl)-5-(tetrahydrofuran-2-yl)-1,3,4-oxadiazole 2-(5-(4-bromophenyl)-1-(2,4-dichlorophenyl)-4-methyl-1H-pyrazol-3-yl)-5-cyclopentyl-1,3,4-thiadiazole
2-(5-(4-chlorophenyl)-1-(2,4-dichlorophenyl)-4-methyl-1H-pyrazol-3-yl)-5-(1-phenylethyl)-1,3,4-thiadiazole
2-sec-butyl-5-(5-(4-chlorophenyl)-1-(2,4-dichlorophenyl)-4-methyl-1H-pyrazol-3-yl)-1,3,4-thiadiazole
2-(5-(4-chlorophenyl)-1-(2,4-dichlorophenyl)-4-methyl-1H-pyrazol-3-yl)-5-(pentan-2-yl)-1,3,4-thiadiazole
2-(5-(4-bromophenyl)-1-(2,4-dichlorophenyl)-4-methyl-1H-pyrazol-3-yl)-5-tert-butyl-1,3,4-thiadiazole
5-(5-(4-chlorophenyl)-1-(2,4-dichlorophenyl)-4-methyl-1H-pyrazol-3-yl)-N-cyclohexyl-1,3,4-thiadiazol-2-amine
2-(5-(4-chlorophenyl)-1-(2,4-dichlorophenyl)-4-methyl-1H-pyrazol-3-yl)-5-(cyclohex-3-enyl)-1,3,4-oxadiazole
2-(5-(4-chlorophenyl)-1-(2,4-dichlorophenyl)-4-methyl-1H-pyrazol-3-yl)-5-(cyclohex-3-enyl)-1,3,4-thiadiazole
5-sec-butyl-3-(5-(4-chlorophenyl)-1-(2,4-dichlorophenyl)-4-methyl-1H-pyrazol-3-yl)-1H-1,2,4-triazole
3-(5-(4-chlorophenyl)-1-(2,4-dichlorophenyl)-4-methyl-1H-pyrazol-3-yl)-5-cyclohexyl-1-isopropyl-1H-1,2,4-triazole
3-(5-(4-chlorophenyl)-1-(2,4-dichlorophenyl)-4-methyl-1H-pyrazol-3-yl)-5-cyclopropyl-1-methyl-1H-1,2,4-triazole
4-(5-(4-chlorophenyl)-1-(2,4-dichlorophenyl)-4-methyl-1H-pyrazol-3-yl)-1-cyclopentyl-1H-1,2,3-triazole
3-(5-(4-chlorophenyl)-1-(2,4-dichlorophenyl)-4-methyl-1H-pyrazol-3-yl)-5-cyclopentyl-1-methyl-1H-1,2,4-triazole
3-(5-(4-chlorophenyl)-1-(2,4-dichlorophenyl)-4-methyl-1H-pyrazol-3-yl)-5-cyclohexyl-1-methyl-1H-1,2,4-triazole
2-(5-(4-chlorophenyl)-1-(2,4-dichlorophenyl)-4-methyl-1H-pyrazol-3-yl)-5-(cyclopropylmethyl)-1,3,4-thiadiazole
2-(4-tert-butylcyclohexyl)-5-(5-(4-chlorophenyl)-1-(2,4-dichlorophenyl)-4-methyl-1H-pyrazol-3-yl)-1,3,4-thiadiazole
2-tert-butyl-5-(5-(4-chlorophenyl)-1-(2,4-dichlorophenyl)-4-methyl-1H-pyrazol-3-yl)-1,3,4-thiadiazole
2-(5-(4-chlorophenyl)-1-(2,4-dichlorophenyl)-4-methyl-1H-pyrazol-3-yl)-5-(cyclopropylmethyl)-1,3,4-oxadiazole
2-(5-(4-bromophenyl)-1-(2,4-dichlorophenyl)-4-methyl-1H-pyrazol-3-yl)-5-cyclohexyl-1,3,4-thiadiazole
3-(5-(4-chlorophenyl)-1-(2,4-dichlorophenyl)-4-methyl-1H-pyrazol-3-yl)-5-cyclopropyl-1-ethyl-1H-1,2,4-triazole
3-(5-(4-chlorophenyl)-1-(2,4-dichlorophenyl)-4-methyl-1H-pyrazol-3-yl)-5-cyclopropyl-1-isopropyl-1H-1,2,4-triazole
2-(5-(4-bromophenyl)-1-(2,4-dichlorophenyl)-4-ethyl-1H-pyrazol-3-yl)-5-cyclohexyl-1,3,4-thiadiazole
2-(5-(4-chlorophenyl)-1-(2,4-dichlorophenyl)-4-methyl-1H-pyrazol-3-yl)-5-(cyclopent-3-enyl)-1,3,4-oxadiazole
2-(5-(4-chlorophenyl)-1-(2,4-dichlorophenyl)-4-methyl-1H-pyrazol-3-yl)-5-(cyclopent-3-enyl)-1,3,4-thiadiazole
5-sec-butyl-3-(5-(4-chlorophenyl)-1-(2,4-dichlorophenyl)-4-methyl-1H-pyrazol-3-yl)-1-methyl-1H-1,2,4-triazole
5-sec-butyl-3-(5-(4-chlorophenyl)-1-(2,4-dichlorophenyl)-4-methyl-1H-pyrazol-3-yl)-1-ethyl-1H-1,2,4-triazole
5-sec-butyl-3-(5-(4-chlorophenyl)-1-(2,4-dichlorophenyl)-4-methyl-1H-pyrazol-3-yl)-1-isopropyl-1H-1,2,4-triazole
3-(5-(4-chlorophenyl)-1-(2,4-dichlorophenyl)-4-methyl-1H-pyrazol-3-yl)-5-isopropyl-1-methyl-1H-1,2,4-triazole
3-(5-(4-chlorophenyl)-1-(2,4-dichlorophenyl)-4-methyl-1H-pyrazol-3-yl)-1-ethyl-5-isopropyl-1H-1,2,4-triazole
3-(5-(4-chlorophenyl)-1-(2,4-dichlorophenyl)-4-methyl-1H-pyrazol-3-yl)-1,5-diisopropyl-1H-1,2,4-triazole
2-(5-(4-bromophenyl)-1-(2,4-dichlorophenyl)-4-ethyl-1H-pyrazol-3-yl)-5-cyclobutyl-1,3,4-thiadiazole
2-(5-(4-bromophenyl)-1-(2,4-dichlorophenyl)-4-ethyl-1H-pyrazol-3-yl)-5-yclopentyl-1,3,4-thiadiazole
2-(5-(4-bromophenyl)-1-(2,4-dichlorophenyl)-4-ethyl-1H-pyrazol-3-yl)-5-tert-butyl-1,3,4-thiadiazole
2-(5-(4-bromophenyl)-1-(2,4-dichlorophenyl)-4-methyl-1H-pyrazol-3-yl)-5-cycloheptyl-1,3,4-thiadiazole
2-(5-(4-chlorophenyl)-1-(2,4-dichlorophenyl)-4-methyl-1H-pyrazol-3-yl)-5-(hexan-2-yl)-1,3,4-thiadiazole
2-(5-(4-bromophenyl)-1-(2,4-dichlorophenyl)-4-methyl-1H-pyrazol-3-yl)-5-(hexan-2-yl)-1,3,4-thiadiazole
2-(5-(4-chlorophenyl)-1-(2,4-dichlorophenyl)-4-methyl-1H-pyrazol-3-yl)-5-(1-phenylpropan-2-yl)-1,3,4-thiadiazole
5-butyl-2-(5-(4-chlorophenyl)-1-(2,4-dichlorophenyl)-4-methyl-1H-pyrazol-3-yl)oxazole
2-(5-(4-chlorophenyl)-1-(2,4-dichlorophenyl)-4-methyl-1H-pyrazol-3-yl)-5-ethyloxazole
2-(5-(4-chlorophenyl)-1-(2,4-dichlorophenyl)-4-methyl-1H-pyrazol-3-yl)-5-isobutyloxazole
2-(5-(4-chlorophenyl)-1-(2,4-dichlorophenyl)-4-methyl-1H-pyrazol-3-yl)-5-isobutylthiazole
2-(5-(4-chlorophenyl)-1-(2,4-dichlorophenyl)-4-methyl-1H-pyrazol-3-yl)-5-(1-cyclobutylpropan-2-yl)-1,3,4-oxadiazole
2-(5-(4-chlorophenyl)-1-(2,4-dichlorophenyl)-4-methyl-1H-pyrazol-3-yl)-5-cyclohexyloxazole
2-(5-(4-chlorophenyl)-1-(2,4-dichlorophenyl)-4-methyl-1H-pyrazol-3-yl)-5-cyclohexylthiazole
2-(5-(4-bromophenyl)-1-(2,4-dichlorophenyl)-4-ethyl-1H-pyrazol-3-yl)-5-(cyclohexylmethyl)-1,3,4-thiadiazole
2-(5-(4-bromophenyl)-1-(2,4-dichlorophenyl)-4-methyl-1H-pyrazol-3-yl)-5-(cyclohexylmethyl)-1,3,4-thiadiazole
2-(5-(4-bromophenyl)-1-(2,4-dichlorophenyl)-4-ethyl-1H-pyrazol-3-yl)-5-(cyclohexylmethyl)-1,3,4-oxadiazole
2-(5-(4-bromophenyl)-1-(2,4-dichlorophenyl)-4-methyl-1H-pyrazol-3-yl)-5-(cyclohexylmethyl)-1,3,4-oxadiazole
2-(5-(4-bromophenyl)-1-(2,4-dichlorophenyl)-4-ethyl-1H-pyrazol-3-yl)-5-(hexan-2-yl)-1,3,4-thiadiazole
2-tert-butyl-5-(5-(4-chlorophenyl)-1-(2,4-dichlorophenyl)-4-ethyl-1H-pyrazol-3-yl)-1,3,4-thiadiazole
2-(5-(4-chlorophenyl)-1-(2,4-dichlorophenyl)-4-methyl-1H-pyrazol-3-yl)-5,6-dihydro-4H-cyclopenta[d]thiazole
2-(5-(4-chlorophenyl)-1-(2,4-dichlorophenyl)-4-methyl-1H-pyrazol-3-yl)-4,5,6,7-tetrahydrobenzo[d]oxazole
2-(5-(4-chlorophenyl)-1-(2,4-dichlorophenyl)-4-methyl-1H-pyrazol-3-yl)-4,5,6,7-tetrahydrobenzo[d]thiazole
2-(5-(4-chlorophenyl)-1-(2,4-dichlorophenyl)-4-ethyl-1H-pyrazol-3-yl)-5-cyclohexyl-1,3,4-thiadiazole
2-(5-(4-chlorophenyl)-1-(2,4-dichlorophenyl)-4-methyl-1H-pyrazol-3-yl)-5-cyclopentyloxazole
2-(5-(4-chlorophenyl)-1-(2,4-dichlorophenyl)-4-methyl-1H-pyrazol-3-yl)-5-cyclopentylthiazole
2-(5-(4-chlorophenyl)-1-(2,4-dichlorophenyl)-4-methyl-1H-pyrazol-3-yl)-5-(1-cyclopentylethyl)-1,3,4-oxadiazole
2-(5-(4-chlorophenyl)-1-(2,4-dichlorophenyl)-4-methyl-1H-pyrazol-3-yl)-5-(1-cyclopentylethyl)-1,3,4-thiadiazole
2-(5-(4-chlorophenyl)-1-(2,4-dichlorophenyl)-4-methyl-1H-pyrazol-3-yl)-5-(1-cyclohexylethyl)-1,3,4-oxadiazole
2-(5-(4-chlorophenyl)-1-(2,4-dichlorophenyl)-4-methyl-1H-pyrazol-3-yl)-5-(1-cyclohexylethyl)-1,3,4-thiadiazole 2-(5-(4-chlorophenyl)-1-(2,4-dichlorophenyl)-4-methyl-1H-pyrazol-3-yl)-5-(2-cyclopentylpropan-2-yl)-1,3,4-oxadiazole 2-(5-(4-chlorophenyl)-1-(2,4-dichlorophenyl)-4-methyl-1H-pyrazol-3-yl)-5-(2-cyclopentylpropan-2-yl)-1,3,4-thiadiazole 2-(5-(4-chlorophenyl)-1-(2,4-dichlorophenyl)-4-methyl-1H-pyrazol-3-yl)-5-(2-cyclohexylpropan-2-yl)-1,3,4-oxadiazole 2-(5-(4-chlorophenyl)-1-(2,4-dichlorophenyl)-4-methyl-1H-pyrazol-3-yl)-5-(2-cyclohexylpropan-2-yl)-1,3,4-thiadiazole 2-(5-(4-chlorophenyl)-1-(2,4-dichlorophenyl)-4-methyl-1H-pyrazol-3-yl)-5-(2,2-dichloro-1-methylcyclopropyl)-1,3,4-oxadiazole 2-(5-(4-chlorophenyl)-1-(2,4-dichlorophenyl)-4-methyl-1H-pyrazol-3-yl)-5-(1-(4-chlorophenyl)cyclopropyl)-1,3,4-oxadiazole 2-(5-(4-chlorophenyl)-1-(2,4-dichlorophenyl)-4-ethyl-1H-pyrazol-3-yl)-5-cyclobutyl-1,3,4-thiadiazole 2-(5-(4-chlorophenyl)-1-(2,4-dichlorophenyl)-4-ethyl-1H-pyrazol-3-yl)-5-cyclopentyl-1,3,4-thiadiazole 5-tert-butyl-2-(5-(4-chlorophenyl)-1-(2,4-dichlorophenyl)-4-methyl-1H-pyrazol-3-yl)oxazole 5-tert-butyl-2-(5-(4-chlorophenyl)-1-(2,4-dichlorophenyl)-4-methyl-1H-pyrazol-3-yl)thiazole 2-(5-(4-chlorophenyl)-1-(2,4-dichlorophenyl)-4-methyl-1H-pyrazol-3-yl)-5-(1-phenylcyclopropyl)-1,3,4-oxadiazole 2-(5-(4-chlorophenyl)-1-(2,4-dichlorophenyl)-4-ethyl-1H-pyrazol-3-yl)-5-cycloheptyl-1,3,4-thiadiazole 2-sec-butyl-5-(5-(4-chlorophenyl)-1-(2,4-dichlorophenyl)-4-ethyl-1H-pyrazol-3-yl)-1,3,4-thiadiazole 2-(5-(4-bromophenyl)-1-(2,4-dichlorophenyl)-4-ethyl-1H-pyrazol-3-yl)-5-sec-butyl-1,3,4-thiadiazole 2-(5-(4-bromophenyl)-1-(2,4-dichlorophenyl)-4-ethyl-1H-pyrazol-3-yl)-5-cycloheptyl-1,3,4-thiadiazole 2-(5-(4-chlorophenyl)-1-(2,4-dichlorophenyl)-4-methyl-1H-pyrazol-3-yl)-5-(2-phenylpropan-2-yl)-1,3,4-thiadiazole 2-(5-(4-chlorophenyl)-1-(2,4-dichlorophenyl)-4-methyl-1H-pyrazol-3-yl)-5-(2-(4-chlorophenyl)propan-2-yl)-1,3,4-thiadiazole 2-(5-(4-bromophenyl)-1-(2,4-dichlorophenyl)-4-methyl-1H-pyrazol-3-yl)-5-sec-butyl-1,3,4-thiadiazole 2-(5-(4-bromophenyl)-1-(2,4-dichlorophenyl)-4-ethyl-1H-pyrazol-3-yl)-5-(2-phenylpropan-2-yl)-1,3,4-thiadiazole 2-(5-(4-chlorophenyl)-1-(2,4-dichlorophenyl)-4-methyl-1H-pyrazol-3-yl)-5-(2-(pyridin-2-yloxy)propan-2-yl)-1,3,4-oxadiazole 2-(5-(4-chlorophenyl)-1-(2,4-dichlorophenyl)-4-methyl-1H-pyrazol-3-yl)-5-(2-(5-(trifluoromethyl)pyridin-2-yloxy)propan-2-yl)-1,3,4-oxadiazole 2-tert-butyl-5-(1-(2-chlorophenyl)-5-(4-chlorophenyl)-4-methyl-1H-pyrazol-3-yl)-1,3,4-thiadiazole 2-(5-(4-chlorophenyl)-1-(2,4-dichlorophenyl)-4-methyl-1H-pyrazol-3-yl)-5-(2-methylhexan-2-yl)-1,3,4-thiadiazole 2-sec-butyl-5-(1-(2-chlorophenyl)-5-(4-chlorophenyl)-4-methyl-1H-pyrazol-3-yl)-1,3,4-thiadiazole 2-(1-(2-chlorophenyl)-5-(4-chlorophenyl)-4-methyl-1H-pyrazol-3-yl)-5-cyclohexyl-1,3,4-thiadiazole 2-(1-(2-chlorophenyl)-5-(4-chlorophenyl)-4-methyl-1H-pyrazol-3-yl)-5-cyclobutyl-1,3,4-thiadiazole 2-(1-(2-chlorophenyl)-5-(4-chlorophenyl)-4-methyl-1H-pyrazol-3-yl)-5-tert-pentyl-1,3,4-thiadiazole 2-(1-(2-chlorophenyl)-5-(4-chlorophenyl)-4-methyl-1H-pyrazol-3-yl)-5-(hexan-2-yl)-1,3,4-thiadiazole 2-(5-(4-chlorophenyl)-1-(2,4-dichlorophenyl)-4-ethyl-1H-pyrazol-3-yl)-5-(pentan-2-yl)-1,3,4-thiadiazole 2-(5-(4-bromophenyl)-1-(2,4-dichlorophenyl)-4-methyl-1H-pyrazol-3-yl)-5-(pentan-2-yl)-1,3,4-thiadiazole 2-(5-(4-bromophenyl)-1-(2,4-dichlorophenyl)-4-ethyl-1H-pyrazol-3-yl)-5-(pentan-2-yl)-1,3,4-thiadiazole 2-(1-(2-chlorophenyl)-5-(4-chlorophenyl)-4-methyl-1H-pyrazol-3-yl)-5-(2-methylhexan-2-yl)-1,3,4-thiadiazole 2-(1-(2-chlorophenyl)-5-(4-chlorophenyl)-4-methyl-1H-pyrazol-3-yl)-5-(2-phenylpropan-2-yl)-1,3,4-thiadiazole 2-(5-(4-bromophenyl)-1-(4-chlorophenyl)-4-methyl-1H-pyrazol-3-yl)-5-tert-pentyl-1,3,4-thiadiazole 2-(5-(4-bromophenyl)-1-(4-chlorophenyl)-4-methyl-1H-pyrazol-3-yl)-5-sec-butyl-1,3,4-thiadiazole 2-(1-(allyloxy)-2-methylpropan-2-yl)-5-(5-(4-chlorophenyl)-1-(2,4-dichlorophenyl)-4-methyl-1H-pyrazol-3-yl)-1,3,4-oxadiazole 2-(5-(4-chlorophenyl)-1-(2,4-dichlorophenyl)-4-methyl-1H-pyrazol-3-yl)-5-(2-methoxypropan-2-yl)-1,3,4-thiadiazole 2-(5-(4-chlorophenyl)-1-(2,4-dichlorophenyl)-4-methyl-1H-pyrazol-3-yl)-5-(2-methoxypropan-2-yl)-1,3,4-oxadiazole 2-(1-(2,4-dichlorophenyl)-4-methyl-5-phenyl-1H-pyrazol-3-yl)-5-tert-pentyl-1,3,4-thiadiazole 2-tert-butyl-5-(1-(2,4-dichlorophenyl)-4-methyl-5-phenyl-1H-pyrazol-3-yl)-1,3,4-thiadiazole 2-sec-butyl-5-(1-(2,4-dichlorophenyl)-4-methyl-5-phenyl-1H-pyrazol-3-yl)-1,3,4-thiadiazole 2-cyclobutyl-5-(1-(2,4-dichlorophenyl)-4-methyl-5-phenyl-1H-pyrazol-3-yl)-1,3,4-thiadiazole 2-(5-(4-bromophenyl)-1-(4-chlorophenyl)-4-methyl-1H-pyrazol-3-yl)-5-cyclobutyl-1,3,4-thiadiazole 2-(5-(4-bromophenyl)-1-(4-chlorophenyl)-4-methyl-1H-pyrazol-3-yl)-5-tert-butyl-1,3,4-thiadiazole 2-(5-(4-bromophenyl)-1-(2-chlorophenyl)-4-methyl-1H-pyrazol-3-yl)-5-tert-butyl-1,3,4-thiadiazole 2-(5-(4-bromophenyl)-1-(2-chlorophenyl)-4-methyl-1H-pyrazol-3-yl)-5-cyclohexyl-1,3,4-thiadiazole 2-(5-(4-bromophenyl)-1-(2-chlorophenyl)-4-methyl-1H-pyrazol-3-yl)-5-cyclobutyl-1,3,4-thiadiazole 2-(5-(4-bromophenyl)-1-(2-chlorophenyl)-4-methyl-1H-pyrazol-3-yl)-5-sec-butyl-1,3,4-thiadiazole 2-(5-(4-bromophenyl)-1-(2-chlorophenyl)-4-methyl-1H-pyrazol-3-yl)-5-tert-pentyl-1,3,4-thiadiazole (3-(5-tert-butyl-1,3,4-oxadiazol-2-yl)-5-(4-chlorophenyl)-1-(2,4-dichlorophenyl)-1H-pyrazol-4-yl)methyl acetate (3-(5-tert-butyl-1,3,4-oxadiazol-2-yl)-5-(4-chlorophenyl)-1-(2,4-dichlorophenyl)-1H-pyrazol-4-yl)methyl benzoate 2-(5-(4-chlorophenyl)-1-(2,4-dichlorophenyl)-4-methyl-1H-pyrazol-3-yl)-5-(1-(4-chlorophenyl)cyclopropyl)-1,3,4-thiadiazole 2-(5-(4-chlorophenyl)-1-(2,4-dichlorophenyl)-4-methyl-1H-pyrazol-3-yl)-5-(1-(4-chlorophenyl)cyclobutyl)-1,3,4-thiadiazole 2-(5-(4-chlorophenyl)-1-(2,4-dichlorophenyl)-4-methyl-1H-pyrazol-3-yl)-5-(1-(4-chlorophenyl)cyclobutyl)-1,3,4-oxadiazole 2-(5-(4-bromophenyl)-1-(2,4-dichlorophenyl)-4-ethyl-1H-pyrazol-3-yl)-5-(1-(4-chlorophenyl)cyclopropyl)-1,3,4-oxadiazole 2-(5-(4-bromophenyl)-1-(2,4-dichlorophenyl)-4-ethyl-1H-pyrazol-3-yl)-5-(1-(4-chlorophenyl)cyclopropyl)-1,3,4-thiadiazole 2-(1-(2-chlorophenyl)-5-(4-chlorophenyl)-4-methyl-1H-pyrazol-3-yl)-5-(1-(4-chlorophenyl)cyclopropyl)-1,3,4-oxadiazole 2-(1-(2-chlorophenyl)-5-(4-chlorophenyl)-4-methyl-1H-pyrazol-3-yl)-5-(1-(4-chlorophenyl)cyclopropyl)-1,3,4-thiadiazole 2-tert-butyl-5-(5-(3-chlorophenyl)-1-(2,4-dichlorophenyl)-4-methyl-1H-pyrazol-3-yl)-1,3,4-thiadiazole 2-sec-butyl-5-(5-(3-chlorophenyl)-1-(2,4-dichlorophenyl)-4-methyl-1H-pyrazol-3-yl)-1,3,4-thiadiazole 2-(5-(3-chlorophenyl)-1-(2,4-dichlorophenyl)-4-methyl-1H-pyrazol-3-yl)-5-cyclobutyl-1,3,4-thiadiazole 2-(5-(4-chlorophenyl)-1-(2,4-dichlorophenyl)-4-methyl-1H-pyrazol-3-yl)-5-(2-ethoxypropan-2-yl)-1,3,4-thiadiazole 2-(5-(4-chlorophenyl)-1-(2,4-dichlorophenyl)-4-methyl-1H-pyrazol-3-yl)-5-(2-ethoxypropan-2-yl)-1,3,4-oxadiazole 2-tert-butyl-5-(5-(4-chlorophenyl)-1-(2,4-dichlorophenyl)-4-(fluoromethyl)-1H-pyrazol-3-yl)-1,3,4-oxadiazole 2-(4-(butoxymethyl)-5-(4-chlorophenyl)-1-(2,4-dichlorophenyl)-1H-pyrazol-3-yl)-5-tert-butyl-1,3,4-oxadiazole (3-(5-tert-butyl-1,3,4-oxadiazol-2-yl)-5-(4-chlorophenyl)-1-(2,4-dichlorophenyl)-1H-pyrazol-4-yl)methanol 2-(1,5-bis(4-chlorophenyl)-4-methyl-1H-pyrazol-3-yl)-5-(1-(4-chlorophenyl)cyclopropyl)-1,3,4-oxadiazole 2-(5-(3-chlorophenyl)-1-(2,4-dichlorophenyl)-4-methyl-1H-pyrazol-3-yl)-5-tert-pentyl-1,3,4-thiadiazole 2-tert-butyl-5-(5-(4-chlorophenyl)-1-(2,4-dichlorophenyl)-4-(methoxymethyl)-1H-pyrazol-3-yl)-1,3,4-oxadiazole 2-(1,5-bis(4-chlorophenyl)-4-methyl-1H-pyrazol-3-yl)-5-tert-butyl-1,3,4-thiadiazole 2-(1,5-bis(4-chlorophenyl)-4-methyl-1H-pyrazol-3-yl)-5-sec-butyl-1,3,4-thiadiazole 2-(1,5-bis(4-chlorophenyl)-4-methyl-1H-pyrazol-3-yl)-5-(1-(4-chlorophenyl)cyclopropyl)-1,3,4-thiadiazole 2-(1,5-bis(4-chlorophenyl)-4-methyl-1H-pyrazol-3-yl)-5-tert-pentyl-1,3,4-thiadiazole 2-tert-butyl-5-(5-(4-chlorophenyl)-1-(2,4-dichlorophenyl)-4-(phenoxymethyl)-1H-pyrazol-3-yl)-1,3,4-oxadiazole 2-(5-(4-chlorophenyl)-1-(2,4-dichlorophenyl)-4-methyl-1H-pyrazol-3-yl)-5-(2-propoxypropan-2-yl)-1,3,4-oxadiazole 2-(5-(4-chlorophenyl)-1-(2,4-dichlorophenyl)-4-methyl-1H-pyrazol-3-yl)-5-(2-propoxypropan-2-yl)-1,3,4-thiadiazole 3-(5-tert-butyl-1,3,4-oxadiazol-2-yl)-5-(4-chlorophenyl)-1-(2,4-dichlorophenyl)-1H-pyrazole-4-carbaldehyde 2-tert-butyl-5-(5-(4-chlorophenyl)-1-(2,4-dichlorophenyl)-4-((pyridin-2-yloxy)methyl)-1H-pyrazol-3-yl)-1,3,4-oxadiazole 2-(4-chloro-5-(4-chlorophenyl)-1-(2,4-dichlorophenyl)-1H-pyrazol-3-yl)-5-cyclobutyl-1,3,4-oxadiazole 2-(4-chloro-5-(4-chlorophenyl)-1-(2,4-dichlorophenyl)-1H-pyrazol-3-yl)-5-cyclobutyl-1,3,4-thiadiazole 2-(4-chloro-5-(4-chlorophenyl)-1-(2,4-dichlorophenyl)-1H-pyrazol-3-yl)-5-tert-pentyl-1,3,4-oxadiazole 2-(4-chloro-5-(4-chlorophenyl)-1-(2,4-dichlorophenyl)-1H-pyrazol-3-yl)-5-tert-pentyl-1,3,4-thiadiazole 2-(4-chloro-5-(4-chlorophenyl)-1-(2,4-dichlorophenyl)-1H-pyrazol-3-yl)-5-cyclohexyl-1,3,4-oxadiazole 2-(4-chloro-5-(4-chlorophenyl)-1-(2,4-dichlorophenyl)-1H-pyrazol-3-yl)-5-cyclohexyl-1,3,4-thiadiazole 2-sec-butyl-5-(4-chloro-5-(4-chlorophenyl)-1-(2,4-dichlorophenyl)-1H-pyrazol-3-yl)-1,3,4-oxadiazole 2-sec-butyl-5-(4-chloro-5-(4-chlorophenyl)-1-(2,4-dichlorophenyl)-1H-pyrazol-3-yl)-1,3,4-thiadiazole 2-tert-butyl-5-(4-chloro-5-(4-chlorophenyl)-1-(2,4-dichlorophenyl)-1H-pyrazol-3-yl)-1,3,4-oxadiazole 2-tert-butyl-5-(4-chloro-5-(4-chlorophenyl)-1-(2,4-dichlorophenyl)-1H-pyrazol-3-yl)-1,3,4-thiadiazole 2-tert-butyl-5-(5-(4-chlorophenyl)-1-(2,4-dichlorophenyl)-4-(difluoromethyl)-1H-pyrazol-3-yl)-1,3,4-oxadiazole 2-tert-butyl-5-(5-(4-chlorophenyl)-1-(2,4-dichlorophenyl)-4-(1-methoxyethyl)-1H-pyrazol-3-yl)-1,3,4-oxadiazole 1-(3-(5-tert-butyl-1,3,4-oxadiazol-2-yl)-5-(4-chlorophenyl)-1-(2,4-dichlorophenyl)-1H-pyrazol-4-yl)ethanone 2-tert-butyl-5-(1-(2,4-dichlorophenyl)-5-(4-(methylthio)phenyl)-4-(methylthiomethyl)-1H-pyrazol-3-yl)-1,3,4-oxadiazole 2-tert-butyl-5-(5-(4-chlorophenyl)-1-(2,4-dichlorophenyl)-4-(piperidin-1-ylmethyl)-1H-pyrazol-3-yl)-1,3,4-oxadiazole 2-(5-(4-bromophenyl)-1-(2,4-dichlorophenyl)-4-ethyl-1H-pyrazol-3-yl)-5-(1-phenylcyclopropyl)-1,3,4-oxadiazole 2-(5-(4-bromophenyl)-1-(2,4-dichlorophenyl)-4-ethyl-1H-pyrazol-3-yl)-5-(1-phenylcyclopropyl)-1,3,4-thiadiazole 2-(5-(4-bromophenyl)-1-(2,4-dichlorophenyl)-4-ethyl-1H-pyrazol-3-yl)-5-tert-pentyl-1,3,4-thiadiazole 2-(bicyclo[2.2.1]heptan-2-yl)-5-(5-(4-bromophenyl)-1-(2,4-dichlorophenyl)-4-ethyl-1H-pyrazol-3-yl)-1,3,4-thiadiazole 2-(5-(4-bromophenyl)-1-(2,4-dichlorophenyl)-4-ethyl-1H-pyrazol-3-yl)-5-isopropyl-1,3,4-thiadiazole 2-(5-(4-bromophenyl)-1-(2,4-dichlorophenyl)-4-ethyl-1H-pyrazol-3-yl)-5-(pentan-3-yl)-1,3,4-thiadiazole 2-(5-(4-Bromophenyl)-1-(2,4-dichlorophenyl)-4-ethyl-1H-pyrazol-3-yl)-5-(1-methylcyclohexyl)-1,3,4-thiadiazole Methyl (3-(5-tert-butyl-1,3,4-oxadiazol-2-yl)-5-(4-chlorophenyl)-1-(2,4-dichlorophenyl)-1H-pyrazol-4-yl)methylcarbamate N-((3-(5-tert-butyl-1,3,4-oxadiazol-2-yl)-5-(4-chlorophenyl)-1-(2,4-dichlorophenyl)-1H-pyrazol-4-yl)methyl)-N-methylethanamine 5'-tert-butyl-5-(4-chlorophenyl)-1-(2,4-dichlorophenyl)-4-methyl-1H,1'H-3,3'-bipyrazole 2-(4-((1H-imidazol-1-yl)methyl)-5-(4-chlorophenyl)-1-(2,4-dichlorophenyl)-1H-pyrazol-3-yl)-5-tert-butyl-1,3,4-oxadiazole 5-tert-butyl-3-(5-(4-chlorophenyl)-1-(2,4-dichlorophenyl)-4-methyl-1H-pyrazol-3-yl)isoxazole 3-tert-butyl-5-(5-(4-chlorophenyl)-1-(2,4-dichlorophenyl)-4-methyl-1H-pyrazol-3-yl)isoxazole 2-(1-(benzyloxy)pentyl)-5-(5-(4-chlorophenyl)-1-(2,4-dichlorophenyl)-4-methyl-1H-pyrazol-3-yl)-1,3,4-oxadiazole 2-(2-(allyloxy)propan-2-yl)-5-(5-(4-chlorophenyl)-1-(2,4-dichlorophenyl)-4-methyl-1H-pyrazol-3-yl)-1,3,4-oxadiazole 2-(2-(allyloxy)propan-2-yl)-5-(5-(4-chlorophenyl)-1-(2,4-dichlorophenyl)-4-methyl-1H-pyrazol-3-yl)-1,3,4-thiadiazole 1-(5-(5-(4-chlorophenyl)-1-(2,4-dichlorophenyl)-4-methyl-1H-pyrazol-3-yl)-1,3,4-oxadiazol-2-yl)pentan-1-ol 2-tert-butyl-5-(5-(4-chlorophenyl)-1-(2,4-dichlorophenyl)-4-(pyrrolidin-1-ylmethyl)-1H-pyrazol-3-yl)-1,3,4-oxadiazole 2-(4-((1H-1,2,4-triazol-1-yl)methyl)-5-(4-chlorophenyl)-1-(2,4-dichlorophenyl)-1H-pyrazol-3-yl)-5-tert-butyl-1,3,4-oxadiazole 1-((3-(5-tert-butyl-1,3,4-oxadiazol-2-yl)-5-(4-chlorophenyl)-1-(2,4-dichlorophenyl)-1H-pyrazol-4-yl)methyl)pyrrolidine-2,5-dione 1-(3-(5-tert-butyl-1,3,4-oxadiazol-2-yl)-5-(4-chlorophenyl)-1-(2,4-dichlorophenyl)-1H-pyrazol-4-yl)ethanol 2-tert-butyl-5-(5-(4-chlorophenyl)-1-(2,4-dichlorophenyl)-4-(1-fluoroethyl)-1H-pyrazol-3-yl)-1,3,4-oxadiazole 1-((3-(5-tert-butyl-1,3,4-oxadiazol-2-yl)-5-(4-chlorophenyl)-1-(2,4-dichlorophenyl)-1H-pyrazol-4-yl)methyl)pyrrolidin-2-one 3-((3-(5-tert-butyl-1,3,4-oxadiazol-2-yl)-5-(4-chlorophenyl)-1-(2,4-dichlorophenyl)-1H-pyrazol-4-yl)methyl)oxazolidin-2-one S-(3-(5-tert-butyl-1,3,4-oxadiazol-2-yl)-5-(4-chlorophenyl)-1-(2,4-dichlorophenyl)-1H-pyrazol-4-yl)methyl ethanethioate 4-((3-(5-tert-butyl-1,3,4-oxadiazol-2-yl)-5-(4-chlorophenyl)-1-(2,4-dichlorophenyl)-1H-pyrazol-4-yl)methyl)morpholine 2-(4-bromo-5-(4-chlorophenyl)-1-(2,4-dichlorophenyl)-1H-pyrazol-3-yl)-5-tert-butyl-1,3,4-oxadiazole 2-(4-bromo-5-(4-chlorophenyl)-1-(2,4-dichlorophenyl)-1H-pyrazol-3-yl)-5-tert-butyl-1,3,4-thiadiazole 2-(4-bromo-5-(4-chlorophenyl)-1-(2,4-dichlorophenyl)-1H-pyrazol-3-yl)-5-sec-butyl-1,3,4-oxadiazole 2-(4-bromo-5-(4-chlorophenyl)-1-(2,4-dichlorophenyl)-1H-pyrazol-3-yl)-5-sec-butyl-1,3,4-thiadiazole 2-(4-bromo-5-(4-chlorophenyl)-1-(2,4-dichlorophenyl)-1H-pyrazol-3-yl)-5-cyclobutyl-1,3,4-oxadiazole 2-(4-bromo-5-(4-chlorophenyl)-1-(2,4-dichlorophenyl)-1H-pyrazol-3-yl)-5-cyclobutyl-1,3,4-thiadiazole 2-(4-bromo-5-(4-chlorophenyl)-1-(2,4-dichlorophenyl)-1H-pyrazol-3-yl)-5-cyclohexyl-1,3,4-oxadiazole 2-(4-bromo-5-(4-chlorophenyl)-1-(2,4-dichlorophenyl)-1H-pyrazol-3-yl)-5-cyclohexyl-1,3,4-thiadiazole 2-(4-bromo-5-(4-chlorophenyl)-1-(2,4-dichlorophenyl)-1H-pyrazol-3-yl)-5-tert-pentyl-1,3,4-oxadiazole 2-(4-bromo-5-(4-chlorophenyl)-1-(2,4-dichlorophenyl)-1H-pyrazol-3-yl)-5-tert-pentyl-1,3,4-thiadiazole 2-(4-bromo-5-(4-chlorophenyl)-1-(2,4-dichlorophenyl)-1H-pyrazol-3-yl)-5-(2-(4-chlorophenyl)propan-2-yl)-1,3,4-oxadiazole 2-(4-bromo-5-(4-chlorophenyl)-1-(2,4-dichlorophenyl)-1H-pyrazol-3-yl)-5-(2-(4-chlorophenyl)propan-2-yl)-1,3,4-thiadiazole 2-tert-butyl-5-(5-(4-chlorophenyl)-1-(2,4-dichlorophenyl)-4-vinyl-1H-pyrazol-3-yl)-1,3,4-oxadiazole 2-(3-(5-tert-butyl-1,3,4-oxadiazol-2-yl)-5-(4-chlorophenyl)-1-(2,4-dichlorophenyl)-1H-pyrazol-4-yl)propan-2-ol ((1R,2S)-2-(5-(5-(4-chlorophenyl)-1-(2,4-dichlorophenyl)-4-methyl-1H-pyrazol-3-yl)-1,3,4-oxadiazol-2-yl)cyclopropyl)(piperidin-1-yl)methanone 2-(2-butoxypropan-2-yl)-5-(5-(4-chlorophenyl)-1-(2,4-dichlorophenyl)-4-methyl-1H-pyrazol-3-yl)-1,3,4-oxadiazole 2-(2-butoxypropan-2-yl)-5-(5-(4-chlorophenyl)-1-(2,4-dichlorophenyl)-4-methyl-1H-pyrazol-3-yl)-1,3,4-thiadiazole 2-(5-(4-chlorophenyl)-1-(2,4-dichlorophenyl)-4-methyl-1H-pyrazol-3-yl)-5-(1-(4-methoxyphenyl)cyclopropyl)-1,3,4-oxadiazole 2-(5-(4-chlorophenyl)-1-(2,4-dichlorophenyl)-4-methyl-1H-pyrazol-3-yl)-5-(1-(4-methoxyphenyl)cyclopropyl)-1,3,4-thiadiazole 2-(5-(4-chlorophenyl)-1-(2,4-dichlorophenyl)-4-methyl-1H-pyrazol-3-yl)-5-(1-(2,4-dichlorophenyl)cyclopropyl)-1,3,4-oxadiazole 2-(5-(4-chlorophenyl)-1-(2,4-dichlorophenyl)-4-methyl-1H-pyrazol-3-yl)-5-(1-(2,4-dichlorophenyl)cyclopropyl)-1,3,4-thiadiazole 2-(5-(4-chlorophenyl)-1-(2,4-dichlorophenyl)-4-methyl-1H-pyrazol-3-yl)-5-(1-p-tolylcyclopropyl)-1,3,4-oxadiazole 2-tert-butyl-5-(5-(4-chlorophenyl)-1-(2,4-dichlorophenyl)-4-(prop-1-en-2-yl)-1H-pyrazol-3-yl)-1,3,4-oxadiazole 2-(5-(4-chlorophenyl)-1-(2,4-dichlorophenyl)-4-methyl-1H-pyrazol-3-yl)-5-(1-p-tolylcyclopropyl)-1,3,4-thiadiazole 2-(5-(4-chlorophenyl)-1-(2,4-dichlorophenyl)-4-methyl-1H-pyrazol-3-yl)-5-(2-(pentyloxy)propan-2-yl)-1,3,4-oxadiazole 2-(5-(4-chlorophenyl)-1-(2,4-dichlorophenyl)-4-methyl-1H-pyrazol-3-yl)-5-(2-(pentyloxy)propan-2-yl)-1,3,4-thiadiazole 2-(5-(4-chlorophenyl)-1-(2,4-dichlorophenyl)-4-methyl-1H-pyrazol-3-yl)-5-(1-(trifluoromethyl)cyclopropyl)-1,3,4-oxadiazole 2-(5-(4-chlorophenyl)-1-(2,4-dichlorophenyl)-4-methyl-1H-pyrazol-3-yl)-5-(1-(trifluoromethyl)cyclopropyl)-1,3,4-thiadiazole 5-tert-butyl-3-(5-(4-chlorophenyl)-1-(2,4-dichlorophenyl)-4-methyl-1H-pyrazol-3-yl)isothiazole 2-(5-(4-chlorophenyl)-1-(2,4-dichlorophenyl)-4-ethyl-1H-pyrazol-3-yl)-5-(1-(4-chlorophenyl)cyclopropyl)-1,3,4-oxadiazole 2-(5-(4-chlorophenyl)-1-(2,4-dichlorophenyl)-4-ethyl-1H-pyrazol-3-yl)-5-(1-(4-chlorophenyl)cyclopropyl)-1,3,4-thiadiazole (3-(5-tert-butyl-1,3,4-oxadiazol-2-yl)-5-(4-chlorophenyl)-1-(2,4-dichlorophenyl)-1H-pyrazol-4-yl)methanethiol 2-(4-((1H-pyrazol-1-yl)methyl)-5-(4-chlorophenyl)-1-(2,4-dichlorophenyl)-1H-pyrazol-3-yl)-5-tert-butyl-1,3,4-oxadiazole 2-(5-(4-bromophenyl)-1-(2-chlorophenyl)-4-ethyl-1H-pyrazol-3-yl)-5-(1-(4-chlorophenyl)cyclopropyl)-1,3,4-oxadiazole 2-(5-(4-bromophenyl)-1-(2-chlorophenyl)-4-ethyl-1H-pyrazol-3-yl)-5-(1-(4-chlorophenyl)cyclopropyl)-1,3,4-thiadiazole 3-(5-tert-butyl-1,3,4-oxadiazol-2-yl)-5-(4-chlorophenyl)-1-(2,4-dichlorophenyl)-1H-pyrazol-4-yl acetate (5-(4-bromophenyl)-3-(5-tert-butyl-1,3,4-oxadiazol-2-yl)-1-(2,4-dichlorophenyl)-1H-pyrazol-4-yl)methyl acetate 2-(4-((1H-pyrrol-1-yl)methyl)-5-(4-chlorophenyl)-1-(2,4-dichlorophenyl)-1H-pyrazol-3-yl)-5-tert-butyl-1,3,4-oxadiazole 2-(4-bromo-5-(4-chlorophenyl)-1-(2,4-dichlorophenyl)-1H-pyrazol-3-yl)-5-(1-(4-chlorophenyl)cyclopropyl)-1,3,4-oxadiazole 2-(4-bromo-5-(4-chlorophenyl)-1-(2,4-dichlorophenyl)-1H-pyrazol-3-yl)-5-(1-(4-chlorophenyl)cyclopropyl)-1,3,4-thiadiazole 2-(5-(4-chlorophenyl)-1-(2,4-dichlorophenyl)-4-methyl-1H-pyrazol-3-yl)-5-(1-(trifluoromethyl)cyclobutyl)-1,3,4-oxadiazole 2-(5-(4-chlorophenyl)-1-(2,4-dichlorophenyl)-4-methyl-1H-pyrazol-3-yl)-5-(1-(trifluoromethyl)cyclobutyl)-1,3,4-thiadiazole 2-(2-(benzyloxy)propan-2-yl)-5-(5-(4-chlorophenyl)-1-(2,4-dichlorophenyl)-4-methyl-1H-pyrazol-3-yl)-1,3,4-oxadiazole 2-(5-(4-chlorophenyl)-1-(2,4-dichlorophenyl)-4-methyl-1H-pyrazol-3-yl)-5-(2,2,2-trifluoroethyl)-1,3,4-oxadiazole 2-(5-(4-chlorophenyl)-1-(2,4-dichlorophenyl)-4-methyl-1H-pyrazol-3-yl)-5-(2,2,2-trifluoroethyl)-1,3,4-thiadiazole 2-(5-(4-chlorophenyl)-1-(2,3-dichlorophenyl)-4-methyl-1H-pyrazol-3-yl)-5-(1-(4-chlorophenyl)cyclobutyl)-1,3,4-oxadiazole
2-(1-(4-chlorophenyl)cyclopropyl)-5-(1-(2,4-dichlorophenyl)-5-(4-methoxyphenyl)-4-methyl-1H-pyrazol-3-yl)-1,3,4-oxadiazole
2-(5-(4-chlorophenyl)-1-(2,3-dichlorophenyl)-4-methyl-1H-pyrazol-3-yl)-5-(1-(4-chlorophenyl)cyclopropyl)-1,3,4-oxadiazole
2-(3-(5-tert-butyl-1,3,4-oxadiazol-2-yl)-5-(4-chlorophenyl)-1-(2,4-dichlorophenyl)-1H-pyrazol-4-yl)acetonitrile
2-(1-(2-chlorophenyl)-5-(4-chlorophenyl)-4-ethyl-1H-pyrazol-3-yl)-5-(1-(4-chlorophenyl)cyclopropyl)-1,3,4-oxadiazole
2-(1-(2-chlorophenyl)-5-(4-chlorophenyl)-4-ethyl-1H-pyrazol-3-yl)-5-(1-(4-chlorophenyl)cyclobutyl)-1,3,4-oxadiazole
N-((3-(5-tert-butyl-1,3,4-oxadiazol-2-yl)-5-(4-chlorophenyl)-1-(2,4-dichlorophenyl)-1H-pyrazol-4-yl)methyl)-2-methylpropan-2-amine
N-((3-(5-tert-butyl-1,3,4-oxadiazol-2-yl)-5-(4-chlorophenyl)-1-(2,4-dichlorophenyl)-1H-pyrazol-4-yl)methyl)propan-2-amine
2-(5-(4-chlorophenyl)-1-(2,4-dichlorophenyl)-4-ethyl-1H-pyrazol-3-yl)-5-(1-phenylcyclopropyl)-1,3,4-oxadiazole
2-(5-(4-chlorophenyl)-1-(2,4-dichlorophenyl)-4-ethyl-1H-pyrazol-3-yl)-5-(1-p-tolylcyclopropyl)-1,3,4-oxadiazole
2-(5-(4-chlorophenyl)-1-(2,4-dichlorophenyl)-4-ethyl-1H-pyrazol-3-yl)-5-(1-(4-methoxyphenyl)cyclopropyl)-1,3,4-oxadiazole
2-(5-(4-chlorophenyl)-1-(2,4-dichlorophenyl)-4-ethyl-1H-pyrazol-3-yl)-5-(1-(2,4-dichlorophenyl)cyclopropyl)-1,3,4-oxadiazole
2-(5-(4-chlorophenyl)-1-(2,4-dichlorophenyl)-4-ethyl-1H-pyrazol-3-yl)-5-(1-(4-chlorophenyl)cyclobutyl)-1,3,4-oxadiazole
2-(5-(4-chlorophenyl)-1-(2,4-dichlorophenyl)-4-ethyl-1H-pyrazol-3-yl)-5-(1-(trifluoromethyl)cyclopropyl)-1,3,4-oxadiazole
2-(5-(4-chlorophenyl)-1-(2,4-dichlorophenyl)-4-methyl-1H-pyrazol-3-yl)-5-(1-(3-chlorophenyl)cyclopropyl)-1,3,4-oxadiazole
2-(5-(4-chlorophenyl)-1-(2,4-dichlorophenyl)-4-ethyl-1H-pyrazol-3-yl)-5-(1-(3-chlorophenyl)cyclopropyl)-1,3,4-oxadiazole
2-(1-allylcyclopropyl)-5-(5-(4-bromophenyl)-1-(2,4-dichlorophenyl)-4-ethyl-1H-pyrazol-3-yl)-1,3,4-oxadiazole
5-(5-(4-bromophenyl)-1-(2,4-dichlorophenyl)-4-methyl-1H-pyrazol-3-yl)-1-cyclopentyl-1H-tetrazole
5-(5-(4-bromophenyl)-1-(2,4-dichlorophenyl)-4-methyl-1H-pyrazol-3-yl)-1-cyclohexyl-1H-tetrazole
5-(5-(4-bromophenyl)-1-(2,4-dichlorophenyl)-4-methyl-1H-pyrazol-3-yl)-1-cycloheptyl-1H-tetrazole
2-(1-(2-bromophenyl)-5-(4-chlorophenyl)-4-methyl-1H-pyrazol-3-yl)-5-(1-(4-chlorophenyl)cyclopropyl)-1,3,4-oxadiazole
2-(1-(2-bromophenyl)-5-(4-chlorophenyl)-4-methyl-1H-pyrazol-3-yl)-5-(1-(4-chlorophenyl)cyclobutyl)-1,3,4-oxadiazole
2-(5-(4-chlorophenyl)-1-(2,6-dichlorophenyl)-4-methyl-1H-pyrazol-3-yl)-5-(1-(4-chlorophenyl)cyclopropyl)-1,3,4-oxadiazole
2-(5-(4-chlorophenyl)-1-(2,6-dichlorophenyl)-4-methyl-1H-pyrazol-3-yl)-5-(1-(4-chlorophenyl)cyclobutyl)-1,3,4-oxadiazole
(5-(4-bromophenyl)-3-(5-tert-butyl-1,3,4-oxadiazol-2-yl)-1-(2,4-dichlorophenyl)-1H-pyrazol-4-yl)methanol
5-(5-(4-bromophenyl)-1-(2,4-dichlorophenyl)-4-ethyl-1H-pyrazol-3-yl)-1-cyclopentyl-1H-tetrazole
2-(5-(4-bromophenyl)-1-(2,4-dichlorophenyl)-4-(fluoromethyl)-1H-pyrazol-3-yl)-5-tert-butyl-1,3,4-oxadiazole
5-(5-(4-chlorophenyl)-1-(2,4-dichlorophenyl)-4-ethyl-1H-pyrazol-3-yl)-1-cyclopentyl-1H-tetrazole
5-(4-bromophenyl)-3-(5-tert-butyl-1,3,4-oxadiazol-2-yl)-1-(2,4-dichlorophenyl)-1H-pyrazole-4-carbaldehyde
2-(4-((1H-1,2,3-triazol-1-yl)methyl)-5-(4-chlorophenyl)-1-(2,4-dichlorophenyl)-1H-pyrazol-3-yl)-5-tert-butyl-1,3,4-oxadiazole
2-(4-((1H-1,2,4-triazol-1-yl)methyl)-5-(4-chlorophenyl)-1-(2,4-dichlorophenyl)-1H-pyrazol-3-yl)-5-tert-butyl-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopropyl)-1,3,4-oxadiazole
2-(5-(4-chlorophenyl)-1-(2,5-dichlorophenyl)-4-methyl-1H-pyrazol-3-yl)-5-(1-(4-chlorophenyl)cyclopropyl)-1,3,4-oxadiazole
2-(5-(4-chlorophenyl)-1-(2,5-dichlorophenyl)-4-methyl-1H-pyrazol-3-yl)-5-(1-(4-chlorophenyl)cyclobutyl)-1,3,4-oxadiazole
2-tert-butyl-5-(5-(4-chlorophenyl)-1-(2,4-dichlorophenyl)-4-ethynyl-1H-pyrazol-3-yl)-1,3,4-oxadiazole
2-(5-(4-bromophenyl)-1-(2,4-dichlorophenyl)-4-ethyl-1H-pyrazol-3-yl)-5-(1-propylcyclopropyl)-1,3,4-oxadiazole
2-tert-butyl-5-(5-(4-chlorophenyl)-1-(2,4-dichlorophenyl)-4-(prop-1-ynyl)-1H-pyrazol-3-yl)-1,3,4-oxadiazole
2-tert-butyl-5-(5-(4-chlorophenyl)-1-(2,4-dichlorophenyl)-4-(3-(trimethylsilyl)prop-2-ynyl)-1H-pyrazol-3-yl)-1,3,4-oxadiazole
2-(4-((1H-tetrazol-1-yl)methyl)-5-(4-chlorophenyl)-1-(2,4-dichlorophenyl)-1H-pyrazol-3-yl)-5-tert-butyl-1,3,4-oxadiazole
2-(4-((1H-tetrazol-5-yl)methyl)-5-(4-chlorophenyl)-1-(2,4-dichlorophenyl)-1H-pyrazol-3-yl)-5-tert-butyl-1,3,4-oxadiazole
2-tert-butyl-5-(5-(4-chlorophenyl)-1-(2,4-dichlorophenyl)-4-(propa-1,2-dienyl)-1H-pyrazol-3-yl)-1,3,4-oxadiazole
2-(5-(4-bromophenyl)-3-(5-tert-butyl-1,3,4-oxadiazol-2-yl)-1-(2,4-dichlorophenyl)-1H-pyrazol-4-yl)propan-2-ol
2-(5-(4-bromophenyl)-1-(2,4-dichlorophenyl)-4-(prop-1-en-2-yl)-1H-pyrazol-3-yl)-5-tert-butyl-1,3,4-oxadiazole
2-(1-(2,4-dichlorophenyl)-5-(4-methoxyphenyl)-4-methyl-1H-pyrazol-3-yl)-5-(1-(4-methoxyphenyl)cyclopropyl)-1,3,4-oxadiazole
2-(5-(4-bromophenyl)-1-(2,4-dichlorophenyl)-4-ethyl-1H-pyrazol-3-yl)-5-(1-(trifluoromethyl)cyclopropyl)-1,3,4-oxadiazole
2-(5-(4-bromophenyl)-1-(2,4-dichlorophenyl)-4-ethyl-1H-pyrazol-3-yl)-5-(1-(2,4-dichlorophenyl)cyclopropyl)-1,3,4-oxadiazole
2-(5-(4-bromophenyl)-1-(2,4-dichlorophenyl)-4-ethyl-1H-pyrazol-3-yl)-5-(1-(4-methoxyphenyl)cyclopropyl)-1,3,4-oxadiazole
2-(5-(4-bromophenyl)-1-(2,4-dichlorophenyl)-4-ethyl-1H-pyrazol-3-yl)-5-(1-p-tolylcyclopropyl)-1,3,4-oxadiazole
2-(5-(4-bromophenyl)-1-(2,4-dichlorophenyl)-4-(1-fluoroethyl)-1H-pyrazol-3-yl)-5-tert-butyl-1,3,4-oxadiazole
1-(5-(4-bromophenyl)-3-(5-tert-butyl-1,3,4-oxadiazol-2-yl)-1-(2,4-dichlorophenyl)-1H-pyrazol-4-yl)ethanol
2-(5-(4-bromophenyl)-1-(2,4-dichlorophenyl)-4-vinyl-1H-pyrazol-3-yl)-5-tert-butyl-1,3,4-oxadiazole
Methyl 1-(5-(4-bromophenyl)-3-(5-tert-butyl-1,3,4-oxadiazol-2-yl)-1-(2,4-dichlorophenyl)-1H-pyrazol-4-yl)ethylcarbamate 1-(5-(4-bromophenyl)-3-(5-tert-butyl-1,3,4-oxadiazol-2-yl)-1-(2,4-dichlorophenyl)-1H-pyrazol-4-yl)ethanone
1-(5-(4-bromophenyl)-3-(5-tert-butyl-1,3,4-oxadiazol-2-yl)-1-(2,4-dichlorophenyl)-1H-pyrazol-4-yl)ethanone
1-(5-(5-(4-chlorophenyl)-1-(2,4-dichlorophenyl)-4-methyl-1H-pyrazol-3-yl)-1,3,4-oxadiazol-2-yl)cyclopropanecarbonitrile
2-(5-(4-chlorophenyl)-1-(2,4-dichlorophenyl)-4-methyl-1H-pyrazol-3-yl)-5-(1-(pyridin-2-yl)cyclopropyl)-1,3,4-oxadiazole
2-(5-(4-chlorophenyl)-1-(2,4-dichlorophenyl)-4-isopropyl-1H-pyrazol-3-yl)-5-(1-(4-chlorophenyl)cyclopropyl)-1,3,4-oxadiazole
2-(5-(4-chlorophenyl)-1-(2,4-dichlorophenyl)-4-isopropyl-1H-pyrazol-3-yl)-5-(1-(4-chlorophenyl)cyclobutyl)-1,3,4-oxadiazole
2-(5-(4-chlorophenyl)-1-(2,4-dichlorophenyl)-4-propyl-1H-pyrazol-3-yl)-5-(1-(4-chlorophenyl)cyclopropyl)-1,3,4-oxadiazole
2-(5-(4-chlorophenyl)-1-(2,4-dichlorophenyl)-4-propyl-1H-pyrazol-3-yl)-5-(1-(4-chlorophenyl)cyclobutyl)-1,3,4-oxadiazole
(5-(4-bromophenyl)-3-(5-tert-butyl-1,3,4-thiadiazol-2-yl)-1-(2,4-dichlorophenyl)-1H-pyrazol-4-yl)methyl acetate
(5-(4-bromophenyl)-3-(5-tert-butyl-1,3,4-thiadiazol-2-yl)-1-(2,4-dichlorophenyl)-1H-pyrazol-4-yl)methanol
2-(1-benzylcyclopropyl)-5-(5-(4-chlorophenyl)-1-(2,4-dichlorophenyl)-4-methyl-1H-pyrazol-3-yl)-1,3,4-oxadiazole
2-(1-benzylcyclopropyl)-5-(5-(4-bromophenyl)-1-(2,4-dichlorophenyl)-4-ethyl-1H-pyrazol-3-yl)-1,3,4-oxadiazole
2-(1-benzylcyclopropyl)-5-(5-(4-chlorophenyl)-1-(2,4-dichlorophenyl)-4-methyl-1H-pyrazol-3-yl)-1,3,4-thiadiazole
2-(1-benzylcyclopropyl)-5-(5-(4-bromorophenyl)-1-(2,4-dichlorophenyl)-4-ethyl-1H-pyrazol-3-yl)-1,3,4-thiadiazole
2-(5-(4-chlorophenyl)-1-(2,4-dichlorophenyl)-4-methyl-1H-pyrazol-3-yl)-5-(1-methylcyclopropyl)-1,3,4-oxadiazole
2-(5-(4-chlorophenyl)-1-(2,4-dichlorophenyl)-4-methyl-1H-pyrazol-3-yl)-5-(1-methylcyclopropyl)-1,3,4-thiadiazole
2-(5-(4-bromophenyl)-1-(2,4-dichlorophenyl)-4-ethyl-1H-pyrazol-3-yl)-5-(1-methylcyclopropyl)-1,3,4-oxadiazole
2-(5-(4-bromophenyl)-1-(2,4-dichlorophenyl)-4-ethyl-1H-pyrazol-3-yl)-5-(1-methylcyclopropyl)-1,3,4-thiadiazole
2-(1-(4-chlorobenzyl)cyclopropyl)-5-(5-(4-chlorophenyl)-1-(2,4-dichlorophenyl)-4-methyl-1H-pyrazol-3-yl)-1,3,4-oxadiazole
2-(1-(4-chlorobenzyl)cyclopropyl)-5-(5-(4-chlorophenyl)-1-(2,4-dichlorophenyl)-4-methyl-1H-pyrazol-3-yl)-1,3,4-thiadiazole
2-(1-(4-chlorobenzyl)cyclopropyl)-5-(5-(4-bromophenyl)-1-(2,4-dichlorophenyl)-4-ethyl-1H-pyrazol-3-yl)-1,3,4-oxadiazole
2-(1-(4-chlorobenzyl)cyclopropyl)-5-(5-(4-bromophenyl)-1-(2,4-dichlorophenyl)-4-ethyl-1H-pyrazol-3-yl)-1,3,4-thiadiazole
2-(5-(4-bromophenyl)-1-(2,4-dichlorophenyl)-4-(methoxymethyl)-1H-pyrazol-3-yl)-5-tert-butyl-1,3,4-thiadiazole
2-(5-(4-bromophenyl)-1-(2,4-dichlorophenyl)-4-ethyl-1H-pyrazol-3-yl)-5-(1-(4-methoxyphenyl)cyclopropyl)-1,3,4-thiadiazole
2-(5-(4-bromophenyl)-1-(2,4-dichlorophenyl)-4-ethyl-1H-pyrazol-3-yl)-5-(1-p-tolylcyclopropyl)-1,3,4-thiadiazole
2-(5-(4-bromophenyl)-1-(2,4-dichlorophenyl)-4-ethyl-1H-pyrazol-3-yl)-5-(1-phenylcyclopropyl)-1,3,4-thiadiazole
2-(5-(4-bromophenyl)-1-(2,4-dichlorophenyl)-4-ethyl-1H-pyrazol-3-yl)-5-(1-(4-chlorophenyl)cyclobutyl)-1,3,4-thiadiazole
2-(5-(4-bromophenyl)-1-(2,4-dichlorophenyl)-4-ethyl-1H-pyrazol-3-yl)-5-(1-(4-chlorophenyl)cyclopropyl)-1,3,4-thiadiazole
2-(5-(4-bromophenyl)-1-(2,4-dichlorophenyl)-4-ethyl-1H-pyrazol-3-yl)-5-(1-(2,4-dichlorophenyl)cyclopropyl)-1,3,4-thiadiazole
2-(5-(4-chlorophenyl)-1-(2,4-dichlorophenyl)-4-ethyl-1H-pyrazol-3-yl)-5-(1-phenylcyclopropyl)-1,3,4-thiadiazole
2-(5-(4-chlorophenyl)-1-(2,4-dichlorophenyl)-4-ethyl-1H-pyrazol-3-yl)-5-(1-p-tolylcyclopropyl)-1,3,4-thiadiazole
2-(5-(4-chlorophenyl)-1-(2,4-dichlorophenyl)-4-ethyl-1H-pyrazol-3-yl)-5-(1-(4-methoxyphenyl)cyclopropyl)-1,3,4-thiadiazole
2-(5-(4-chlorophenyl)-1-(2,4-dichlorophenyl)-4-ethyl-1H-pyrazol-3-yl)-5-(1-(2,4-dichlorophenyl)cyclopropyl)-1,3,4-thiadiazole
2-(5-(4-chlorophenyl)-1-(2,4-dichlorophenyl)-4-ethyl-1H-pyrazol-3-yl)-5-(1-(4-chlorophenyl)cyclobutyl)-1,3,4-thiadiazole
(5-(4-chlorophenyl)-3-(5-(1-(4-chlorophenyl)cyclopropyl)-1,3,4-oxadiazol-2-yl)-1-(2,4-dichlorophenyl)-1H-pyrazol-4-yl)methyl acetate
(5-(4-chlorophenyl)-3-(5-(1-(4-chlorophenyl)cyclopropyl)-1,3,4-oxadiazol-2-yl)-1-(2,4-dichlorophenyl)-1H-pyrazol-4-yl)methanol
2-(5-(4-chlorophenyl)-1-(2,4-dichlorophenyl)-4-(fluoromethyl)-1H-pyrazol-3-yl)-5-(1-(4-chlorophenyl)cyclopropyl)-1,3,4-oxadiazole
5-(4-chlorophenyl)-3-(5-(1-(4-chlorophenyl)cyclopropyl)-1,3,4-oxadiazol-2-yl)-1-(2,4-dichlorophenyl)-1H-pyrazole-4-carbaldehyde
2-(5-(4-chlorophenyl)-1-(2,4-dichlorophenyl)-4-ethyl-1H-pyrazol-3-yl)-5-(1-methylcyclopropyl)-1,3,4-oxadiazole
2-(5-(4-chlorophenyl)-1-(2,4-dichlorophenyl)-4-ethyl-1H-pyrazol-3-yl)-5-(1-methylcyclopropyl)-1,3,4-thiadiazole
1-(1-(5-(5-(4-chlorophenyl)-1-(2,4-dichlorophenyl)-4-methyl-1H-pyrazol-3-yl)-1,3,4-oxadiazol-2-yl)cyclopropyl)ethanone
2-(5-(4-bromophenyl)-1-(2,4-dichlorophenyl)-4-(fluoromethyl)-1H-pyrazol-3-yl)-5-tert-butyl-1,3,4-thiadiazole
2-(5-(4-bromophenyl)-1-(2,4-dichlorophenyl)-4-((5-(trifluoromethyl)pyridin-2-yloxy)methyl)-1H-pyrazol-3-yl)-5-tert-butyl-1,3,4-thiadiazole
2-(4-((1H-1,2,4-triazol-1-yl)methyl)-5-(4-bromophenyl)-1-(2,4-dichlorophenyl)-1H-pyrazol-3-yl)-5-tert-butyl-1,3,4-thiadiazole
5-(4-bromophenyl)-3-(5-tert-butyl-1,3,4-thiadiazol-2-yl)-1-(2,4-dichlorophenyl)-1H-pyrazole-4-carbaldehyde
2-(4-((1H-1,2,4-triazol-1-yl)methyl)-5-(4-chlorophenyl)-1-(2,4-dichlorophenyl)-1H-pyrazol-3-yl)-5-cyclobutyl-1,3,4-oxadiazole
2-(4-((1H-1,2,4-triazol-1-yl)methyl)-5-(4-chlorophenyl)-1-(2,4-dichlorophenyl)-1H-pyrazol-3-yl)-5-cyclohexyl-1,3,4-oxadiazole
2-(4-((1H-1,2,4-triazol-1-yl)methyl)-5-(4-chlorophenyl)-1-(2,4-dichlorophenyl)-1H-pyrazol-3-yl)-5-(1-phenylcyclopropyl)-1,3,4-oxadiazole
2-(4-((1H-1,2,4-triazol-1-yl)methyl)-5-(4-chlorophenyl)-1-(2,4-dichlorophenyl)-1H-pyrazol-3-yl)-5-(1-p-tolylcyclopropyl)-1,3,4-oxadiazole 2-(4-((1H-1,2,4-triazol-1-yl)methyl)-5-(4-chlorophenyl)-1-(2,4-dichlorophenyl)-1H-pyrazol-3-yl)-5-(1-(4-methoxyphenyl)cyclopropyl)-1,3,4-oxadiazole
2-(4-((1H-1,2,4-triazol-1-yl)methyl)-5-(4-chlorophenyl)-1-(2,4-dichlorophenyl)-1H-pyrazol-3-yl)-5-(1-(2,4-dichlorophenyl)cyclopropyl)-1,3,4-oxadiazole
2-(4-((1H-1,2,4-triazol-1-yl)methyl)-5-(4-chlorophenyl)-1-(2,4-dichlorophenyl)-1H-pyrazol-3-yl)-5-cyclobutyl-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-cyclohexyl-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopropyl)-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-(1-phenylcyclopropyl)-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-(1-p-tolylcyclopropyl)-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-(1-(4-methoxyphenyl)cyclopropyl)-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-(1-(2,4-dichlorophenyl)cyclopropyl)-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-(1-(trifluoromethyl)cyclopropyl)-1,3,4-thiadiazole
2-(5-(4-chlorophenyl)-1-(2,4-dichlorophenyl)-4-methyl-1H-pyrazol-3-yl)-5-(1-ethylcyclopropyl)-1,3,4-oxadiazole
2-(5-(4-chlorophenyl)-1-(2,4-dichlorophenyl)-4-ethyl-1H-pyrazol-3-yl)-5-(1-ethylcyclopropyl)-1,3,4-oxadiazole
2-(5-(4-bromophenyl)-1-(2,4-dichlorophenyl)-4-ethyl-1H-pyrazol-3-yl)-5-(1-ethylcyclopropyl)-1,3,4-oxadiazole
2-(5-(4-bromophenyl)-1-(2,4-dichlorophenyl)-4-ethyl-1H-pyrazol-3-yl)-5-(1-phenylcyclopentyl)-1,3,4-oxadiazole
2-(5-(4-bromophenyl)-1-(2,4-dichlorophenyl)-4-ethyl-1H-pyrazol-3-yl)-5-(1-phenylcyclopentyl)-1,3,4-thiadiazole
2-(5-(4-bromophenyl)-1-(2,4-dichlorophenyl)-4-ethyl-1H-pyrazol-3-yl)-5-(1-(4-chlorophenyl)cyclopentyl)-1,3,4-oxadiazole
2-(5-(4-bromophenyl)-1-(2,4-dichlorophenyl)-4-ethyl-1H-pyrazol-3-yl)-5-(1-(4-chlorophenyl)cyclopentyl)-1,3,4-thiadiazole
2-(5-(4-chlorophenyl)-1-(2,4-dichlorophenyl)-4-methyl-1H-pyrazol-3-yl)-5-(1-phenylcyclopropyl)-1,3,4-thiadiazole
2-(5-(4-chlorophenyl)-1-(2,4-dichlorophenyl)-4-methyl-1H-pyrazol-3-yl)-5-(1-ethylcyclopropyl)-1,3,4-thiadiazole
2-(5-(4-chlorophenyl)-1-(2,4-dichlorophenyl)-4-ethyl-1H-pyrazol-3-yl)-5-(1-ethylcyclopropyl)-1,3,4-thiadiazole
2-(5-(4-bromophenyl)-1-(2,4-dichlorophenyl)-4-ethyl-1H-pyrazol-3-yl)-5-(1-ethylcyclopropyl)-1,3,4-thiadiazole
1-(5-(5-(4-chlorophenyl)-1-(2,4-dichlorophenyl)-4-ethyl-1H-pyrazol-3-yl)-1,3,4-oxadiazol-2-yl)cyclopropanecarbonitrile
1-(5-(5-(4-chlorophenyl)-1-(2,4-dichlorophenyl)-4-ethyl-1H-pyrazol-3-yl)-1,3,4-thiadiazol-2-yl)cyclopropanecarbonitrile
2-(4-((1H-1,2,4-triazol-1-yl)methyl)-5-(4-chlorophenyl)-1-(2,4-dichlorophenyl)-1H-pyrazol-3-yl)-5-(1-(trifluoromethyl)cyclobutyl)-1,3,4-oxadiazole
2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclobutyl)-1,3,4-oxadiazole
2-(4-((1H-1,2,4-triazol-1-yl)methyl)-5-(4-chlorophenyl)-1-(2,4-dichlorophenyl)-1H-pyrazol-3-yl)-5-(1-phenylcyclopentyl)-1,3,4-oxadiazole
2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopentyl)-1,3,4-oxadiazole
2-(4-((1H-1,2,4-triazol-1-yl)methyl)-5-(4-chlorophenyl)-1-(2,4-dichlorophenyl)-1H-pyrazol-3-yl)-5-(1-(trifluoromethyl)cyclobutyl)-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclobutyl)-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-(1-phenylcyclopentyl)-1,3,4-thiadiazole
2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopentyl)-1,3,4-thiadiazole
2-(5-(4-bromophenyl)-1-(2,4-dichlorophenyl)-4-ethyl-1H-pyrazol-3-yl)-5-(1-(4-fluorophenyl)cyclopropyl)-1,3,4-oxadiazole
2-(5-(4-bromophenyl)-1-(2,4-dichlorophenyl)-4-ethyl-1H-pyrazol-3-yl)-5-(1-(4-fluorophenyl)cyclopropyl)-1,3,4-thiadiazole
2-(5-(4-chlorophenyl)-1-(2,4-dichlorophenyl)-4-methyl-1H-pyrazol-3-yl)-5-(1-(3-chlorophenyl)cyclopropyl)-1,3,4-thiadiazole
2-(5-(4-chlorophenyl)-1-(2,4-dichlorophenyl)-4-ethyl-1H-pyrazol-3-yl)-5-(1-(3-chlorophenyl)cyclopropyl)-1,3,4-thiadiazole
2-(5-(4-bromophenyl)-1-(2,4-dichlorophenyl)-4-ethyl-1H-pyrazol-3-yl)-5-(1-(3-chlorophenyl)cyclopropyl)-1,3,4-oxadiazole
2-(5-(4-bromophenyl)-1-(2,4-dichlorophenyl)-4-ethyl-1H-pyrazol-3-yl)-5-(1-(3-chlorophenyl)cyclopropyl)-1,3,4-thiadiazole
5-(4-bromophenyl)-3-(5-tert-butyl-1,3,4-thiadiazol-2-yl)-1-(2,4-dichlorophenyl)-1H-pyrazole-4-carbaldehyde
2-(5-(4-bromophenyl)-1-(2,4-dichlorophenyl)-4-(prop-1-en-2-yl)-1H-pyrazol-3-yl)-5-tert-butyl-1,3,4-thiadiazole
2-(4-((2H-tetrazol-2-yl)methyl)-5-(4-bromophenyl)-1-(2,4-dichlorophenyl)-1H-pyrazol-3-yl)-5-tert-butyl-1,3,4-oxadiazole
2-(4-((1H-tetrazol-1-yl)methyl)-5-(4-bromophenyl)-1-(2,4-dichlorophenyl)-1H-pyrazol-3-yl)-5-tert-butyl-1,3,4-oxadiazole
2-(5-(4-chlorophenyl)-1-(2,4-dichlorophenyl)-4-methyl-1H-pyrazol-3-yl)-5-(1-(4-fluorophenyl)cyclopropyl)-1,3,4-oxadiazole
2-(5-(4-chlorophenyl)-1-(2,4-dichlorophenyl)-4-methyl-1H-pyrazol-3-yl)-5-(1-(4-fluorophenyl)cyclopropyl)-1,3,4-thiadiazole
2-(1-(5-(5-(4-chlorophenyl)-1-(2,4-dichlorophenyl)-4-methyl-1H-pyrazol-3-yl)-1,3,4-oxadiazol-2-yl)cyclopropyl)propan-2-ol
1-(1-(5-(5-(4-chlorophenyl)-1-(2,4-dichlorophenyl)-4-methyl-1H-pyrazol-3-yl)-1,3,4-oxadiazol-2-yl)cyclopropyl)ethanol
2-(5-(5-(4-chlorophenyl)-1-(2,4-dichlorophenyl)-4-methyl-1H-pyrazol-3-yl)-1,3,4-oxadiazol-2-yl)-2-methylpropyl acetate
2-(5-(5-(4-chlorophenyl)-1-(2,4-dichlorophenyl)-4-methyl-1H-pyrazol-3-yl)-1,3,4-oxadiazol-2-yl)-2-methylpropan-1-ol 2-(5-(4-Chlorophenyl)-1-(2,4-dichlorophenyl)-4-methyl-1H-pyrazol-3-yl)-5-(2-(2-fluorobenzyloxy)propan-2-yl)-1,3,4-oxadiazole 2-(2-(3-Chlorobenzyloxy)propan-2-yl)-5-(5-(4-chlorophenyl)-1-(2,4-dichlorophenyl)-4-methyl-1H-pyrazol-3-yl)-1,3,4-oxadiazole 2-(2-(allyloxy)propan-2-yl)-5-(5-(4-bromophenyl)-1-(2,4-dichlorophenyl)-4-ethyl-1H-pyrazol-3-yl)-1,3,4-oxadiazole 3-(2-(5-(5-(4-bromophenyl)-1-(2,4-dichlorophenyl)-4-ethyl-1H-pyrazol-3-yl)-1,3,4-oxadiazol-2-yl)propan-2-yloxy)propan-1-ol 2-(2-(allyloxy)propan-2-yl)-5-(5-(4-chlorophenyl)-1-(2,4-dichlorophenyl)-4-ethyl-1H-pyrazol-3-yl)-1,3,4-oxadiazole 2-tert-butyl-5-(5-(4-chlorophenyl)-1-(2,4-dichlorophenyl)-4-((2-methyl-2H-tetrazol-5-yl)methyl)-1H-pyrazol-3-yl)-1,3,4-oxadiazole 2-tert-butyl-5-(5-(4-chlorophenyl)-1-(2,4-dichlorophenyl)-4-((1-methyl-1H-tetrazol-5-yl)methyl)-1H-pyrazol-3-yl)-1,3,4-oxadiazole 2-(4-((1H-1,2,4-triazol-1-yl)methyl)-1-(2-chlorophenyl)-5-(4-chlorophenyl)-1H-pyrazol-3-yl)-5-tert-butyl-1,3,4-oxadiazole 1-(5-(4-bromophenyl)-3-(5-tert-butyl-1,3,4-thiadiazol-2-yl)-1-(2,4-dichlorophenyl)-1H-pyrazol-4-yl)ethanol 2-(5-(4-bromophenyl)-1-(2,4-dichlorophenyl)-4-(1-fluoroethyl)-1H-pyrazol-3-yl)-5-tert-butyl-1,3,4-thiadiazole 2-(5-(4-bromophenyl)-1-(2,4-dichlorophenyl)-4-vinyl-1H-pyrazol-3-yl)-5-tert-butyl-1,3,4-thiadiazole Methyl 1-(5-(4-bromophenyl)-3-(5-tert-butyl-1,3,4-thiadiazol-2-yl)-1-(2,4-dichlorophenyl)-1H-pyrazol-4-yl)ethylcarbamate 1-(5-(4-bromophenyl)-3-(5-tert-butyl-1,3,4-thiadiazol-2-yl)-1-(2,4-dichlorophenyl)-1H-pyrazol-4-yl)ethanone 2-(1-(Benzyloxy)-2-methylpropan-2-yl)-5-(5-(4-chlorophenyl)-1-(2,4-dichlorophenyl)-4-methyl-1H-pyrazol-3-yl)-1,3,4-oxadiazole 1-(5-(4-chlorophenyl)-3-(5-(1-(4-chlorophenyl)cyclopropyl)-1,3,4-oxadiazol-2-yl)-1-(2,4-dichlorophenyl)-1H-pyrazol-4-yl)ethanol 2-(5-(4-chlorophenyl)-1-(2,4-dichlorophenyl)-4-(difluoromethyl)-1H-pyrazol-3-yl)-5-(1-(4-chlorophenyl)cyclopropyl)-1,3,4-oxadiazole 2-(5-(4-chlorophenyl)-1-(2,4-dichlorophenyl)-4-isopropyl-1H-pyrazol-3-yl)-5-(1-(4-chlorophenyl)cyclopropyl)-1,3,4-thiadiazole 2-(5-(4-chlorophenyl)-1-(2,4-dichlorophenyl)-4-isopropyl-1H-pyrazol-3-yl)-5-(1-(trifluoromethyl)cyclopropyl)-1,3,4-oxadiazole 2-(5-(4-chlorophenyl)-1-(2,4-dichlorophenyl)-4-isopropyl-1H-pyrazol-3-yl)-5-(1-(trifluoromethyl)cyclopropyl)-1,3,4-thiadiazole 2-(5-(4-chlorophenyl)-1-(2,4-dichlorophenyl)-4-propyl-1H-pyrazol-3-yl)-5-(1-(trifluoromethyl)cyclopropyl)-1,3,4-oxadiazole 2-(5-(4-chlorophenyl)-1-(2,4-dichlorophenyl)-4-propyl-1H-pyrazol-3-yl)-5-(1-(trifluoromethyl)cyclopropyl)-1,3,4-thiadiazole 2-(5-(4-chlorophenyl)-1-(2,4-dichlorophenyl)-4-(1-fluoroethyl)-1H-pyrazol-3-yl)-5-(1-(4-chlorophenyl)cyclopropyl)-1,3,4-oxadiazole 1-(5-(4-chlorophenyl)-3-(5-(1-(4-chlorophenyl)cyclopropyl)-1,3,4-oxadiazol-2-yl)-1-(2,4-dichlorophenyl)-1H-pyrazol-4-yl)ethanone 2-(5-(4-chlorophenyl)-1-(2,4-dichlorophenyl)-4-ethyl-1H-pyrazol-3-yl)-5-(1-(trifluoromethyl)cyclopropyl)-1,3,4-thiadiazole 2-(5-(4-chlorophenyl)-1-(2,4-dichlorophenyl)-4-ethyl-1H-pyrazol-3-yl)-5-(1-(2-fluorophenyl)cyclopropyl)-1,3,4-oxadiazole 2-(5-(4-chlorophenyl)-1-(2,4-dichlorophenyl)-4-ethyl-1H-pyrazol-3-yl)-5-(1-(2-fluorophenyl)cyclopropyl)-1,3,4-thiadiazole 2-(4-((1H-1,2,4-triazol-1-yl)methyl)-5-(4-bromophenyl)-1-(2,4-dichlorophenyl)-1H-pyrazol-3-yl)-5-tert-butyl-1,3,4-oxadiazole 2-(4-((1H-1,2,4-triazol-1-yl)methyl)-1-(2-chlorophenyl)-5-(4-chlorophenyl)-1H-pyrazol-3-yl)-5-tert-butyl-1,3,4-thiadiazole (3-(5-tert-butyl-1,3,4-thiadiazol-2-yl)-5-(4-chlorophenyl)-1-(2,4-dichlorophenyl)-1H-pyrazol-4-yl)methyl acetate (3-(5-tert-butyl-1,3,4-thiadiazol-2-yl)-5-(4-chlorophenyl)-1-(2,4-dichlorophenyl)-1H-pyrazol-4-yl)methanol 2-(5-(4-chlorophenyl)-1-(2,4-dichlorophenyl)-4-vinyl-1H-pyrazol-3-yl)-5-(1-(4-chlorophenyl)cyclopropyl)-1,3,4-oxadiazole Methyl 1-(5-(4-chlorophenyl)-3-(5-(1-(4-chlorophenyl)cyclopropyl)-1,3,4-oxadiazol-2-yl)-1-(2,4-dichlorophenyl)-1H-pyrazol-4-yl)ethylcarbamate 2-(5-(5-(4-chlorophenyl)-1-(2,4-dichlorophenyl)-4-methyl-1H-pyrazol-3-yl)-1,3,4-oxadiazol-2-yl)propan-2-yl acetate 2-(5-(5-(4-chlorophenyl)-1-(2,4-dichlorophenyl)-4-methyl-1H-pyrazol-3-yl)-1,3,4-oxadiazol-2-yl)propan-2-ol 2-(4-((1H-1,2,4-triazol-1-yl)methyl)-5-(4-chlorophenyl)-1-(2,4-dichlorophenyl)-1H-pyrazol-3-yl)-5-(1-methylcyclopropyl)-1,3,4-oxadiazole 2-(4-((1H-1,2,4-triazol-1-yl)methyl)-5-(4-bromophenyl)-1-(2,4-dichlorophenyl)-1H-pyrazol-3-yl)-5-(1-(trifluoromethyl)cyclopropyl)-1,3,4-oxadiazole 2-(4-((1H-1,2,4-triazol-1-yl)methyl)-5-(4-bromophenyl)-1-(2,4-dichlorophenyl)-1H-pyrazol-3-yl)-5-(1-(4-chlorophenyl)cyclopropyl)-1,3,4-oxadiazole 2-(4-((1H-1,2,4-triazol-1-yl)methyl)-5-(4-chlorophenyl)-1-(2,4-dichlorophenyl)-1H-pyrazol-3-yl)-5-(1-methylcyclopropyl)-1,3,4-thiadiazole 2-(4-((1H-1,2,4-triazol-1-yl)methyl)-5-(4-bromophenyl)-1-(2,4-dichlorophenyl)-1H-pyrazol-3-yl)-5-(1-(trifluoromethyl)cyclopropyl)-1,3,4-thiadiazole 2-(4-((1H-1,2,4-triazol-1-yl)methyl)-5-(4-bromophenyl)-1-(2,4-dichlorophenyl)-1H-pyrazol-3-yl)-5-(1-(4-chlorophenyl)cyclopropyl)-1,3,4-thiadiazole 2-(5-(4-Chlorophenyl)-1-(2,4-dichlorophenyl)-4-methyl-1H-pyrazol-3-yl)-5-(2-methyl-1-(4-(trifluoromethyl)benzyloxy)propan-2-yl)-1,3,4-oxadiazole 2-(1-(4-Chlorobenzyloxy)-2-methylpropan-2-yl)-5-(5-(4-chlorophenyl)-1-(2,4-dichlorophenyl)-4-methyl-1H-pyrazol-3-yl)-1,3,4-oxadiazole 2-(5-(4-chlorophenyl)-1-(2,4-dichlorophenyl)-4-methyl-1H-pyrazol-3-yl)-5-(1-(1-fluoroethyl)cyclopropyl)-1,3,4-oxadiazole 2-(5-(4-chlorophenyl)-1-(2,4-dichlorophenyl)-4-ethyl-1H-pyrazol-3-yl)-5-(1-(cyclopropylmethyl)cyclopropyl)-1,3,4-oxadiazole 2-(5-(4-bromophenyl)-1-(2,4-dichlorophenyl)-4-ethyl-1H-pyrazol-3-yl)-5-(1-(cyclopropylmethyl)cyclopropyl)-1,3,4-oxadiazole 2-(5-(4-bromophenyl)-3-(5-tert-butyl-1,3,4-thiadiazol-2-yl)-1-(2,4-dichlorophenyl)-1H-pyrazol-4-yl)propan-2-ol 1-(3-(5-tert-butyl-1,3,4-thiadiazol-2-yl)-5-(4-chlorophenyl)-1-(2,4-dichlorophenyl)-1H-pyrazol-4-yl)ethanol

General Synthetic Sequence

The following synthetic schemes are merely illustrative of the methods by which the compounds of the invention may be prepared and are not intended to limit the scope of the invention as defined in the appended claims.

The compound of formula (Ia) may be prepared by (i) reacting a carboxylic acid derivative (5) with a hydrazide compound (7) or a semicarbazide compound (12) in the presence of a coupling agent, e.g., 1-ethyl-3-[3-dimethylaminopropyl]carbodiimide hydrochloride (EDCI), 4-dimethylaminopyridine (DMAP), and (ii) cyclizing the resulting product using a dehydrating agent to obtain an 1,3,4-oxadiazole compound of formula (Ia), as shown in Reaction Scheme 1.

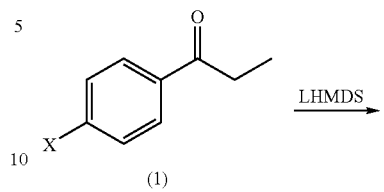

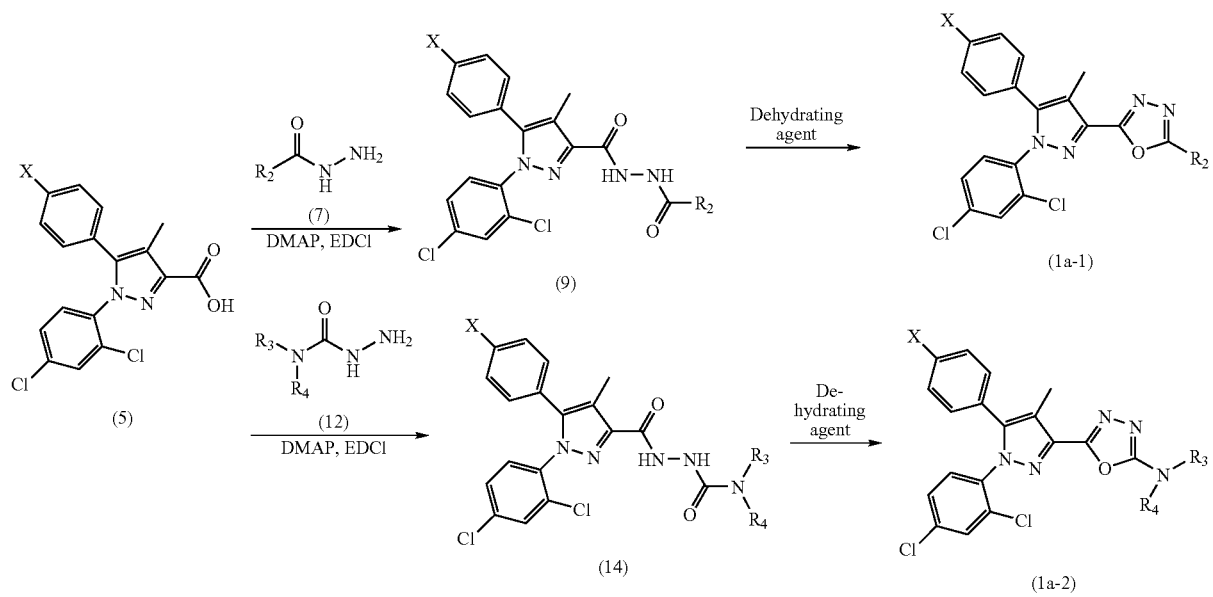

wherein, $R_1$ to $R_4$ have the same meanings as defined above.

The cyclization may be conducted using Burgess reagent as a dehydrating agent while applying microwave irradiation thereon (See Leber, J. D. et al., WO 2005/032550), or using triphenylphosphine with carbon tetrachloride and a base such triethylamine in a suitable solvent such as acetonitrile and THF.

The carboxylic acid derivative (5) used as a starting material in preparing the compound of formula (Ia) may be prepared by a conventional method, e.g., by treating an acetophenone derivative (1) with an organic base such as lithium hexamethyldisilazide (LHMDS) to produce a corresponding alkali metal salt (2), reacting the resulting salt with an equimolar amount of diethyl oxalate to provide a ketoester salt (3), reacting the salt (3) with a hydrazine derivative in refluxing acetic acid to obtain a pyrazole-3-carboxylic ester (4), and transforming the ester (4) into an acid form (5) using an alkaline agent such as potassium hydroxide or lithium hydroxide, followed by acidification (See Barth, F. et al., U.S. Pat. No. 5,462,960), as shown in Reaction Scheme 2.

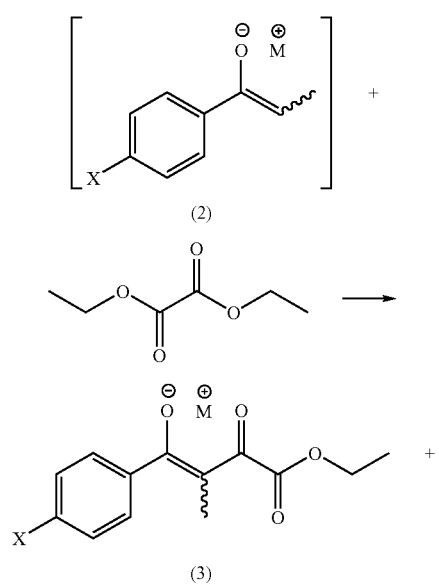

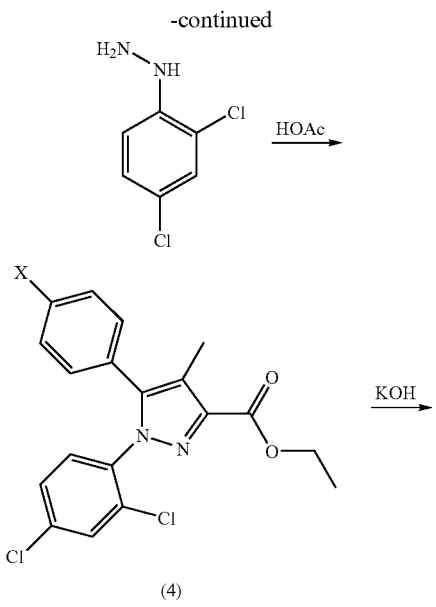

wherein, $R_1$ to $R_4$ have the same meanings as defined above.

The compound of formula (Ib) may be prepared by (i) reacting a carboxylic acid derivative (5) with a hydrazide compound (7) in the presence of coupling agents, e.g., EDCI, DMAP, and (ii) cyclizing the resulting product using a Lawesson's reagent, which can be conducted with microwave irradiation (See Kiryanov, A. A., Sampson, P., Seed, A. J., *J. Org. Chem.* 2001, 665, 7925-7929), as shown in Reaction Scheme 4.

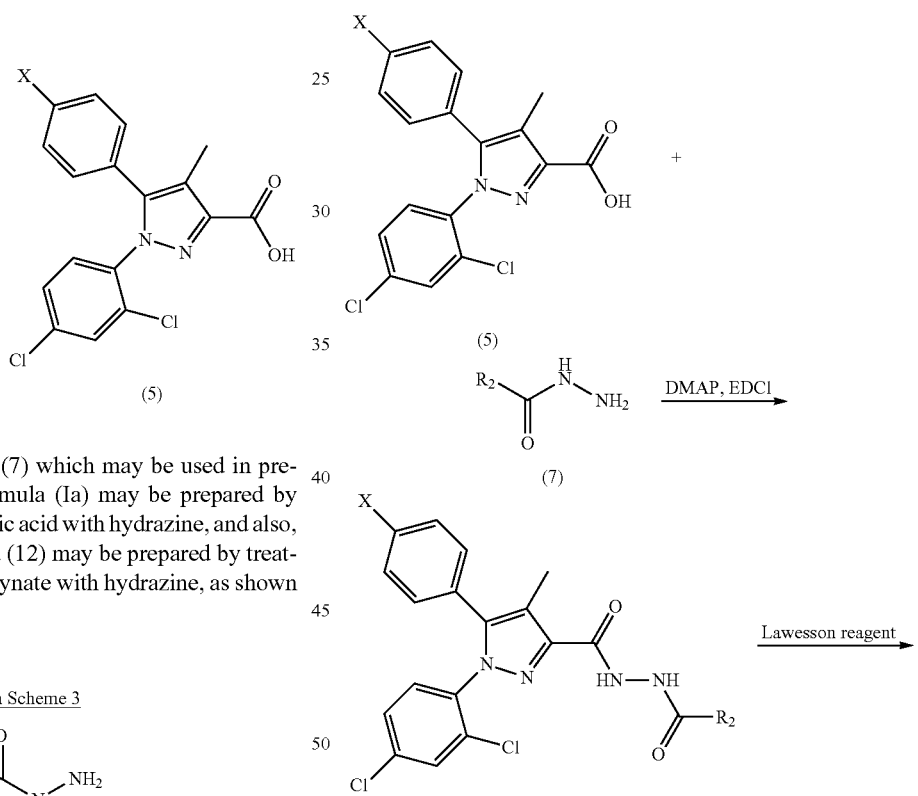

The hydrazide compound (7) which may be used in preparing the compound of formula (Ia) may be prepared by treating an ester or a carboxylic acid with hydrazine, and also, the semicarbazide compound (12) may be prepared by treating carbamyl chloride or isocynate with hydrazine, as shown in Reaction Scheme 3.

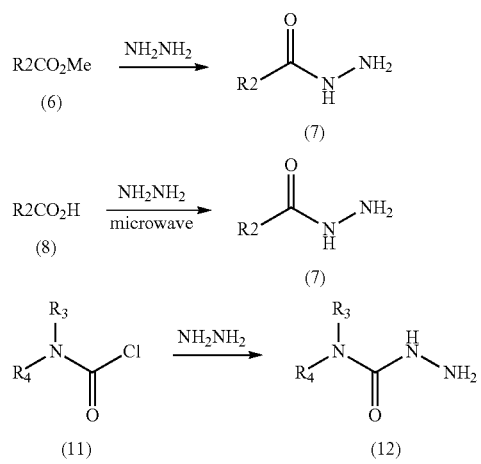

-continued

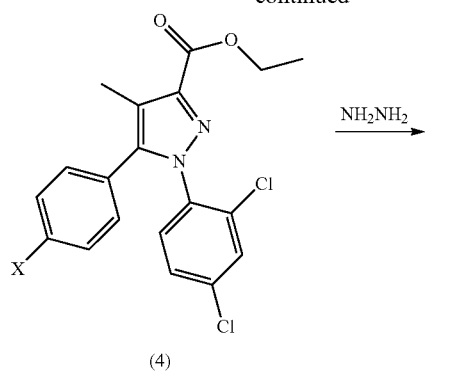
(4)

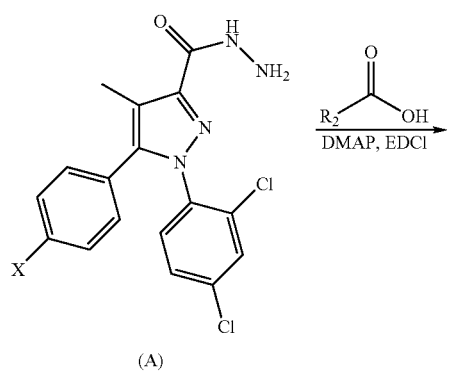
(A)

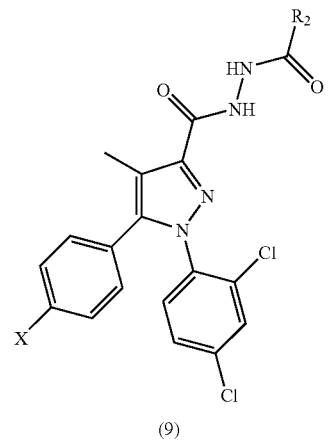
(9)

wherein, R₁ and R₂ have the same meanings as defined above.

As demonstrated above, the acylhydrazide intermediate (9) is also available through a coupling of the hydrazide (A) with a corresponding acid in the presence of coupling reagents: DMAP, EDCI; EDCI, 1-hydroxybezotriazole (HOBt), N-methyl morpholine (NMM) In turn, the requisite hydrazide (A) is prepared by treating ester (4) with hydrazine in refluxing ethanol (EtOH).

The compound of formula (Ic) may be prepared by (i) reacting a nitrile intermediate (19) with hydroxylamine in a solvent, e.g., MeOH, (ii) acylating the resulting N-hydroxyamidine (20) with an activated carboxylic acid in the presence of a coupling agent, e.g., dicyclohexylcarbodiimide (DCC), EDCI or 1,1-carbonyldiimidazole (CDI), and (iii) cyclizing the acylated compound (21) in the presence of a base by heating, e.g., microwave irradiation, as shown in Reaction Scheme 5.

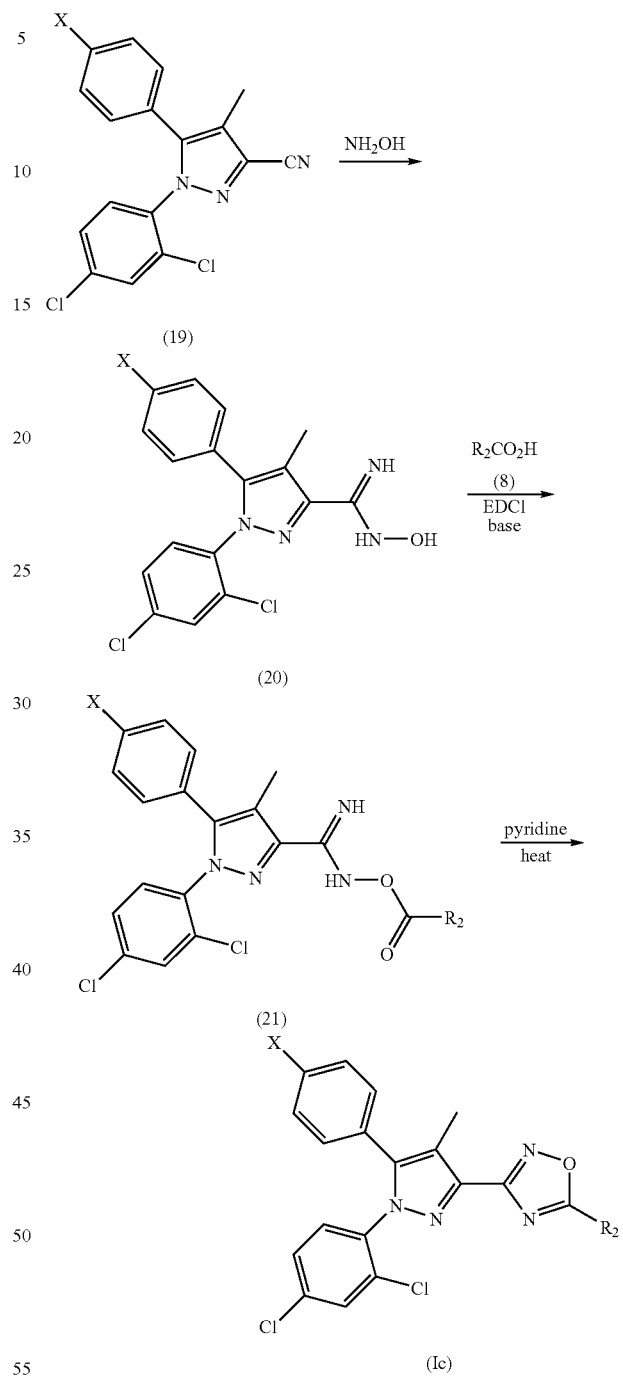

wherein, R₁ and R₂ have the same meanings as defined above.

In Reaction Scheme 5, step (i) may be conducted in heated methyl alcohol. The acylation of step (ii) may be conducted in the presence of a suitable base such as triethylamine (TEA) or N-methyl morpholine (NMM) in a solvent such as methylene chloride, THF or acetonitrile. The cyclization step (iii) may be conducted in a solvent such as acetonitrile or THF, and exemplary bases which may be used in this step include pyridine, N,N-diisopropylethylamine or tetrabutylammonium fluoride. Also, the process of isolating N-acyloxyamidine (21) may be omitted, in case N-hydroxyamidine (20) was converted to 1,2,4-oxadiazole (Ic) in a continuous process (See, Colandrea, V. J. et al., WO 2005/058848).

The nitrile intermediate (19) used in preparing the compound of formula (Ic) may be prepared by [3+2] cycloaddition reaction disclosed in *J. Med. Chem.* 1999, 42, 769-776, as shown in Reaction Scheme 6.

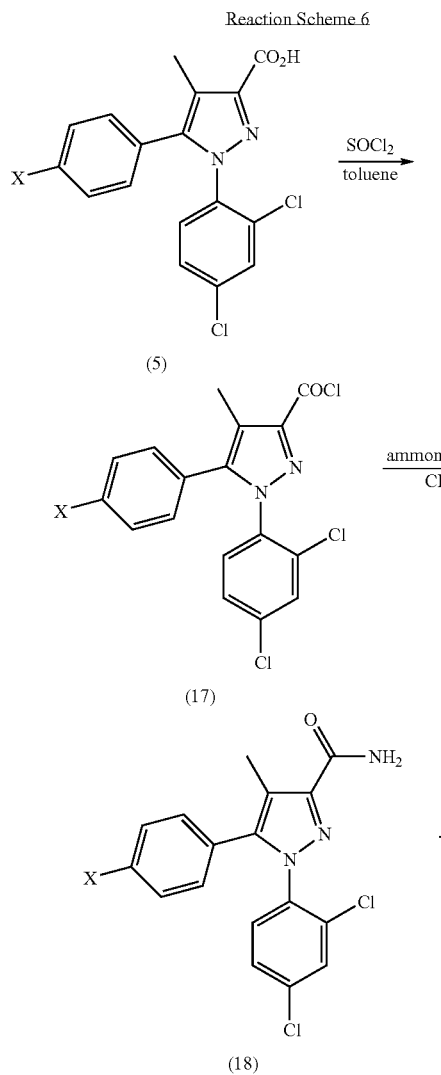

The compound of formula (Id) may be prepared by reacting a nitrile intermediate (19) with a hydrazide compound (7) in the presence of a catalyst such as potassium carbonate in a suitable solvent such as 1-butanol under a reflux condition, to obtain a triazole, as shown in Reaction Scheme 7.

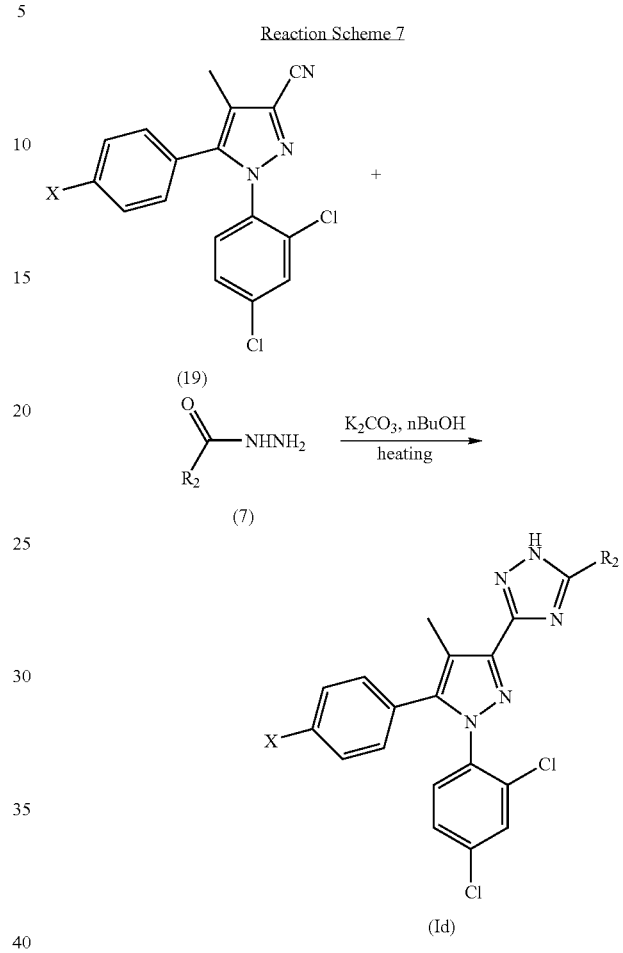

wherein, $R_2$ has the same meaning as defined above.

The compound of formula (Ie) or (If) may be prepared by reacting a nitrile intermediate (19) with sodium azide in the presence of a base (e.g., ammonium chloride) in a solvent (e.g., N,N-dimethylformamide: DMF) with microwave irradiation, according to [3+2] cycloaddition reaction, to obtain a tetrazole, which may be alkylated by a reaction with an alkyl halide in the presence of potassium carbonate in DMF to obtain alkyl tetrazoles, as shown in Reaction Scheme 8.

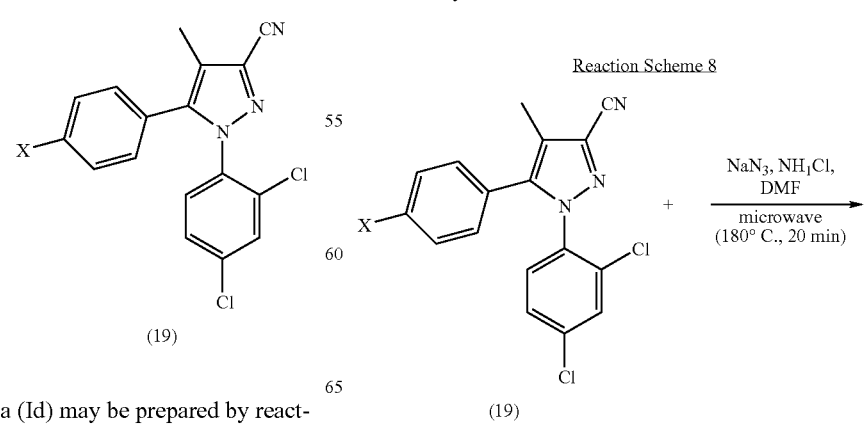

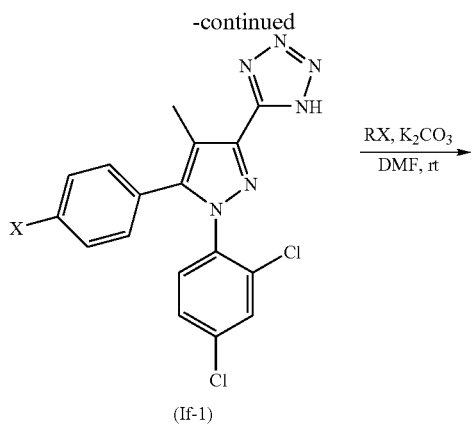
(If-1)

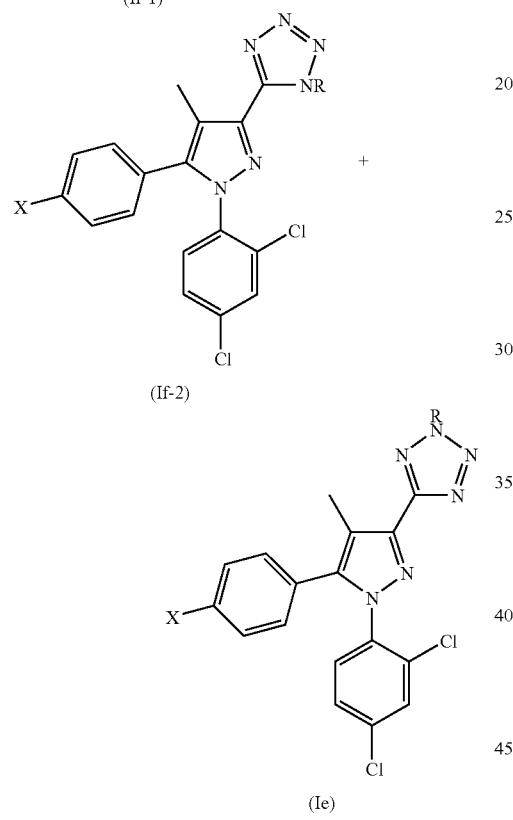

(If-2)

(Ie)

R = Me, Et, nPr, nBu, nPentyl, iPr, cyPentyl, cyHexyl, Bn

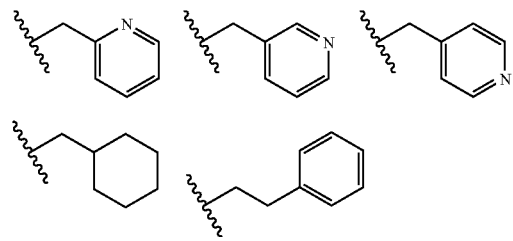

In Reaction Scheme 8, when RX is a primary alkyl halide, the alkylation can be conducted at room temperature. However, when a secondary alkyl halide is used, the reaction is preferably conducted at 80° C.

Also, the alkylation of the tetrazole may be conducted using an aliphatic alcohol in the presence of diisopropylazodicarboxylate (DIAD) and triphenylphosphine (PPh$_3$) in THF at 0° C., as shown in Reaction Scheme 9.

Reaction Scheme 9

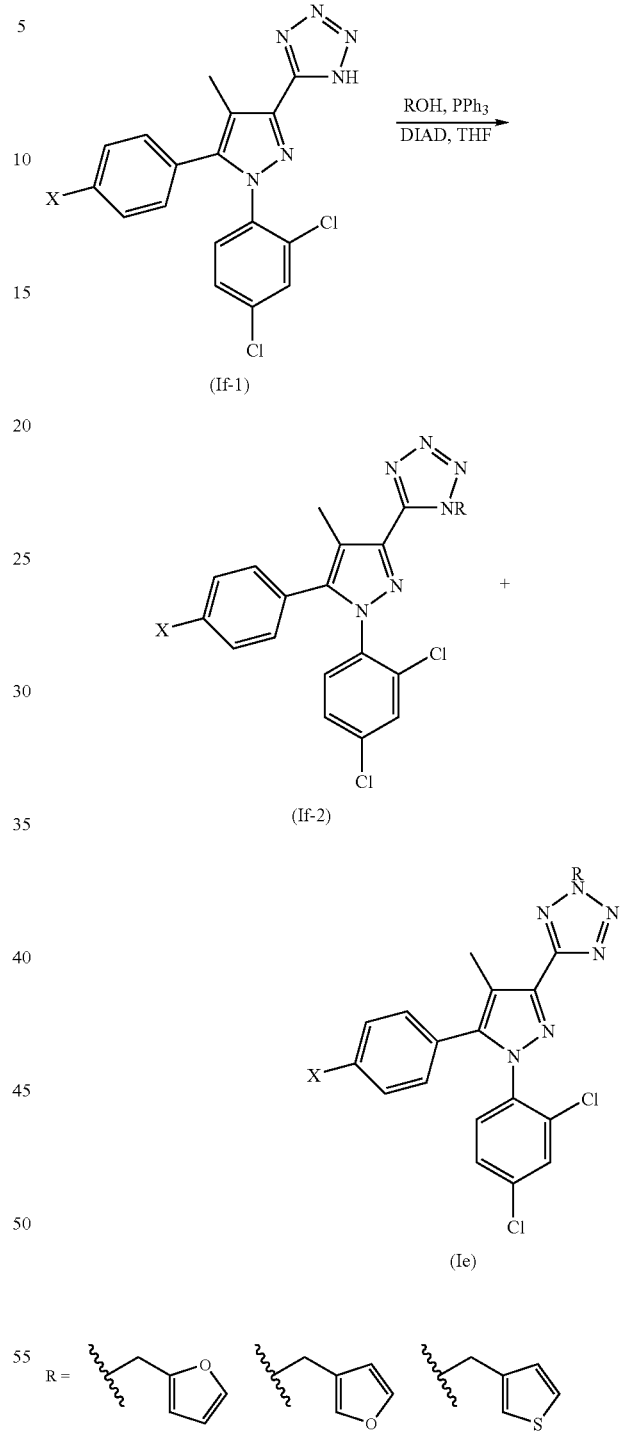

Alternatively, the compound of formula (If) may be prepared by treating acyl chloride (17) with an amine in the presence of triethylamine in methylene chloride to produce an amide (26) and reacting the resulting amide with hydrazoic acid in the presence of phosphorus pentachloride in toluene as shown in Reaction Scheme 10.

Reaction Scheme 10

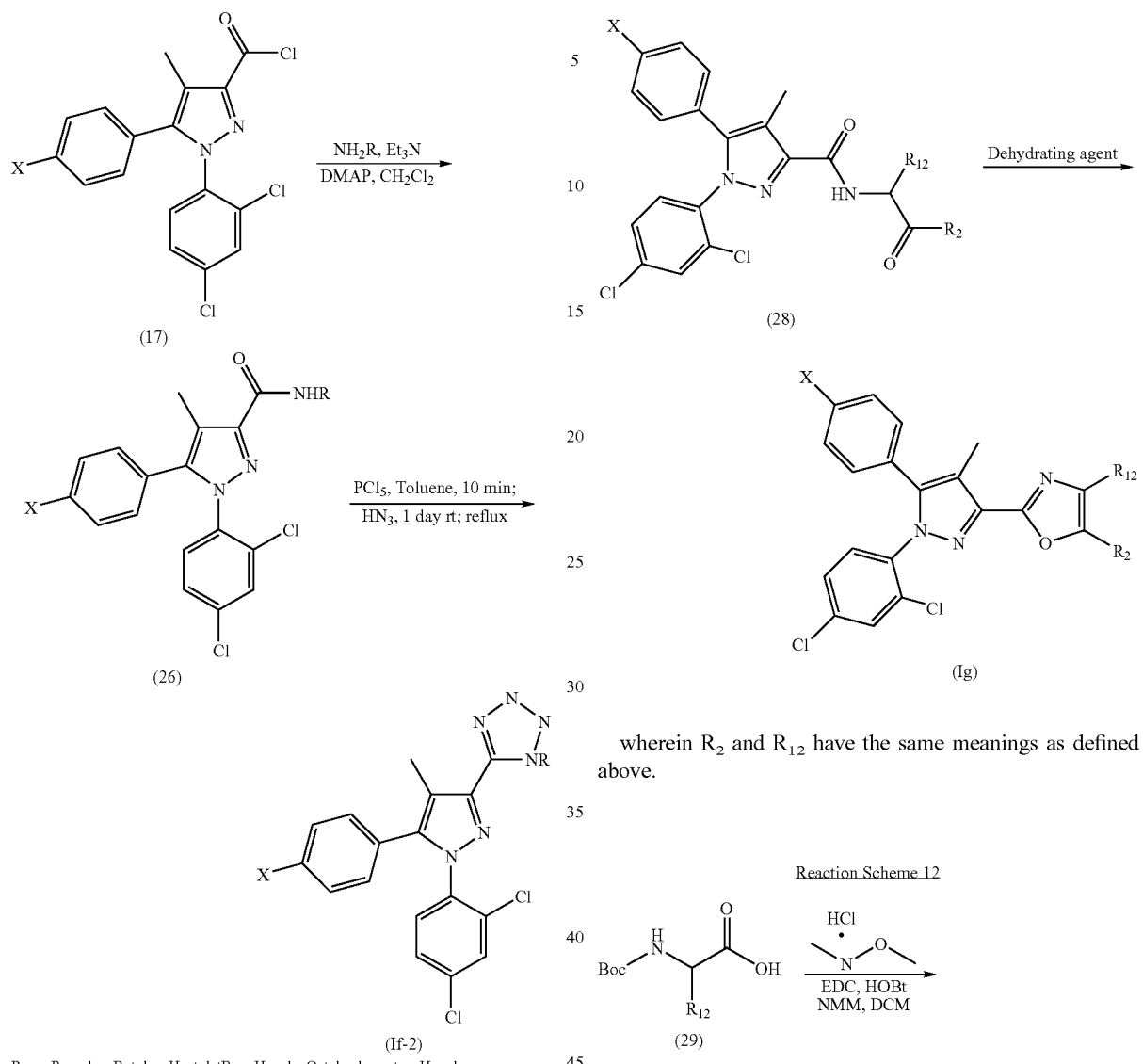

R = cyPropyl, cyButyl, cyHeptyl, tBu, nHexyl, nOctyl, adamant. cyHexyl

The compound of formula (Ig) may be prepared by (i) reacting a carboxylic acid intermediate (5) with an aminoketone (27) in the presence of a coupling reagent, e.g. EDCI, DMAP, and (ii) cyclizing the resulting product (28) using a dehydrating agent to obtain an oxazole compound of formula (Ig), as shown in Reaction Scheme 11.

Reaction Scheme 11

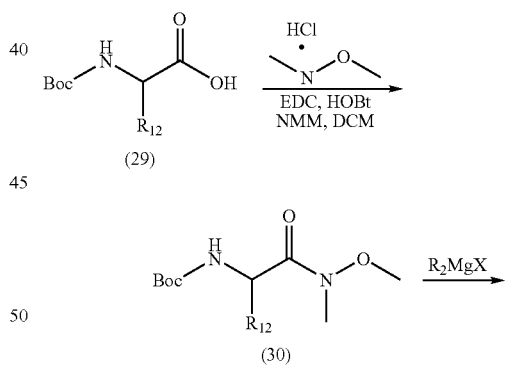

wherein $R_2$ and $R_{12}$ have the same meanings as defined above.

Reaction Scheme 12

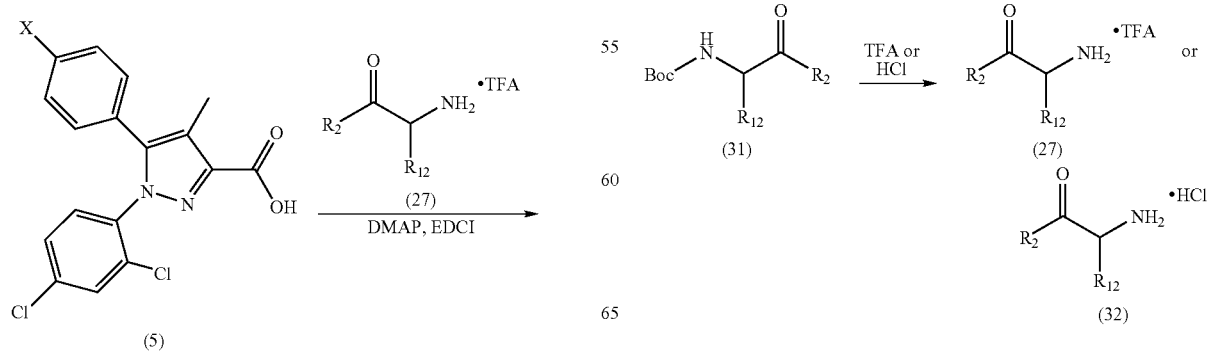

The aminoketone compound (27) or (32) which may be used in preparing the compound of formula (Ig) may be prepared as shown in Reaction Scheme 12. The starting N-Boc protected aminoacid (29) is converted into the corresponding Weinreb amide (30) using N,O-dimethylhydroxylamine hydrochloride in the presence of coupling reagents such as EDCI, HOBt, NMM in an appropriate solvent such as dichloromethane (DCM) or DMF. The Weinreb amide (30) may be transformed into a corresponding ketone (31) by action of a Grignard reagent in an appropriate solvent such as ether or THF under $N_2$ atmosphere. Then final deprotection of Boc group using either trifluoroacetic acid (TFA) or HCl may provide a corresponding aminoketone (27) or (32) in a salt form, respectively.

The compound of formula (Ih) may be prepared by (i) reacting a carboxylic acid intermediate (5) with an aminoketone (27) or (32) in the presence of a coupling reagent, e.g. EDCI, DMAP, and (ii) cyclizing the resulting product (28) using a Lawesson's reagent, which may be conducted with microwave irradiation (See Kiryanov, A. A., Sampson, P., Seed, A. J., *J. Org. Chem.* 2001, 665, 7925-7929), as shown in Reaction Scheme 13.

Reaction Scheme 13

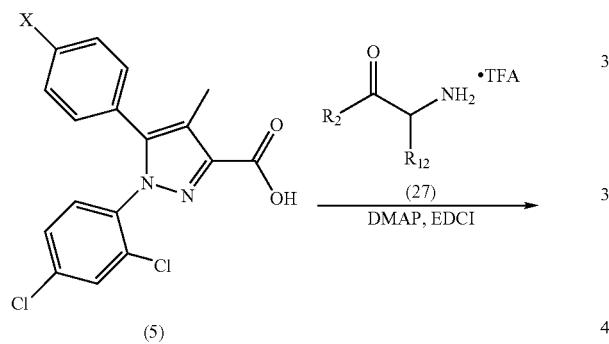

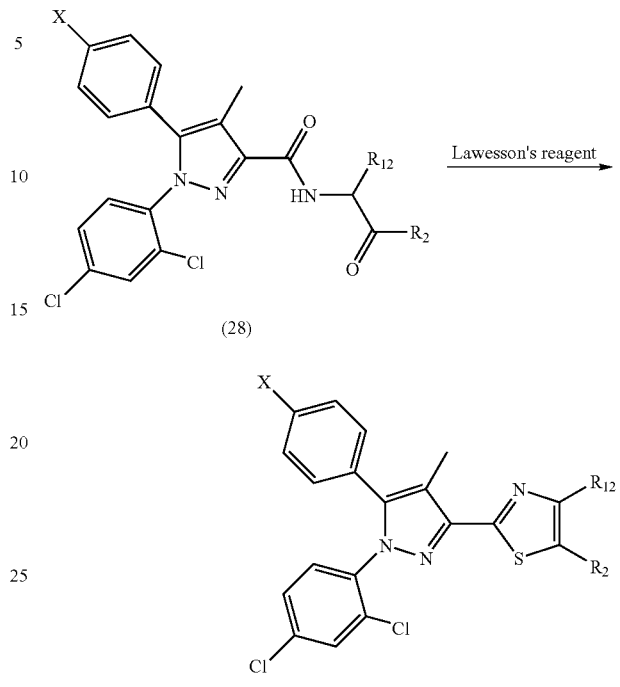

Further derivatization may be started with activated 4-pyrazole intermediate such as the bromomethyl derivative (33) as illustrated in Reaction Scheme 14. Thus, hydroxyl group is introduced by reacting the bromo derivative (33) with sodium acetate, and subsequent hydrolysis of the acetate (34). Oxidation of the alcohol (35) to aldehyde (36) is achieved by action of an oxidant such as Dess-Martin periodinane.

Reaction Scheme 14

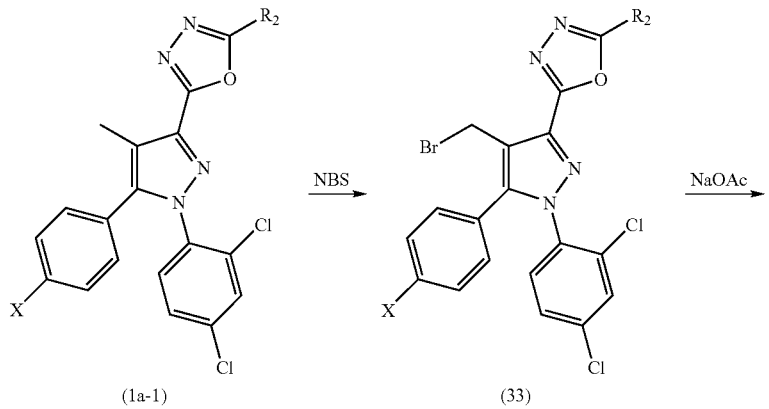

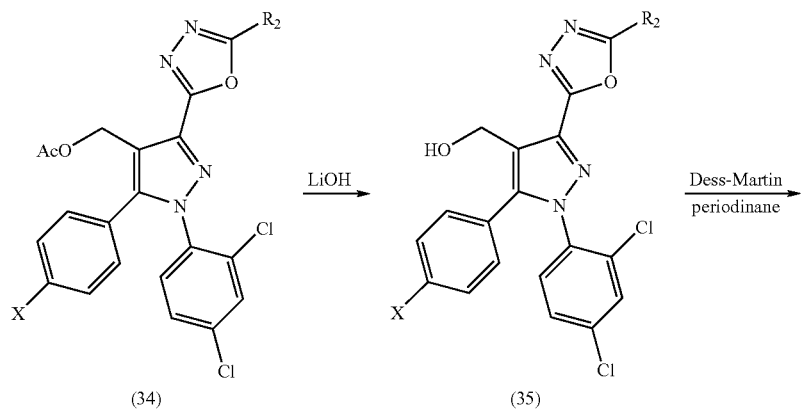

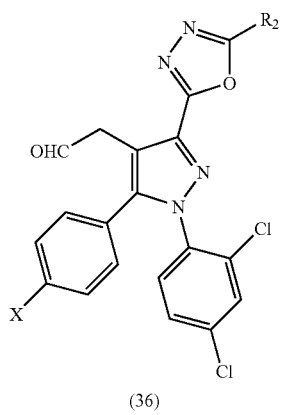

A bromide of structure (33) may be utilized to provide the corresponding cyanide (37) by reaction with sodium cyanide in a mixture of acetonitrile and water. A bromide (33) also undergoes acetylenylation to afford a 4-(3-(trimethylsilyl)prop-2-ynyl)-pyrazole (38), which is further desilylated in the presence of TBAF to provide a 4-(prop-2-ynyl)-pyrazole (39) as shown in Reaction Scheme 15.

Reaction Scheme 15

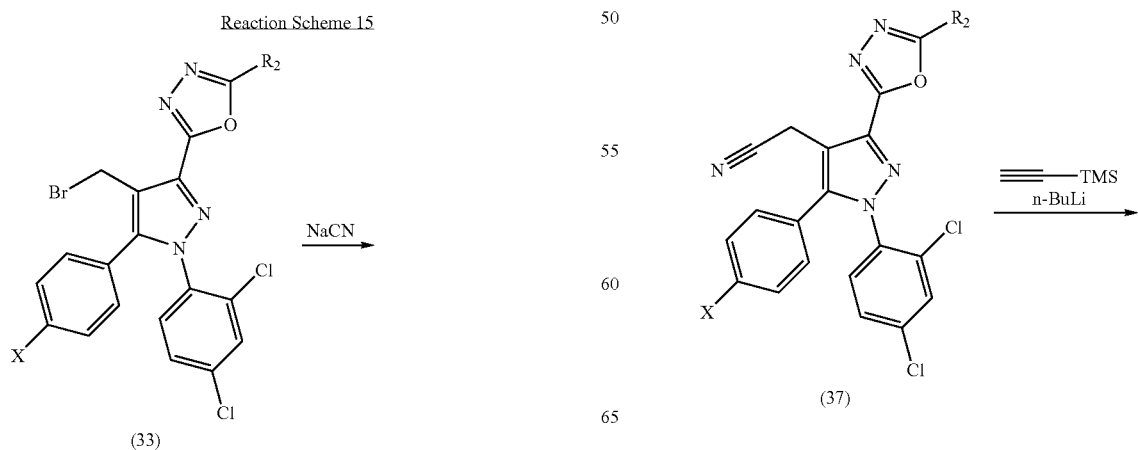

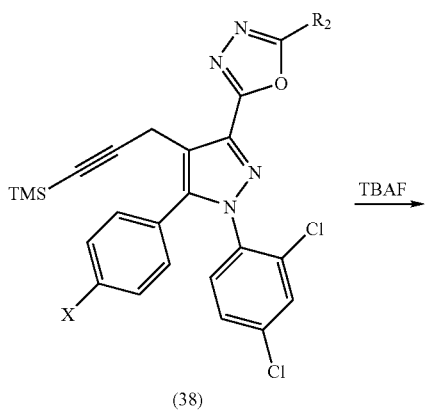

(38)

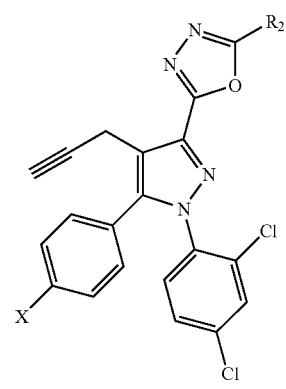

(39)

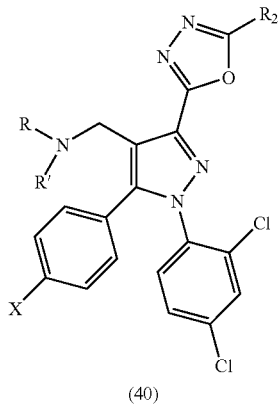

(40)

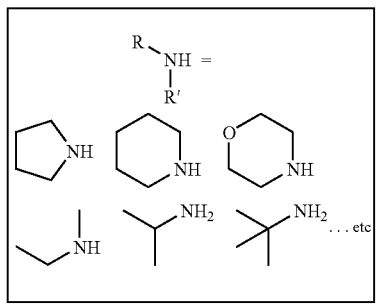

A bromide of structure (33) may be further utilized by reacting a bromide (33) with various primary or secondary amines in the presence of a suitable base such as diisopropylethylamine (DIPEA) in a suitable solvent such as acetonitrile to afford the corresponding amines of structure (40) as described in Reaction Scheme 16.

Further derivatization may be conducted on a bromide of structure (33) by reacting a bromide (33) with a pyrrole or various azoles including pyrazole, imidazole, 1,2,4-triazole, 1,2,3-triazole, tetrazole in the presence of a base such as sodium hydride in an appropriate solvent such as THF.

Reaction Scheme 16

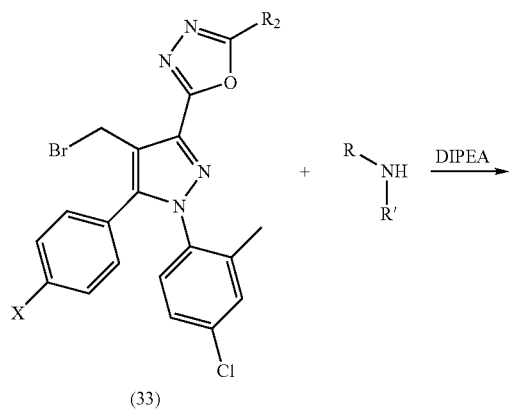

(33)

Reaction Scheme 17

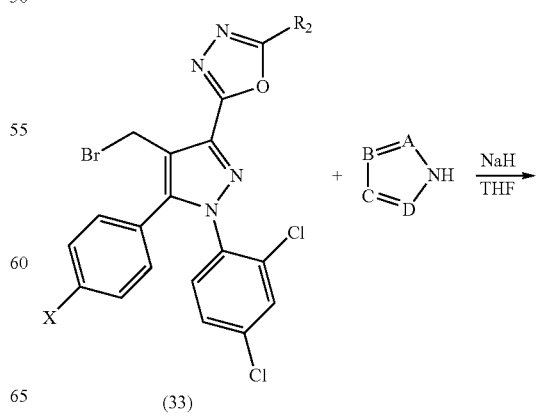

(33)

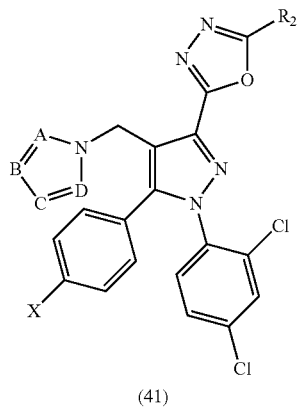

(41)

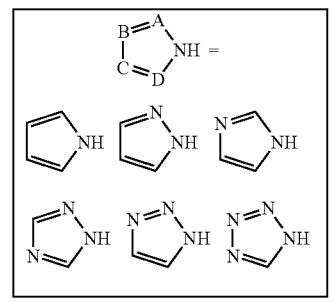

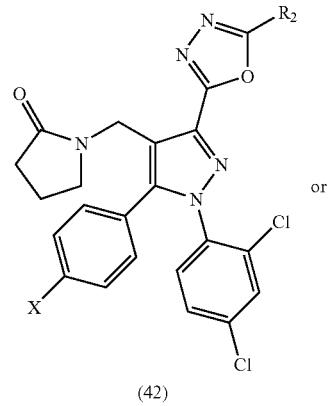

or (42)

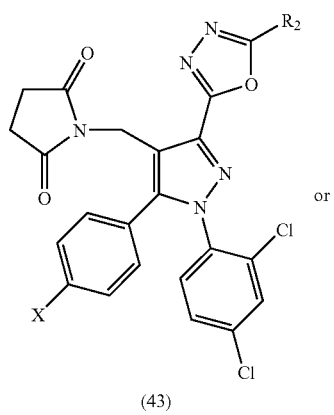

or (43)

A derivatization may come from alkylation of the anion of pyrrolidin-2-one, succinimide, or oxazolidini-2-one with a bromide of structure (33) to lead to the corresponding alkylated products (42), (43), or (44), respectively as depicted in Reaction Scheme (18).

Reaction Scheme 18

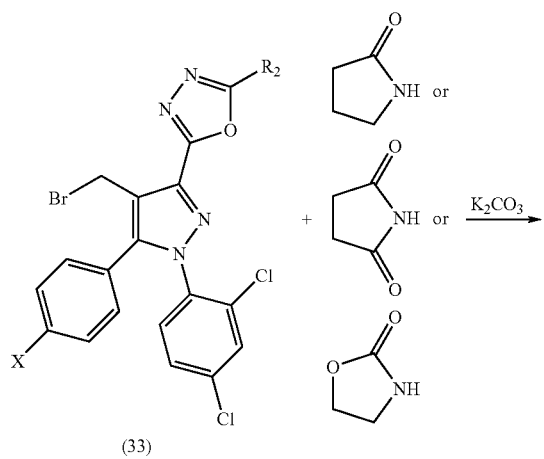

(33)

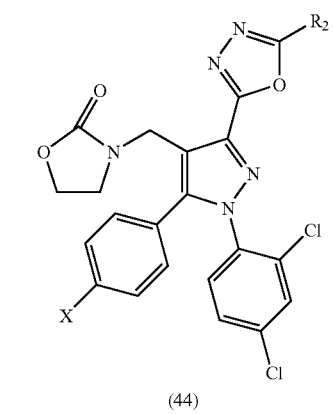

(44)

Another derivatization may come from alkylation of the anion of hydroxyl-aryl or hydroxyl-hetero-aryl such as phenol or pyridin-2-ol with a bromide of structure (33) to produce the corresponding alkylated products (45) or (46), respectively as demonstrated in Reaction Scheme 19.

Reaction Scheme 19

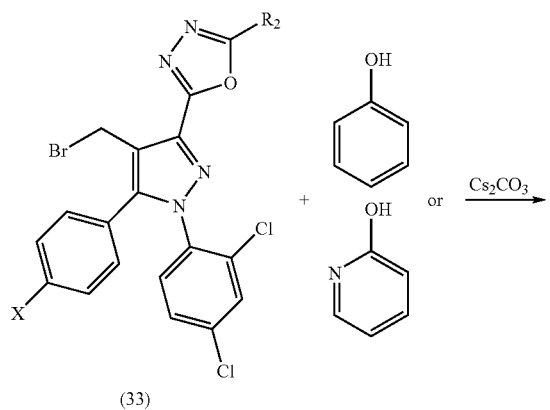

Reaction Scheme 20

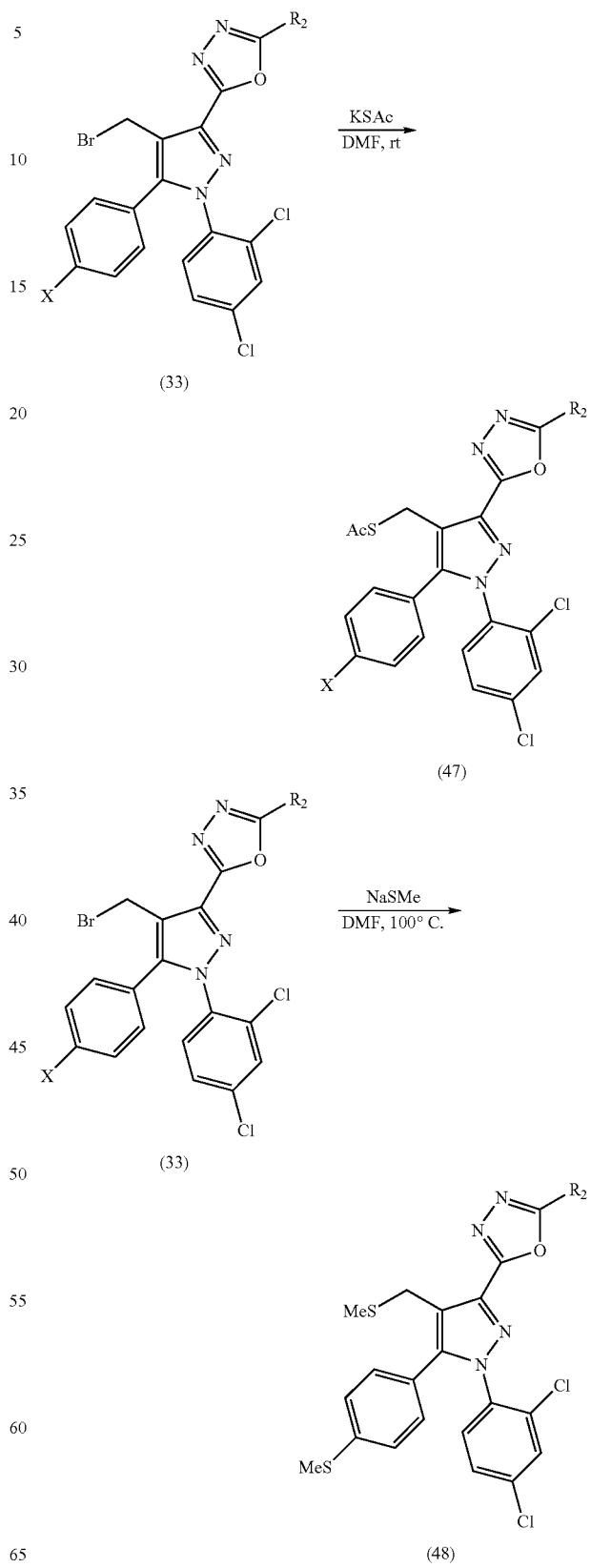

Another derivatization may result from a nucleophilic sulfur reagent such as potassium thioacetate or sodium thiomethoxide with a bromide of structure (33). For example, a bromide (33) is smoothly converted to a thioacetate (47) in a suitable solvent such as DMF at ambient temperature. A thioacetate of structure (47) may be used to prepare the corresponding thiol. Another example includes reacting a bromide of structure (33, X=Cl) with sodium thiomethoxide in heated DMF to generate a disulfide of structure (48) as shown in Reaction Scheme 20.

An alcohol of structure (35) can be alkylated with an alkyl iodide or an alkyl bromide in the presence of a suitable base such as sodium hydride (Williamson ether synthesis conditions) to furnish the corresponding ether of structure (49). Also, an alcohol of structure (35) may be converted into the corresponding fluoride of structure (50) by action of a fluorinating agent such as diethylaminosulfur trifluoride (DAST) in an appropriate solvent such as methylene chloride at ambient temperature. On the other hand, Burgess reagent may convert an alcohol of structure (35) to the corresponding carbamate of structure (51) as described in Reaction Scheme 21.

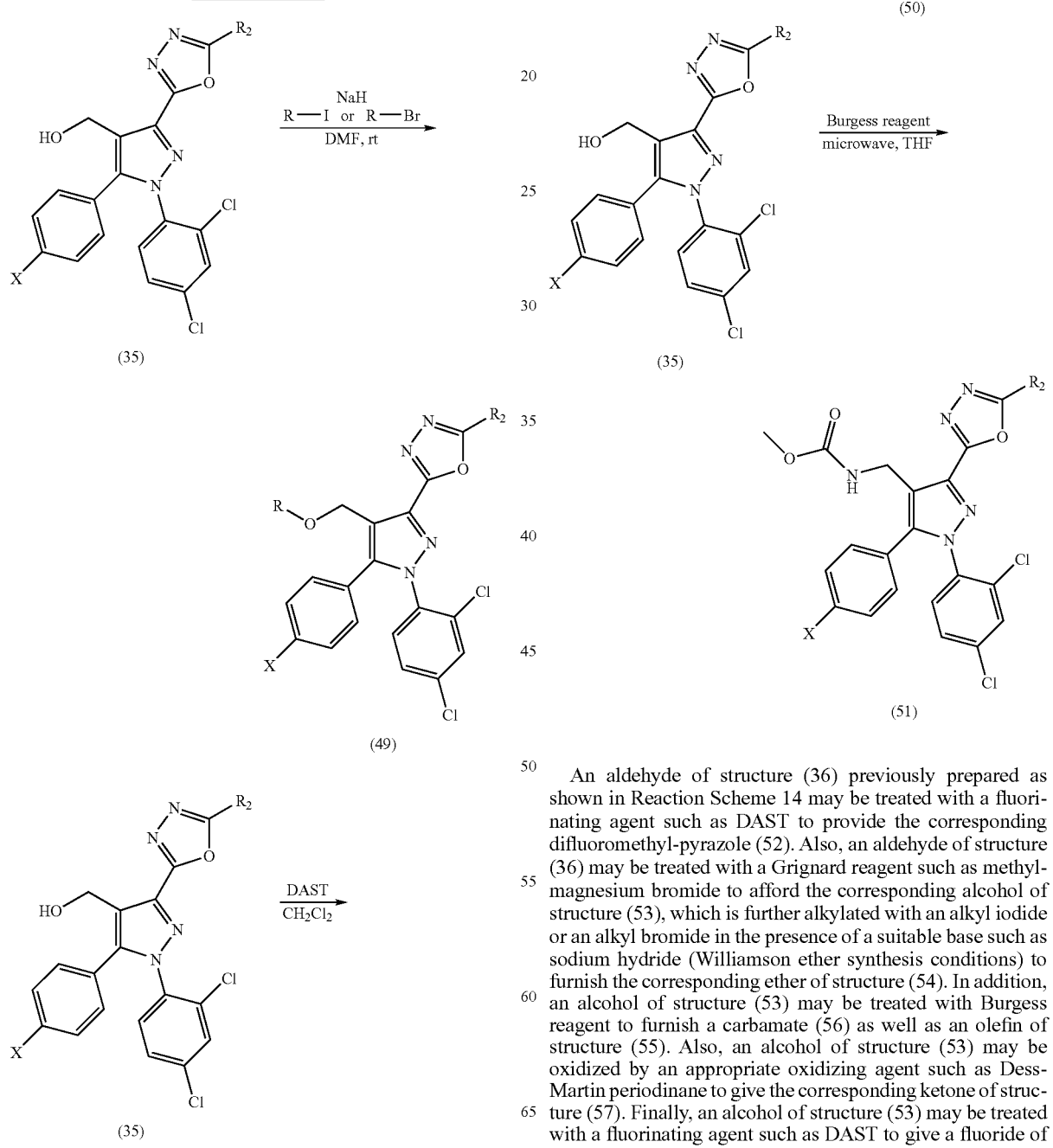

An aldehyde of structure (36) previously prepared as shown in Reaction Scheme 14 may be treated with a fluorinating agent such as DAST to provide the corresponding difluoromethyl-pyrazole (52). Also, an aldehyde of structure (36) may be treated with a Grignard reagent such as methylmagnesium bromide to afford the corresponding alcohol of structure (53), which is further alkylated with an alkyl iodide or an alkyl bromide in the presence of a suitable base such as sodium hydride (Williamson ether synthesis conditions) to furnish the corresponding ether of structure (54). In addition, an alcohol of structure (53) may be treated with Burgess reagent to furnish a carbamate (56) as well as an olefin of structure (55). Also, an alcohol of structure (53) may be oxidized by an appropriate oxidizing agent such as Dess-Martin periodinane to give the corresponding ketone of structure (57). Finally, an alcohol of structure (53) may be treated with a fluorinating agent such as DAST to give a fluoride of structure (58) as described in Reaction Scheme 22.

Reaction Scheme 22
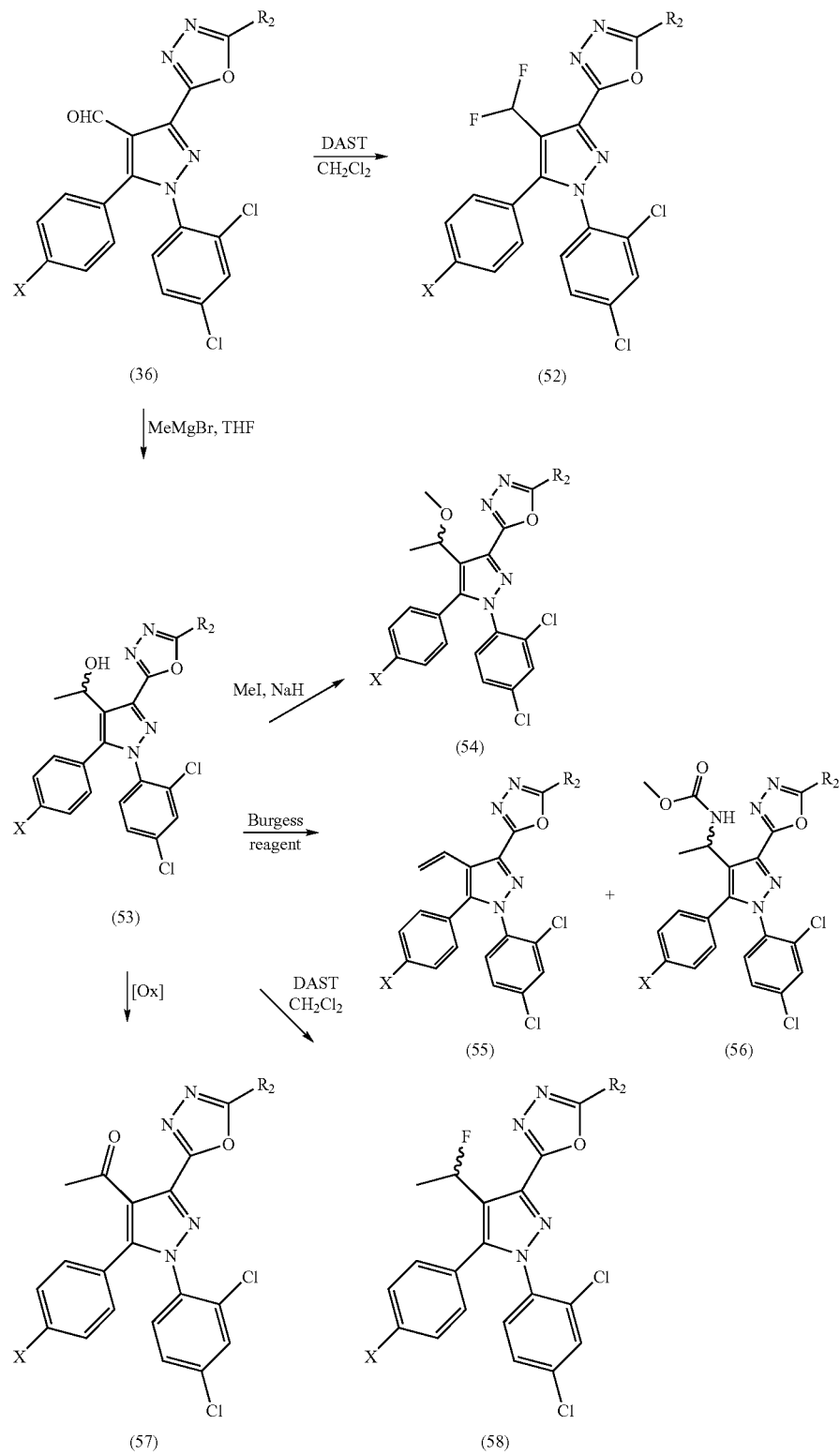
A ketone of structure (57) may be further reacted with a Grignard reagent such as methylmagnesium bromide to provide the alcohol of structure (59), which may be dehydrated by using a suitable dehydrating agent such as Burgess reagent to give the corresponding olefin of structure (60) as demonstrated in Reaction Scheme 23.

Reaction Scheme 23

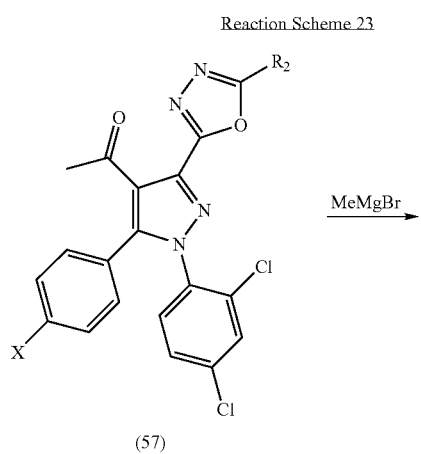

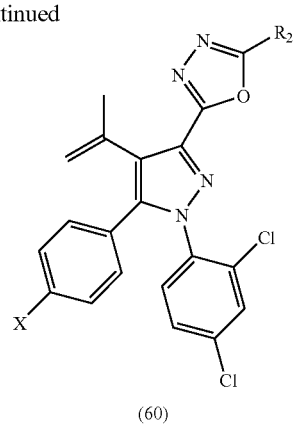

The compounds containing 1,2,4-triazole at C-4 on pyrazole may be obtained by a series of reaction sequence involving a key intermediate bromide of structure (61). Thus, a bromide of structure (61), which is obtained by reaction of a pyrazole of structure (4) with N-bromosuccinimide (NBS) in the presence of a catalytic amount of AIBN, may be reacted with 1H-1,2,4-triazole in the presence of a suitable base such as sodium hydride in a suitable solvent such as THF to furnish 1,2,4-triazole of structure (62). Hydrolysis of an ester (62) may provide the corresponding acid of structure (63). Activation of an acid of structure (63) followed by coupling with a hydrazide in the presence of an appropriate base such as triethylamine may produce an acylhydrazide of structure (64). As an alternative, hydrazynolysis of an ester (62) may provide the corresponding hydrazide, which may be coupled with a particular acid in the presence of coupling reagents such as EDCI, HOBt and NMM to provide an acylhydrazide of structure (64).

The cyclization may be conducted using Burgess reagent as a dehydrating agent while applying microwave irradiation thereon, or using triphenylphosphine with carbon tetrachloride and a base such as triethylamine in a suitable solvent such as acetonitrile and THF, or alternatively using phosphorus (III) oxychloride in a solvent such as acetonitrile or 1,4-dioxane at reflux temperature to give an oxadiazole of structure (65). On the other hand, a compound of formula (66) may be prepared by cyclizing the acylhydrazide intermediate (64) using a Lawesson's reagent, which may be conducted with microwave irradiation as shown in Reaction Scheme 24.

Reaction Scheme 24

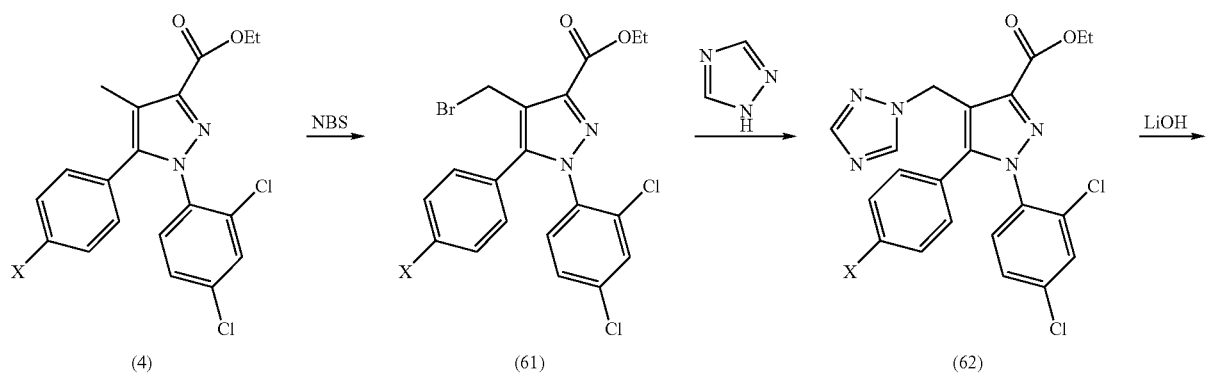

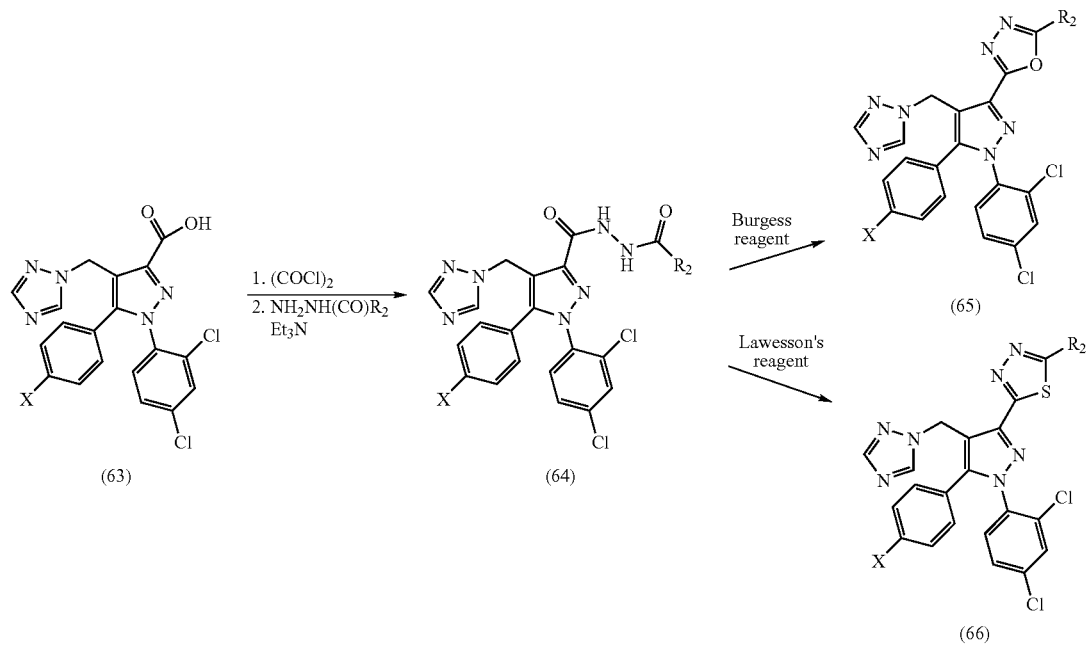

The 4-cyclopropyl-pyrazole compound may be prepared as shown in Reaction Scheme 25. Thus, 4-bromo-pyrazole of structure (68), which may be prepared by following a generic procedure (Andrew G. Horti et al, *J. Med. Chem.* 2003, 46, 642-645), may be coupled with a cyclopropylboronic acid under Suzuki-Miyaura coupling reaction conditions to afford a 4-cyclopropyl-pyrazole of structure (69). The ester (69) may undergo a series of reaction sequence previously described to give rise to an oxadiazole of structure (72). The thiadiazole compound of formula (73) may be prepared by cyclizing the acylhydrazide intermediate (71) using a Lawesson's reagent, which may be conducted with microwave irradiation as shown in Reaction Scheme 25.

Reaction Scheme 25

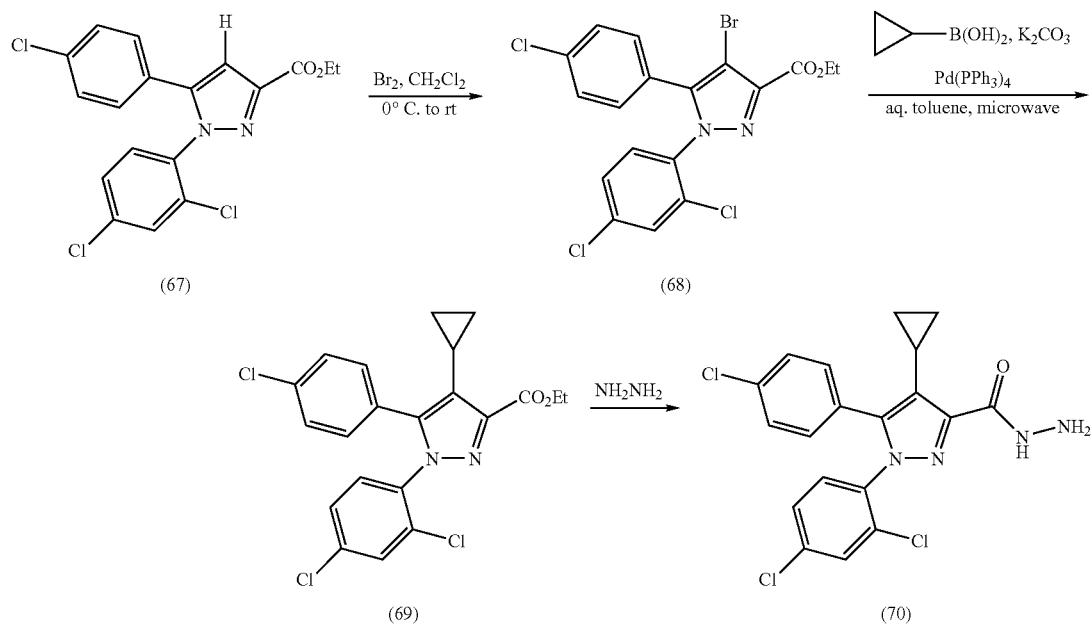

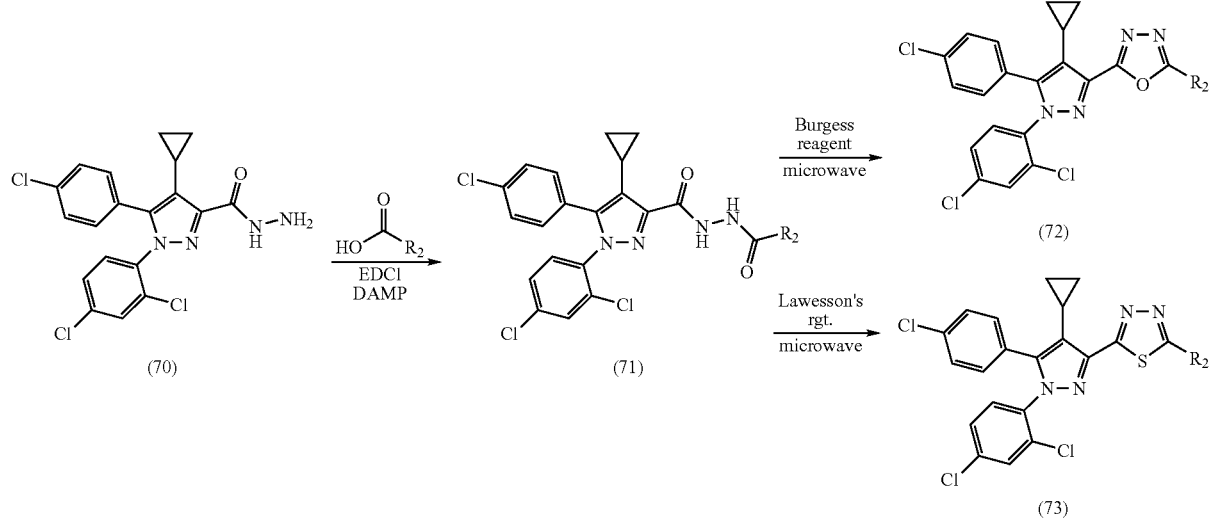

The 4-ethynyl-pyrazole compound of structure (75) may be prepared through two steps from a starting aldehyde of structure (36). Thus, an aldehyde of structure (36) prepared in Reaction Scheme 14 may be converted to a corresponding 4-(2,2-dibromovinyl)-pyrazole (74), which could be treated with a suitable base such as potassium hexamethyldisilazane (KHMDS) at −78° C. in an appropriate solvent such as THF to afford a 4-ethynyl-pyrazole of structure (75). A compound of structure (75) may be further alkylated by action of a base such as lithium hexamethyldisilazide (LHMDS) with an alkylating agent such as methyl iodide in an appropriate solvent such as THF to produce 4-(prop-1-ynyl)-pyrazole of structure (76) as shown in Reaction Scheme 26.

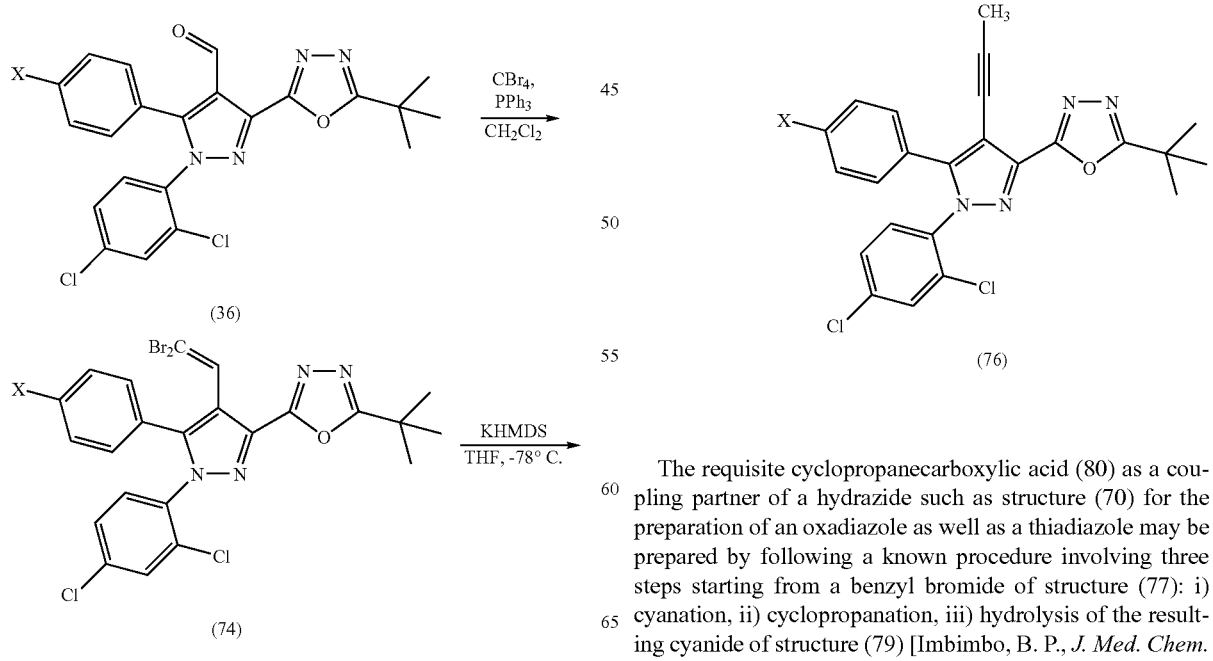

The requisite cyclopropanecarboxylic acid (80) as a coupling partner of a hydrazide such as structure (70) for the preparation of an oxadiazole as well as a thiadiazole may be prepared by following a known procedure involving three steps starting from a benzyl bromide of structure (77): i) cyanation, ii) cyclopropanation, iii) hydrolysis of the resulting cyanide of structure (79) [Imbimbo, B. P., *J. Med. Chem.* 2005, 48, 5707-7520] as described in Reaction Scheme 27.

Reaction Scheme 27

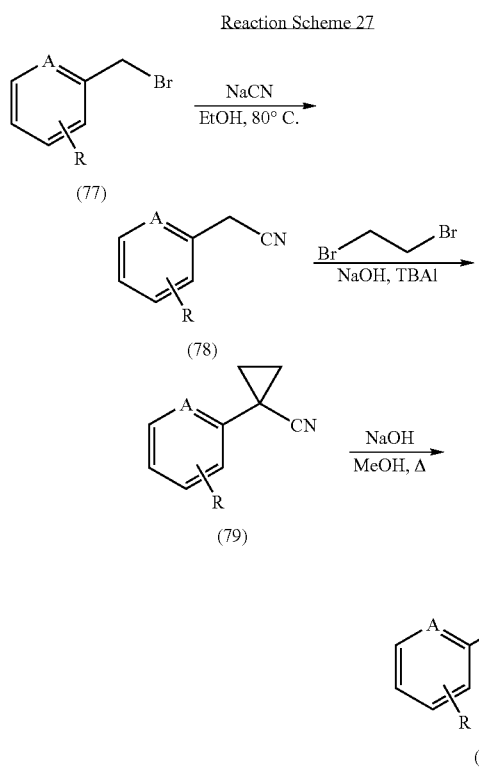

Reaction Scheme 28

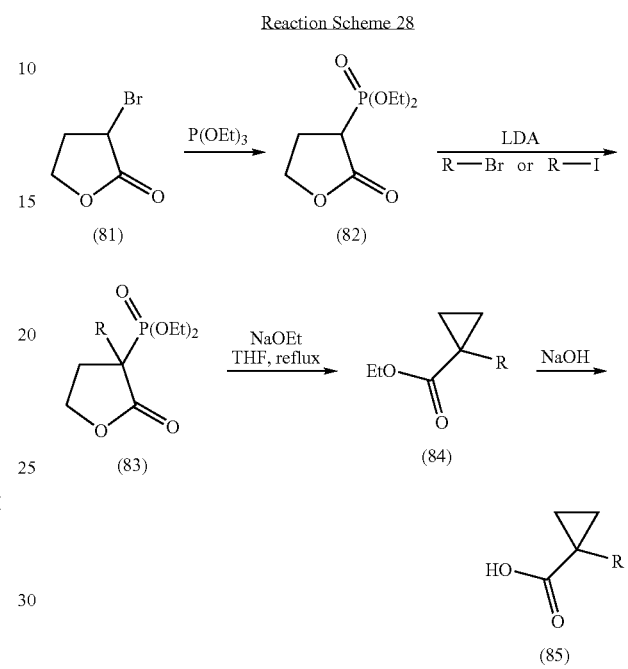

structure (83) with in situ generated sodium ethoxide in refluxed THF would afford a cyclopropanecarboxylic ester of structure (84), which in turn could be hydrolyzed to a corresponding cyclopropanecarboxylic acid (85) as shown in Reaction Scheme 28.

wherein A is carbon or nitrogen; R is halogen, $C_1$-$C_6$ alkyl, $C_1$-$C_4$ alkoxy, $NR_iR_j$, carbocycle, heterocycle, aryl, or heteroaryl; and $R_i$ and $R_j$ are independently hydrogen, $C_{1-4}$ alkyl or $C_{3-5}$ carbocycle.

Alternatively, a requisite cyclopropanecarboxylic acid such as structure (85) may be provided by following a known method [Krawczyk, H., *Synlett.*, 2005, 17, 2648-2652]. Thus, a commercially available 3-bromodihydrofuran-2(3H)-one (81) may undergo Arbuzov reaction to afford diethyl 2-oxotetrahydrofuran-3-ylphosphonate (82), which could be alkylated with an alkyl bromide or an alkyl iodide in the presence of a suitable base such as lithium diisopropylamide (LDA) in an appropriate solvent such as THF to give a compound of structure (83). Treatment of a lactone compound of structure (83) with in situ generated sodium ethoxide in refluxed THF would afford a cyclopropanecarboxylic ester of structure (84), which in turn could be hydrolyzed to a corresponding cyclopropanecarboxylic acid (85) as shown in Reaction Scheme 28.

As an alternative scaffold, a pyrazole of structure (88) may be prepared by treatment of 1,3-dione of structure (87) with hydrazine at reflux temperature. In turn, a 1,3-dione of structure (87) in equilibrium with a keto-enol of structure (88) may be obtained by treating an ester of structure (4) with a methyl ketone such as 3,3-dimethylbutan-2-one (86) in the presence of a base such as sodium amide. On the other hand, an isoxazole (90) or its isomer (91) may be prepared by treatment of 1,3-dione of structure (87) with hydroxylamine. These two isomers may be separated by preparative HPLC as shown in Reaction Scheme 29.

Reaction Scheme 29

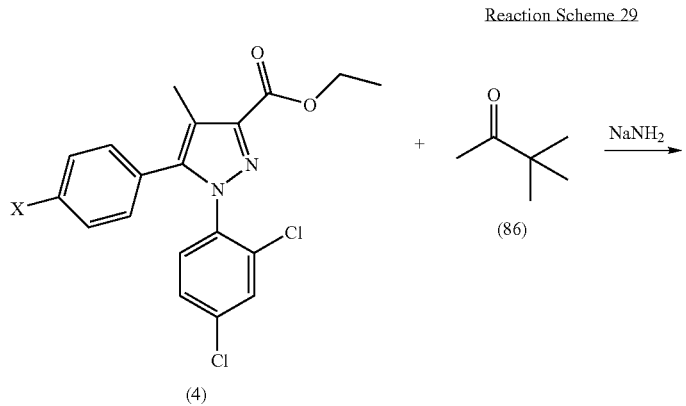

-continued

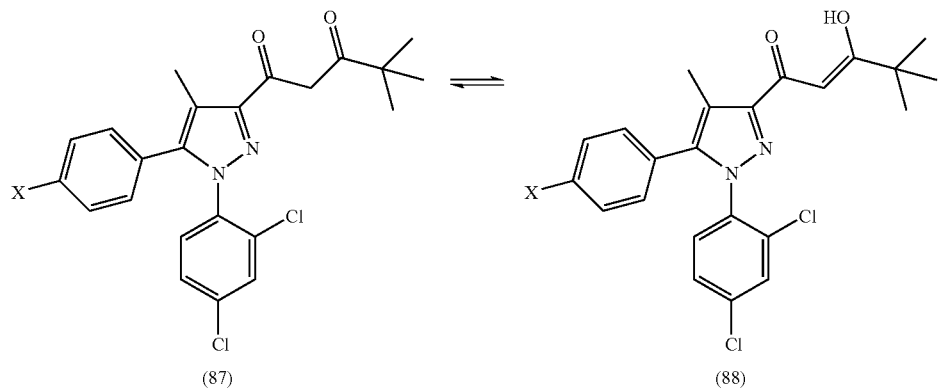

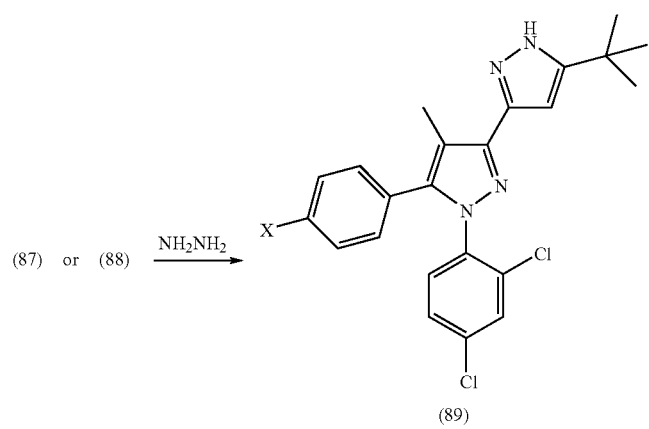

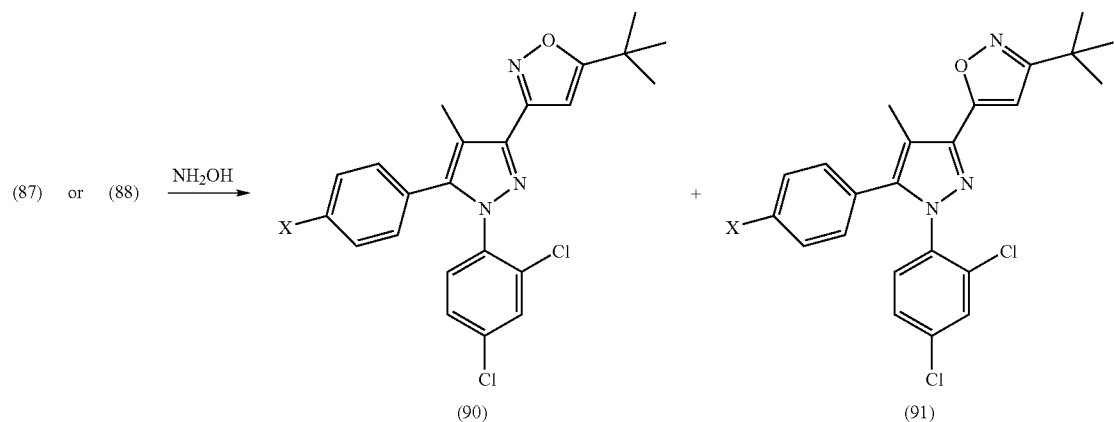

Further derivatization on a thiadiazole compound may be done in a similar fashion as done on an oxadiazole compound as illustrated in Reaction Scheme 14. Thus, as shown in Reaction Scheme 30, bromination may be achieved by NBS in the presence of either benzoyl peroxide or AIBN. Subsequently, hydroxyl group is introduced by reacting a bromide of structure (92) with sodium acetate followed by subsequent hydrolysis of the acetate (93). Oxidation of the alcohol (94) to aldehyde (95) may be achieved by action of a mild oxidant such as Dess-Martin periodinane.

Reaction Scheme 30

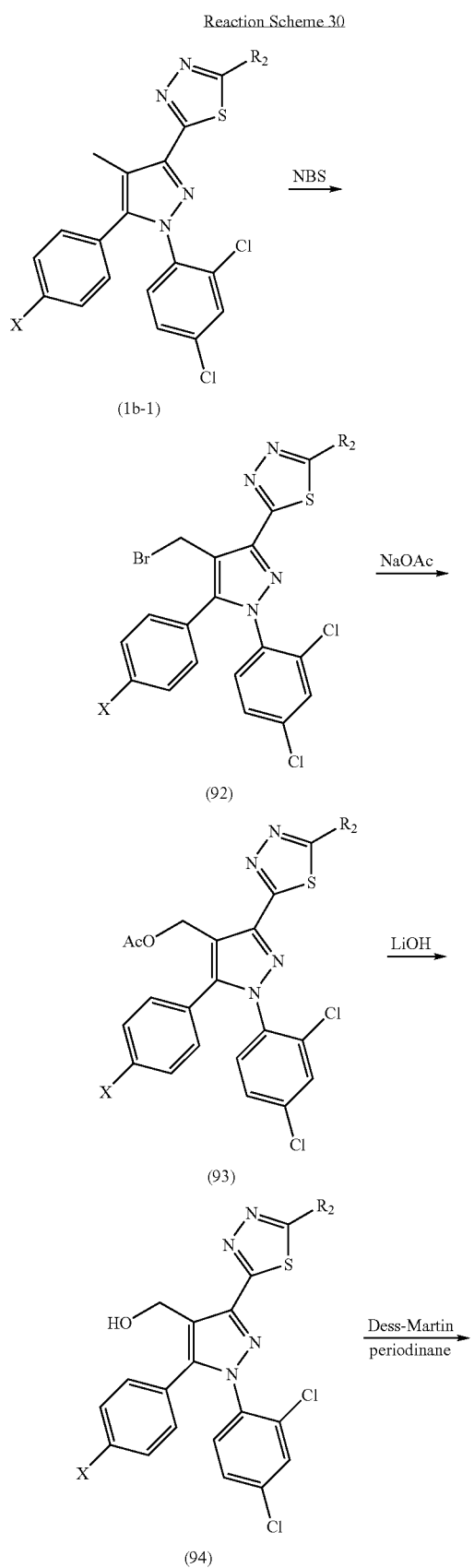

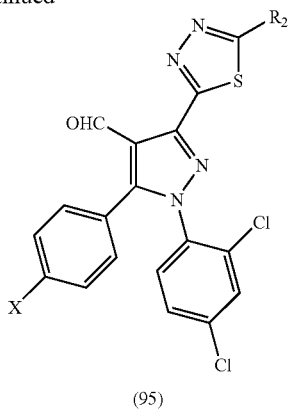

All the other transformations demonstrated in Reaction Scheme 15-24, and Reaction Scheme 26 can be applied on a thiadiazole compound to prepare inventive compounds in a similar way.

The inventive heteroaryl-pyrazole compound of formula (I) is effective as a cannabinoid $CB_1$ receptor inverse agonist or antagonist, thereby preventing or treating obesity and obesity-related metabolic disorders.

Accordingly, the present invention provides a pharmaceutical composition for preventing or treating obesity and obesity-related metabolic disorders, which comprises the compound of formula (I) or a pharmaceutically acceptable salt thereof as an active ingredient and a pharmaceutically acceptable carrier.

Further, the present invention provides a method for preventing or treating obesity and obesity-related metabolic disorders in a mammal, which comprises administering the compound of formula (I) of claim 1 to the mammal.

Also, the present invention provides a method for inhibiting cannabinoid $CB_1$ receptor in a mammal, which comprises administering the compound of formula (I) of claim 1 to the mammal.

As used herein, the term "obesity-related metabolic disorders" refers to chronic diseases that require treatment to reduce the excessive health risks associated with obesity and exemplary disorders include type 2 diabetes mellitus, cardiovascular and hypertension, hyperlipidaemia, fibrinolytic abnormalities.

The pharmaceutical composition may be administered orally, intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerine or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg/Kg, and preferably from 1 mg to 100 mg/Kg of the compound of Formula (I) or its pharmaceutically acceptable salt.

The suitable daily dosage for oral administration is about 0.01 mg/Kg to 40 mg/Kg of the compound of Formula (I) or its pharmaceutically acceptable salt, may be administered 1 to 6 times a day, depending on the patient's condition.

SYNTHETIC EXAMPLES

As used herein the symbols and conventions used describing the processes, schemes and examples of the present invention are consistent with those used in the contemporary scientific literature, for example, the *Journal of the American Chemical Society* or the *Journal of Biological Chemistry*. Unless otherwise noted, all starting materials were obtained from commercial suppliers and used without further purification.

Hz (Hertz) TLC (thin layer chromatography)
$T_r$ (retention time) RP (reverse phase)
MeOH (methanol) i-PrOH (isopropanol)
TFA (trifluoroacetic acid) TEA (triethylamine)
EtOH (ethanol) THF (tetrahydrofuran)
DMSO (dimethylsulfoxide) EtOAc (ethyl acetate)
DCM (dichloromethane) HOAc (acetic acid)
DMF (N,N-dimethylformamide) Ac (acetyl)
CDI (1,1-carbonyldiimidazole) Bn (benzyl)
HOSu (N-hydroxysuccinimide)
HOBT (1-hydroxybenzotriazole)
Boc (tert-butyloxycarbonyl)
mCPBA (meta-chloroperbenzoic acid)
FMOC (9-fluorenylmethoxycarbonyl)
DCC (dicyclohexylcarbodiimide)
Cbz (benzyloxycarbonyl)
NMM (N-methyl morpholine)
HOAt (1-hydroxy-7-azabenzotriazole)
TBAF (tetra-n-butylammonium fluoride)
THP (tetrahydro-2H-pyran-2-yl)
DMAP (4-dimethylaminopyridine)
HPLC (high pressure liquid chromatography)
BOP (bis(2-oxo-3-oxazolidinyl)phosphinic chloride);
EDCI (1-ethyl-3-[3-dimethylaminopropyl]carbodiimide hydrochloride)
HBTU (O-Benzotriazolel-yl-N,N,N',N'-tetramethyluronium hexafluorophosphate)
AIBN (α,α'-azobis(isobutyronitrile))
MeI (iodomethane)
LDA (lithium diisopropylamide)
DIPEA (diisopropylethylamine)
NaSMe (sodium thiomethoxide)

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are of the highest available purity unless otherwise indicated.

Microwave reaction was conducted with a Biotage microwave reactor.

$^1$H NMR spectra were recorded on either a Jeol ECX-400, or a Jeol JNM-LA300 spectrometer. Chemical shifts were expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were obtained with either a Micromass, Quattro LC Triple Quadruple Tandem Mass Spectometer, ESI or Agilent, 1100 LC/MSD, ESI.

For preparative HPLC, ca 100 mg of a product was injected in 1 mL of DMSO onto a SunFire™ Prep C18 OBD 5 um 19×100 mm Column with a 10 min gradient from 10% $CH_3CN$ to 90% $CH_3CN$ in $H_2O$. Flash chromatography was carried using Merck silica gel 60 (230-400 mesh). Most of the reactions were monitored by thin-layer chromatography on 0.25 mm E. Merck silica gel plates (60F-254), visualized with UV light using a 5% ethanolic phosphomolybdic acid or p-anisaldehyde solution.

Preparation of 1,3,4-oxadiazole (Formula (Ia))

Example 1

2-(5-(4-chlorophenyl)-1-(2,4-dichlorophenyl)-4-methyl-1H-pyrazol-3-yl)-5-propyl-1,3,4-oxadiazole Step 1: N-butanoyl-N'-[5-(4-Chlorophenyl)-1-(2,4-dichlorophenyl)-4-methyl-1H-pyrazole-3-carbonyl]-hydrazine Added to a solution of 5-(4-chlorophenyl)-1-(2,4-dichlorophenyl)-4-methyl-1H-pyrazole-3-carboxylic acid (0.40 g, 1.05 mmol), N-butanoyl-hydrazine (0.11 g, 1.05 mmol) and EDCI (0.24 g, 1.26 mmol) dissolved in DCM (11 ml), was DMAP (0.15 g, 1.26 mmol) in one portion at room temperature. The reaction mixture was stirred at room temperature for 6 hrs, and then treated with 10% aq. HCl. The organic layer was collected, and evaporated under a vacuum. The crude mixture was further purified by preparative HPLC, to obtain 0.38 g (0.81 mmol, 77%) of the title compound as yellow solid.

$^1$H NMR (400 MHz, $CDCl_3$) δ 7.40 (br s, 1H), 7.31-7.27 (m, 4H), 7.08-7.03 (m, 2H), 2.33 (s, 3H), 2.31 (t, J=7.8 Hz, 2H), 1.72 (m, 2H), 0.97 (t, J=7.3 Hz, 3H).

MH+ 463.

Step 2: 2-(5-(4-chlorophenyl)-1-(2,4-dichlorophenyl)-4-methyl-1H-pyrazol-3-yl)-5-propyl-1,3,4-oxadiazole N-butanoyl-N'-[5-(4-Chlorophenyl)-1-(2,4-dichlorophenyl)-4-methyl-1H-pyrazole-3-carbonyl]-hydrazine (0.35 g, 0.75 mmol) obtained in Step 1 was added to a microwave reactor containing Burgess reagent (0.45 g, 1.88 mmol) in THF (2 mL). The capped reactor was placed in a microwave reactor and the mixture was irradiated at 140° C. for 15 min. The reaction product was purified by preparative HPLC to provide the title compound (0.21 g, 0.46 mmol, 61%) as yellow solid.

$^1$H NMR (400 MHz, $CDCl_3$) δ 7.41 (d, J=2.3 Hz, 1H), 7.34-7.28 (m, 4H), 7.09-7.13 (m, 2H), 2.90 (t, J=7.6 Hz, 2H), 2.45 (s, 3H), 1.88 (m, 2H), 1.03 (t, J=7.6 Hz, 3H).

MH+ 447.

The following compounds of Examples 2 to 344 were obtained by using corresponding starting materials and repeating the procedure of Example 1.

Example 2

2-(5-(4-chlorophenyl)-1-(2,4-dichlorophenyl)-4-methyl-1H-pyrazol-3-yl)-5-(pyridin-4-yl)-1,3,4-oxadiazole $^1$H NMR (400 MHz, CDCl$_3$) δ 8.78 (d, J=7.43 Hz, 1H), 8.01 (d, J=5.04 Hz, 1H), 7.41 (d, J=1.84 Hz, 1H), 7.37-7.29 (m, 4H), 7.11 (d, J=8.72 Hz, 2H), 2.48 (s, 3H).
MH+ 482.

Example 3

2-(5-(4-chlorophenyl)-1-(2,4-dichlorophenyl)-4-methyl-1H-pyrazol-3-yl)-5-methyl-1,3,4-oxadiazole $^1$H NMR (400 MHz, CDCl$_3$) δ 7.43 (d, J=1.84 Hz, 1H), 7.37-7.29 (m, 4H), 7.11 (dt, J=2.28, 8.24 Hz, 2H), 2.63 (s, 3H), 2.46 (s, 3H).
MH+ 419.

Example 4

2-butyl-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.43 (d, J=1.84 Hz, 1H), 7.37-7.29 (m, 4H), 7.12 (dt, J=2.28, 8.24 Hz, 2H), 2.94 (t, J=7.56 Hz, 2H), 2.46 (s, 3H), 1.85 (m, 2H), 1.45 (m, 2H), 0.96 (t, J=7.36 Hz, 3H).
MH+ 461.

Example 5

2-(5-(4-chlorophenyl)-1-(2,4-dichlorophenyl)-4-methyl-1H-pyrazol-3-yl)-5-cyclopentyl-1,3,4-oxadiazole $^1$H NMR (400 MHz, CDCl$_3$) δ 7.41 (d, J=1.84 Hz, 1H), 7.37-7.29 (m, 4H), 7.11 (dt, J=2.28, 8.24 Hz, 2H), 3.39 (m, 1H), 2.45 (s, 3H), 2.14 (m, 2H), 2.04 (m, 2H), 1.84 (m, 2H), 1.71 (m, 2H).
MH+ 473.

Example 6

2-(5-(4-chlorophenyl)-1-(2,4-dichlorophenyl)-4-methyl-1H-pyrazol-3-yl)-5-cyclohexyl-1,3,4-oxadiazole $^1$H NMR (400 MHz, CDCl$_3$) δ 7.41 (d, J=1.84 Hz, 1H), 7.37-7.29 (m, 4H), 7.11 (dt, J=2.28, 8.24 Hz, 2H), 3.00 (m, 1H), 2.44 (s, 3H), 2.16-2.12 (m, 2H), 1.87-1.81 (m, 2H), 1.78-1.65 (m, 3H), 1.44-1.28 (m, 3H).
MH+ 487.

Example 7

2-(5-(4-chlorophenyl)-1-(2,4-dichlorophenyl)-4-methyl-1H-pyrazol-3-yl)-5-cyclopropyl-1,3,4-oxadiazole

MH+ 445.

Example 8

2-(5-(4-chlorophenyl)-1-(2,4-dichlorophenyl)-4-methyl-1H-pyrazol-3-yl)-5-(furan-2-yl)-1,3,4-oxadiazole

MH+ 471.

Example 9

2-(5-(4-chlorophenyl)-1-(2,4-dichlorophenyl)-4-methyl-1H-pyrazol-3-yl)-5-cyclobutyl-1,3,4-oxadiazole $^1$H NMR (400 MHz, CDCl$_3$) δ 7.43 (d, J=2.3 Hz, 1H), 7.34-7.28 (m, 4H), 7.13-7.09 (m, 2H), 4.01 (m, 1H), 2.62-2.52 (m, 2H), 2.49 (s, 3H), 2.47-2.39 (m, 2H), 2.20-2.00 (m, 2H).
MH+ 459.

Example 10

2-(5-(4-chlorophenyl)-1-(2,4-dichlorophenyl)-4-methyl-1H-pyrazol-3-yl)-5-(pyrazin-2-yl)-1,3,4-oxadiazole $^1$H NMR (400 MHz, CDCl$_3$) δ 9.53 (s, 1H), 8.76 (m, 1H), 7.43 (d, J=1.84 Hz, 1H), 7.39 (d, J=8.68 Hz, 1H), 7.36-7.30 (m, 4H), 7.15 (d, J=8.24 Hz, 2H), 2.55 (s, 3H).
MH+ 483.

Example 11

2-(5-(4-chlorophenyl)-1-(2,4-dichlorophenyl)-4-methyl-1H-pyrazol-3-yl)-5-(thiophen-2-yl)-1,3,4-oxadiazole

MH+ 487.

Example 12

2-(5-(4-chlorophenyl)-1-(2,4-dichlorophenyl)-4-methyl-1H-pyrazol-3-yl)-5-(pyridin-2-ylmethyl)-1,3,4-oxadiazole 1H NMR (400 MHz, CDCl$_3$) δ 8.55 (d, J=4.12 Hz, 1H), 7.66 (dt, J=1.84, 7.80 Hz, 1H), 7.41 (d, J=1.84 Hz, 1H), 7.35-7.29 (m, 5H), 7.20 (dd, J=5.04, 7.32 Hz, 1H), 7.13-7.09 (m, 2H), 4.52 (s, 2H), 2.45 (s, 3H).
MH+ 496.

Example 13

2-(5-(4-chlorophenyl)-1-(2,4-dichlorophenyl)-4-methyl-1H-pyrazol-3-yl)-5-isopropyl-1,3,4-oxadiazole $^1$H NMR (400 MHz, CDCl$_3$) δ 7.41 (d, J=2.28 Hz, 1H), 7.38-7.29 (m, 4H), 7.13-7.09 (m, 2H), 3.28 (m, 1H), 2.44 (s, 3H), 1.46 (d, J=6.88 Hz, 6H).
MH+ 447.

Example 14

2-(5-(4-chlorophenyl)-1-(2,4-dichlorophenyl)-4-methyl-1H-pyrazol-3-yl)-5-(pentan-3-yl)-1,3,4-oxadiazole $^1$H NMR (400 MHz, CDCl$_3$) δ 7.42 (d, J=2.28 Hz, 1H), 7.38-7.30 (m, 4H), 7.13-7.10 (m, 2H), 2.96 (m, 1H), 2.46 (s, 3H), 1.93-1.79 (m, 2H), 0.94 (t, J=7.32 Hz, 3H).
MH+ 475.

Example 15

2-Benzyl-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.41 (d, J=1.84 Hz, 1H), 7.38-7.27 (m, 9H), 7.12-7.08 (m, 2H), 4.29 (s, 2H), 2.43 (s, 3H).
MH+ 495.

Example 16

2-(5-(4-Chlorophenyl)-1-(2,4-dichlorophenyl)-4-methyl-1H-pyrazol-3-yl)-5-phenyl-1,3,4-oxadiazole $^1$H NMR (300 MHz, CDCl$_3$) δ 8.22-8.18 (m, 2H), 7.57-7.49 (m, 3H), 7.45-7.44 (m, 1H), 7.41-7.32 (m, 4H), 7.16-7.12 (m, 2H), 2.51 (s, 3H).
MH+ 483.

Example 17

2-(4-Chlorophenyl)-5-(5-(4-chlorophenyl)-1-(2,4-dichlorophenyl)-4-methyl-1H-pyrazol-3-yl)-1,3,4-oxadiazole $^1$H-NMR (300 MHz, CDCl$_3$) δ 8.16-8.12 (m, 2H), 7.52-7.48 (m, 2H), 7.45-7.44 (m, 1H), 7.37-7.32 (m, 4H), 7.16-7.12 (m, 2H), 2.50 (s, 3H).
MH+ 517.

Example 18

2-(Benzofuran-2-yl)-5-(5-(4-chlorophenyl)-1-(2,4-dichlorophenyl)-4-methyl-1H-pyrazol-3-yl)-1,3,4-oxadiazole $^1$H-NMR (400 MHz, CDCl$_3$) δ 7.70 (d, J=7.7 Hz, 1H), 7.64-7.62 (m, 2H), 7.47-7.42 (m, 2H), 7.40-7.38 (m, 1H), 7.36-7.30 (m, 4H), 7.16-7.13 (m, 2H), 2.53 (s, 3H).
MH+ 521.

Example 19

2-(5-(4-Chlorophenyl)-1-(2,4-dichlorophenyl)-4-methyl-1H-pyrazol-3-yl)-5-pentyl-1,3,4-oxadiazole $^1$H-NMR (400 MHz, CDCl$_3$) δ 7.43-7.42 (m, 1H), 7.37-7.30 (m, 4H), 7.13-7.10 (m, 2H), 2.93 (t, J=7.8 Hz, 2H), 2.46 (s, 3H), 1.90-1.83 (m, 2H), 1.45-1.32 (m, 4H), 0.91 (t, J=7.3 Hz, 3H).
MH+ 475.

Example 20

2-(5-(4-Chlorophenyl)-1-(2,4-dichlorophenyl)-4-methyl-1H-pyrazol-3-yl)-5-cycloheptyl-1,3,4-oxadiazole $^1$H-NMR (400 MHz, CDCl$_3$) δ 7.43-7.41 (m, 1H), 7.37-7.29 (m, 4H), 7.13-7.10 (m, 2H), 3.23-3.16 (m, 1H), 2.45 (s, 3H), 2.21-2.14 (m, 4H), 1.98-1.89 (m, 2H), 1.85-1.79 (m, 2H), 1.68-1.53 (m, 4H).
MH+ 501.

Example 21

2-(5-(4-Chlorophenyl)-1-(2,4-dichlorophenyl)-4-methyl-1H-pyrazol-3-yl)-5-(2,4-dichlorophenyl)-1,3,4-oxadiazole $^1$H-NMR (400 MHz, CDCl$_3$) δ 8.04 (d, J=8.4 Hz, 1H), 7.60 (d, J=1.8 Hz, 1H), 7.44 (d, J=2.2 Hz, 1H), 7.41 (d, J=2.2 Hz, 1H), 7.39-7.31 (m, 4H), 7.15-7.12 (m, 2H), 2.51 (s, 3H).
MH+ 548.

Example 22

2-(5-(4-Chlorophenyl)-1-(2,4-dichlorophenyl)-4-methyl-1H-pyrazol-3-yl)-5-(cyclopentylmethyl)-1,3,4-oxadiazole $^1$H-NMR (400 MHz, CDCl$_3$) δ 7.41 (d, J=2.3 Hz, 1H), 7.37-7.29 (m, 4H), 7.14-7.10 (m, 2H), 2.93 (d, J=7.3 Hz, 2H), 2.46 (s, 3H), 2.45-2.39 (m, 1H), 1.90-1.82 (m, 2H), 1.71-1.63 (m, 2H), 1.61-1.54 (m, 2H), 1.35-1.26 (m, 2H).
MH+ 487.

Example 23

2-(5-(4-Chlorophenyl)-1-(2,4-dichlorophenyl)-4-methyl-1H-pyrazol-3-yl)-5-(tetrahydro-2H-pyran-4-yl)-1,3,4-oxadiazole $^1$H-NMR (400 MHz, CDCl$_3$) δ 7.43-7.42 (m, 1H), 7.37-7.30 (m, 4H), 7.13-7.10 (m, 2H), 4.08-4.03 (m, 2H), 3.59-3.52 (m, 2H), 3.29-3.21 (m, 1H), 2.45 (s, 3H), 2.10-2.05 (m, 4H).
MH+ 489.

Example 24

2-(5-(4-Chlorophenyl)-1-(2,4-dichlorophenyl)-4-methyl-1H-pyrazol-3-yl)-5-(cyclohexylmethyl)-1,3,4-oxadiazole $^1$H-NMR (400 MHz, CDCl$_3$) δ 7.43-7.42 (m, 1H), 7.37-7.29 (m, 4H), 7.13-7.10 (m, 2H), 2.82 (d, J=7.3 Hz, 2H), 2.46 (s, 3H), 1.98-1.87 (m, 1H), 1.79-1.63 (m, 4H), 1.31-1.03 (m, 6H).
MH+ 501.

Example 25

2-(5-(4-Chlorophenyl)-1-(2,4-dichlorophenyl)-4-methyl-1H-pyrazol-3-yl)-5-(tetrahydrofuran-2-yl)-1,3,4-oxadiazole $^1$H-NMR (400 MHz, CDCl$_3$) δ 7.45-7.42 (m, 1H), 7.34-7.29 (m, 4H), 7.13-7.10 (m, 2H), 5.28-5.24 (m, 1H), 4.10-

4.04 (m, 1H), 3.99-3.96 (m, 1H), 2.45 (s, 3H), 2.42-2.33 (m, 2H), 2.25-2.14 (m, 1H), 2.11-2.00 (m, 1H).
MH+ 475.

Example 26

2-(5-(4-Bromophenyl)-1-(2,4-dichlorophenyl)-4-methyl-1H-pyrazol-3-yl)-5-cyclobutyl-1,3,4-oxadiazole $^1$H-NMR (400 MHz, CDCl$_3$) δ 7.50-7.46 (m, 2H), 7.42 (d, J=2.3 Hz, 1H), 7.36 (d, J=8.7 Hz, 1H), 7.33-7.30 (m, 1H), 7.07-7.04 (m, 2H), 3.86-3.77 (m, 1H), 2.61-2.51 (m, 2H), 2.49-2.41 (m, 2H), 2.45 (s, 3H), 2.16-2.00 (m, 2H).
MH+ 503.

Example 27

2-(5-(4-Bromophenyl)-1-(2,4-dichlorophenyl)-4-methyl-1H-pyrazol-3-yl)-5-cyclopentyl-1,3,4-oxadiazole $^1$H-NMR (400 MHz, CDCl$_3$) δ 7.50-7.46 (m, 2H), 7.42 (d, J=2.3 Hz, 1H), 7.36 (d, J=8.2 Hz, 1H), 7.32-7.29 (m, 1H), 7.07-7.03 (m, 2H), 3.43-3.35 (m, 1H), 2.45 (s, 3H), 2.19-2.11 (m, 2H), 2.08-1.99 (m, 2H), 1.89-1.80 (m, 2H), 1.75-1.67 (m, 2H).
MH+ 517.

Example 28

2-(5-(4-Bromophenyl)-1-(2,4-dichlorophenyl)-4-methyl-1H-pyrazol-3-yl)-5-cyclohexyl-1,3,4-oxadiazole $^1$H-NMR (400 MHz, CDCl$_3$) δ 7.50-7.46 (m, 2H), 7.42 (d, J=2.3 Hz, 1H), 7.36 (d, J=8.2 Hz, 1H), 7.32-7.29 (m, 1H), 7.06-7.03 (m, 2H), 3.03-2.96 (m, 1H), 2.45 (s, 3H), 2.17-2.12 (m, 2H), 1.88-1.83 (m, 2H) 1.76-1.66 (m, 4H), 1.45-1.26 (m, 2H).
MH+ 531.

Example 29

2-sec-Butyl-5-(5-(4-chlorophenyl)-1-(2,4-dichlorophenyl)-4-methyl-1H-pyrazol-3-yl)-1,3,4-oxadiazole $^1$H-NMR (400 MHz, CDCl$_3$) δ 7.42-7.41 (m, 1H), 7.36 (d, J=8.2 Hz, 1H), 7.34-7.30 (m, 3H), 7.13-7.09 (m, 2H), 3.16-3.07 (m, 1H), 2.45 (s, 3H), 2.00-1.89 (m, 1H), 1.80-1.70 (m, 1H), 1.43 (d, J=6.9 Hz, 3H), 0.97 (t, J=7.4 Hz, 3H).
MH+ 461.

Example 30

2-(5-(4-Chlorophenyl)-1-(2,4-dichlorophenyl)-4-methyl-1H-pyrazol-3-yl)-5-(pentan-2-yl)-1,3,4-oxadiazole $^1$H-NMR (400 MHz, CDCl$_3$) δ 7.42-7.41 (m, 1H), 7.38-7.30 (m, 4H), 7.13-7.09 (m, 2H), 3.24-3.15 (m, 1H), 2.45 (s, 3H), 1.95-1.86 (m, 1H), 1.71-1.63 (m, 1H), 1.46-1.32 (m, 5H), 0.92 (t, J=7.4 Hz, 3H).
MH+ 475.

Example 31

2-(5-(4-Chlorophenyl)-1-(2,4-dichlorophenyl)-4-methyl-1H-pyrazol-3-yl)-5-(hexan-2-yl)-1,3,4-oxadiazole $^1$H-NMR (400 MHz, CDCl$_3$) δ 7.42-7.41 (m, 1H), 7.38-7.30 (m, 4H), 7.13-7.09 (m, 2H), 3.22-3.13 (m, 1H), 2.45 (s, 3H), 1.95-1.89 (m, 1H), 1.73-1.64 (m, 1H), 1.42 (d, J=6.9 Hz, 3H), 1.38-1.25 (m, 4H), 0.91-1.87 (m, 3H).
MH+ 489.

Example 32

2-(5-(4-Bromophenyl)-1-(2,4-dichlorophenyl)-4-methyl-1H-pyrazol-3-yl)-5-tert-butyl-1,3,4-oxadiazole $^1$H-NMR (400 MHz, CDCl$_3$) δ 7.49-7.46 (m, 2H), 7.42-7.41 (m, 1H), 7.39-7.37 m, 1H), 7.33-7.30 (m, 1H), 7.05-7.03 (m, 2H), 2.45 (s, 3H), 1.50 (s, 9H).
MH+ 505.

Example 33

2-tert-Butyl-5-(5-(4-chlorophenyl)-1-(2,4-dichlorophenyl)-4-methyl-1H-pyrazol-3-yl)-1,3,4-oxadiazole $^1$H-NMR (400 MHz, CDCl$_3$) δ 7.42-7.41 (m, 1H), 7.38 (d, J=8.2 Hz, 1H), 7.34-7.30 (m, 3H), 7.12-7.09 (m, 2H), 2.45 (s, 3H), 1.52 (s, 9H).
MH+ 461.

Example 34

2-(5-(4-Chlorophenyl)-1-(2,4-dichlorophenyl)-4-methyl-1H-pyrazol-3-yl)-5-(cyclopropylmethyl)-1,3,4-oxadiazole $^1$H-NMR (400 MHz, CDCl$_3$) δ 7.42-7.41 (m, 1H), 7.37-7.30 (m, 4H), 7.13-7.09 (m, 2H), 2.87 (d, J=6.9 Hz, 2H), 2.45 (s, 3H), 2.29-2.24 (m, 2H), 1.29-1.21 (m, 1H), 0.64-0.60 (m, 2H), 0.36-0.32 (m, 2H).
MH+ 459.

Example 35

2-(4-tert-Butylcyclohexyl)-5-(5-(4-chlorophenyl)-1-(2,4-dichlorophenyl)-4-methyl-1H-pyrazol-3-yl)-1,3,4-oxadiazole $^1$H-NMR (400 MHz, CDCl$_3$) δ 7.42-7.41 (m, 1H), 7.37-7.30 (m, 4H), 7.13-7.09 (m, 2H), 2.92-2.85 (m, 1H), 2.45 (s, 3H), 2.28-2.24 (m, 2H), 1.94-1.91 (m, 2H), 1.71-1.63 (m, 2H), 1.17-1.08 (m, 3H), 0.87 (s, 9H).
MH+ 543.

Example 36

2-(5-(4-Bromophenyl)-1-(2,4-dichlorophenyl)-4-methyl-1H-pyrazol-3-yl)-5-cycloheptyl-1,3,4-oxadiazole $^1$H-NMR (400 MHz, CDCl$_3$) δ 7.50-7.46 (m, 2H), 7.42-7.41 (m, 1H), 7.36 (d, J=8.7 Hz, 1H), 7.31 (dd, J=8.7, 2.3 Hz, 1H), 7.07-7.03 (m, 2H), 3.23-3.15 (m, 1H), 2.45 (s, 3H), 2.21-2.14 (m, 2H), 1.98-1.89 (m, 2H), 1.84-1.79 (m, 2H), 1.69-1.52 (m, 6H).

MH+ 545.

Example 37

2-(5-(4-Bromophenyl)-1-(2,4-dichlorophenyl)-4-ethyl-1H-pyrazol-3-yl)-5-cyclohexyl-1,3,4-oxadiazole $^1$H-NMR (400 MHz, CDCl$_3$) δ 7.50-7.46 (m, 2H), 7.41-7.40 (m, 1H), 7.36 (d, J=8.7 Hz, 1H), 7.30 (dd, J=8.7, 2.3 Hz, 1H), 7.07-7.03 (m, 2H), 3.02-2.96 (m, 1H), 2.94-2.89 (m, 2H), 2.22-2.13 (m, 2H), 1.87-1.84 (m, 2H), 1.76-1.67 (m, 2H), 1.45-1.20 (m, 7H).

MH+ 545.

Example 38

2-(5-(4-Bromophenyl)-1-(2,4-dichlorophenyl)-4-ethyl-1H-pyrazol-3-yl)-5-cyclobutyl-1,3,4-oxadiazole $^1$H-NMR (400 MHz, CDCl$_3$) δ 7.50-7.46 (m, 2H), 7.42-7.41 (m, 1H), 7.36 (d, J=8.2 Hz, 1H), 7.30 (dd, J=8.2, 2.3 Hz, 1H), 7.09-7.05 (m, 2H), 3.86-3.77 (m, 1H), 2.91-2.85 (m, 2H), 2.61-2.51 (m, 2H), 2.49-2.40 (m, 2H), 2.19-1.99 (m, 2H), 1.25-1.21 (m, 3H).

MH+ 517.

Example 39

2-(5-(4-Bromophenyl)-1-(2,4-dichlorophenyl)-4-ethyl-1H-pyrazol-3-yl)-5-cyclopentyl-1,3,4-oxadiazole $^1$H-NMR (400 MHz, CDCl$_3$) δ 7.50-7.46 (m, 2H), 7.41-7.40 (m, 1H), 7.36 (d, J=8.2 Hz, 1H), 7.32-7.29 (m, 1H), 7.07-7.03 (m, 2H), 3.45-3.35 (m, 1H), 2.90-2.84 (m, 2H), 2.19-2.11 (m, 2H), 2.08-1.99 (m, 2H), 1.89-1.80 (m, 2H), 1.75-1.65 m, 2H), 1.25-1.20 (m, 3H).

MH+ 531.

Example 40

2-(5-(4-Bromophenyl)-1-(2,4-dichlorophenyl)-4-ethyl-1H-pyrazol-3-yl)-5-tert-butyl-1,3,4-oxadiazole $^1$H-NMR (400 MHz, CDCl$_3$) δ 7.50-7.46 (m, 2H), 7.41-7.40 (m, 1H), 7.37 (d, J=8.2 Hz, 1H), 7.32-7.29 (m, 1H), 7.07-7.03 (m, 2H), 2.88-2.82 (m, 2H), 1.50 (s, 9H), 1.25-1.18 (m, 3H).

MH+ 519.

Example 41

2-(5-(4-Bromophenyl)-1-(2,4-dichlorophenyl)-4-methyl-1H-pyrazol-3-yl)-5-(hexan-2-yl)-1,3,4-oxadiazole $^1$H-NMR (300 MHz, CDCl$_3$) δ 7.50-7.46 (m, 2H), 7.42-7.41 (m, 1H), 7.37 (d, J=8.4 Hz, 1H), 7.33-7.29 (m, 1H), 7.07-7.03 (m, 2H), 3.21-3.14 (m, 1H), 2.45 (s, 3H), 1.96-1.89 (m, 1H), 1.71-1.64 (m, 1H), 1.43 (d, J=7.0 Hz, 3H), 1.34-1.32 (m, 4H), 0.91-0.86 (m, 3H).

MH+ 533.

Example 42

2-(5-(4-chlorophenyl)-1-(2,4-dichlorophenyl)-4-methyl-1H-pyrazol-3-yl)-5-(1-phenylethyl)-1,3,4-oxadiazole $^1$H NMR (400 MHz, CDCl$_3$) δ 7.40 (d, J=2.3 Hz, 1H), 7.37-7.23 (m, 9H), 7.12-7.09 (m, 2H), 4.45 (m, 1H), 2.42 (s, 3H), 1.82 (d, J=7.3 Hz, 3H).

(M+Na)+ 531.

Example 43

4-(5-(5-(4-chlorophenyl)-1-(2,4-dichlorophenyl)-4-methyl-1H-pyrazol-3-yl)-1,3,4-oxadiazol-2-yl)morpholine $^1$H NMR (400 MHz, CDCl$_3$) δ 7.41 (d, J=2.3 Hz, 1H), 7.35-7.28 (m, 4H), 7.13-7.09 (m, 2H), 3.81 (m, 4H), 3.62 (m, 4H), 2.41 (s, 3H).

MH+ 490.

Example 44

5-(5-(4-chlorophenyl)-1-(2,4-dichlorophenyl)-4-methyl-1H-pyrazol-3-yl)-N-cyclohexyl-1,3,4-oxadiazol-2-amine $^1$H NMR (400 MHz, CDCl$_3$) δ 7.41 (d, J=1.8 Hz, 1H), 7.34-7.27 (m, 4H), 7.13-7.09 (m, 2H), 4.62 (br d, J=8.2 Hz, 1H), 3.68 (m, 1H), 2.42 (s, 3H), 2.15-2.07 (m, 2H), 1.78-1.70 (m, 2H), 1.67-1.59 (m, 1H), 1.47-1.18 (m, 7H).

MH+ 502.

Example 45

2-(5-(4-chlorophenyl)-1-(2,4-dichlorophenyl)-4-methyl-1H-pyrazol-3-yl)-5-(4-methylcyclohexyl)-1,3,4-oxadiazole $^1$H NMR (400 MHz, CDCl$_3$) δ 7.42 (d, J=2.3 Hz, 1H), 7.38-7.29 (m, 4H), 7.14-7.10 (m, 2H), 3.20 (m, 1H), 2.46 (s, 3H), 2.25-2.15 (m, 3H), 1.87-1.79 (m, 2H), 1.47-1.35 (m, 2H), 0.93 (d, J=6.4 Hz, 3H).

MH+ 501.

Example 46

2-(5-(4-chlorophenyl)-1-(2,4-dichlorophenyl)-4-methyl-1H-pyrazol-3-yl)-5-(3-methylcyclohexyl)-1,3,4-oxadiazole $^1$H NMR (400 MHz, CDCl$_3$) δ 7.42 (d, J=2.3 Hz, 1H), 7.38-7.29 (m, 4H), 7.14-7.10 (m, 2H), 3.01 (m, 1H), 2.45 (s, 3H), 2.17-2.13 (m, 2H), 1.91-1.33 (m, 7H), 0.95 (d, J=6.4 Hz, 3H).

MH+ 501.

Example 47

2-(5-(4-chlorophenyl)-1-(2,4-dichlorophenyl)-4-methyl-1H-pyrazol-3-yl)-5-(2-methylcyclohexyl)-1,3,4-oxadiazole $^1$H NMR (400 MHz, CDCl$_3$) δ 7.42 (d, J=1.8 Hz, 1H), 7.38-7.09 (m, 4H), 7.13-7.10 (m, 2H), 3.25 (m, 1H), 2.46 (s, 3H), 2.26 (m, 1H), 2.05 (m, 1H), 1.92-1.57 (m, 5H), 1.49-1.40 (m, 2H), 0.92 (d, J=6.9 Hz, 3H).
MH+ 501.

Example 48

N-tert-butyl-5-(5-(4-chlorophenyl)-1-(2,4-dichlorophenyl)-4-methyl-1H-pyrazol-3-yl)-1,3,4-oxadiazol-2-amine

MH+ 476.

Example 49

2-(5-(4-chlorophenyl)-1-(2,4-dichlorophenyl)-4-methyl-1H-pyrazol-3-yl)-5-(cyclohex-3-enyl)-1,3,4-oxadiazole

MH+ 485.

Example 50

2-(5-(4-chlorophenyl)-1-(2,4-dichlorophenyl)-4-methyl-1H-pyrazol-3-yl)-5-(1-methylcyclohexyl)-1,3,4-oxadiazole

MH+ 501.

Example 51

2-(5-(4-chlorophenyl)-1-(2,4-dichlorophenyl)-4-methyl-1H-pyrazol-3-yl)-5-(cyclopent-3-enyl)-1,3,4-oxadiazole $^1$H NMR (400 MHz, CDCl$_3$) δ 7.42 (d, J=2.3 Hz, 1H), 7.38-7.30 (m, 4H), 7.14-7.10 (m, 2H), 5.76 (s, 2H), 3.79 (m, 1H), 2.89 (d, J=8.2 Hz, 2H), 2.45 (s, 3H).
MH+ 471.

Example 52

2-(bicyclo[2.2.1]heptan-2-yl)-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.42 (d, J=1.8 Hz, 1H), 7.38-7.30 (m, 4H), 7.14-7.10 (m, 2H), 3.34 (m, 1H), 2.74 (m, 1H), 2.46 (s, 3H), 2.40 (m, 1H), 2.05-1.98 (m, 2H), 1.65-1.21 (m, 6H).
MH+ 499.

Example 53

2-(5-(4-chlorophenyl)-1-(2,4-dichlorophenyl)-4-methyl-1H-pyrazol-3-yl)-5-(1-phenylpropan-2-yl)-1,3,4-oxadiazole $^1$H NMR (300 MHz, CDCl$_3$) δ 7.43 (d, J=2.22 Hz, 2H), 7.38-7.24 (m, 5H), 7.24-7.19 (m, 3H), 7.13-7.10 (m, 2H), 3.48-3.43 (m, 1H), 3.37-3.30 (m, 1H), 2.95-2.88 (dd, J=13.56, 8.79 Hz, 1H), 2.45 (s, 3H), 1.40 (d, J=6.93 Hz, 3H).
MH+ 525.

Example 54

2-(5-(4-chlorophenyl)-1-(2,4-dichlorophenyl)-4-methyl-1H-pyrazol-3-yl)-5-(1-cyclobutylpropan-2-yl)-1,3,4-oxadiazole $^1$H NMR (300 MHz, CDCl$_3$) δ 7.43-7.13 (m, 5H), 7.13-7.10 (m, 2H), 3.15-3.13 (m, 1H), 2.46 (s, 3H), 2.26-2.33 (m, 1H), 2.04-1.97 (m, 3H), 1.81-1.75 (m, 3H), 1.41 (d, J=7.14 Hz, 3H).
MH+ 503.

Example 55

2-(5-(4-bromophenyl)-1-(2,4-dichlorophenyl)-4-ethyl-1H-pyrazol-3-yl)-5-(cyclohexylmethyl)-1,3,4-oxadiazole $^1$H NMR (300 MHz, CDCl$_3$) δ 7.50-7.47 (m, 2H), 7.42-7.41 (m, 1H), 7.38-7.28 (m, 2H), 7.09-7.06 (m, 2H), 2.92-2.80 (m, 4H), 1.99-1.88 (m, 1H), 1.80-1.62 (m, 4H), 1.26-1.04 (m, 9H).
MH+ 560.

Example 56

2-(5-(4-bromophenyl)-1-(2,4-dichlorophenyl)-4-methyl-1H-pyrazol-3-yl)-5-(cyclohexylmethyl)-1,3,4-oxadiazole $^1$H NMR (300 MHz, CDCl$_3$) δ 7.50-7.47 (m, 2H), 7.43-7.30 (m, 3H), 7.07-7.04 (m, 2H), 2.82 (d, J=6.9 Hz, 2H), 2.46 (s, 3H), 1.99-1.87 (m, 1H), 1.79-1.61 (m, 4H), 1.25-1.04 (m, 6H).
MH+ 545.

Example 57

2-(5-(4-bromophenyl)-1-(2,4-dichlorophenyl)-4-ethyl-1H-pyrazol-3-yl)-5-(hexan-2-yl)-1,3,4-oxadiazole $^1$H NMR (300 MHz, CDCl$_3$) δ 7.49-7.46 (m, 2H), 7.41-7.40 (m, 1H), 7.38-7.28 (m, 2H), 7.08-7.05 (m, 2H), 3.21-3.13 (m, 1H), 2.91-2.83 (m, 2H), 1.98-1.88 (m, 1H), 1.75-1.65 (m, 1H), 1.43 (d, J=6.9 Hz, 3H), 1.37-1.28 (m, 4H), 1.23 (t, J=7.3 Hz, 3H), 0.91-0.86 (m, 3H).
MH+ 547.

Example 58

2-tert-butyl-5-(5-(4-chlorophenyl)-1-(2,4-dichlorophenyl)-4-ethyl-1H-pyrazol-3-yl)-1,3,4-oxadiazole $^1$H NMR (300 MHz, CDCl$_3$) δ 7.42-7.40 (m, 1H), 7.37-7.28 (m, 4H), 7.15-7.11 (m, 2H), 2.89-2.82 (m, 2H), 1.50 (s, 9H), 1.23 (t, J=7.3 Hz, 3H).
MH+ 475.

Example 59

2-(5-(4-chlorophenyl)-1-(2,4-dichlorophenyl)-4-ethyl-1H-pyrazol-3-yl)-5-cyclohexyl-1,3,4-oxadiazole $^1$H NMR (300 MHz, CDCl$_3$) δ 7.42-7.40 (m, 1H), 7.38-7.27 (m, 4H), 7.15-7.12 (m, 2H), 3.04-2.96 (m, 1H), 2.91-2.83 (m, 2H), 2.18-2.13 (m, 2H), 1.84-1.61 (m, 6H), 1.44-1.34 (m, 2H), 1.23 (t, J=7.3 Hz, 3H).
MH+ 501.

Example 60

2-(5-(4-chlorophenyl)-1-(2,4-dichlorophenyl)-4-methyl-1H-pyrazol-3-yl)-5-tert-pentyl-1,3,4-oxadiazole $^1$H NMR (400 MHz, CDCl$_3$) δ 7.42-7.31 (m, 5H), 7.12-7.10 (m, 2H), 2.44 (s, 3H), 1.83 (q, J=7.6 Hz, 2H), 1.47 (s, 6H), 0.87 (t, J=7.6 Hz, 3H).
MH+ 475.

Example 61

2-(5-(4-chlorophenyl)-1-(2,4-dichlorophenyl)-4-methyl-1H-pyrazol-3-yl)-5-(1-cyclopentylethyl)-1,3,4-oxadiazole $^1$H NMR (300 MHz, CDCl$_3$) δ 7.43-7.12 (m, 5H), 7.13-7.11 (m, 2H), 3.15-3.13 (m, 1H), 2.46 (s, 3H), 1.89-1.73 (m, 1H), 1.70-1.50 (m, 4H), 1.44-1.40 (m, 4H), 1.41 (d, J=7.23 Hz, 3H).
MH+ 503.

Example 62

2-(5-(4-chlorophenyl)-1-(2,4-dichlorophenyl)-4-methyl-1H-pyrazol-3-yl)-5-(1-cyclohexylethyl)-1,3,4-oxadiazole $^1$H NMR (300 MHz, CDCl$_3$) δ 7.44-7.12 (m, 5H), 7.13-7.12 (m, 2H), 3.11-3.12 (m, 1H), 2.49 (s, 3H), 1.92-1.73 (m, 2H), 1.72-1.50 (m, 5H), 1.44-1.40 (m, 4H), 1.44 (d, J=7.21 Hz, 3H).
MH+ 517.

Example 63

2-(5-(4-chlorophenyl)-1-(2,4-dichlorophenyl)-4-methyl-1H-pyrazol-3-yl)-5-(2-cyclopentylpropan-2-yl)-1,3,4-oxadiazole $^1$H NMR (300 MHz, CDCl$_3$) δ 7.55-7.53 (m, 2H), 7.39-7.34 (m, 2H), 7.26-7.20 (m, 2H), 7.13-7.12 (m, 1H), 2.51 (s, 3H), 1.92-1.73 (m, 1H), 1.74-1.50 (m, 5H), 1.45 (s, 6H), 1.43-1.40 (m, 3H).
MH+ 517.

Example 64

2-(5-(4-chlorophenyl)-1-(2,4-dichlorophenyl)-4-methyl-1H-pyrazol-3-yl)-5-(2-cyclohexylpropan-2-yl)-1,3,4-oxadiazole $^1$H NMR (300 MHz, CDCl$_3$) δ 7.55-7.53 (m, 2H), 7.39-7.34 (m, 2H), 7.26-7.20 (m, 2H), 7.13-7.12 (m, 1H), 2.54 (s, 3H), 1.97-1.88 (m, 1H), 1.74-1.50 (m, 6H), 1.45 (s, 6H), 1.43-1.40 (m, 3H).
MH+ 531.

Example 65

2-(5-(4-chlorophenyl)-1-(2,4-dichlorophenyl)-4-methyl-1H-pyrazol-3-yl)-5-(2,2-dichloro-1-methyl-cyclopropyl)-1,3,4-oxadiazole $^1$H NMR (400 MHz, CDCl$_3$) δ 7.43-7.31 (m, 5H), 7.14-7.10 (m, 2H), 2.69 (d, J=7.8 Hz, 1H), 2.46 (s, 3H), 1.86 (s, 1H), 1.78 (d, J=7.8 Hz, 1H).
MH+ 527.

Example 66

5-(5-(4-chlorophenyl)-1-(2,4-dichlorophenyl)-4-methyl-1H-pyrazol-3-yl)-N-cyclohexyl-N-methyl-1,3,4-oxadiazol-2-amine $^1$H NMR (400 MHz, CDCl$_3$) δ 7.41-7.30 (m, 5H), 7.12-7.08 (m, 2H), 3.98 (m, 1H), 3.04 (s, 3H), 2.41 (s, 3H), 1.88-1.80 (m, 4H), 1.70-1.05 (m, 6H).
MH+ 516.

Example 67

2-(5-(4-chlorophenyl)-1-(2,4-dichlorophenyl)-4-methyl-1H-pyrazol-3-yl)-5-(1-(4-chlorophenyl)cyclopropyl)-1,3,4-oxadiazole $^1$H NMR (400 MHz, CDCl$_3$) δ 7.42-7.39 (m, 3H), 7.35-7.29 (m, 6H), 7.08 (m, 2H), 2.38 (s, 3H), 1.79 (dd, J=7.1, 4.6 Hz, 2H), 1.45 (dd, J=7.1, 4.6 Hz, 2H).
MH+ 555.

Example 68

2-(5-(4-chlorophenyl)-1-(2,4-dichlorophenyl)-4-ethyl-1H-pyrazol-3-yl)-5-cyclobutyl-1,3,4-oxadiazole $^1$H NMR (400 MHz, CDCl$_3$) δ 7.42-7.41 (m, 1H), 7.37-7.29 (m, 4H), 7.15-7.12 (m, 2H), 3.84-3.80 (m, 1H), 2.91-2.85 (m, 2H), 2.61-2.52 (m, 2H), 2.48-2.40 (m, 2H), 2.17-2.02 (m, 2H), 1.23 (t, J=7.2 Hz, 3H).
MH+ 473.

Example 69

2-(5-(4-chlorophenyl)-1-(2,4-dichlorophenyl)-4-ethyl-1H-pyrazol-3-yl)-5-cyclopentyl-1,3,4-oxadiazole $^1$H NMR (400 MHz, CDCl$_3$) δ 7.42-7.41 (m, 1H), 7.38-7.29 (m, 4H), 7.15-7.12 (m, 2H), 3.43-3.35 (m, 1H), 2.90-2.84 (m, 2H), 2.19-2.08 (m, 2H), 2.06-1.99 (m, 2H), 1.88-1.80 (m, 2H), 1.75-1.68 (m, 2H), 1.23 (t, J=7.2 Hz, 3H).
MH+ 487.

Example 70

2-(5-(4-chlorophenyl)-1-(2,4-dichlorophenyl)-4-ethyl-1H-pyrazol-3-yl)-5-cycloheptyl-1,3,4-oxadiazole $^1$H NMR (400 MHz, CDCl$_3$) δ 7.41-7.40 (m, 1H), 7.37-7.28 (m, 4H), 7.15-7.11 (m, 2H), 3.23-3.15 (m, 1H), 2.90-2.84 (m, 2H), 2.22-2.15 (m, 2H), 1.98-1.89 (m, 2H), 1.85-1.78 (m, 2H), 1.69-1.52 (m, 6H), 1.22 (t, J=7.3 Hz, 3H).
MH+ 515.

Example 71

2-(5-(4-chlorophenyl)-1-(2,4-dichlorophenyl)-4-methyl-1H-pyrazol-3-yl)-5-(1-phenylcyclopropyl)-1,3,4-oxadiazole $^1$H NMR (400 MHz, CDCl$_3$) δ 7.49-7.46 (m, 2H), 7.41-7.27 (m, 8H), 7.15-7.08 (m, 2H), 2.38 (s, 3H), 1.78 (dd, J=7.0, 5.0 Hz, 2H), 1.48 (dd, J=7.0, 5.0 Hz, 2H).
MH+ 521.

Example 72

2-sec-butyl-5-(5-(4-chlorophenyl)-1-(2,4-dichlorophenyl)-4-ethyl-1H-pyrazol-3-yl)-1,3,4-oxadiazole $^1$H NMR (400 MHz, CDCl$_3$) δ 7.41-7.40 (m, 1H), 7.38-7.29 (m, 4H), 7.15-7.11 (m, 2H), 3.15-3.06 (m, 1H), 2.90-2.84 (m, 2H), 2.01-1.90 (m, 1H), 1.80-1.69 (m, 1H), 1.43 (d, J=6.88 Hz, 3H), 1.23 (t, J=7.3 Hz, 3H), 0.98 (t, J=7.3 Hz, 3H).
MH+ 475.

Example 73

2-(5-(4-bromophenyl)-1-(2,4-dichlorophenyl)-4-ethyl-1H-pyrazol-3-yl)-5-sec-butyl-1,3,4-oxadiazole $^1$H NMR (400 MHz, CDCl$_3$) δ 7.49-7.46 (m, 2H), 7.42-7.41 (m, 2H), 7.36 (d, J=8.28 Hz, 1H), 7.32-7.29 (m, 1H), 7.08-7.05 (m, 2H), 3.16-3.06 (m, 1H), 2.90-2.84 (m, 2H), 2.01-1.90 (m, 1H), 1.80-1.69 (m, 1H), 1.43 (d, J=7.32 Hz, 3H), 1.23 (t, J=7.32 Hz, 3H), 0.98 (t, J=7.32 Hz, 3H).
MH+ 519.

Example 74

2-(5-(4-bromophenyl)-1-(2,4-dichlorophenyl)-4-ethyl-1H-pyrazol-3-yl)-5-cycloheptyl-1,3,4-oxadiazole $^1$H NMR (400 MHz, CDCl$_3$) δ 7.49-7.46 (m, 2H), 7.41 (d, J=2.28 Hz, 1H), 7.36 (d, J=8.24 Hz, 1H), 7.30 (dd, J=8.24, 2.28 Hz, 1H), 7.08-7.05 (m, 2H), 3.22-3.15 (m, 1H), 2.90-2.84 (m, 2H), 2.22-2.15 (m, 2H), 1.98-1.89 (m, 2H), 1.85-1.79 (m, 2H), 1.68-1.53 (m, 6H), 1.23 (t, J=7.8 Hz, 3H).
MH+ 560.

Example 75

2-(5-(4-bromophenyl)-1-(2,4-dichlorophenyl)-4-methyl-1H-pyrazol-3-yl)-5-sec-butyl-1,3,4-oxadiazole $^1$H NMR (400 MHz, CDCl$_3$) δ 7.50-7.46 (m, 2H), 7.42 (d, J=2.32 Hz, 1H), 7.37 (d, J=8.72 Hz, 1H), 7.32 (dd, J=8.68, 2.28 Hz, 1H), 7.07-7.03 (m, 2H), 3.16-3.07 (m, 1H), 2.45 (s, 3H), 2.00-1.90 (m, 1H), 1.80-1.70 (m, 2H), 1.43 (d, J=6.88 Hz, 3H), 0.97 (t, J=7.32 Hz, 3H).
MH+ 505.

Example 76

2-(5-(4-bromophenyl)-1-(2,4-dichlorophenyl)-4-ethyl-1H-pyrazol-3-yl)-5-(2-phenylpropan-2-yl)-1,3,4-oxadiazole $^1$H NMR (400 MHz, CDCl$_3$) δ 7.48-7.45 (m, 2H), 7.37 (d, J=2.32 Hz, 1H), 7.35-7.30 (m, 4H), 7.29-7.20 (m, 3H), 7.05-7.01 (m, 2H), 2.83-2.78 (m, 2H), 1.90 (s, 6H), 1.18 (t, J=7.32 Hz, 3H).
MH+ 581.

Example 77

N-tert-butyl-5-(5-(4-chlorophenyl)-1-(2,4-dichlorophenyl)-4-methyl-1H-pyrazol-3-yl)-N-methyl-1,3,4-oxadiazol-2-amine $^1$H NMR (400 MHz, CDCl$_3$) δ 7.41-7.29 (m, 7H), 7.12-7.08 (m, 2H), 3.15 (s, 3H), 2.41 (s, 3H), 1.51 (s, 9H).
MH+ 490.

Example 78

2-(5-(4-chlorophenyl)-1-(2,4-dichlorophenyl)-4-methyl-1H-pyrazol-3-yl)-5-(2-phenylpropan-2-yl)-1,3,4-oxadiazole $^1$H NMR (400 MHz, CDCl$_3$) δ 7.40-7.38 (d, J=2 Hz, 1H), 7.36-7.27 (m, 7H), 7.26-7.21 (m, 1H), 7.10-7.07 (m, 2H), 2.42 (s, 3H), 1.90 (s, 6H).
MH+ 523.

Example 79

2-(5-(4-chlorophenyl)-1-(2,4-dichlorophenyl)-4-methyl-1H-pyrazol-3-yl)-5-(2-(4-chlorophenyl)propan-2-yl)-1,3,4-oxadiazole $^1$H NMR (400 MHz, CDCl$_3$) δ 7.40-7.38 (m, 1H), 7.35-7.27 (m, 6H), 7.26-7.21 (m, 1H), 7.10-7.07 (m, 2H), 2.42 (s, 3H), 1.88 (s, 6H).
MH+ 559.

Example 80

2-(5-(4-chlorophenyl)-1-(2,4-dichlorophenyl)-4-methyl-1H-pyrazol-3-yl)-5-(2-(pyridin-2-yloxy)propan-2-yl)-1,3,4-oxadiazole $^1$H NMR (400 MHz, CDCl$_3$) δ 7.90-7.89 (m, 1H), 7.55-7.51 (m, 1H), 7.43-7.29 (m, 5H), 7.11-7.07 (m, 2H), 6.79-6.74 (m, 2H), 2.37 (s, 3H), 1.99 (s, 6H).
MH+ 542.

Example 81

2-(5-(4-chlorophenyl)-1-(2,4-dichlorophenyl)-4-methyl-1H-pyrazol-3-yl)-5-(2-(5-(trifluoromethyl)pyridin-2-yloxy)propan-2-yl)-1,3,4-oxadiazole $^1$H NMR (400 MHz, CDCl$_3$) δ 8.00 (m, 1H), 7.77-7.74 (m, 1H), 7.40-7.26 (m, 5H), 7.10-7.08 (m, 2H), 6.88-6.86 (d, J=9.2 Hz, 1H), 2.41 (s, 3H), 2.02 (s, 6H).
MH+ 610.

Example 82

2-tert-butyl-5-(1-(2-chlorophenyl)-5-(4-chlorophenyl)-4-methyl-1H-pyrazol-3-yl)-1,3,4-oxadiazole $^1$H NMR (400 MHz, CDCl$_3$) δ 7.45-7.27 (m, 6H), 7.14-7.10 (m, 2H), 2.45 (s, 3H), 1.50 (s, 9H).
MH+ 427.

Example 83

2-sec-butyl-5-(1-(2-chlorophenyl)-5-(4-chlorophenyl)-4-methyl-1H-pyrazol-3-yl)-1,3,4-oxadiazole $^1$H NMR (400 MHz, CDCl$_3$) δ 7.45-7.27 (m, 6H), 7.16-7.11 (m, 2H), 3.12 (sextet, J=6.8 Hz, 1H), 2.47 (s, 3H), 1.95 (septet, J=6.8 Hz, 1H), 1.75 (septet, J=6.8 Hz, 1H), 1.43 (d, J=7.2 Hz, 3H), 0.97 (t, J=7.4 Hz, 3H).
MH+ 427.

Example 84

2-(1-(2-chlorophenyl)-5-(4-chlorophenyl)-4-methyl-1H-pyrazol-3-yl)-5-cyclohexyl-1,3,4-oxadiazole $^1$H NMR (400 MHz, CDCl$_3$) δ 7.46-7.26 (m, 6H), 7.18-7.11 (m, 2H), 3.01-2.98 (m, 1H), 2.47 (s, 3H), 2.41-2.20 (m, 2H), 1.91-1.83 (m, 2H), 1.80-1.65 (m, 3H), 1.48-1.24 (m, 4H).
MH+ 453.

Example 85

2-(5-(4-chlorophenyl)-1-(2,4-dichlorophenyl)-4-methyl-1H-pyrazol-3-yl)-5-(2-methylhexan-2-yl)-1,3,4-oxadiazole $^1$H NMR (400 MHz, CDCl$_3$) δ 7.43-7.38 (m, 2H), 7.34-7.30 (m, 3H), 7.15-7.09 (m, 2H), 2.44 (s, 3H), 1.78 (m, 2H), 1.47 (s, 6H), 1.25 (m, 4H), 0.87 (t, J=7.0 Hz, 3H).
MH+ 503.

Example 86

2-(5-(4-chlorophenyl)-1-(2,4-dichlorophenyl)-4-ethyl-1H-pyrazol-3-yl)-5-(pentan-2-yl)-1,3,4-oxadiazole $^1$H NMR (400 MHz, CDCl$_3$) δ 7.42-7.41 (m, 2H), 7.38-7.36 (m, 1H), 7.34-7.29 (m, 2H), 7.14-7.12 (m, 2H), 3.24-3.15 (m, 1H), 2.90-2.84 (m, 2H), 1.96-1.87 (m, 2H), 1.71-1.65 (m, 2H), 1.44-1.42 (m, 2H), 1.24 (t, J=7.2 Hz, 3H), 0.93 (t, J=7.6 Hz, 3H).
MH+ 489.

Example 87

2-(1-(2-chlorophenyl)-5-(4-chlorophenyl)-4-methyl-1H-pyrazol-3-yl)-5-cyclobutyl-1,3,4-oxadiazole $^1$H NMR (400 MHz, CDCl$_3$) δ 7.44-7.26 (m, 6H), 7.18-7.10 (m, 2H), 3.82 (quintet, J=8.8 Hz, 1H), 2.63-2.51 (m, 2H), 2.50-2.48 (m, 4H), 2.19-2.01 (m, 2H).
MH+ 425.

Example 88

2-(1-(2-chlorophenyl)-5-(4-chlorophenyl)-4-methyl-1H-pyrazol-3-yl)-5-tert-pentyl-1,3,4-oxadiazole $^1$H NMR (400 MHz, CDCl$_3$) δ 7.47-7.28 (m, 6H), 7.14-7.10 (m, 2H), 2.45 (s, 3H), 1.84 (quartet, J=7.2 Hz, 2H), 1.46 (s, 6H), 0.87 (t, J=7.6 Hz, 3H).
MH+ 441.

Example 89

2-(1-(2-chlorophenyl)-5-(4-chlorophenyl)-4-methyl-1H-pyrazol-3-yl)-5-(hexan-2-yl)-1,3,4-oxadiazole $^1$H NMR (400 MHz, CDCl$_3$) δ 7.46-7.28 (m, 6H), 7.18-7.11 (m, 2H), 3.18 (sextet, J=6.8 Hz, 1H), 2.47 (s, 3H), 1.96-1.88 (m, 1H), 1.75-1.62 (m, 1H), 1.43 (d, J=6.8 Hz, 3H), 1.39-1.28 (m, 4H), 0.90 (t, J=7.2 Hz, 3H).
MH+ 455.

Example 90

2-(5-(4-bromophenyl)-1-(2,4-dichlorophenyl)-4-methyl-1H-pyrazol-3-yl)-5-(pentan-2-yl)-1,3,4-oxadiazole $^1$H NMR (400 MHz, CDCl$_3$) δ 7.49-7.46 (m, 2H), 7.42 (d, J=2.4 Hz, 1H), 7.38-7.36 (d, J=8.4 Hz, 1H), 7.30 (dd, J=8.4, 2.4 Hz, 1H), 7.06-7.04 (m, 2H), 3.22-3.17 (m, 1H), 2.45 (s, 3H), 1.92-1.89 (m, 1H), 1.68-1.66 (m, 1H), 1.43-1.42 (m, 3H), 1.41-1.37 (m, 2H), 0.93 (t, J=7.6 Hz, 3H).
MH+ 519.

Example 91

2-(5-(4-bromophenyl)-1-(2,4-dichlorophenyl)-4-ethyl-1H-pyrazol-3-yl)-5-(pentan-2-yl)-1,3,4-oxadiazole $^1$H NMR (400 MHz, CDCl$_3$) δ 7.50-7.46 (m, 2H), 7.41 (d, J=2.0 Hz, 1H), 7.37 (d, J=8.4 Hz, 1H), 7.32-7.29 (m, 1H), 7.08-7.05 (m, 2H), 3.22-3.17 (m, 1H), 2.90-2.84 (m, 2H), 1.93-1.88 (m, 1H), 1.70-1.64 (m, 1H), 1.44-1.42 (d, J=6.8 Hz, 3H), 1.41-1.35 (m, 2H), 1.23 (t, J=7.2 Hz, 3H), 0.93 (t, J=7.6 Hz, 3H).
MH+ 533.

Example 92

2-(1-(2-chlorophenyl)-5-(4-chlorophenyl)-4-methyl-1H-pyrazol-3-yl)-5-(2-methylhexan-2-yl)-1,3,4-oxadiazole $^1$H NMR (400 MHz, CDCl$_3$) δ 7.46-7.27 (m, 6H), 7.30-7.11 (m, 2H), 2.45 (s, 3H), 1.83-1.74 (m, 2H), 1.47 (s, 6H), 1.33-1.18 (m, 4H), 0.88 (t, J=6.8 Hz, 3H).
MH+ 469.

Example 93

2-(1-(2-chlorophenyl)-5-(4-chlorophenyl)-4-methyl-1H-pyrazol-3-yl)-5-(2-phenylpropan-2-yl)-1,3,4-oxadiazole $^1$H NMR (400 MHz, CDCl$_3$) δ 7.44-7.20 (m, 11H), 7.12-7.07 (m, 2H), 2.43 (s, 3H), 1.90 (s, 6H).
MH+ 489.

Example 94

2-(5-(4-bromophenyl)-1-(4-chlorophenyl)-4-methyl-1H-pyrazol-3-yl)-5-tert-pentyl-1,3,4-oxadiazole $^1$H NMR (400 MHz, CDCl$_3$) δ 7.55 (d, J=8.4 Hz, 2H), 7.32 (d, J=6.4 Hz, 2H), 7.22 (d, J=6.4 Hz, 2H), 7.06 (d, J=8.4 Hz, 2H), 2.41 (s, 3H), 1.86 (q, J=7.2 Hz, 2H), 1.48 (s, 6H), 0.88 (t, J=7.2 Hz, 3H).
MH+ 487.

Example 95

2-(5-(4-bromophenyl)-1-(4-chlorophenyl)-4-methyl-1H-pyrazol-3-yl)-5-cyclohexyl-1,3,4-oxadiazole $^1$H NMR (400 MHz, CDCl$_3$) δ 7.55-7.52 (m, 2H), 7.33-7.30 (m, 2H), 7.23-7.20 (m, 2H), 7.08-7.05 (m, 2H), 3.08-2.98 (m, 1H), 2.41 (s, 3H), 2.18-2.14 (m, 2H), 1.90-1.85 (m, 2H), 1.77-1.68 (m, 2H), 1.46-1.25 (m, 3H).
MH+ 499.

Example 96

2-(5-(4-bromophenyl)-1-(4-chlorophenyl)-4-methyl-1H-pyrazol-3-yl)-5-sec-butyl-1,3,4-oxadiazole $^1$H NMR (400 MHz, CDCl$_3$) δ 7.55-7.53 (m, 2H), 7.33-7.30 (m, 2H), 7.23-7.20 (m, 2H), 7.08-7.06 (m, 2H), 3.15-3.13 (m, 1H), 2.42 (s, 3H), 1.98-1.92 (m, 2H), 1.79-1.75 (m, 2H), 1.45 (d, J=6.8 Hz, 3H), 0.99 (t, J=7.2 Hz, 3H).
MH+ 473.

Example 97

2-(1-(allyloxy)-2-methylpropan-2-yl)-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.42-7.30 (m, 5H), 7.15-7.09 (m, 2H), 4.00 (br d, 5.6 Hz, 2H), 3.67 (s, 2H), 2.44 (s, 3H), 1.56 (s, 3H), 1.51 (s, 3H).
MH+ 517.

Example 98

2-(5-(4-chlorophenyl)-1-(2,4-dichlorophenyl)-4-methyl-1H-pyrazol-3-yl)-5-(2-methoxypropan-2-yl)-1,3,4-oxadiazole $^1$H NMR (400 MHz, CDCl$_3$) δ 7.42-7.31 (m, 5H), 7.14-7.10 (m, 2H), 3.23 (s, 3H), 2.45 (s, 3H), 1.74 (s, 6H).
MH+ 477.

Example 99

2-(1-(2,4-dichlorophenyl)-4-methyl-5-phenyl-1H-pyrazol-3-yl)-5-tert-pentyl-1,3,4-oxadiazole $^1$H NMR (400 MHz, CDCl$_3$) δ 7.40 (d, J=2.4 Hz, 1H), 7.39-7.32 (m, 3H), 7.31-7.28 (m, 2H), 7.20-7.16 (m, 2H), 2.46 (s, 3H), 1.84 (q, J=7.6 Hz, 2H), 1.47 (s, 6H), 0.88 (t, J=7.2 Hz, 3H).
MH+ 441.

Example 100

2-tert-butyl-5-(1-(2,4-dichlorophenyl)-4-methyl-5-phenyl-1H-pyrazol-3-yl)-1,3,4-oxadiazole $^1$H NMR (400 MHz, CDCl$_3$) δ 7.41 (d, J=2.4 Hz, 1H), 7.38-7.32 (m, 3H), 7.31-7.28 (m, 2H), 7.20-7.16 (m, 2H), 2.46 (s, 3H), 1.51 (s, 9H).
MH+ 427.

Example 101

2-cyclohexyl-5-(1-(2,4-dichlorophenyl)-4-methyl-5-phenyl-1H-pyrazol-3-yl)-1,3,4-oxadiazole $^1$H NMR (400 MHz, CDCl$_3$) δ 7.41 (d, J=2.0 Hz, 1H), 7.36-7.32 (m, 3H), 7.30-7.28 (m, 2H), 7.19-7.17 (m, 2H), 3.04-2.97 (m, 1H), 2.47 (s, 3H), 2.17-2.13 (m, 2H), 1.88-1.84 (m, 2H), 1.77-1.67 (m, 3H), 1.45-1.29 (m, 3H).
MH+ 453.

Example 102

2-sec-butyl-5-(1-(2,4-dichlorophenyl)-4-methyl-5-phenyl-1H-pyrazol-3-yl)-1,3,4-oxadiazole $^1$H NMR (400 MHz, CDCl$_3$) δ 7.41 (d, J=2.0 Hz, 1H), 7.37-7.31 (m, 3H), 7.30-7.26 (m, 2H), 7.20-7.16 (m, 2H), 3.15-3.09 (m, 1H), 2.47 (s, 3H), 1.99-1.90 (m, 1H), 1.81-1.72 (m, 1H), 1.44 (d, J=6.8 Hz, 3H), 0.98 (t, J=7.6 Hz, 3H).
MH+ 427.

Example 103

2-cyclobutyl-5-(1-(2,4-dichlorophenyl)-4-methyl-5-phenyl-1H-pyrazol-3-yl)-1,3,4-oxadiazole $^1$H NMR (400 MHz, CDCl$_3$) δ 7.41 (d, J=2.0 Hz, 1H), 7.36-7.32 (m, 3H), 7.30-7.27 (m, 2H), 7.20-7.17 (m, 2H), 3.87-3.78 (m, 1H), 2.62-2.52 (m, 2H), 2.49-2.41 (m, 5H), 2.17-2.03 (m, 2H).
MH+ 425.

Example 104

2-(5-(4-bromophenyl)-1-(4-chlorophenyl)-4-methyl-1H-pyrazol-3-yl)-5-tert-butyl-1,3,4-oxadiazole $^1$H NMR (400 MHz, CDCl$_3$) δ 7.56-7.55 (m, 2H), 7.39-7.31 (m, 2H), 7.23-7.21 (m, 2H), 7.08-7.06 (m, 2H), 2.41 (s, 3H), 1.52 (s, 9H).
MH+ 473.

Example 105

2-(5-(4-bromophenyl)-1-(2-chlorophenyl)-4-methyl-1H-pyrazol-3-yl)-5-tert-butyl-1,3,4-oxadiazole $^1$H NMR (400 MHz, CDCl$_3$) δ 7.46-7.43 (m, 3H), 7.41-7.38 (m, 1H), 7.36-7.31 (m, 2H), 7.07-7.04 (m, 2H), 2.5 (s, 3H), 1.50 (s, 9H).
MH+ 471.

Example 106

2-(5-(4-bromophenyl)-1-(2-chlorophenyl)-4-methyl-1H-pyrazol-3-yl)-5-cyclohexyl-1,3,4-oxadiazole $^1$H NMR (400 MHz, CDCl$_3$) δ 7.46-7.43 (m, 3H), 7.41-7.39 (m, 1H), 7.38-7.34 (m, 2H), 7.07-7.05 (m, 2H), 3.02-2.97 (m, 1H), 2.46 (s, 3H), 2.16-2.12 (m, 2H), 1.88-1.84 (m, 2H), 1.77-1.58 (m, 2H), 1.41-1.25 (m, 4H).
MH+ 497.

Example 107

2-(5-(4-bromophenyl)-1-(2-chlorophenyl)-4-methyl-1H-pyrazol-3-yl)-5-cyclobutyl-1,3,4-oxadiazole $^1$H NMR (400 MHz, CDCl$_3$) δ 7.46-7.42 (m, 3H), 7.41-7.39 (m, 1H), 7.38-7.33 (m, 2H), 7.08-7.06 (m, 2H), 3.86-3.77 (m, 1H), 2.63-2.48 (m, 2H), 2.50 (s, 3H), 2.44-2.40 (m, 2H), 2.18-1.98 (m, 2H).
MH+ 469.

Example 108

2-(5-(4-bromophenyl)-1-(2-chlorophenyl)-4-methyl-1H-pyrazol-3-yl)-5-sec-butyl-1,3,4-oxadiazole $^1$H NMR (400 MHz, CDCl$_3$) δ 7.47-7.31 (m, 6H), 7.08-7.05 (m, 2H), 3.16-3.07 (m, 1H), 2.49 (s, 3H), 2.01-1.90 (m, 1H), 1.80-1.69 (m, 1H), 1.43 (d, J=7.2 Hz, 3H), 0.97 (t, J=7.6 Hz, 3H).
MH+ 471.

Example 109

2-(5-(4-bromophenyl)-1-(2-chlorophenyl)-4-methyl-1H-pyrazol-3-yl)-5-tert-pentyl-1,3,4-oxadiazole $^1$H NMR (400 MHz, CDCl$_3$) δ 7.46-7.42 (m, 2H), 7.41-7.31 (m, 4H), 7.07-7.04 (m, 2H), 2.45 (s, 3H), 1.83 (q, J=7.6 Hz, 2H), 1.46 (s, 6H), 0.87 (t, J=7.6 Hz, 3H).
MH+ 485.

Example 110

2-(5-(4-chlorophenyl)-1-(2,4-dichlorophenyl)-4-methyl-1H-pyrazol-3-yl)-5-(1-(4-chlorophenyl)cyclobutyl)-1,3,4-oxadiazole $^1$H NMR (400 MHz, CDCl$_3$) δ 7.40 (m, 1H), 7.35-7.29 (m, 8H), 7.10-7.06 (m, 2H), 3.09 (m, 2H), 2.73 (m, 2H), 2.40 (s, 3H), 2.25 (s, 1H), 2.02 (m, 1H).
MH+ 569.

Example 111

2-(5-(4-bromophenyl)-1-(2,4-dichlorophenyl)-4-ethyl-1H-pyrazol-3-yl)-5-(1-(4-chlorophenyl)cyclopropyl)-1,3,4-oxadiazole $^1$H NMR (400 MHz, CDCl$_3$) δ 7.48-7.40 (m, 5H), 7.35-7.28 (m, 4H), 7.06-7.02 (m, 2H), 2.79 (q, J=7.2 Hz, 2H), 1.79 (dd, J=7.2, 4.8 Hz, 2H), 1.45 (dd, J=7.2, 4.8 Hz, 2H), 1.16 (t, J=7.2 Hz, 3H).
MH+ 613.

Example 112

2-(1-(2-chlorophenyl)-5-(4-chlorophenyl)-4-methyl-1H-pyrazol-3-yl)-5-(1-(4-chlorophenyl)cyclopropyl)-1,3,4-oxadiazole $^1$H NMR (400 MHz, CDCl$_3$) δ 7.43-7.25 (m, 10H), 7.12-7.08 (m, 2H), 2.39 (s, 3H), 1.79 (m, 2H), 1.44 (m, 2H).
MH+ 521.

Example 113

2-tert-butyl-5-(5-(3-chlorophenyl)-1-(2,4-dichlorophenyl)-4-methyl-1H-pyrazol-3-yl)-1,3,4-oxadiazole $^1$H NMR (400 MHz, CDCl$_3$) δ 7.42 (d, 1H, J=2.4 Hz), 7.38 (d, 1H, J=8.8 Hz), 7.34-7.31 (m, 2H), 7.29-7.25 (m, 1H), 7.21-7.20 (m, 1H), 7.03 (dt, 1H, J=7.6 Hz, 1.2 Hz), 2.45 (s, 3H), 1.50 (s, 9H).
MH+ 461.

Example 114

2-sec-butyl-5-(5-(3-chlorophenyl)-1-(2,4-dichlorophenyl)-4-methyl-1H-pyrazol-3-yl)-1,3,4-oxadiazole $^1$H NMR (400 MHz, CDCl$_3$) δ 7.42 (d, 1H, J=2.4 Hz), 7.37 (d, 1H, J=7.6 Hz), 7.34-7.31 (m, 2H), 7.29-7.25 (m, 1H), 7.21-7.20 (m, 1H), 7.03 (dt, 1H, J=8.0 Hz, 1.2 Hz), 3.14-3.09 (m, 1H), 2.46 (s, 3H), 1.98-1.91 (m, 1H), 1.78-1.73 (m, 1H), 1.43 (d, 3H), 0.97 (t, 3H).
MH+ 461.

Example 115

2-(5-(3-chlorophenyl)-1-(2,4-dichlorophenyl)-4-methyl-1H-pyrazol-3-yl)-5-cyclobutyl-1,3,4-oxadiazole $^1$H NMR (400 MHz, CDCl$_3$) δ 7.43 (dd, 1H, J=2.0 Hz, 0.4 Hz), 7.36 (d, 1H, J=8.0 Hz), 7.35-7.32 (m, 2H), 7.31-7.25 (m, 1H), 7.22-7.21 (m, 1H), 7.04 (dt, 1H, J=7.6 Hz, 1.2 Hz), 3.82 (m, 1H), 2.59-2.51 (m, 2H), 2.48-2.42 (m, 2H), 2.47 (s, 3H), 2.14-2.05 (m, 2H).
MH+ 461.

Example 116

2-(5-(4-chlorophenyl)-1-(2,4-dichlorophenyl)-4-methyl-1H-pyrazol-3-yl)-5-(2-ethoxypropan-2-yl)-1,3,4-oxadiazole $^1$H NMR (400 MHz, CDCl$_3$) δ 7.42-7.32 (m, 5H), 7.14-7.10 (m, 2H), 3.40 (q, J=7.2 Hz, 2H), 2.45 (s, 3H), 1.74 (s, 6H), 1.16 (t, J=7.2 Hz, 3H).
MH+ 491.

Example 117

2-(1,5-bis(4-chlorophenyl)-4-methyl-1H-pyrazol-3-yl)-5-tert-butyl-1,3,4-oxadiazole $^1$H NMR (400 MHz, CDCl$_3$) δ 7.38 (d, J=8.8 Hz, 2H), 7.31 (d, J=8.8 Hz, 2H), 7.22 (d, J=8.8 Hz, 2H), 7.13 (d, J=8.8 Hz, 2H), 2.40 (s, 3H), 1.51 (s, 9H).
MH+ 427.

Example 118

2-(1,5-bis(4-chlorophenyl)-4-methyl-1H-pyrazol-3-yl)-5-sec-butyl-1,3,4-oxadiazole $^1$H NMR (400 MHz, CDCl$_3$) δ 7.38 (d, J=8.8 Hz, 2H), 7.31 (d, J=8.8 Hz, 2H), 7.21 (d, J=9.2 Hz, 2H), 7.13 (d, J=8.8 Hz, 2H), 3.16-3.11 (m, 1H), 2.42 (s, 3H), 1.99-1.92 (m, 1H), 1.80-1.73 (m, 1H), 1.45 (d, J=7.2 Hz, 3H), 0.99 (t, J=7.6 Hz, 3H).
MH+ 427.

Example 119

2-(1,5-Bis(4-chlorophenyl)-4-methyl-1H-pyrazol-3-yl)-5-(1-(4-chlorophenyl)cyclopropyl)-1,3,4-oxadiazole $^1$H NMR (400 MHz, CDCl$_3$) δ 7.42 (d, J=8.8 Hz, 2H), 7.37 (d, J=8.4 Hz, 2H), 7.35-7.29 (m, 4H), 7.18 (d, J=8.8 Hz, 2H), 7.11 (d, J=8.8 Hz, 2H), 2.34 (s, 3H), 1.82-1.79 (m, 2H), 1.48-1.45 (m, 2H).
MH+ 521.

Example 120

2-(1,5-Bis(4-chlorophenyl)-4-methyl-1H-pyrazol-3-yl)-5-tert-pentyl-1,3,4-oxadiazole $^1$H NMR (400 MHz, CDCl$_3$) δ 7.38 (d, J=8.4 Hz, 2H), 7.31 (d, J=9.2 Hz, 2H), 7.22 (d, J=9.2 Hz, 2H), 7.13 (d, J=8.8 Hz, 2H), 2.40 (s, 3H), 1.85 (q, J=Hz, 2H), 1.48 (s, 6H), 0.88 (t, J=7.6 Hz, 3H).
MH+ 441.

Example 121

2-(5-(3-Chlorophenyl)-1-(2,4-dichlorophenyl)-4-methyl-1H-pyrazol-3-yl)-5-cyclohexyl-1,3,4-oxadiazole $^1$H NMR (400 MHz, CDCl$_3$) δ 7.43 (d, J=2.4 Hz, 1H), 7.36 (d, J=8.8 Hz, 1H), 7.35-7.32 (m, 2H), 7.31-7.25 (m, 1H), 7.21-7.20 (m, 1H), 7.04 (dt, J=7.2 Hz, 1.2 Hz, 1H), 3.04-3.00 (m, 1H), 2.46 (s, 3H), 2.17-2.13 (m, 2H), 1.88-1.84 (m, 2H), 1.77-1.67 (m, 3H), 1.46-1.26 (m, 3H).
MH+ 487.

Example 122

2-(5-(3-Chlorophenyl)-1-(2,4-dichlorophenyl)-4-methyl-1H-pyrazol-3-yl)-5-tert-pentyl-1,3,4-oxadiazole $^1$H NMR (400 MHz, CDCl$_3$) δ 7.42 (d, J=2.4 Hz, 1H), 7.38 (d, J=8.0 Hz, 1H), 7.34-7.31 (m, 2H), 7.29-7.25 (m, 1H), 7.21-7.20 (m, 1H), 7.03 (dt, J=7.6 Hz, 1.6 Hz 1H), 2.45 (s, 3H), 1.83 (q, 2H, J=7.6 Hz), 1.46 (s, 6H), 0.88 (t, J=7.2 Hz, 3H).
MH+ 477.

Example 123

2-(5-(4-bromophenyl)-1-(2,4-dichlorophenyl)-4-ethyl-1H-pyrazol-3-yl)-5-(1-phenylcyclopropyl)-1,3,4-oxadiazole $^1$H NMR (400 MHz, CDCl$_3$) δ 7.49-7.43 (m, 3H), 7.39-7.25 (m, 7H), 7.05-7.02 (m, 2H), 2.76 (quartet, J=7.6 Hz, 2H), 1.77 (m, 2H), 1.48 (m, 2H), 1.15 (t, J=7.6 Hz, 3H).
MH+ 581.

Example 124

2-(5-(4-bromophenyl)-1-(2,4-dichlorophenyl)-4-ethyl-1H-pyrazol-3-yl)-5-tert-pentyl-1,3,4-oxadiazole $^1$H NMR (400 MHz, CDCl$_3$) δ 7.49-7.45 (m, 2H), 7.41-7.35 (m, 2H), 7.31-7.27 (m, 1H), 7.07-7.03 (m, 2H), 2.84 (quartet, J=7.6 Hz, 2H), 1.83 (quartet, J=7.2 Hz, 2H), 1.46 (s, 6H), 1.22 (t, J=7.2 Hz, 3H), 0.87 (t, J=7.6 Hz, 3H).
MH+ 535.

Example 125

2-(bicyclo[2.2.1]heptan-2-yl)-5-(5-(4-bromophenyl)-1-(2,4-dichlorophenyl)-4-ethyl-1H-pyrazol-3-yl)-1,3,4-oxadiazole $^1$H NMR (400 MHz, CDCl$_3$) δ 7.49-7.45 (m, 2H), 7.42-7.39 (m, 1H), 7.37-7.33 (m, 1H), 7.31-7.27 (m, 1H), 7.08-7.04 (m, 2H), 7.08-7.04 (m, 2H), 2.90 (quartet, J=7.6 Hz, 2H), 2.56 (br d, J=3.6 Hz, 1H), 2.49-2.37 (m, 1H), 2.20-2.02 (m, 1H), 1.95-1.85 (m, 1H), 1.70-1.18 (m, 9H).
MH+ 559.

Example 126

2-(5-(4-bromophenyl)-1-(2,4-dichlorophenyl)-4-ethyl-1H-pyrazol-3-yl)-5-isopropyl-1,3,4-oxadiazole $^1$H NMR (400 MHz, CDCl$_3$) δ 7.49-7.45 (m, 2H), 7.41-7.28 (m, 3H), 7.08-7.04 (m, 2H), 3.28 (quintet, J=6.8 Hz, 1H), 2.86 (quartet, J=6.8 Hz, 2H), 1.46 (d, J=6.8 Hz, 6H), 1.22 (t, J=7.6 Hz, 3H).
MH+ 506.

Example 127

2-(5-(4-bromophenyl)-1-(2,4-dichlorophenyl)-4-ethyl-1H-pyrazol-3-yl)-5-(pentan-3-yl)-1,3,4-oxadiazole $^1$H NMR (400 MHz, CDCl$_3$) δ 7.50-7.45 (m, 2H), 7.41-7.27 (m, 3H), 7.08-7.04 (m, 2H), 2.99-2.91 (m, 1H), 2.86 (quartet, J=7.6 Hz, 2H), 1.94-1.74 (m, 4H), 1.22 (t, J=7.2 Hz, 3H), 0.92 (t, J=7.6 Hz, 3H).
MH+ 534.

Example 128

2-(5-(4-bromophenyl)-1-(2,4-dichlorophenyl)-4-ethyl-1H-pyrazol-3-yl)-5-(1-methylcyclohexyl)-1,3,4-oxadiazole $^1$H NMR (400 MHz, CDCl$_3$) δ 7.49-7.45 (m, 2H), 7.41-7.36 (m, 2H), 7.31-7.29 (m, 1H), 7.07-7.03 (m, 2H), 2.85 (quartet, J=7.2 Hz, 2H), 2.32-2.25 (m, 2H), 1.68-1.45 (m, 8H), 1.40 (s, 3H), 1.21 (t, J=7.6 Hz, 3H).
MH+ 561.

Example 129

2-(5-(4-chlorophenyl)-1-(2,4-dichlorophenyl)-4-methyl-1H-pyrazol-3-yl)-5-(1-(4-methoxyphenyl)cyclopropyl)-1,3,4-oxadiazole $^1$H NMR (400 MHz, CDCl$_3$) δ 7.42-7.38 (m, 3H), 7.35-7.28 (m, 4H), 7.07 (m, 2H), 6.87 (m, 2H), 3.79 (s, 3H), 2.54 (s, 3H), 1.73 (dd, J=7.2, 4.4 Hz, 2H), 1.42 (dd, J=7.2, 4.4 Hz, 2H).
MH+ 551.

Example 130

2-(5-(4-chlorophenyl)-1-(2,4-dichlorophenyl)-4-methyl-1H-pyrazol-3-yl)-5-(1-(2,4-dichlorophenyl)cyclopropyl)-1,3,4-oxadiazole $^1$H NMR (400 MHz, CDCl$_3$) δ 7.44-7.39 (m, 3H), 7.36-7.25 (m, 5H), 7.07 (m, 2H), 2.35 (s, 3H), 1.94 (dd, J=7.6, 5.2 Hz, 2H), 1.48 (dd, J=7.6, 5.2 Hz, 2H).
MH+ 589.

Example 131

2-(5-(4-chlorophenyl)-1-(2,4-dichlorophenyl)-4-methyl-1H-pyrazol-3-yl)-5-(1-p-tolylcyclopropyl)-1,3,4-oxadiazole $^1$H NMR (400 MHz, CDCl$_3$) δ 7.39-7.25 (m, 7H), 7.14 (m, 2H), 7.08 (m, 2H), 2.36 (s, 3H), 2.33 (s, 3H), 1.73 (dd, J=7.2, 4.4 Hz, 2H), 1.44 (dd, J=7.2, 4.4 Hz, 2H).
MH+ 535.

Example 132

2-(5-(4-chlorophenyl)-1-(2,4-dichlorophenyl)-4-methyl-1H-pyrazol-3-yl)-5-(1-(trifluoro methyl)cyclopropyl)-1,3,4-oxadiazole $^1$H NMR (400 MHz, CDCl$_3$) δ 7.41 (br d, J=2.0 Hz, 1H), 7.38-7.30 (m, 4H), 7.10 (m, 2H), 2.42 (s, 3H), 1.63 (m, 2H), 1.61 (m, 2H).
MH+ 513.

Example 133

2-(5-(4-chlorophenyl)-1-(2,4-dichlorophenyl)-4-ethyl-1H-pyrazol-3-yl)-5-(1-(4-chlorophenyl)cyclopropyl)-1,3,4-oxadiazole $^1$H NMR (400 MHz, CDCl$_3$) δ 7.42-7.37 (m, 3H), 7.34-7.27 (m, 6H), 7.11-7.07 (m, 2H), 2.78 (quartet, J=7.6 Hz, 2H), 1.79 (m, 2H), 1.44 (m, 2H), 1.16 (t, J=7.6 Hz, 3H).
MH+ 571.

Example 134

2-(5-(4-bromophenyl)-1-(2-chlorophenyl)-4-ethyl-1H-pyrazol-3-yl)-5-(1-(4-chlorophenyl)cyclopropyl)-1,3,4-oxadiazole $^1$H NMR (400 MHz, CDCl$_3$) δ 7.45-7.40 (m, 4H), 7.39-7.34 (m, 4H), 7.33-7.31 (m, 2H), 7.05 (d, 2H, J=8.4 Hz), 2.80 (q, 2H, J=7.2 Hz), 1.82-1.79 (m, 2H), 1.47-1.44 (m, 2H), 1.17 (t, 3H, J=7.2 Hz).
MH+ 581.

Example 135

2-(5-(4-chlorophenyl)-1-(2,4-dichlorophenyl)-4-methyl-1H-pyrazol-3-yl)-5-(1-(trifluoromethyl)cyclobutyl)-1,3,4-oxadiazole $^1$H NMR (400 MHz, CDCl$_3$) δ 7.41 (d, J=2.0 Hz, 1H), 7.38-7.30 (m, 4H), 7.10 (m, 2H), 2.81 (m, 4H), 2.44 (s, 3H), 2.16 (m, 2H).
MH+ 527.

Example 136

2-(5-(4-chlorophenyl)-1-(2,4-dichlorophenyl)-4-methyl-1H-pyrazol-3-yl)-5-(2,2,2-trifluoroethyl)-1,3,4-oxadiazole $^1$H NMR (400 MHz, CDCl$_3$) δ 7.42 (br d, J=2.0 Hz, 1H), 7.36-7.30 (m, 4H), 7.11 (m, 2H), 3.84 (q, J=9.6 Hz, 2H), 2.45 (s, 3H).
MH+ 487.

Example 137

2-(5-(4-chlorophenyl)-1-(2,3-dichlorophenyl)-4-methyl-1H-pyrazol-3-yl)-5-(1-(4-chlorophenyl)cyclobutyl)-1,3,4-oxadiazole $^1$H NMR (400 MHz, CDCl$_3$) δ 7.53-7.50 (m, 1H), 7.34-7.23 (m, 9H), 7.10-7.07 (m, 1H), 3.14-3.04 (m, 2H), 2.78-2.69 (m, 2H), 2.40 (s, 3H), 2.26-2.18 (m, 2H).
MH+ 571.

Example 138

2-(1-(4-chlorophenyl)cyclopropyl)-5-(1-(2,4-dichlorophenyl)-5-(4-methoxyphenyl)-4-methyl-1H-pyrazol-3-yl)-1,3,4-oxadiazole $^1$H NMR (400 MHz, CDCl$_3$) δ 7.42-7.47 (m, 2H), 7.33-7.25 (m, 5H), 7.07-7.04 (m, 2H), 6.85-6.81 (m, 2H), 3.79 (s, 3H), 2.37 (s, 3H), 1.78 (m, 2H), 1.43 (m, 2H).
MH+ 553.

Example 139

2-tert-butyl-5-(5-(4-chlorophenyl)-1-(2,3-dichlorophenyl)-4-methyl-1H-pyrazol-3-yl)-1,3,4-oxadiazole $^1$H NMR (400 MHz, CDCl$_3$) δ 7.54-7.49 (m, 1H), 7.34-7.22 (m, 4H), 7.14-7.10 (m, 2H), 2.44 (s, 3H), 1.49 (s, 9H).
MH+ 463.

Example 140

2-tert-butyl-5-(1-(2,4-dichlorophenyl)-5-(4-methoxyphenyl)-4-methyl-1H-pyrazol-3-yl)-1,3,4-oxadiazole $^1$H NMR (400 MHz, CDCl$_3$) δ 7.41-7.39 (m, 1H), 7.37-7.33 (m, 1H), 7.29-7.24 (m, 1H), 7.11-7.06 (m, 2H), 6.86-6.83 (m, 2H), 3.79 (s, 3H), 2.42 (s, 3H), 1.49 (s, 9H).
MH+ 457.

Example 141

2-(5-(4-chlorophenyl)-1-(2,3-dichlorophenyl)-4-methyl-1H-pyrazol-3-yl)-5-cyclobutyl-1,3,4-oxadiazole $^1$H NMR (400 MHz, CDCl$_3$) δ 7.52 (dd, J=8.0 Hz, 1.6 Hz, 1H), 7.33-7.24 (m, 4H), 7.15-7.10 (m, 2H), 3.85-3.75 (m, 1H), 2.61-2.50 (m, 2H), 2.48-2.39 (m, 5H), 2.24-2.02 (m, 2H).
MH+ 461.

Example 142

2-(5-(4-chlorophenyl)-1-(2,3-dichlorophenyl)-4-methyl-1H-pyrazol-3-yl)-5-cyclohexyl-1,3,4-oxadiazole $^1$H NMR (400 MHz, CDCl$_3$) δ 7.51 (dd, J=8.0 Hz, 1.6 Hz, 1H), 7.33-7.22 (m, 4H), 7.14-7.09 (m, 2H), 3.05-2.94 (m, 1H), 2.45 (s, 3H), 2.18-2.10 (m, 2H), 1.89-1.80 (m, 2H), 1.79-1.63 (m, 2H), 1.45-1.25 (m, 4H).
MH+ 487.

Example 143

2-(5-(4-chlorophenyl)-1-(2,3-dichlorophenyl)-4-methyl-1H-pyrazol-3-yl)-5-(1-(4-chlorophenyl)cyclopropyl)-1,3,4-oxadiazole $^1$H NMR (400 MHz, CDCl$_3$) δ 7.53-7.49 (m, 1H), 7.42-7.37 (m, 2H), 7.32-7.22 (m, 6H), 7.12-7.06 (m, 2H), 2.83 (s, 3H), 1.78 (m, 2H), 1.39 (m, 2H).
MH+ 557.

Example 144

2-(1-(2-chlorophenyl)-5-(4-chlorophenyl)-4-ethyl-1H-pyrazol-3-yl)-5-(1-(4-chlorophenyl)cyclopropyl)-1,3,4-oxadiazole $^1$H NMR (400 MHz, CDCl$_3$) δ 7.43-7.36 (m, 4H), 7.34-7.26 (m, 6H), 7.14-7.10 (m, 2H), 2.80 (q, 2H), 1.84-1.78 (m, 2H), 1.46-1.43 (m, 2H), 1.73 (t, 3H, J=7.2 Hz).
MH+ 537.

Example 145

2-tert-butyl-5-(1-(2-chlorophenyl)-5-(4-chlorophenyl)-4-ethyl-1H-pyrazol-3-yl)-1,3,4-oxadiazole $^1$H NMR (400 MHz, CDCl$_3$) δ 7.45-7.42 (m, 1H), 7.40-7.36 (m, 1H), 7.35-7.27 (m, 4H), 7.16-7.13 (m, 2H), 2.87 (q, 2H), 1.50 (s, 9H), 1.24 (t, 3H, J=7.2 Hz).
MH+ 442.

Example 146

2-(1-(2-chlorophenyl)-5-(4-chlorophenyl)-4-ethyl-1H-pyrazol-3-yl)-5-cyclobutyl-1,3,4-oxadiazole $^1$H NMR (400 MHz, CDCl$_3$) δ 7.43-7.40 (m, 1H), 7.39-7.36 (m, 1H), 7.35-7.28 (m, 4H), 7.17-7.14 (m, 2H), 3.86-3.77 (m, 1H), 2.88 (q, 2H), 2.62-2.52 (m, 2H), 2.49-2.40 (m, 2H), 2.18-2.01 (m, 2H), 1.24 (t, 3H, J=7.6 Hz).
MH+ 439.

Example 147

2-(1-(2-chlorophenyl)-5-(4-chlorophenyl)-4-ethyl-1H-pyrazol-3-yl)-5-(1-(4-chlorophenyl)cyclobutyl)-1,3,4-oxadiazole $^1$H NMR (400 MHz, CDCl$_3$) δ 7.41-7.35 (m, 2H), 7.34-7.26 (m, 6H), 7.27-7.25 (m, 2H), 7.13-7.09 (m, 2H), 3.12-3.06 (m, 2H), 2.81 (q, 2H), 2.78-2.70 (m, 2H), 2.30-2.19 (m, 1H), 2.07-1.97 (m, 1H), 1.19 (t, 3H, J=7.2 Hz).
MH+ 551.

Example 148

2-(5-(4-chlorophenyl)-1-(2,4-dichlorophenyl)-4-methyl-1H-pyrazol-3-yl)-5-(1-phenylpropyl)-1,3,4-oxadiazole $^1$H NMR (400 MHz, CDCl$_3$) δ 7.39 (br d, J=2.0 Hz, 1H), 7.37-7.22 (m, 9H), 7.08 (m, 2H), 4.17 (t, J=7.6 Hz, 2H), 2.42 (s, 3H), 2.37 (m, 1H), 2.12 (m, 1H), 0.97 (t, J=7.2 Hz, 3H).
MH+ 523.

Example 149

2-(5-(4-chlorophenyl)-1-(2,4-dichlorophenyl)-4-methyl-1H-pyrazol-3-yl)-5-(2-phenylpropyl)-1,3,4-oxadiazole $^1$H NMR (400 MHz, CDCl$_3$) δ 7.42 (d, J=2.0 Hz, 1H), 7.36-7.18 (m, 9H), 7.11 (m, 2H), 3.44 (m, 1H), 3.20 (m, 2H), 2.42 (s, 3H), 1.36 (d, J=6.8 Hz).
MH+ 523.

Example 150

2-(5-(4-chlorophenyl)-1-(2,4-dichlorophenyl)-4-ethyl-1H-pyrazol-3-yl)-5-(1-phenylcyclopropyl)-1,3,4-oxadiazole $^1$H NMR (400 MHz, CDCl$_3$) δ 7.48-7.45 (m, 2H), 7.38-7.26 (m, 8H), 7.09 (d, J=8.8 Hz, 2H), 2.77 (q, J=7.2 Hz, 2H), 1.79-1.76 (m, 2H), 1.48-1.46 (m, 2H), 1.14 (t, J=7.6 Hz, 3H). MH+ 537.

Example 151

2-(5-(4-chlorophenyl)-1-(2,4-dichlorophenyl)-4-ethyl-1H-pyrazol-3-yl)-5-(1-p-tolylcyclopropyl)-1,3,4-oxadiazole $^1$H NMR (400 MHz, CDCl$_3$) δ 7.38-7.34 (m, 3H), 7.32-7.26 (m, 4H), 7.16-7.13 (m, 2H), 7.09 (d, J=8.4 Hz, 2H), 2.77 (q, J=7.2 Hz, 2H), 2.33 (s, 3H), 1.76-1.73 (m, 2H), 1.45-1.42 (m, 2H), 1.14 (t, J=7.2 Hz, 3H).
MH+ 549.

Example 152

2-(5-(4-chlorophenyl)-1-(2,4-dichlorophenyl)-4-ethyl-1H-pyrazol-3-yl)-5-(1-(4-methoxyphenyl)cyclopropyl)-1,3,4-oxadiazole $^1$H NMR (400 MHz, CDCl$_3$) δ 7.43-7.38 (m, 3H), 7.34-7.26 (m, 4H), 7.09 (d, J=8.8 Hz, 2H), 6.87 (d, J=8.8 Hz, 2H), 3.79 (s, 3H), 2.77 (q, J=7.6 Hz, 2H), 1.75-1.72 (m, 2H), 1.44-1.41 (m, 2H), 1.14 (t, J=7.2 Hz, 3H).
MH+ 565.

Example 153

2-(5-(4-chlorophenyl)-1-(2,4-dichlorophenyl)-4-ethyl-1H-pyrazol-3-yl)-5-(1-(2,4-dichlorophenyl)cyclopropyl)-1,3,4-oxadiazole $^1$H NMR (400 MHz, CDCl$_3$) δ 7.44-7.42 (m, 2H), 7.39-7.27 (m, 6H), 7.09 (d, J=8.4 Hz, 2H), 2.75 (q, J=7.6 Hz, 2H), 1.97-1.94 (m, 2H), 1.50-1.47 (m, 2H), 1.12 (t, J=7.6 Hz, 3H).
MH+ 605.

Example 154

2-(5-(4-chlorophenyl)-1-(2,4-dichlorophenyl)-4-ethyl-1H-pyrazol-3-yl)-5-(1-(4-chlorophenyl)cyclobutyl)-1,3,4-oxadiazole $^1$H NMR (400 MHz, CDCl$_3$) δ 7.38 (d, J=2.0 Hz, 1H), 7.34-7.25 (m, 8H), 7.09 (d, J=8.8 Hz, 2H), 3.11-3.05 (m, 2H), 2.82-2.70 (m, 4H), 2.30-2.18 (m, 1H), 2.06-1.97 (m, 1H), 1.16 (t, J=7.2 Hz, 3H).
MH+ 585.

Example 155

2-(5-(4-chlorophenyl)-1-(2,4-dichlorophenyl)-4-ethyl-1H-pyrazol-3-yl)-5-(1-(trifluoromethyl)cyclopropyl)-1,3,4-oxadiazole $^1$H NMR (400 MHz, CDCl$_3$) δ 7.40 (d, J=2.4 Hz, 1H), 7.36-7.28 (m, 4H), 7.12 (d, J=8.8 Hz, 2H), 2.84 (q, J=7.6 Hz, 2H), 1.67-1.61 (m, 4H), 1.21 (t, J=7.2 Hz, 3H).
MH+ 527.

Example 156

2-(1-(2-bromophenyl)-5-(4-chlorophenyl)-4-methyl-1H-pyrazol-3-yl)-5-cyclohexyl-1,3,4-oxadiazole $^1$H NMR (400 MHz, CDCl$_3$) δ 7.59-7.57 (m, 1H), 7.41-7.34 (m, 2H), 7.30-7.25 (m, 3H), 7.16-7.12 (m, 2H), 3.02-2.97 (m, 1H), 2.46 (s, 3H), 2.16-2.12 (m, 2H), 1.88-1.84 (m, 2H), 1.73-1.71 (m, 2H), 1.41-1.33 (m, 4H).
MH+ 497.

Example 157

2-(1-(2-bromophenyl)-5-(4-chlorophenyl)-4-methyl-1H-pyrazol-3-yl)-5-tert-butyl-1,3,4-oxadiazole $^1$H NMR (400 MHz, CDCl$_3$) δ 7.59-7.57 (m, 1H), 7.43-7.35 (m, 2H), 7.30-7.26 (m, 3H), 7.15-7.12 (m, 2H), 2.45 (s, 3H), 1.50 (s, 9H).
MH+ 471.

Example 158

2-(1-(2-bromophenyl)-5-(4-chlorophenyl)-4-methyl-1H-pyrazol-3-yl)-5-(1-(4-chlorophenyl)cyclopropyl)-1,3,4-oxadiazole $^1$H NMR (400 MHz, CDCl$_3$) δ 7.58-7.56 (m, 1H), 7.42-7.36 (m, 4H), 7.34-7.25 (m, 5H), 7.13-7.09 (m, 2H), 2.39 (s, 3H), 1.80-1.77 (m, 2H), 1.45-1.42 (m, 2H).
MH+ 565.

Example 159

2-(1-(2-bromophenyl)-5-(4-chlorophenyl)-4-methyl-1H-pyrazol-3-yl)-5-(1-(4-chlorophenyl)cyclobutyl)-1,3,4-oxadiazole $^1$H NMR (400 MHz, CDCl$_3$) δ 7.58-7.55 (m, 1H), 7.37-7.25 (m, 9H), 7.18-7.09 (m, 2H), 3.12-3.06 (m, 2H), 2.78-2.70 (m, 2H), 2.41 (s, 3H), 2.27-2.20 (m, 1H), 2.04-1.99 (m, 1H).
MH+ 579.

Example 160

2-tert-butyl-5-(5-(4-chlorophenyl)-1-(2,6-dichlorophenyl)-4-methyl-1H-pyrazol-3-yl)-1,3,4-oxadiazole $^1$H NMR (400 MHz, CDCl$_3$) δ 7.36-7.35 (m, 1H), 7.34-7.33 (m, 1H), 7.31-7.30 (m, 1H), 7.29-7.28 (m, 2H), 7.22-7.19 (m, 2H), 2.43 (s, 3H), 1.49 (s, 9H).
MH+ 461.

Example 161

2-(5-(4-chlorophenyl)-1-(2,6-dichlorophenyl)-4-methyl-1H-pyrazol-3-yl)-5-(1-(4-chlorophenyl)cyclopropyl)-1,3,4-oxadiazole $^1$H NMR (400 MHz, CDCl$_3$) δ 7.41-7.38 (m, 2H), 7.36-7.33 (m, 2H), 7.32-7.29 (m, 3H), 7.28-7.26 (m, 2H), 7.20-7.17 (m, 2H), 2.37 (s, 3H), 1.80-1.77 (m, 2H), 1.44-1.41 (m, 2H).
MH+ 555.

Example 162

2-(5-(4-chlorophenyl)-1-(2,6-dichlorophenyl)-4-methyl-1H-pyrazol-3-yl)-5-(1-(4-chlorophenyl)cyclobutyl)-1,3,4-oxadiazole $^1$H NMR (400 MHz, CDCl$_3$) δ 7.35-7.34 (m, 1H), 7.33-7.32 (m, 2H), 7.31-7.29 (m, 4H), 7.28-7.27 (m, 2H), 7.20-7.16 (m, 2H), 3.12-3.06 (m, 2H), 2.77-2.69 (m, 2H), 2.25 (s, 3H), 2.24-2.18 (m, 1H), 2.05-1.97 (m, 1H).
MH+ 569.

Example 163

2-(1-(2-bromophenyl)-5-(4-chlorophenyl)-4-methyl-1H-pyrazol-3-yl)-5-cyclobutyl-1,3,4-oxadiazole $^1$H NMR (400 MHz, CDCl$_3$) δ 7.59-7.56 (m, 1H), 7.40-7.30 (m, 2H), 7.29-7.27 (m, 3H), 7.24-7.12 (m, 2H), 3.83-3.78 (m, 1H), 2.58-2.53 (m, 2H), 2.51 (s, 3H), 2.47-2.41 (m, 2H), 2.15-1.03 (m, 2H).
MH+ 469.

Example 164

2-tert-butyl-5-(5-(4-chlorophenyl)-1-(2,5-dichlorophenyl)-4-methyl-1H-pyrazol-3-yl)-1,3,4-oxadiazole $^1$H NMR (400 MHz, CDCl$_3$) δ 7.51 (d, J=2.4 Hz, 1H), 7.35-7.29 (m, 4H), 7.12 (d, J=8.8 Hz, 2H), 2.43 (s, 3H), 1.50 (s, 9H).
MH+ 461.

Example 165

2-(5-(4-chlorophenyl)-1-(2,5-dichlorophenyl)-4-methyl-1H-pyrazol-3-yl)-5-cyclobutyl-1,3,4-oxadiazole $^1$H NMR (400 MHz, CDCl$_3$) δ 7.49 (d, J=2.0 Hz, 1H), 7.35-7.30 (m, 4H), 7.13 (d, J=8.8 Hz, 2H), 3.83-3.79 (m, 1H), 2.58-2.51 (m, 2H), 2.47-2.42 (m, 5H), 2.14-2.05 (m, 2H).
MH+ 459.

Example 166

2-(5-(4-chlorophenyl)-1-(2,5-dichlorophenyl)-4-methyl-1H-pyrazol-3-yl)-5-cyclohexyl-1,3,4-oxadiazole $^1$H NMR (400 MHz, CDCl$_3$) δ 7.49 (d, J=2.0 Hz, 1H), 7.35-7.29 (m, 4H), 7.13 (d, J=8.8 Hz, 2H), 3.02-2.97 (m, 1H), 2.45 (s, 3H), 2.16-2.12 (m, 2H), 1.87-1.83 (m, 2H), 1.76-1.66 (m, 3H), 1.44-1.29 (m, 3H).
MH+ 487.

Example 167

2-(5-(4-chlorophenyl)-1-(2,5-dichlorophenyl)-4-methyl-1H-pyrazol-3-yl)-5-(1-(4-chlorophenyl)cyclopropyl)-1,3,4-oxadiazole $^1$H NMR (400 MHz, CDCl$_3$) δ 7.47 (d, J=2.0 Hz, 1H), 7.40 (d, J=8.8 Hz, 2H), 7.35-7.28 (m, 6H), 7.10 (d, J=8.4 Hz, 2H), 2.38 (s, 3H), 1.80-1.77 (m, 2H), 1.46-1.43 (m, 2H).
MH+ 557.

Example 168

2-(5-(4-chlorophenyl)-1-(2,5-dichlorophenyl)-4-methyl-1H-pyrazol-3-yl)-5-(1-(4-chlorophenyl)cyclobutyl)-1,3,4-oxadiazole $^1$H NMR (400 MHz, CDCl$_3$) δ 7.47 (d, J=2.4 Hz, 1H), 7.34-7.27 (m, 8H), 7.09 (d, J=8.4 Hz, 2H), 3.12-3.05 (m, 2H), 2.78-2.70 (m, 2H), 2.39 (s, 3H), 2.24-2.19 (m, 1H), 2.05-1.18 (m, 1H).
MH+ 571.

Example 169

2-(1-(2-chlorophenyl)-5-(4-chlorophenyl)-4-ethyl-1H-pyrazol-3-yl)-5-cyclohexyl-1,3,4-oxadiazole $^1$H NMR (400 MHz, CDCl$_3$) δ 7.42-7.39 (m, 1H), 7.38-7.35 (m, 1H), 7.33-7.26 (m, 4H), 7.16-7.12 (m, 2H), 3.02-2.95 (m, 1H), 2.88 (q, 2H), 2.16-2.12 (m, 2H), 1.87-1.83 (m, 2H), 1.76-1.66 (m, 3H), 1.44-1.26 (m, 3H), 1.23 (t, J=7.6 Hz, 3H).
MH+ 467.

Example 170

2-tert-butyl-5-(5-(4-chlorophenyl)-1-(3,4-dichlorophenyl)-4-methyl-1H-pyrazol-3-yl)-1,3,4-oxadiazole $^1$H NMR (400 MHz, CDCl$_3$) δ 7.57 (d, J=2.4 Hz, 2H), 7.42-7.39 (m, 2H), 7.34 (d, J=8.4 Hz, 1H), 7.16-7.12 (m, 2H), 6.96 (dd, J=8.8 Hz, 2.4 Hz, 1H), 2.38 (s, 3H), 1.51 (s, 9H).
MH+ 461.

Example 171

2-(5-(4-chlorophenyl)-1-(3,4-dichlorophenyl)-4-methyl-1H-pyrazol-3-yl)-5-cyclobutyl-1,3,4-oxadiazole $^1$H NMR (400 MHz, CDCl$_3$) δ 7.57 (d, J=2.4 Hz, 2H), 7.42-7.39 (m, 2H), 7.34 (d, J=8.4 Hz, 1H), 7.16-7.12 (m, 2H), 6.96 (dd, J=8.8 Hz, 2.4 Hz, 1H), 3.86-3.81 (m, 1H), 2.59-2.54 (m, 2H), 2.51-2.45 (m, 2H), 2.40 (s, 3H), 2.18-2.07 (m, 2H).
MH+ 459.

Example 172

2-(1-(2,4-dichlorophenyl)-5-(4-methoxyphenyl)-4-methyl-1H-pyrazol-3-yl)-5-(1-(4-methoxyphenyl)cyclopropyl)-1,3,4-oxadiazole $^1$H NMR (400 MHz, CDCl$_3$) δ 7.42-7.36 (m, 2H), 7.34-7.24 (m, 3H), 7.08-7.03 (m, 2H), 6.90-6.80 (m, 4H), 3.78 (s, 6H), 2.35 (d, J=4.0 Hz, 3H), 1.81-1.71 (m, 2H), 1.45-1.38 (m, 2H).
MH+ 547.

Example 173

2-(5-(4-bromophenyl)-1-(2,4-dichlorophenyl)-4-ethyl-1H-pyrazol-3-yl)-5-(1-(trifluoromethyl)cyclopropyl)-1,3,4-oxadiazole $^1$H NMR (400 MHz, CDCl$_3$) δ 7.49-7.46 (m, 2H), 7.40 (br d, J=2.0 Hz, 1H), 7.37-7.28 (m, 2H), 7.07-7.04 (m, 2H), 2.83

(q, J=7.6 Hz, 2H), 1.64 (m, 2H), 1.61 (m, 2H), 1.21 (t, J=7.6 Hz, 3H).
MH+ 571.

Example 174

2-(5-(4-bromophenyl)-1-(2,4-dichlorophenyl)-4-ethyl-1H-pyrazol-3-yl)-5-(1-(2,4-dichlorophenyl)cyclopropyl)-1,3,4-oxadiazole $^1$H NMR (400 MHz, CDCl$_3$) δ 7.47-7.25 (m, 8H), 7.04-7.00 (m, 2H), 2.74 (q, J=7.6 Hz, 2H), 1.95 (dd, J=7.4, 5.0 Hz, 2H), 1.49 (dd, J=7.4, 5.0 Hz, 2H), 1.12 (t, J=7.6 Hz, 3H).
MH+ 647.

Example 175

2-(5-(4-bromophenyl)-1-(2,4-dichlorophenyl)-4-ethyl-1H-pyrazol-3-yl)-5-(1-(4-methoxyphenyl)cyclopropyl)-1,3,4-oxadiazole $^1$H NMR (400 MHz, CDCl$_3$) δ 7.47-7.44 (m, 2H), 7.42-7.39 (m, 2H), 7.38-7.27 (m, 3H), 7.04-7.00 (m, 2H), 6.88-6.86 (m, 2H), 3.79 (s, 3H), 2.76 (q, J=7.6 Hz, 2H), 1.74 (dd, J=7.2, 4.8 Hz, 2H), 1.42 (dd, J=7.2, 4.8 Hz, 2H), 1.14 (t, J=7.6 Hz, 3H).
MH+ 609.

Example 176

2-(5-(4-bromophenyl)-1-(2,4-dichlorophenyl)-4-ethyl-1H-pyrazol-3-yl)-5-(1-p-tolylcyclopropyl)-1,3,4-oxadiazole $^1$H NMR (400 MHz, CDCl$_3$) δ 7.47-7.44 (m, 2H), 7.38-7.27 (m, 5H), 7.16-7.14 (m, 2H), 7.04-7.00 (m, 2H), 2.76 (q, J=7.6 Hz, 2H), 2.31 (s, 3H), 1.74 (dd, J=7.2, 4.8 Hz, 2H), 1.44 (dd, J=7.2, 4.8 Hz, 2H), 1.14 (t, J=7.6 Hz, 3H).
MH+ 593.

Example 177

2-(5-(4-bromophenyl)-1-(2,4-dichlorophenyl)-4-ethyl-1H-pyrazol-3-yl)-5-(1-phenylcyclopropyl)-1,3,4-oxadiazole $^1$H NMR (400 MHz, CDCl$_3$) δ 7.48-7.44 (m, 4H), 7.38-7.27 (m, 6H), 7.04-7.00 (m, 2H), 2.76 (q, J=7.6 Hz, 2H), 1.77 (dd, J=7.2, 4.8 Hz, 2H), 1.47 (dd, J=7.2, 4.8 Hz, 2H), 1.14 (t, J=7.6 Hz, 3H).
MH+ 579.

Example 178

2-tert-butyl-5-(5-(4-chlorophenyl)-1-(2,4-dichlorophenyl)-4-isopropyl-1H-pyrazol-3-yl)-1,3,4-oxadiazole $^1$H NMR (400 MHz, CDCl$_3$) δ 7.38 (d, J=2.0 Hz, 1H), 7.31-7.24 (m, 4H), 7.14 (d, J=8.8 Hz, 2H), 3.48-3.43 (m, 1H), 1.49 (s, 9H), 1.26 (d, J=7.2 Hz, 6H).
MH+ 489.

Example 179

2-(5-(4-chlorophenyl)-1-(2,4-dichlorophenyl)-4-isopropyl-1H-pyrazol-3-yl)-5-cyclobutyl-1,3,4-oxadiazole $^1$H NMR (400 MHz, CDCl$_3$) δ 7.39 (d, J=2.4 Hz, 1H), 7.31-7.23 (m, 4H), 7.15 (d, J=8.4 Hz, 2H), 3.85-3.76 (m, 1H), 3.54-3.47 (m, 1H), 2.60-2.40 (m, 3H), 2.18-2.00 (m, 3H), 1.27 (d, J=7.2 Hz, 6H).
MH+ 487.

Example 180

2-(5-(4-chlorophenyl)-1-(2,4-dichlorophenyl)-4-isopropyl-1H-pyrazol-3-yl)-5-cyclohexyl-1,3,4-oxadiazole $^1$H NMR (400 MHz, CDCl$_3$) δ 7.38 (d, J=2.4 Hz, 1H), 7.31-7.22 (m, 4H), 7.15 (d, J=8.0 Hz, 2H), 3.52-3.45 (m, 1H), 3.02-2.95 (m, 1H), 2.16-2.12 (m, 2H), 1.87-1.83 (m, 2H), 1.75-1.65 (m, 3H), 1.44-1.29 (m, 3H), 1.26 (d, J=6.8 Hz, 6H).
MH+ 515.

Example 181

2-(5-(4-chlorophenyl)-1-(2,4-dichlorophenyl)-4-isopropyl-1H-pyrazol-3-yl)-5-(1-(4-chlorophenyl)cyclopropyl)-1,3,4-oxadiazole $^1$H NMR (400 MHz, CDCl$_3$) δ 7.41 (d, J=8.4 Hz, 2H), 7.37 (d, J=2.0 Hz, 1H), 7.33-7.23 (m, 6H), 7.11 (d, J=8.4 Hz, 2H), 3.40-3.33 (m, 1H), 1.80-1.77 (m, 2H), 1.46-1.43 (m, 2H), 1.20 (d, J=7.2 Hz, 6H).
MH+ 585.

Example 182

2-(5-(4-chlorophenyl)-1-(2,4-dichlorophenyl)-4-isopropyl-1H-pyrazol-3-yl)-5-(1-(4-chlorophenyl)cyclobutyl)-1,3,4-oxadiazole $^1$H NMR (400 MHz, CDCl$_3$) δ 7.36 (d, J=2.0 Hz, 1H), 7.31-7.22 (m, 8H), 7.11 (d, J=8.4 Hz, 2H), 3.43-3.36 (m, 1H), 3.11-3.05 (m, 2H), 2.77-2.70 (m, 2H), 2.28-2.21 (m, 1H), 2.05-1.97 (m, 1H), 1.19 (d, J=7.2 Hz, 6H).
MH+ 599.

Example 183

2-tert-butyl-5-(5-(4-chlorophenyl)-1-(2,4-dichlorophenyl)-4-propyl-1H-pyrazol-3-yl)-1,3,4-oxadiazole $^1$H NMR (400 MHz, CDCl$_3$) δ 7.40 (d, J=2.4 Hz, 1H), 7.37-7.27 (m, 4H), 7.11 (d, J=8.4 Hz, 2H), 2.81-2.77 (m, 2H), 1.66-1.57 (m, 2H), 1.49 (s, 9H), 0.88 (t, J=7.2 Hz, 3H).
MH+ 489.

Example 184

2-(5-(4-chlorophenyl)-1-(2,4-dichlorophenyl)-4-propyl-1H-pyrazol-3-yl)-5-cyclobutyl-1,3,4-oxadiazole $^1$H NMR (400 MHz, CDCl$_3$) δ 7.40 (d, J=2.0 Hz, 1H), 7.35-7.27 (m, 4H), 7.12 (d, J=8.0 Hz, 2H), 3.82-3.78 (m, 1H), 2.84-2.80 (m, 2H), 2.58-2.50 (m, 2H), 2.48-2.42 (m, 2H), 2.16-2.05 (m, 2H), 1.65-1.59 (m, 2H), 0.88 (t, J=7.2 Hz, 3H).
MH+ 487.

Example 185

2-(5-(4-chlorophenyl)-1-(2,4-dichlorophenyl)-4-propyl-1H-pyrazol-3-yl)-5-cyclohexyl-1,3,4-oxadiazole $^1$H NMR (400 MHz, CDCl$_3$) δ 7.40 (d, J=2.0 Hz, 1H), 7.35-7.27 (m, 4H), 7.12 (d, J=8.4 Hz, 2H), 3.02-2.94 (m, 1H), 2.83-2.79 (m, 2H), 2.17-2.12 (m, 2H), 1.87-1.83 (m, 2H), 1.75-1.57 (m, 4H), 1.44-1.25 (m, 4H), 0.88 (t, J=7.2 Hz, 3H).
MH+ 515.

Example 186

2-(5-(4-chlorophenyl)-1-(2,4-dichlorophenyl)-4-propyl-1H-pyrazol-3-yl)-5-(1-(4-chlorophenyl)cyclopropyl)-1,3,4-oxadiazole $^1$H NMR (400 MHz, CDCl$_3$) δ 7.42-7.38 (m, 3H), 7.34-7.26 (m, 6H), 7.09 (d, J=8.8 Hz, 2H), 2.74-2.70 (m, 2H), 1.80-1.77 (m, 2H), 1.58-1.50 (m, 2H), 1.46-1.43 (m, 2H), 0.82 (t, J=7.6 Hz, 3H).
MH+ 585.

Example 187

2-(5-(4-chlorophenyl)-1-(2,4-dichlorophenyl)-4-propyl-1H-pyrazol-3-yl)-5-(1-(4-chlorophenyl)cyclobutyl)-1,3,4-oxadiazole $^1$H NMR (400 MHz, CDCl$_3$) δ 7.38 (d, J=2.4 Hz, 1H), 7.33-7.26 (m, 8H), 7.08 (d, J=8.8 Hz, 2H), 3.11-3.04 (m, 2H), 2.77-2.70 (m, 4H), 2.27-2.20 (m, 1H), 2.04-2.00 (m, 1H), 1.61-1.53 (m, 2H), 0.85 (t, J=7.2 Hz, 3H).
MH+ 599.

Example 188

2-(5-(4-bromophenyl)-1-(2,4-dichlorophenyl)-4-ethyl-1H-pyrazol-3-yl)-5-(1-phenylcyclopentyl)-1,3,4-oxadiazole $^1$H NMR (400 MHz, CDCl$_3$) δ 7.46-7.38 (m, 4H), 7.37 (d, J=2.4 Hz, 1H), 7.34-7.26 (m, 4H), 7.23-7.19 (m, 1H), 7.03-6.95 (m, 2H), 2.91 (m, 2H), 2.77 (q, J=7.6 Hz, 2H), 2.24 (m, 2H), 1.83 (m, 4H), 1.15 (t, J=7.6 Hz, 3H).
MH+ 607.

Example 189

2-(5-(4-bromophenyl)-1-(2,4-dichlorophenyl)-4-ethyl-1H-pyrazol-3-yl)-5-(1-(4-chlorophenyl)cyclopentyl)-1,3,4-oxadiazole $^1$H NMR (400 MHz, CDCl$_3$) δ 7.46-7.44 (m, 2H), 7.35-7.25 (m, 7H), 7.04-7.01 (m, 2H), 2.88 (m, 2H), 2.78 (q, J=7.6 Hz, 2H), 2.19 (m, 2H), 1.83 (m, 4H), 1.16 (t, J=7.6 Hz, 3H).
MH+ 641.

Example 190

2-(5-(4-chlorophenyl)-1-(2,4-dichlorophenyl)-4-isopropyl-1H-pyrazol-3-yl)-5-(1-(trifluoromethyl)cyclopropyl)-1,3,4-oxadiazole $^1$H NMR (400 MHz, CDCl$_3$) δ 7.41 (s, 1H), 7.33-7.26 (m, 4H), 7.16 (d, J=8.8 Hz, 2H), 3.48-3.41 (m, 1H), 1.66-1.63 (m, 4H), 1.28 (d, J=7.2 Hz, 6H).
MH+ 541.

Example 191

2-(5-(4-chlorophenyl)-1-(2,4-dichlorophenyl)-4-propyl-1H-pyrazol-3-yl)-5-(1-(trifluoromethyl)cyclopropyl)-1,3,4-oxadiazole $^1$H NMR (400 MHz, CDCl$_3$) δ 7.34 (s, 1H), 7.30-7.22 (m, 4H), 7.06 (d, J=8.8 Hz, 2H), 2.74-2.71 (m, 2H), 1.58-1.52 (m, 6H), 0.82 (t, J=7.2 Hz, 2H).
MH+ 541.

Example 192

2-(5-(4-chlorophenyl)-4-cyclopropyl-1-(2,4-dichlorophenyl)-1H-pyrazol-3-yl)-5-cyclohexyl-1,3,4-oxadiazole Step 1: Ethyl 4-bromo-5-(4-chlorophenyl)-1-(2,4-dichlorophenyl)-1H-pyrazole-3-carboxylate (68)

To a solution of ethyl 5-(4-chlorophenyl)-1-(2,4-dichlorophenyl)-1H-pyrazole-3-carboxylate (1 g, 2.4 mmol) in methylene chloride (30 ml) at room temperature was added bromine (4.9 ml, prepared 1.0 M solution in methylenechlordie, 4.9 mmol) dropwisely. The reaction mixture was stirred at room temperature for 1 hour and the resulting solution was diluted with ethyl ether (50 ml). The reaction mixture was quenched with saturated sodium bicarbonate solution (30 ml) and extracted with ethyl ether (50 ml twice). The organic solution was evaporated under reduced pressure, and crude residue was purified with silica gel column (hexane/ethyl acetate=5/1) to recover starting material (401 mg, 40%) and produce the title compound (520 mg, 45% yield) as white solid.

$^1$H NMR (400 MHz, CDCl$_3$) δ 7.41 (d, J=2.0 Hz, 1H), 7.37 (d, J=8.4, 2H), 7.35-7.31 (m, 3H), 7.21-7.19 (m, 2H), 4.50 (q, J=7.2 Hz, 2H), 1.44 (t, J=7.2 Hz, 3H).
MH+ 473.

Step 2: Ethyl 5-(4-chlorophenyl)-4-cyclopropyl-1-(2,4-dichlorophenyl)-1H-pyrazole-3-carboxylate (69)

To a solution of ethyl 4-bromo-5-(4-chlorophenyl)-1-(2,4-dichlorophenyl)-1H-pyrazole-3-carboxylate (68) (500 mg, 1.1 mmol) in aqueous toluene, tetrakis(triphenylphsophine)palladium (122 mg, 0.11 mmol) and potassium carbonate (510 mg, 3.9 mmol) were added. The reaction mixture was placed under microwave irradiation with the temperature set to 140° C. The resulting solution was filtered with syringe filter, and then solvent was evaporated under reduced pressure. The residue was purified with silica gel column chromatography to obtain the title compound (283 mg, 44%) as white solid.

$^1$H NMR (400 MHz, CDCl$_3$) δ 7.46-7.43 (m, 1H), 7.38-7.35 (m, 4H), 7.13-7.11 (m, 2H), 4.48 (q, J=7.1 Hz, 2H), 2.02-1.98 (m, 1H), 1.44 (t, J=7.1, 3H), 1.26-1.23 (m, 1H), 0.89-0.86 (m, 1H).
MH+ 436.

Step 3: 2-(5-(4-chlorophenyl)-4-cyclopropyl-1-(2,4-dichlorophenyl)-1H-pyrazol-3-yl)-5-cyclohexyl-1,3,4-oxadiazole $^1$H NMR (400 MHz, CDCl$_3$) δ 7.52-7.48 (m, 2H), 7.31-7.22 (m, 2H), 7.17-7.04 (m, 1H), 7.02-7.00 (m, 2H), 3.08-2.98 (m, 1H), 2.18-2.14 (m, 2H), 1.90-1.85 (m, 2H), 1.77-1.68 (m, 2H), 1.46-1.25 (m, 4H), 0.63-0.60 (m, 2H), 0.38-0.34 (m, 2H).
MH+ 515.

Example 193

2-tert-butyl-5-(5-(4-chlorophenyl)-4-cyclopropyl-1-(2,4-dichlorophenyl)-1H-pyrazol-3-yl)-1,3,4-oxadiazole $^1$H NMR (400 MHz, CDCl$_3$) δ 7.55-7.50 (m, 2H), 7.37-7.31 (m, 2H), 7.22-7.20 (m, 1H), 7.15-7.10 (m, 2H), 1.45 (m, 1H), 1.34 (s, 9H), 0.62-0.59 (m, 2H), 0.38-0.34 (m, 2H).
MH+ 489.

Example 194

2-(5-(4-chlorophenyl)-4-cyclopropyl-1-(2,4-dichlorophenyl)-1H-pyrazol-3-yl)-5-cyclobutyl-1,3,4-oxadiazole $^1$H NMR (400 MHz, CDCl$_3$) δ 7.54-7.51 (m, 2H), 7.33-7.31 (m, 2H), 7.20-7.17 (m, 1H), 7.14-7.11 (m, 2H), 3.25-2.22 (m, 1H), 1.50 (m, 1H), 1.45-1.44 (m, 4H), 1.37-1.30 (m, 2H), 0.61-0.59 (m, 2H), 0.37-0.34 (m, 2H).
MH+ 487.

Example 195

(5-(4-bromophenyl)-3-(5-tert-butyl-1,3,4-oxadiazol-2-yl)-1-(2,4-dichlorophenyl)-1H-pyrazol-4-yl)methyl acetate To the solution of bromide (33) (2.7 g, 4.614 mmol) in DMF (20 mL) was added sodium acetate (1.13 mg, 13.842 mmol). The reaction mixture was heated for 12 hrs at 60° C. The reaction mixture was diluted with EtOAc and washed with brine. The organic layer was dried over anhydrous MgSO$_4$, filtered, and concentrated in vacuo. Purification by silica gel column chromatography (eluent: hexane/EtOAc=3/1) provided 1.75 g (76%) of desired acetate as solid.
$^1$H NMR (400 MHz, CDCl$_3$) δ 7.51-7.47 (m, 2H), 7.44-7.39 (m, 1H), 7.40-7.38 (m, 1H), 7.35-7.32 (m, 1H), 7.25-7.06 (m, 2H), 5.30 (s, 2H), 2.03 (s, 3H), 1.49 (s, 9H).
MH+ 563.

Example 196

(3-(5-tert-butyl-1,3,4-oxadiazol-2-yl)-5-(4-chlorophenyl)-1-(2,4-dichlorophenyl)-1H-pyrazol-4-yl)methyl acetate $^1$H NMR (400 MHz, CDCl$_3$) δ 7.44-7.43 (m, 1H), 7.39 (d, J=8.4 Hz, 1H), 7.35-7.32 (m, 3H), 7.15-7.13 (m, 2H), 5.30 (s, 2H), 2.03 (s, 3H), 1.50 (s, 9H).
MH+ 519.

Example 197

(5-(4-chlorophenyl)-3-(5-(1-(4-chlorophenyl)cyclopropyl)-1,3,4-oxadiazol-2-yl)-1-(2,4-dichlorophenyl)-1H-pyrazol-4-yl)methyl acetate $^1$H NMR (300 MHz, CDCl$_3$) δ 7.42-7.38 (m, 3H), 7.35-7.31 (m, 6H), 7.12 (d, J=8.4 Hz, 2H), 5.24 (s, 2H), 1.99 (s, 3H), 1.81-1.77 (m, 2H), 1.48-1.46 (m, 2H).
MH+ 615.

Example 198

(3-(5-tert-butyl-1,3,4-oxadiazol-2-yl)-5-(4-chlorophenyl)-1-(2,4-dichlorophenyl)-1H-pyrazol-4-yl)methyl benzoate $^1$H NMR (400 MHz, CDCl$_3$) δ 7.93-7.91 (m, 2H), 7.56-7.52 (m, 1H), 7.45-7.26 (m, 7H), 7.19-7.17 (m, 2H), 5.58 (s, 2H), 1.46 (s, 9H).
MH+ 581.

Example 199

(3-(5-tert-butyl-1,3,4-oxadiazol-2-yl)-5-(4-chlorophenyl)-1-(2,4-dichlorophenyl)-1H-pyrazol-4-yl)methanol To the solution of acetate (34) (1.57 g, 3.020 mmol) in THF(9 mL)/MeOH(9 mL)/H$_2$O(2 mL) was added LiOH monohydrate (380 mg, 9.060 mmol). The reaction mixture was stirred for 12 hrs at room temperature. The reaction mixture was diluted with EtOAc and washed with brine. The organic layer was dried over anhydrous MgSO$_4$, filtered, and concentrated in vacuo to provide 1.37 g (95%) of desired alcohol (35) as solid. The obtained acid was used without further purification.
$^1$H NMR (400 MHz, CDCl$_3$) δ 7.45-7.44 (m, 1H), 7.34-7.32 (m, 4H), 7.16-7.14 (m, 2H), 4.82-4.78 (m, 1H), 4.72-4.70 (m, 2H), 1.51 (s, 9H).
MH+ 478.

Example 200

(5-(4-bromophenyl)-3-(5-tert-butyl-1,3,4-oxadiazol-2-yl)-1-(2,4-dichlorophenyl)-1H-pyrazol-4-yl)methanol $^1$H NMR (400 MHz, CDCl$_3$) δ 7.49-7.46 (m, 2H), 7.44-7.43 (m, 1H), 7.33-7.32 (m, 2H), 7.08-7.06 (m, 2H), 4.69 (s, 2H), 1.50 (s, 9H).
MH+ 521.

Example 201

(5-(4-chlorophenyl)-3-(5-(1-(4-chlorophenyl)cyclopropyl)-1,3,4-oxadiazol-2-yl)-1-(2,4-dichlorophenyl)-1H-pyrazol-4-yl)methanol $^1$H NMR (400 MHz, CDCl$_3$) δ 7.43-7.39 (m, 3H), 7.35-7.30 (m, 6H), 7.12 (d, J=8.4 Hz, 2H), 4.66 (s, 2H), 1.82-1.79 (m, 2H), 1.50-1.47 (m, 2H).
MH+ 573.

Example 202

3-(5-tert-butyl-1,3,4-oxadiazol-2-yl)-5-(4-chlorophenyl)-1-(2,4-dichlorophenyl)-1H-pyrazole-4-carbaldehyde To the solution of alcohol (35) (100 mg, 0.209 mmol) and Dess-Martin periodinane (132 mg, 0.313 mmol) in $CH_2Cl_2$ (5 mL) was stirred at room temperature. The reaction mixture was filtered off the white solid and then diluted with $CH_2Cl_2$ (50 mL) and washed with brine. The organic layer was dried over anhydrous $MgSO_4$, filtered, and concentrated in vacuo. Purification by silica gel column chromatography (eluent: hexane/EtOAc=3/1) provided 78 mg (78%) of desired aldehyde (36) as solid.

$^1$H NMR (400 MHz, $CDCl_3$) δ 10.65 (s, 1H), 7.46-7.45 (m, 1H), 7.38-7.31 (m, 4H), 7.36-7.23 (m, 2H), 1.52 (s, 9H).
MH+ 475.

Example 203

5-(4-bromophenyl)-3-(5-tert-butyl-1,3,4-oxadiazol-2-yl)-1-(2,4-dichlorophenyl)-1H-pyrazole-4-carbaldehyde $^1$H NMR (400 MHz, $CDCl_3$) δ 10.63 (s, 1H), 7.48-7.44 (m, 3H), 7.35-7.33 (m, 2H), 7.18-7.15 (m, 2H), 1.50 (s, 9H).
MH+ 519.

Example 204

5-(4-chlorophenyl)-3-(5-(1-(4-chlorophenyl)cyclopropyl)-1,3,4-oxadiazol-2-yl)-1-(2,4-dichlorophenyl)-1H-pyrazole-4-carbaldehyde $^1$H NMR (300 MHz, $CDCl_3$) δ 10.55 (s, 1H), 7.45-7.41 (m, 3H), 7.36-7.30 (m, 6H), 7.23 (d, J=8.6 Hz, 2H), 1.85-1.81 (m, 2H), 1.52-1.48 (m, 2H).
MH+ 571.

Example 205

2-tert-butyl-5-(5-(4-chlorophenyl)-1-(2,4-dichlorophenyl)-4-(methoxymethyl)-1H-pyrazol-3-yl)-1,3,4-oxadiazole To the suspension of alcohol (35) (120 mg, 0.251 mmol), NaH (20 mg, 60% dispersion in mineral oil) in DMF (5 mL) was stirred at room temperature. After 1 hr, the reaction mixture was added MeI (40 μL, 0.33 mmol) and stirred for 12 hrs. The reaction mixture was filtered off the white solid and then extracted with EtOAc (50 mL). The organic layer was dried over anhydrous $MgSO_4$, filtered, and concentrated in vacuo. Purification by silica gel column chromatography (eluent: hexane/EtOAc=4/1) provided 103 mg (84%) of desired ether (49) as solid.

$^1$H NMR (400 MHz, $CDCl_3$) δ 7.45-7.44 (m, 1H), 7.36-7.31 (m, 4H), 7.26-7.23 (m, 2H), 4.66 (s, 2H), 3.48 (s, 3H), 1.50 (s, 9H).
MH+ 491.

Example 206

2-(4-(butoxymethyl)-5-(4-chlorophenyl)-1-(2,4-dichlorophenyl)-1H-pyrazol-3-yl)-5-tert-butyl-1,3,4-oxadiazole $^1$H NMR (400 MHz, $CDCl_3$) δ 7.45-7.36 (m, 1H), 7.34-7.31 (m, 4H), 7.28-7.26 (m, 2H), 4.70 (s, 2H), 3.60 (t, J=6.4 Hz, 2H), 1.66-1.57 (m, 2H), 1.50 (s, 9H), 1.41-1.26 (m, 2H), 0.91 (t, J=7.6 Hz, 3H).
MH+ 533.

Example 207

1-(3-(5-tert-butyl-1,3,4-oxadiazol-2-yl)-5-(4-chlorophenyl)-1-(2,4-dichlorophenyl)-1H-pyrazol-4-yl)ethanol To the solution of aldehyde (36) (100 mg, 0.210 mmol) in THF (5 mL) was added methyl magnesium bromide (200 L, 3.0M solution in diethylether). The reaction mixture was stirred for 12 hrs at room temperature. $H_2O$ (20 mL) was added to the reaction mixture and then extracted with $CH_2Cl_2$ (50 mL). The organic layer was dried over anhydrous $MgSO_4$, filtered, and concentrated in vacuo. Purification by silica gel column chromatography (eluent: hexane/EtOAc=2/1) provided 83 mg (80%) of desired secondary alcohol (53) as solid.

$^1$H NMR (400 MHz, $CDCl_3$) δ 7.42-7.41 (m, 1H), 7.34-7.29 (m, 4H), 7.13-7.10 (m, 2H), 5.72 (d, J=11.6 Hz, 1H), 4.86-4.78 (m, 1H), 1.61 (d, J=7.2 Hz, 3H), 1.51 (s, 9H).
MH+ 491.

Example 208

1-(5-(4-bromophenyl)-3-(5-tert-butyl-1,3,4-oxadiazol-2-yl)-1-(2,4-dichlorophenyl)-1H-pyrazol-4-yl)ethanol $^1$H NMR (400 MHz, $CDCl_3$) δ 7.48-7.46 (m, 2H), 7.42-7.41 (m, 1H), 7.31-7.29 (m, 2H), 7.06-7.03 (m, 2H), 4.83-4.78 (m, 1H), 1.60-1.59 (m, 3H), 1.50 (s, 9H).
MH+ 535.

Example 209

1-(5-(4-chlorophenyl)-3-(5-(1-(4-chlorophenyl)cyclopropyl)-1,3,4-oxadiazol-2-yl)-1-(2,4-dichlorophenyl)-1H-pyrazol-4-yl)ethanol $^1$H NMR (400 MHz, $CDCl_3$) δ 7.43-7.40 (m, 3H), 7.35-7.29 (m, 6H), 7.09 (d, J=8.4 Hz, 2H), 4.78 (q, J=6.8 Hz, 1H), 1.85-1.77 (m, 2H), 1.56 (d, J=6.8 Hz, 3H), 1.51-1.46 (m, 2H).
MH+ 587.

Example 210

2-tert-butyl-5-(5-(4-chlorophenyl)-1-(2,4-dichlorophenyl)-4-(1-fluoroethyl)-1H-pyrazol-3-yl)-1,3,4-oxadiazole To the solution of secondary alcohol (53) (50 mg, 0.101 mmol) in $CH_2Cl_2$ (3 mL) in Falcon tube was added DAST (27 L, 0.202 mmol). The reaction mixture was stirred for 2 hrs at room temperature. Saturated $NaHCO_3$ (30 mL) was added to the reaction mixture. After 1 hr, the organic layer was dried over anhydrous $MgSO_4$, filtered, and concentrated in vacuo. Purification by silica gel column chromatography (eluent: hexane/EtOAc=2/1) provided 40 mg (80%) of desired product (58) as solid.

$^1$H NMR (400 MHz, $CDCl_3$) δ 7.42 (bs, 1H), 7.32-7.29 (m, 4H), 7.25-7.22 (m, 2H), 6.49 (q, J=6.8 Hz, 1H), 1.61 (d, J=6.4 Hz, 3H), 1.50 (s, 9H).
MH+ 493.

Example 211

2-(5-(4-bromophenyl)-1-(2,4-dichlorophenyl)-4-(1-fluoroethyl)-1H-pyrazol-3-yl)-5-tert-butyl-1,3,4-oxadiazole $^1$H NMR (400 MHz, CDCl$_3$) δ 7.48-7.46 (m, 2H), 7.41-7.40 (m, 1H), 7.31-7.30 (m, 2H), 7.05-7.03 (m, 2H), 4.82-4.80 (m, 1H), 1.60-1.58 (m, 3H), 1.50 (s, 9H).
MH+ 537.

Example 212

2-(5-(4-chlorophenyl)-1-(2,4-dichlorophenyl)-4-(1-fluoroethyl)-1H-pyrazol-3-yl)-5-(1-(4-chlorophenyl)cyclopropyl)-1,3,4-oxadiazole $^1$H NMR (400 MHz, CDCl$_3$) δ 7.45-7.41 (m, 3H), 7.36-7.30 (m, 6H), 7.22 (d, J=8.4 Hz, 2H), 6.43-6.27 (m, 1H), 1.82-1.80 (m, 2H), 1.58-1.51 (m, 3H), 1.49-1.47 (m, 2H).
MH+ 589.

Example 213

1-(3-(5-tert-butyl-1,3,4-oxadiazol-2-yl)-5-(4-chlorophenyl)-1-(2,4-dichlorophenyl)-1H-pyrazol-4-yl)ethanone To the solution of secondary alcohol (53) (150 mg, 0.305 mmol) and Dess-Martin periodinane (155 mg, 0.366 mmol) in CH$_2$Cl$_2$ (5 mL) was stirred at room temperature. The reaction mixture was filtered off the white solid and then diluted with CH$_2$Cl$_2$ (50 mL) and washed with brine. The organic layer was dried over anhydrous MgSO$_4$, filtered, and concentrated in vacuo. Purification by silica gel column chromatography (eluent: hexane/EtOAc=2/1) provided 117 mg (78%) of desired ketone (57) as solid.

$^1$H NMR (400 MHz, CDCl$_3$) δ 7.44-7.43 (m, 1H), 7.35-7.30 (m, 4H), 7.23-7.19 (m, 2H), 2.40 (s, 3H), 1.50 (s, 9H).
MH+ 489.

Example 214

1-(5-(4-bromophenyl)-3-(5-tert-butyl-1,3,4-oxadiazol-2-yl)-1-(2,4-dichlorophenyl)-1H-pyrazol-4-yl)ethanone $^1$H NMR (400 MHz, CDCl$_3$) δ 7.48-7.45 (m, 2H), 7.43-7.42 (m, 1H), 7.32-7.31 (m, 2H), 7.15-7.11 (m, 2H), 2.39 (s, 3H), 1.49 (s, 9H).
MH+ 533.

Example 215

1-(5-(4-chlorophenyl)-3-(5-(1-(4-chlorophenyl)cyclopropyl)-1,3,4-oxadiazol-2-yl)-1-(2,4-dichlorophenyl)-1H-pyrazol-4-yl)ethanone $^1$H NMR (400 MHz, CDCl$_3$) δ 7.36-7.34 (m, 3H), 7.28-7.23 (m, 6H), 7.12 (d, J=8.8 Hz, 2H), 2.25 (s, 3H), 1.76-1.73 (m, 2H), 1.43-1.40 (m, 2H).
MH+ 585.

Example 216

3-(5-tert-butyl-1,3,4-oxadiazol-2-yl)-5-(4-chlorophenyl)-1-(2,4-dichlorophenyl)-1H-pyrazol-4-yl acetate To the solution of ketone (57) (65 mg, 0.132 mmol) and 3-chloroperoxybenzoic acid (77% max) (66 mg) in CH$_2$Cl$_2$ (10 mL) was stirred at rt. The reaction mixture was diluted with CH$_2$Cl$_2$ (50 mL) and washed with brine. The organic layer was dried over anhydrous MgSO$_4$, filtered, and concentrated in vacuo. Purification by silica gel column chromatography (eluent: hexane/EtOAc=5/1) provided 42 mg (63%) of desired acetate as solid.

$^1$H NMR (400 MHz, CDCl$_3$) δ 7.49 (d, J=8.4 Hz, 1H), 7.45 (d, J=2.0 Hz, 1H), 7.39-7.36 (m, 1H), 7.33-7.29 (m, 2H), 7.16-7.12 (m, 2H), 2.37 (s, 3H), 1.48 (s, 9H).
MH+ 505.

Example 217

2-(3-(5-tert-butyl-1,3,4-oxadiazol-2-yl)-5-(4-chlorophenyl)-1-(2,4-dichlorophenyl)-1H-pyrazol-4-yl)propan-2-ol To the solution of ketone (57) (40 mg, 0.082 mmol) in THF (5 mL) was added methyl magnesium bromide (100 L, 3.0M solution in diethylether). The reaction mixture was stirred for 12 hrs at room temperature. H$_2$O (20 mL) was added to the reaction mixture and then extracted with CH$_2$Cl$_2$ (50 mL). The organic layer was dried over anhydrous MgSO$_4$, filtered, and concentrated in vacuo. Purification by silica gel column chromatography (eluent: hexane/EtOAc=2/1) provided 33 mg (80%) of desired tertiary alcohol (59) as solid.

$^1$H NMR (400 MHz, CDCl$_3$) δ 7.39-7.38 (m, 1H), 7.29-7.17 (m, 6H), 6.77 (s, 1H), 1.51 (s, 9H), 1.42 (s, 6H).
MH+ 505.

Example 218

2-(5-(4-bromophenyl)-3-(5-tert-butyl-1,3,4-oxadiazol-2-yl)-1-(2,4-dichlorophenyl)-1H-pyrazol-4-yl)propan-2-ol $^1$H NMR (400 MHz, CDCl$_3$) δ 7.44-7.41 (m, 2H), 7.38 (d, J=2.0 Hz, 1H), 7.21 (dd, J=8.4 Hz, J=2.0 Hz, 1H), 7.17 (d, J=8.4 Hz, 1H), 7.11-7.09 (m, 2H), 1.50 (s, 9H), 1.41 (s, 6H).
(MH+ —H$_2$O) 531.

Example 219

2-tert-butyl-5-(5-(4-chlorophenyl)-1-(2,4-dichlorophenyl)-4-(prop-1-en-2-yl)-1H-pyrazol-3-yl)-1,3,4-oxadiazole To the solution of tertiary alcohol (59) (52 mg, 0.103 mmol) and Burgess reagent (50 mg, 0.206 mmol) in THF (5 mL) was irradiated in a microwave reactor (Biotage) for 10 minutes at 150° C. The organic layer was washed with brine and dried over anhydrous MgSO$_4$, filtered, and concentrated in vacuo. Purification by silica gel column chromatography (eluent: hexane/EtOAc=4/1) provided 49 mg (98%) of desired product (60) as solid.

$^1$H NMR (400 MHz, CDCl$_3$) δ 7.42 (d, J=2.4 Hz, 1H), 7.39 (d, J=8.4 Hz, 1H), 7.32 (dd, J=8.4, 2.4 Hz, 1H), 7.28-7.26 (m, 2H), 7.14-7.10 (m, 2H), 5.28-5.27 (m, 1H), 4.99-4.98 (m, 1H), 2.02 (s, 3H), 1.48 (s, 9H).
MH+ 487.

Example 220

2-(5-(4-bromophenyl)-1-(2,4-dichlorophenyl)-4-(prop-1-en-2-yl)-1H-pyrazol-3-yl)-5-tert-butyl-1,3,4-oxadiazole $^1$H NMR (400 MHz, CDCl$_3$) δ 7.43-7.37 (m, 3H), 7.39 (d, J=8.4 Hz, 1H), 7.31 (dd, J=8.4 Hz, J=2.4 Hz, 1H), 7.06-7.03 (m, 2H), 5.27-5.26 (m, 1H), 4.98-4.97 (m, 1H), 2.01 (s, 3H), 1.47 (s, 9H).
MH+ 531.

Example 221

2-tert-butyl-5-(5-(4-chlorophenyl)-1-(2,4-dichlorophenyl)-4-(fluoromethyl)-1H-pyrazol-3-yl)-1,3,4-oxadiazole To the solution of alcohol (35) (200 mg, 0.418 mmol) in CH$_2$Cl$_2$ (5 mL) in Falcon tube was added (diethylamino)sulfur trifluoride (DAST, 110 L, 0.836 mmol). The reaction mixture was stirred for 2 hrs at room temperature. Saturated NaHCO$_3$ (30 mL) was added to the reaction mixture. After 1 hr, the organic extract was dried over anhydrous MgSO$_4$, filtered, and concentrated in vacuo. Purification by silica gel column chromatography (eluent: hexane/EtOAc=4/1) provided 106 mg (53%) of desired fluoride (50) as solid.

$^1$H NMR (400 MHz, CDCl$_3$) δ 7.47-7.46 (m, 1H), 7.38-7.32 (m, 4H), 7.24-7.20 (m, 2H), 5.67 (d, J=48.8 Hz, 2H), 1.50 (s, 9H).
MH+ 479.

Example 222

2-(5-(4-bromophenyl)-1-(2,4-dichlorophenyl)-4-(fluoromethyl)-1H-pyrazol-3-yl)-5-tert-butyl-1,3,4-oxadiazole $^1$H NMR (400 MHz, CDCl$_3$) δ 7.51-7.49 (m, 2H), 7.45-7.44 (m, 1H), 7.38-7.32 (m, 2H), 7.15-7.13 (m, 2H), 5.65 (d, J=48.8 Hz, 2H), 1.48 (s, 9H).
MH+ 523.

Example 223

2-(5-(4-chlorophenyl)-1-(2,4-dichlorophenyl)-4-(fluoromethyl)-1H-pyrazol-3-yl)-5-(1-(4-chlorophenyl)cyclopropyl)-1,3,4-oxadiazole $^1$H NMR (300 MHz, CDCl$_3$) δ 7.45-7.39 (m, 3H), 7.36-7.31 (m, 6H), 7.20 (d, J=8.5 Hz, 2H), 5.67 (s, 1H), 5.51 (s, 1H), 1.82-1.78 (m, 2H), 1.49-1.45 (m, 2H).
MH+ 575.

Example 224

2-tert-butyl-5-(5-(4-chlorophenyl)-1-(2,4-dichlorophenyl)-4-(difluoromethyl)-1H-pyrazol-3-yl)-1,3,4-oxadiazole To the solution of aldehyde (36) (50 mg, 0.105 mmol) in CH$_2$Cl$_2$ (5 mL) in Falcon tube was added (diethylamino)sulfur trifluoride (DAST, 30 L, 0.210 mmol). The reaction mixture was stirred for 2 hrs at room temperature. Saturated NaHCO$_3$ (30 mL) was added to the reaction mixture. After 1 hr, the organic extract was dried over anhydrous MgSO$_4$, filtered, and concentrated in vacuo. Purification by silica gel column chromatography (eluent: hexane/EtOAc=4/1) provided 25 mg (48%) of desired difluoride (52) as solid.

$^1$H NMR (400 MHz, CDCl$_3$) δ 7.56 (d, J=53.6 Hz, 1H), 7.45-7.44 (m, 1H), 7.37-7.30 (m, 4H), 7.27-7.24 (m, 2H), 1.50 (s, 9H).
MH+ 497.

Example 225

2-(5-(4-chlorophenyl)-1-(2,4-dichlorophenyl)-4-(difluoromethyl)-1H-pyrazol-3-yl)-5-(1-(4-chlorophenyl)cyclopropyl)-1,3,4-oxadiazole $^1$H NMR (400 MHz, CDCl$_3$) δ 7.45-7.41 (m, 3H), 7.36-7.31 (m, 7H), 7.25 (d, J=8.8 Hz, 2H), 1.83-1.80 (m, 2H), 1.51-1.48 (m, 2H).
MH+ 593.

Example 226

2-tert-butyl-5-(5-(4-chlorophenyl)-1-(2,4-dichlorophenyl)-4-(1-methoxyethyl)-1H-pyrazol-3-yl)-1,3,4-oxadiazole To the suspension of secondary alcohol (53) (50 mg, 0.101 mmol), NaH (25 mg, 60% dispersion in mineral oil) in DMF (5 mL) was stirred at room temperature. After 1 hr, the reaction mixture was added MeI (20 μL, 0.33 mmol) and stirred for 12 hrs. The reaction mixture was filtered off the white solid and then extracted with EtOAc (50 mL). The organic extract was dried over anhydrous MgSO$_4$, filtered, and concentrated in vacuo. Purification by silica gel column chromatography (eluent: Hexane/EtOAc=2/1) provided 42 mg (82%) of desired product (54) as solid.

$^1$H NMR (400 MHz, CDCl$_3$) δ 7.41-7.40 (m, 1H), 7.30-7.22 (m, 6H), 5.27 (q, J=6.4 Hz, 1H), 3.27 (s, 3H), 1.50 (s, 9H), 1.39 (d, J=6.8 Hz, 3H).
MH+ 505.

Example 227

2-tert-butyl-5-(5-(4-chlorophenyl)-1-(2,4-dichlorophenyl)-4-vinyl-1H-pyrazol-3-yl)-1,3,4-oxadiazole To the solution of secondary alcohol (53) (50 mg, 0.093 mmol) and Burgess reagent (45 mg, 0.186 mmol) in THF (5 mL) was irradiated in a microwave reactor (Biotage) for 10 minutes at 150° C. The organic extract was dried over anhydrous MgSO$_4$, filtered, and concentrated in vacuo. Purification by silica gel column chromatography (eluent: hexane/EtOAc=4/1) provided 15 mg (55, 31%) and 16 mg (56, 29%) as solid.

$^1$H NMR (400 MHz, CDCl$_3$) δ 7.42-7.41 (m, 1H), 7.34-7.28 (m, 4H), 7.20-7.18 (m, 2H), 7.12-7.04 (m, 1H), 5.41 (dd, J=18.0, 1.2 Hz, 1H), 5.25 (dd, J=11.6, 1.2 Hz, 1H), 1.50 (s, 9H).
MH+ 473.

Example 228

2-(5-(4-bromophenyl)-1-(2,4-dichlorophenyl)-4-vinyl-1H-pyrazol-3-yl)-5-tert-butyl-1,3,4-oxadiazole $^1$H NMR (400 MHz, CDCl$_3$) δ 7.48-7.44 (m, 2H), 7.42-7.40 (m, 1H), 7.33 (d, J=8.4 Hz, 1H), 7.29 (dd, J=8.4 Hz, J=2.4 Hz, 1H), 7.13-7.09 (m, 2H), 7.07-7.02 (m, 1H), 5.40 (dd, J=18.0, 1.2 Hz, 1H), 5.13 (dd, J=11.6, 1.2 Hz, 1H), 1.49 (s, 9H).
MH+ 517.

Example 229

2-(5-(4-chlorophenyl)-1-(2,4-dichlorophenyl)-4-vinyl-1H-pyrazol-3-yl)-5-(1-(4-chlorophenyl)cyclopropyl)-1,3,4-oxadiazole $^1$H NMR (400 MHz, CDCl$_3$) δ 7.42-7.39 (m, 3H), 7.38-7.23 (m, 6H), 7.16 (d, J=8.8 Hz, 2H), 7.01-6.84 (m, 1H), 5.39 (d, J=18 Hz, 1H), 5.22 (d, J=12 Hz, 1H), 1.81-1.77 (m, 2H), 1.50-1.42 (m, 2H).
MH+ 569.

Example 230

Methyl 1-(5-(4-bromophenyl)-3-(5-tert-butyl-1,3,4-oxadiazol-2-yl)-1-(2,4-dichlorophenyl)-1H-pyrazol-4-yl)ethylcarbamate $^1$H NMR (400 MHz, CDCl$_3$) δ 7.51-7.49 (m, 2H), 7.47-7.44 (m, 1H), 7.41-7.40 (m, 1H), 7.31-7.29 (m, 2H), 7.23-7.21 (m, 1H), 5.10-4.90 (m, 1H), 3.62 (s, 3H), 1.54 (s, 3H), 1.50 (s, 9H).
MH+ 592.

Example 231

Methyl 1-(5-(4-chlorophenyl)-3-(5-(1-(4-chlorophenyl)cyclopropyl)-1,3,4-oxadiazol-2-yl)-1-(2,4-dichlorophenyl)-1H-pyrazol-4-yl)ethylcarbamate $^1$H NMR (400 MHz, CDCl$_3$) δ 7.44-7.40 (m, 3H), 7.36-7.33 (m, 4H), 7.31-7.27 (m, 4H), 5.0-4.94 (m, 1H), 3.60 (s, 3H), 1.85-1.74 (m, 2H), 1.50-1.40 (m, 4H).
MH+ 644.

Example 232

Methyl (3-(5-tert-butyl-1,3,4-oxadiazol-2-yl)-5-(4-chlorophenyl)-1-(2,4-dichlorophenyl)-1H-pyrazol-4-yl)methylcarbamate $^1$H NMR (400 MHz, CDCl$_3$) δ 7.44-7.41 (m, 1H), 7.38-7.27 (m, 6H), 6.86-6.78 (m, 1H), 4.41 (d, J=6.8 Hz, 2H), 3.60 (s, 3H), 1.50 (s, 9H).
MH+ 536.

Example 233

2-tert-butyl-5-(5-(4-chlorophenyl)-1-(2,4-dichlorophenyl)-4-(phenoxymethyl)-1H-pyrazol-3-yl)-1,3,4-oxadiazole To the solution of bromide (33) (150 mg, 0.277 mmol) in DMF (5 mL) was added phenol (40 mg, 0.415 mmol), Cs$_2$CO$_3$ (202 mg, 0.622 mmol). The reaction mixture was refluxed for 12 hrs at room temperature. Reaction mixture was filtered off the white solid and then extracted with EtOAc (50 mL). The organic extract was dried over anhydrous MgSO$_4$, filtered, and concentrated in vacuo. Purification by silica gel column chromatography (eluent: hexane/EtOAc=5/1) provided 86 mg (56%) of desired ether (45) as solid.

$^1$H NMR (400 MHz, CDCl$_3$) δ 7.45 (d, J=2.0 Hz, 1H), 7.39 (d, J=8.4 Hz, 1H), 7.33 (dd, J=8.4, 2.0 Hz, 1H), 7.30-7.22 (m, 6H), 6.97-6.95 (m, 3H), 5.27 (s, 2H), 1.44 (s, 9H).
MH+ 553.

Example 234

2-tert-butyl-5-(5-(4-chlorophenyl)-1-(2,4-dichlorophenyl)-4-((pyridin-2-yloxy)methyl)-1H-pyrazol-3-yl)-1,3,4-oxadiazole $^1$H NMR (400 MHz, CDCl$_3$) δ 8.11-8.09 (m, 1H), 7.56-7.53 (m, 1H), 7.44-7.41 (m, 2H), 7.34-7.32 (m, 1H), 7.28-7.19 (m, 4H), 6.88-6.86 (m, 1H), 6.73-6.71 (m, 1H), 5.52 (s, 2H), 1.52 (s, 9H).
MH+ 554.

Example 235

2-(5-(4-chlorophenyl)-1-(2,4-dichlorophenyl)-4-methyl-1H-pyrazol-3-yl)-5-(2-propoxypropan-2-yl)-1,3,4-oxadiazole $^1$H NMR (400 MHz, CDCl$_3$) δ 7.42-7.30 (m, 5H), 7.14-7.08 (m, 2H), 3.29 (t, J=6.6 Hz, 2H), 2.45 (s, 3H), 1.74 (s, 6H), 1.53 (m, 2H), 0.87 (t, J=7.2 Hz, 3H).
MH+ 505.

Example 236

2-(1-(benzyloxy)pentyl)-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.42 (br d, J=2.0 Hz, 2H), 7.39-7.26 (m, 9H), 7.14-7.10 (m, 2H), 4.75 (dd, J=6.0, 8.0 Hz, 1H), 4.66 (d, J=11.6 Hz, 1H), 4.49 (d, J=11.6 Hz, 1H), 2.46 (s, 3H), 2.09 (m, 1H), 1.97 (m, 1H), 1.48 (m, 1H), 1.31 (m, 3H), 0.87 (t, J=7.2 Hz, 3H).
MH+ 581.

Example 237

2-(2-(allyloxy)propan-2-yl)-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.42 (br d, J=2.0 Hz, 1H), 7.40-7.31 (m, 4H), 7.13-7.10 (m, 2H), 5.86 (m, 1H), 5.26 (br d, J=17.2 Hz, 1H), 5.10 (br d, J=10.4 Hz, 1H), 3.92 (dt, J=5.2, 1.6 Hz, 2H), 2.45 (s, 3H), 1.77 (s, 6H).
MH+ 503.

Example 238

2-(2-(allyloxy)propan-2-yl)-5-(5-(4-bromophenyl)-1-(2,4-dichlorophenyl)-4-ethyl-1H-pyrazol-3-yl)-1,3,4-oxadiazole $^1$H NMR (400 MHz, CDCl$_3$) δ 7.43-7.22 (m, 5H), 7.01-6.98 (m, 2H), 5.79 (m, 1H), 5.17 (dd, J=17.2, 1.4 Hz, 1H), 5.03 (dd, J=10.4, 1.4 Hz, 1H), 3.86 (d, J=6.8 Hz, 2H), 2.78 (q, J=7.6 Hz, 2H), 1.70 (s, 6H), 1.16 (t, J=7.6 Hz, 3H).
MH+ 561.

Example 239

2-(2-(allyloxy)propan-2-yl)-5-(5-(4-chlorophenyl)-1-(2,4-dichlorophenyl)-4-ethyl-1H-pyrazol-3-yl)-1,3,4-oxadiazole $^1$H NMR (400 MHz, CDCl$_3$) δ 7.35-7.22 (m, 5H), 7.08-7.04 (m, 2H), 5.79 (m, 1H), 5.17 (dd, J=17.2, 1.4 Hz, 1H), 5.03 (dd, J=10.4, 1.4 Hz, 1H), 3.86 (d, J=6.8 Hz, 2H), 2.78 (q, J=7.6 Hz, 2H), 1.70 (s, 6H), 1.16 (t, J=7.6 Hz, 3H).
MH+ 517.

Example 240

3-(2-(5-(5-(4-bromophenyl)-1-(2,4-dichlorophenyl)-4-ethyl-1H-pyrazol-3-yl)-1,3,4-oxadiazol-2-yl)propan-2-yloxy)propan-1-ol

MH+ 580.

Example 241

1-(5-(5-(4-chlorophenyl)-1-(2,4-dichlorophenyl)-4-methyl-1H-pyrazol-3-yl)-1,3,4-oxadiazol-2-yl)pentan-1-ol $^1$H NMR (400 MHz, CDCl$_3$) δ 7.42-7.26 (m, 5H), 7.14-7.10 (m, 2H), 4.75 (dd, J=6.0, 8.0 Hz, 1H), 2.46 (s, 3H), 2.09 (m, 1H), 1.97 (m, 1H), 1.48 (m, 1H), 1.31 (m, 3H), 0.87 (t, J=7.2 Hz, 3H).
MH+ 491.

Example 242

((1R,2S)-2-(5-(5-(4-chlorophenyl)-1-(2,4-dichlorophenyl)-4-methyl-1H-pyrazol-3-yl)-1,3,4-oxadiazol-2-yl)cyclopropyl)(piperidin-1-yl)methanone

MH+ 556.

Example 243

2-(2-butoxypropan-2-yl)-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.40 (br d, J=2.0 Hz), 7.37-7.29 (m, 4H), 7.12-7.09 (m, 2H), 3.31 (t, J=6.8 Hz, 2H), 2.43 (s, 3H), 1.72 (s, 6H), 1.49 (m, 2H), 1.31 (m, 2H), 0.84 (t, J=7.2 Hz, 3H).
MH+ 519.

Example 244

2-(5-(4-chlorophenyl)-1-(2,4-dichlorophenyl)-4-methyl-1H-pyrazol-3-yl)-5-(2-(pentyloxy)propan-2-yl)-1,3,4-oxadiazole $^1$H NMR (400 MHz, CDCl$_3$) δ 7.40 (br d, J=2.0 Hz, 1H), 7.38-7.30 (m, 4H), 7.10 (m, 2H), 3.30 (t, J=6.8 Hz, 2H), 2.44 (s, 3H), 1.72 (s, 6H), 1.50 (m, 2H), 1.25 (m, 4H), 0.83 (t, J=5.2 Hz, 3H).
MH+ 533.

Example 245

2-(2-(benzyloxy)propan-2-yl)-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.42 (br d, J=2.0 Hz, 1H), 7.37-7.20 (m, 9H), 7.10 (m, 2H), 4.43 (s, 2H), 2.43 (s, 3H), 1.83 (s, 6H).
MH+ 553.

Example 246

2-(5-(5-(4-chlorophenyl)-1-(2,4-dichlorophenyl)-4-methyl-1H-pyrazol-3-yl)-1,3,4-oxadiazol-2-yl)propan-2-yl acetate $^1$H NMR (400 MHz, CDCl$_3$) δ 7.42-7.30 (s, 5H), 7.12-7.09 (m, 2H), 2.44 (s, 3H), 2.09 (s, 3H), 1.90 (s, 6H).
MH+ 505.

Example 247

2-(5-(5-(4-chlorophenyl)-1-(2,4-dichlorophenyl)-4-methyl-1H-pyrazol-3-yl)-1,3,4-oxadiazol-2-yl)propan-2-ol $^1$H NMR (400 MHz, CDCl$_3$) δ 7.43-7.31 (m, 5H), 7.13-7.10 (m, 2H), 2.45 (s, 3H), 1.77 (s, 6H).
MH+ 463.

Example 248

2-(5-(4-Chlorophenyl)-1-(2,4-dichlorophenyl)-4-methyl-1H-pyrazol-3-yl)-5-(2-(2-fluoro benzyloxy)propan-2-yl)-1,3,4-oxadiazole $^1$H NMR (400 MHz, CDCl$_3$) δ 7.46-7.18 (m, 7H), 7.12-6.94 (m, 4H), 4.51 (s, 2H), 2.43 (s, 3H), 1.83 (s, 6H).
MH+ 571.

Example 249

2-(2-(3-Chlorobenzyloxy)propan-2-yl)-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.42-7.22 (m, 6H), 7.20-7.09 (m, 5H), 4.42 (s, 2H), 2.43 (s, 3H), 1.82 (s, 6H).
MH+ 587.

Example 250

Ethyl 5-(5-(4-chlorophenyl)-1-(2,4-dichlorophenyl)-4-methyl-1H-pyrazol-3-yl)-1,3,4-oxadiazole-2-carboxylate $^1$H NMR (400 MHz, CDCl$_3$) δ 7.42 (d, J=2.0 Hz, 1H), 7.36-7.30 (m, 4H), 7.11 (m, 2H), 4.53 (q, J=7.2 Hz, 2H), 2.47 (s, 3H), 1.45 (t, J=7.2 Hz, 3H).
MH+ 477.

Example 251

2-(5-(4-chlorophenyl)-1-(2,4-dichlorophenyl)-4-methyl-1H-pyrazol-3-yl)-5-(2,2,2-trifluoro-1-methoxy-1-phenylethyl)-1,3,4-oxadiazole $^1$H NMR (400 MHz, CDCl$_3$) δ 7.58 (m, 2H), 7.44-7.29 (m, 8H), 7.10 (m, 2H), 3.49 (s, 3H), 2.44 (s, 3H).
MH+ 593.

Example 252

2-(5-(5-(4-chlorophenyl)-1-(2,4-dichlorophenyl)-4-methyl-1H-pyrazol-3-yl)-1,3,4-oxadiazol-2-yl)-2-methylpropyl acetate $^1$H NMR (400 MHz, CDCl$_3$) δ 7.42-7.31 (m, 5H), 7.12-7.10 (m, 2H), 4.32 (s, 2H), 2.44 (s, 3H), 1.52 (s, 6H).
MH+ 519.

Example 253

2-(5-(5-(4-chlorophenyl)-1-(2,4-dichlorophenyl)-4-methyl-1H-pyrazol-3-yl)-1,3,4-oxadiazol-2-yl)-2-methylpropan-1-ol $^1$H NMR (400 MHz, CDCl$_3$) δ 7.44-7.32 (m, 5H), 7.14-7.13 (m, 2H), 3.85 (s, 2H), 2.45 (s, 3H), 1.47 (s, 6H).
MH+ 477.

Example 254

2-(1-(Benzyloxy)-2-methylpropan-2-yl)-5-(5-(4-chlorophenyl)-1-(2,4-dichlorophenyl)-4-methyl-1H-pyrazol-3-yl)-1,3,4-oxadiazole $^1$H NMR (300 MHz, CDCl$_3$) δ 7.43-7.23 (m, 9H), 7.17-7.04 (m, 3H), 5.11 (s, 2H), 3.93 (s, 2H), 2.12 (s, 3H), 1.21 (s, 6H).
MH+ 567.

Example 255

2-(5-(4-Chlorophenyl)-1-(2,4-dichlorophenyl)-4-methyl-1H-pyrazol-3-yl)-5-(2-methyl-1-(4-(trifluoromethyl)benzyloxy)propan-2-yl)-1,3,4-oxadiazole $^1$H NMR (400 MHz, CDCl$_3$) δ 7.59-7.31 (m, 9H), 7.13-7.10 (m, 2H), 4.58 (s, 2H), 3.70 (s, 2H), 2.42 (s, 3H), 1.53 (s, 6H).
MH+ 635.

Example 256

2-(1-(4-Chlorobenzyloxy)-2-methylpropan-2-yl)-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.44-7.32 (m, 5H), 7.24-7.11 (m, 6H), 4.48 (s, 2H), 3.60 (s, 2H), 2.42 (s, 3H), 1.51 (s, 6H).
MH+ 601.

Example 257

2-(5-(4-chlorophenyl)-1-(2,4-dichlorophenyl)-4-methyl-1H-pyrazol-3-yl)-5-(1-(3-chlorophenyl)cyclopropyl)-1,3,4-oxadiazole Step 1: 2-(3-chlorophenyl)acetonitrile The experimental procedure was followed by the method of Bruno P. Imbimbo et al [*J. Med. Chem.* 2005, 48, 5707-7520]. A solution of 3-chlorobenzylbromide (5 g, 24.3 mmol) and sodium cyanide (1.3 g, 26.8 mmol) in ethanol (50 ml) was heated to 80° C. for 2 hours. After resulting solution was cooled to room temperature and concentrated under reduced pressure. The residue was suspended in water and organic layer was extracted with ethyl acetate. The solution was evaporated and crude compound was purified by silica gel column chromatography (hexane/ethyl acetate=5/1) to yield 2-(3-chlorophenyl)acetonitrile (3.2 g, 87% yield) as colorless oil.

$^1$H NMR (400 MHz, CDCl$_3$) δ 7.36-7.32 (m, 1H), 7.20-7.17 (m, 3H), 7.06-7.04 (m, 1H), 3.68 (s, 2H).

Step 2: 1-(3-chlorophenyl)cyclopropanecarbonitrile

To a solution of 2-(3-chlorophenyl)acetonitrile (3.2 g, 21 mmol) and 1,2-dibromoethane (3 mL, 35 mmol) in toluene (20 ml), 35% sodium hydroxide and tetrabutylammonium iodide (400 mg, 1.3 mmol) were added. The mixture was vigorously stirred at room temperature for 4 hours. The resulting solution was diluted with water and extracted with ethyl acetate. The organic solution was concentrated to afford brown oil. Chromatography on silica gel (hexane/ethyl acetate=5/1) afforded 1-(3-chlorophenyl)cyclopropanecarbonitrile (2.1 g, 56% yield) as light yellow oil.

$^1$H NMR (400 MHz, CDCl$_3$) δ 7.38-7.34 (m, 1H), 7.21-7.18 (m, 3H), 7.07-7.03 (m, 1H), 0.98-0.96 (m, 2H), 0.74-0.72 (m, 2H).

Step 3: 1-(3-chlorophenyl)cyclopropanecarboxylic Acid

To a solution of 1-(3-chlorophenyl)cyclopropanecarbonitrile (2.1 g, 11.8 mmol) in methanol (10 ml), 35% NaOH (40 ml) was added and the mixture was heated to 100° C. for 8 hours. After cooling to room temperature, the resulting solution was evaporated under reduced pressure. And the aqueous layer was washed with ethyl ether, acidified with 2N HCl, and extracted organic layer with ethyl acetate. The organic solution was dried over magnesium sulfate, evaporated volatile solvent and dried under vacuum to obtain 1-(3-chlorophenyl) cyclopropanecarboxylic acid (1.8 g, 77% yield) as white solid.

Step 4: 2-(5-(4-chlorophenyl)-1-(2,4-dichlorophenyl)-4-methyl-1H-pyrazol-3-yl)-5-(1-(3-chlorophenyl)cyclopropyl)-1,3,4-oxadiazole $^1$H NMR (400 MHz, CDCl$_3$) δ 7.55-7.48 (m, 4H), 7.33-7.31 (m, 2H), 7.25-7.17 (m, 3H), 7.14-7.11 (m, 3H), 2.35 (s, 3H), 1.86-1.84 (m, 2H), 1.34-1.29 (m, 2H).
MH+ 555.

Example 258

2-(5-(4-chlorophenyl)-1-(2,4-dichlorophenyl)-4-ethyl-1H-pyrazol-3-yl)-5-(1-(3-chlorophenyl)cyclopropyl)-1,3,4-oxadiazole $^1$H NMR (400 MHz, CDCl$_3$) δ 7.56-7.48 (m, 4H), 7.33-7.32 (m, 2H), 7.25-7.19 (m, 3H), 7.13-7.10 (m, 3H), 2.85 (q, J=7.6 Hz, 2H), 1.23 (t, J=7.6 Hz, 3H).

MH+ 569.

Example 259

2-(1-allylcyclopropyl)-5-(5-(4-bromophenyl)-1-(2,4-dichlorophenyl)-4-ethyl-1H-pyrazol-3-yl)-1,3,4-oxadiazole

Step 1: 1-allylcyclopropanecarboxylic Acid

The experimental procedure was followed by the method of Henryk Krawczyk et al [*Synlett* 2005, 17, 2648-2652]. A solution of -diethoxyphosphoryl-lactone (5 g, 22.5 mmol) in THF (10 ml) was added dropwise under nitrogen atmosphere at −78° C. to a stirred solution of LDA (13.7 ml, 1.8 M in tetrahydrofuran/heptane/ethylbenzene, 24.8 mmol). When the addition was completed the reaction mixture was warmed to 0° C. and stirred for 30 minutes. The reaction mixture was cooled down to −78° C. and ally bromide (2.45 ml, 18.7 mmol) was added. The stirring was continued for 1 hour at this temperature and then the reaction mixture was warmed to room temperature and stirred for overnight. The mixture was quenched and acidified using 1N HCl solution and extracted with methylenechloride (30 ml twice). The crude products was purified by column chromatography (silica gel, acetone/methylenechloride=1/5) to produce diethyl 3-allyl-2-oxotetrahydrofuran-3-ylphosphonate (4.5 g, 76%) as colorless oil.

$^1$H NMR (400 MHz, CDCl$_3$) δ 5.71-5.70 (m, 1H), 5.03-4.97 (m, 2H), 4.35-4.25 (m, 2H), 4.08-4.06 (m, 6H), 2.40-2.38 (m, 1H), 2.32-2.30 (m, 2H), 1.97-1.95 (m, 1H), 1.13-1.10 (m, 9H).

Step 2

To a suspension of sodium hydride (686 mg, 60% in mineral oil, 17.2 mmol) and diethyl 3-allyl-2-oxotetrahydrofuran-3-ylphosphonate (4.5 g, 17.2 mmol) in THF (15 ml) was added dropwise under nitrogen atmosphere at room temperature a solution of ethanol (1.1 ml, 18.9 mmol) in THF (5 ml). The reaction mixture was stirred for 30 minutes and then was heated at reflux for 10 hours. After cooling to room temperature saturated ammonium chloride was added and extracted organic layer with ethyl ether. The residue was dried with magnesium sulfate. Without further purification, the ester was hydrolyzed with sodium hydroxide (1.4 g, 34 mmol) in aqueous acetonitrile (20 ml) at 60° C. for overnight. The reaction mixture was cooled down to room temperature. After acidification of the resulting solution with 1H HCl, organic layer was extracted with ethyl ether. The solution was dried with magnesium sulfate, and then it was evaporated under reduced pressure. Product was dried under vacuum to produce crude title compound (1.4 g, 65% yield) as light yellow oil.

Step 3: 2-(1-allylcyclopropyl)-5-(5-(4-bromophenyl)-1-(2,4-dichlorophenyl)-4-ethyl-1H-pyrazol-3-yl)-1,3,4-oxadiazole $^1$H NMR (400 MHz, CDCl$_3$) δ 7.57-7.47 (m, 4H), 7.34-7.32 (m, 2H), 7.26-7.19 (m, 3H), 7.14-7.10 (m, 3H), 5.71-5.68 (m, 1H), 5.03-4.97 (m, 2H), 2.85 (q, J=7.6 Hz, 2H), 2.23-2.20 (m, 2H), 1.23 (t, J=7.6 Hz, 3H), 0.84 (dd, J=4.4, 6.8 Hz, 2H), 0.43 (dd, J=4.4.68 Hz, 2H).

MH+ 543.

Example 260

2-tert-butyl-5-(5-(4-chlorophenyl)-1-(2,4-dichlorophenyl)-4-ethynyl-1H-pyrazol-3-yl)-1,3,4-oxadiazole

Step 1: 2-tert-butyl-5-(5-(4-chlorophenyl)-4-(2,2-dibromovinyl)-1-(2,4-dichlorophenyl)-1H-pyrazol-3-yl)-1,3,4-oxadiazole (74)

To a solution of carbontetrabromide (313 mg, 0.94 mmol) in methylene chloride (15 ml) at 0° C. was added triphenylphosphine (248 mg, 0.95 mmol). The reaction mixture was stirred at 0° C. for 10 minutes and then 3-(5-tert-butyl-1,3,4-oxadiazol-2-yl)-5-(4-chlorophenyl)-1-(2,4-dichlorophenyl)-1H-pyrazole-4-carbaldehyde (300 mg, 0.63 mmol) in methylenechloride (10 ml) was added slowly. The reaction temperature was warmed slowly to room temperature and stirred overnight. The resulting solution was quenched with saturated ammonium chloride and extracted organic layer with ethyl ether (50 ml twice). After evaporation, crude residue was purified with silica gel column (hexane/ethyl acetate=5/1) to recover starting material (110 mg, 37%) and produce 2-tert-butyl-5-(5-(4-chlorophenyl)-4-(2,2-dibromovinyl)-1-(2,4-dichlorophenyl)-1H-pyrazol-3-yl)-1,3,4-oxadiazole (230 mg, 58% yield) as white solid.

$^1$H NMR (400 MHz, CDCl$_3$) δ 7.51-7.48 (m, 1H), 7.47 (s, 1H), 7.36-7.32 (m, 2H), 7.30-7.28 (m, 1H), 7.18 (d, J=8.68 Hz, 1H), 7.14-7.10 (m, 2H), 1.34 (s, 9H).

MH+ 631.

Step 2: 2-tert-butyl-5-(5-(4-chlorophenyl)-1-(2,4-dichlorophenyl)-4-ethynyl-1H-pyrazol-3-yl)-1,3,4-oxadiazole (75)

To a solution of 2-tert-butyl-5-(5-(4-chlorophenyl)-4-(2,2-dibromovinyl)-1-(2,4-dichlorophenyl)-1H-pyrazol-3-yl)-1,3,4-oxadiazole (230 mg, 0.36 mmol) in tetrahydrofuran (10 ml) at 78° C., potassium bis(trimethysilyl)amide (1.46 ml, 0.5 M solution in tetrahydrofuran, 0.73 mmol) was added slowly. After stirring for 20 minutes at 78° C., the resulting solution was quenched with saturated ammonium chloride (5 ml). After warming up to room temperature, the solution was diluted with ethyl ether, and then the organic layer was extracted with ethyl acetate (50 ml twice). After evaporation, crude residue was purified with silica gel column (hexane/ethyl acetate=5/1) to obtain title compound (150 mg, 91% yield) as light yellow solid.

$^1$H NMR (400 MHz, CDCl$_3$) δ 7.54-7.49 (m, 2H), 7.34-7.31 (m, 2H), 7.20-7.17 (m, 1H), 7.15-7.11 (m, 2H), 3.06 (s, 1H), 1.35 (s, 9H).

MH+ 471.

Example 261

2-tert-butyl-5-(5-(4-chlorophenyl)-1-(2,4-dichlorophenyl)-4-(prop-1-ynyl)-1H-pyrazol-3-yl)-1,3,4-oxadiazole To a solution of 2-tert-butyl-5-(5-(4-chlorophenyl)-1-(2,4-dichlorophenyl)-4-ethynyl-1H-pyrazol-3-yl)-1,3,4-oxadiazole (100 mg, 0.21 mmol) in tetrahydrofuran (15 ml) at 78° C., lithium bis(trimethylsilyl)amide (0.23 ml, 1.0 M solution in tetrahydrofuran, 0.23 mmol) was added slowly not to warm up the reaction solution. After stirring at 78° C. for 10 minutes, iodomethane (0.04 ml, 0.7 mmol) was added quickly. The resulting solution was stirred for 20 minutes, and then it was warmed up to room temperature slowly. After quenching with saturated ammonium solution, the organic layer was separated with ethyl acetate. The organic solution was evaporated in reduced pressure and the residue was purified by silica gel column chromatography (hexane/ethyl acetate=10/1 to hexane/ethyl acetate=5/1) to produce title compound (13 mg, 13% yield) as light yellow solid.

$^1$H NMR (400 MHz, CDCl$_3$) δ 7.55-7.49 (m, 2H), 7.35-7.31 (m, 2H), 7.21-7.17 (m, 1H), 7.16-7.11 (m, 2H), 1.89 (s, 1H), 1.35 (s, 9H).

MH+ 485.

Example 262

2-(5-(4-bromophenyl)-1-(2,4-dichlorophenyl)-4-ethyl-1H-pyrazol-3-yl)-5-(1-propylcyclopropyl)-1,3,4-oxadiazole $^1$H NMR (400 MHz, CDCl$_3$) δ 7.56-7.44 (m, 4H), 7.34-7.32 (m, 2H), 7.27-7.20 (m, 3H), 7.15-7.10 (m, 3H), 2.91 (q, J=7.8 Hz, 2H), 2.23-2.20 (m, 2H), 1.57-1.53 (m, 2H), 1.33-1.30 (m, 2H), 1.27 (t, J=7.8 Hz, 3H), 0.98 (t, J=7.4 Hz, 3H), 0.86-0.82 (m, 2H), 0.45-0.41 (m, 2H).

MH+ 545.

Example 263

2-tert-butyl-5-(5-(4-chlorophenyl)-1-(2,4-dichlorophenyl)-4-(3-(trimethylsilyl)prop-2-ynyl)-1H-pyrazol-3-yl)-1,3,4-oxadiazole To a solution of ethylyltrimethylsilane (0.26 ml, 1.85 mmol) in tetrahydrofuran (10 ml) at 78° C. was added butyllithium (0.74 ml, 2.5 M in hexane, 1.85 mmol) slowly. The reaction mixture was stirred at 78° C. for 10 minutes and then 2-(4-(bromomethyl)-5-(4-chlorophenyl)-1-(2,4-dichlorophenyl)-1H-pyrazol-3-yl)-5-tert-butyl-1,3,4-oxadiazole (500 mg, 0.92 mmol) in tetrahydrofuran (5 ml) was added slowly at 78° C. The reaction temperature was warmed slowly to room temperature for 5 hours and stirred 1 hour at room temperature. The resulting solution was quenched with saturated ammonium chloride and extracted organic layer with ethyl acetate (50 ml twice). After evaporation, crude residue was purified with silica gel column (hexane/ethyl acetate=5/1) to produce 2-tert-butyl-5-(5-(4-chlorophenyl)-1-(2,4-dichlorophenyl)-4-(3-(trimethylsilyl)prop-2-ynyl)-1H-pyrazol-3-yl)-1,3,4-oxadiazole (370 mg, 72% yield) as white solid.

$^1$H NMR (400 MHz, CDCl$_3$) δ 7.54-7.49 (m, 2H), 7.33-7.31 (m, 2H), 7.20-7.17 (m, 1H), 7.14-7.11 (m, 2H), 4.00 (s, 2H), 1.57 (s, 9H), 0.11 (s, 9H).

MH+ 559.

Example 264

2-tert-butyl-5-(5-(4-chlorophenyl)-1-(2,4-dichlorophenyl)-4-(prop-2-ynyl)-1H-pyrazol-3-yl)-1,3,4-oxadiazole To a solution of 2-tert-butyl-5-(5-(4-chlorophenyl)-1-(2,4-dichlorophenyl)-4-(3-(trimethylsilyl)prop-2-ynyl)-1H-pyrazol-3-yl)-1,3,4-oxadiazole (300 mg, 0.46 mmol) in tetrahydrofuran (5 ml) at 0° C. was added tetrabutylammonium fluoride (0.7 ml, 1.0 M in tetrahydrofuran, 0.7 mmol). After reaction mixture was warmed up to room temperature, it was stirred for 10 minutes. After the resulting solution was diluted with ether (20 ml), water was added (10 ml). Organic layer was separated with ethyl acetate (20 ml twice). After evaporation, crude residue was purified with silica gel column (hexane/ethyl acetate=7/1 to hexane/ethyl acetate 5/1). The less polar compound 2-tert-butyl-5-(5-(4-chlorophenyl)-1-(2,4-dichlorophenyl)-4-(propa-1,2-dienyl)-1H-pyrazol-3-yl)-1,3,4-oxadiazole was obtained as light yellow solid (87 mg, 34% yield). And relatively more polar compound 2-tert-butyl-5-(5-(4-chlorophenyl)-1-(2,4-dichlorophenyl)-4-(prop-2-ynyl)-1H-pyrazol-3-yl)-1,3,4-oxadiazole was produced as yellow solid (140 mg, 54% yield).

$^1$H NMR (400 MHz, CDCl$_3$) δ 7.41-7.40 (dd, J=0.4, 2.4 Hz, 1H), 7.34-7.32 (m, 1H), 7.30-7.25 (m, 3H), 7.18-7.16 (m, 2H), 6.83 (t, J=7.2 Hz, 1H), 4.59 (d, J=6.8 Hz, 2H), 1.49 (s, 9H).

MH+ 485.

Example 265

2-tert-butyl-5-(5-(4-chlorophenyl)-1-(2,4-dichlorophenyl)-4-(propa-1,2-dienyl)-1H-pyrazol-3-yl)-1,3,4-oxadiazole $^1$H NMR (400 MHz, CDCl$_3$) δ 7.42-7.41 (m, 2H), 7.35-7.32 (m, 2H), 7.29-7.26 (m, 3H), 3.02-2.93 (m, 2H), 1.49 (s, 9H), 1.51 (m, 1H).

MH+ 485.

Example 266

1-(5-(5-(4-bromophenyl)-1-(2,4-dichlorophenyl)-4-ethyl-1H-pyrazol-3-yl)-1,3,4-oxadiazol-2-yl)cyclopropanecarbonitrile $^1$H NMR (400 MHz, CDCl$_3$) δ 7.49-7.41 (m, 3H), 7.36-7.30 (m, 2H), 7.07-7.04 (m, 2H), 2.84 (q, J=7.6 Hz, 2H), 2.03-1.95 (m, 2H), 1.94-1.91 (m, 2H), 1.21 (t, J=7.6 Hz, 3H).

MH+ 528.

Example 267

1-(5-(5-(4-chlorophenyl)-1-(2,4-dichlorophenyl)-4-methyl-1H-pyrazol-3-yl)-1,3,4-oxadiazol-2-yl)cyclopropanecarbonitrile $^1$H NMR (400 MHz, CDCl$_3$) δ 7.42 (dd, J=0.4, 2.4 Hz, 1H), 7.36-7.30 (m, 4H), 7.12-7.08 (m, 2H), 2.42 (s, 3H), 2.03-1.90 (m, 4H).

MH+ 470.

Example 268

1-(5-(5-(4-chlorophenyl)-1-(2,4-dichlorophenyl)-4-ethyl-1H-pyrazol-3-yl)-1,3,4-oxadiazol-2-yl)cyclopropanecarbonitrile $^1$H NMR (400 MHz, CDCl$_3$) δ 7.42-7.41 (m, 1H), 7.34-7.27 (m, 4H), 7.14-7.10 (m, 2H), 2.86 (q, J=10.0 Hz, 2H), 1.97 (dd, J=4.6, 2.7 Hz, 2H), 1.04 (dd, J=4.6, 2.7 Hz, 2H), 1.21 (t, J=10.0, 3H).
MH+ 484.

Example 269

2-(5-(4-chlorophenyl)-1-(2,4-dichlorophenyl)-4-methyl-1H-pyrazol-3-yl)-5-(1-(pyridin-2-yl)cyclopropyl)-1,3,4-oxadiazole $^1$H NMR (400 MHz, CDCl$_3$) δ 8.45 (m, 1H), 7.43-7.40 (m, 3H), 7.34-7.31 (m, 4H), 7.20-7.18 (m, 1H), 7.12-7.08 (m, 2H), 2.43 (s, 3H), 2.02-1.92 (m, 4H).
MH+ 523.

Example 270

2-(1-benzylcyclopropyl)-5-(5-(4-chlorophenyl)-1-(2,4-dichlorophenyl)-4-methyl-1H-pyrazol-3-yl)-1,3,4-oxadiazole Step 1: 1-benzylcyclopropanecarboxylic Acid A solution of cyclopropyl cyanide (2 g, 30 mmol) in THF (30 ml) was added dropwise under nitrogen atmosphere at −78° C. to a stirred solution of LDA (18 ml, 1.8 M in tetrahydrofuran/heptane/ethylbenzene, 33 mmol). The reaction mixture was stirred 20 minutes at −78° C. and then benzylbromide (7 ml, 60 mmol) in tetrahydrofuran (20 ml) was added at −78° C. After stirring for 30 minutes, the reaction mixture was warmed to room temperature. The stirring was continued for 3 hours at this temperature and then the mixture was quenched using saturated ammonium chloride solution and extracted with ethyl ether. The organic solution was dried with magnesium sulfate. Without further purification, the nitrile compound was hydrolyzed with 35% aqueous sodium hydroxide solution (20 ml) in methanol (30 ml) at 100° C. for 8 hours. After reaction complete, methanol was evaporated under reduced pressure. After washing aqueous solution with diethyl ether (30 ml twice), resulting solution was acidified using 3N HCl. With diethyl ether, the organic phase was worked-up and evaporated under reduced pressure to obtained the title compound (3.2 g, 61%) as light yellow solid.

$^1$H NMR (400 MHz, CDCl$_3$) δ 7.35-7.17 (m, 5H), 2.98 (s, 2H), 1.34 (dd, J=4, 6.8 Hz, 2H), 0.87 (dd, J=4.0, 6.8 Hz, 2H).

Step 2: 2-(1-benzylcyclopropyl)-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.40 (d, J=2 Hz, 1H), 7.35-7.26 (m, 6H), 7.21-7.17 (m, 3H), 7.09-7.07 (m, 2H), 3.22 (s, 2H), 2.38 (s, 3H), 1.44-1.41 (m, 2H), 1.07-1.04 (m, 2H).
MH+ 535.

Example 271

2-(1-benzylcyclopropyl)-5-(5-(4-bromophenyl)-1-(2,4-dichlorophenyl)-4-ethyl-1H-pyrazol-3-yl)-1,3,4-oxadiazole $^1$H NMR (400 MHz, CDCl$_3$) δ 7.48-7.44 (m, 2H), 7.41 (d, J=2 Hz, 1H), 7.37-7.25 (m, 5H), 7.23-7.17 (m, 2H), 7.05-7.02 (m, 2H), 3.31 (s, 2H), 2.81 (q, J=7.6 Hz, 2H), 1.44-1.41 (m, 2H), 1.96 (t, J=7.6 Hz, 3H), 1.06-1.05 (m, 2H).
MH+ 551.

Example 272

2-(5-(4-bromophenyl)-1-(2,4-dichlorophenyl)-4-ethyl-1H-pyrazol-3-yl)-5-(1-(4-fluorophenyl)cyclopropyl)-1,3,4-oxadiazole $^1$H NMR (400 MHz, CDCl$_3$) δ 7.44-7.42 (m, 1H), 7.34-7.30 (m, 6H), 7.20-7.11 (m, 4H), 2.86 (q, J=9.9 Hz, 2H), 2.12 (dd, J=9.3, 6.1, 2H), 1.98 (dd, J=9.3, 6.1, 2H), 1.26 (t, J=9.9 Hz, 3H).
MH+ 597.

Example 273

2-(5-(4-bromophenyl)-1-(2,4-dichlorophenyl)-4-ethyl-1H-pyrazol-3-yl)-5-(1-(3-chlorophenyl)cyclopropyl)-1,3,4-oxadiazole $^1$H NMR (400 MHz, CDCl$_3$) δ 7.47-7.44 (m, 2H), 7.40 (d, J=2.1 Hz, 1H), 7.37-7.31 (m, 2H), 7.30 (d, J=2.4 Hz, 1H), 7.27-7.23 (m, 4H), 7.05-7.03 (m, 2H), 2.77 (q, J=7.7 Hz, 2H), 1.94 (dd, J=9.2, 6.2 Hz, 2H), 1.46 (dd, J=9.2, 6.2 Hz, 2H), 1.19 (t, J=7.7 Hz, 3H).
MH+ 615.

Example 274

2-(5-(4-chlorophenyl)-1-(2,4-dichlorophenyl)-4-methyl-1H-pyrazol-3-yl)-5-(1-(4-fluorophenyl)cyclopropyl)-1,3,4-oxadiazole $^1$H NMR (400 MHz, CDCl$_3$) δ 7.48-7.45 (m, 3H), 7.38-7.35 (m, 2H), 7.29-7.22 (m, 4H), 7.04-7.01 (m, 2H), 2.23 (s, 3H), 1.92 (dd, J=9.2, 6.7 Hz, 2H), 1.51 (dd, J=9.2, 6.7 Hz, 2H).
MH+ 539.

Example 275

2-(5-(4-chlorophenyl)-1-(2,4-dichlorophenyl)-4-methyl-1H-pyrazol-3-yl)-5-(1-methylcyclopropyl)-1,3,4-oxadiazole $^1$H NMR (400 MHz, CDCl$_3$) δ 7.41 (d, J=2 Hz, 2H), 7.36 (d, J=8.4 Hz, 1H), 7.33-7.23 (m, 3H), 7.11-7.08 (m, 2H), 2.41 (s, 3H), 1.61 (s, 3H), 1.42-1.40 (m, 2H), 0.97-0.94 (m, 2H).
MH+ 459.

Example 276

2-(5-(4-bromophenyl)-1-(2,4-dichlorophenyl)-4-ethyl-1H-pyrazol-3-yl)-5-(1-methylcyclopropyl)-1,3,4-oxadiazole $^1$H NMR (400 MHz, CDCl$_3$) δ 7.47-7.45 (m, 2H), 7.40 (d, J=3.6 Hz, 1H), 7.35-7.27 (m, 2H), 7.06-7.04 (m, 2H), 2.83 (q, J=7.6 Hz, 2H), 1.62 (s, 3H), 1.45-1.42 (m, 2H), 1.22 (t, J=7.6 Hz, 3H), 0.96-0.95 (m, 2H).
MH+ 517.

Example 277

2-(5-(4-chlorophenyl)-1-(2,4-dichlorophenyl)-4-methyl-1H-pyrazol-3-yl)-5-(1-ethylcyclopropyl)-1,3,4-oxadiazole $^1$H NMR (400 MHz, CDCl$_3$) δ 7.44-7.42 (m, 1H), 7.34-7.31 (m, 4H), 7.14-7.10 (m, 2H), 2.45 (s, 3H), 1.90 (q, J=9.7 Hz, 2H), 1.39 (dd, J=9.3, 6.2 Hz, 2H), 1.11 (t, J=9.7 Hz, 3H), 1.06 (dd, J=9.3, 6.2 Hz).
MH+ 473.

Example 278

2-(5-(4-chlorophenyl)-1-(2,4-dichlorophenyl)-4-ethyl-1H-pyrazol-3-yl)-5-(1-ethylcyclopropyl)-1,3,4-oxadiazole $^1$H NMR (400 MHz, CDCl$_3$) δ 7.43-7.42 (m, 1H), 7.34-7.29 (m, 4H), 7.16-7.11 (m, 2H), 2.89 (q, J=9.8 Hz, 2H), 1.90 (q, J=9.6 Hz, 2H), 1.38 (dd, J=9.3, 6.2 Hz, 2H), 1.27 (t, J=9.8 Hz, 3H), 1.03 (t, J=9.6 Hz, 3H), 1.01 (dd, J=9.3, 6.2 Hz).
MH+ 487.

Example 279

2-(5-(4-bromophenyl)-1-(2,4-dichlorophenyl)-4-ethyl-1H-pyrazol-3-yl)-5-(1-ethylcyclopropyl)-1,3,4-oxadiazole $^1$H NMR (400 MHz, CDCl$_3$) δ 7.44-7.42 (m, 1H), 7.33-7.30 (m, 4H), 7.14-7.11 (m, 2H), 2.91 (q, J=9.8 Hz, 2H), 1.91 (q, J=9.6 Hz, 2H), 1.36 (dd, J=9.3, 6.2 Hz, 2H), 1.27 (t, J=9.8 Hz, 3H), 1.03 (t, J=9.6 Hz, 3H), 1.01 (dd, J=9.3, 6.2 Hz).
MH+ 531.

Example 280

2-(1-(4-chlorobenzyl)cyclopropyl)-5-(5-(4-chlorophenyl)-1-(2,4-dichlorophenyl)-4-methyl-1H-pyrazol-3-yl)-1,3,4-oxadiazole $^1$H NMR (400 MHz, CDCl$_3$) δ 7.41 (d, J=2.4 Hz, 1H), 7.34-7.28 (m, 4H), 7.23-7.20 (m, 3H), 7.10-7.07 (m, 2H), 3.24 (s, 2H), 2.39 (s, 3H), 1.45 (dd, J=2, 6.8 Hz, 2H), 1.07 (dd, J=2, 6.8 Hz, 2H).
MH+ 571.

Example 281

2-(1-(4-chlorobenzyl)cyclopropyl)-5-(5-(4-bromophenyl)-1-(2,4-dichlorophenyl)-4-ethyl-1H-pyrazol-3-yl)-1,3,4-oxadiazole $^1$H NMR (400 MHz, CDCl$_3$) δ 7.51-7.45 (m, 2H), 7.40 (d, J=2 Hz, 1H), 7.34-7.26 (m, 3H), 7.23-7.20 (m, 3H), 7.05-6.96 (m, 2H), 3.24 (s, 2H), 2.80 (q, J=7.6 Hz, 2H), 1.46 (dd, J=5.2, 7.2 Hz, 2H), 1.25 (t, J=7.6 Hz, 3H), 1.06 (dd, J=4.8, 6.8 Hz, 2H).
MH+ 629.

Example 282

2-(5-(4-chlorophenyl)-1-(2,4-dichlorophenyl)-4-ethyl-1H-pyrazol-3-yl)-5-(1-(2-fluorophenyl)cyclopropyl)-1,3,4-oxadiazole $^1$H NMR (400 MHz, CDCl$_3$) δ 7.46-7.38 (m, 2H), 7.34-7.27 (m, 5H), 7.16-7.06 (m, 4H), 2.74 (q, J=7.6 Hz, 2H), 1.89-1.82 (m, 2H), 1.51-1.45 (m, 2H), 1.12 (t, J=7.2 Hz, 3H).
MH+ 553.

Example 283

2-(5-(4-chlorophenyl)-1-(2,4-dichlorophenyl)-4-ethyl-1H-pyrazol-3-yl)-5-(1-methylcyclopropyl)-1,3,4-oxadiazole $^1$H NMR (400 MHz, CDCl$_3$) δ 7.39 (d, J=2.0 Hz, 1H), 7.34 (d, J=8.4 HZ, 1H), 7.32-7.27 (m, 3H), 7.13-7.09 (m, 2H), 2.84 (q, J=7.6 Hz, 2H), 1.61 (s, 3H), 1.40 (dd, J=4.4, 6.8 Hz, 2H), 1.21 (t, J=7.6 Hz, 3H), 0.95 (dd, J=4.4, 6.8 Hz, 2H).
MH+ 473.

Example 284

2-(5-(4-chlorophenyl)-1-(2,4-dichlorophenyl)-4-ethyl-1H-pyrazol-3-yl)-5-(1-(cyclopropylmethyl)cyclopropyl)-1,3,4-oxadiazole

MH+ 513.

Example 285

2-(5-(4-bromophenyl)-1-(2,4-dichlorophenyl)-4-ethyl-1H-pyrazol-3-yl)-5-(1-(cyclopropylmethyl)cyclopropyl)-1,3,4-oxadiazole

MH+ 557.

Example 286

1-(1-(5-(5-(4-chlorophenyl)-1-(2,4-dichlorophenyl)-4-methyl-1H-pyrazol-3-yl)-1,3,4-oxadiazol-2-yl)cyclopropyl)ethanone $^1$H NMR (400 MHz, CDCl$_3$) δ 7.42 (dd, J=0.4, 2.4 Hz, 1H), 7.36-7.30 (m, 4H), 7.13-7.09 (m, 2H), 2.46 (s, 3H), 2.35 (s, 3H), 1.78 (dd, J=4.8, 8.4 Hz, 2H), 1.66 (dd, J=4.8, 8.4 Hz, 2H).
MH+ 487.

Example 287

2-(1-(5-(5-(4-chlorophenyl)-1-(2,4-dichlorophenyl)-4-methyl-1H-pyrazol-3-yl)-1,3,4-oxadiazol-2-yl)cyclopropyl)propan-2-ol $^1$H NMR (400 MHz, CDCl$_3$) δ 7.41 (d, J=2.0, 1H), 7.35-7.28 (m, 4H), 7.10-7.08 (m, 2H), 2.42 (s, 3H), 1.39 (s, 6H), 1.33-1.30 (m, 2H), 1.27-1.23 (m, 2H).
MH+ 503.

Example 288

1-(1-(5-(5-(4-chlorophenyl)-1-(2,4-dichlorophenyl)-4-methyl-1H-pyrazol-3-yl)-1,3,4-oxadiazol-2-yl)cyclopropyl)ethanol $^1$H NMR (400 MHz, CDCl$_3$) δ 7.41-7.41 (m, 1H), 7.35-7.29 (m, 4H), 7.12-7.08 (m, 2H), 3.86 (q, J=6.4 Hz, 1H), 2.42

(s, 3H), 1.38 (d, J=6.4 Hz, 3H), 1.33-1.30 (m, 2H), 1.27-1.23 (m, 2H).
MH+ 489.

Example 289

2-(5-(4-chlorophenyl)-1-(2,4-dichlorophenyl)-4-methyl-1H-pyrazol-3-yl)-5-(1-(1-fluoroethyl)cyclopropyl)-1,3,4-oxadiazole

MH+ 491.

Example 290

N-((3-(5-tert-butyl-1,3,4-oxadiazol-2-yl)-5-(4-chlorophenyl)-1-(2,4-dichlorophenyl)-1H-pyrazol-4-yl)methyl)-N-methylethanamine To the suspension of bromide (33) (150 mg, 0.28 mmol) in $CH_3CN$ (5 mL) was added N-ethylmethylamine (30 μL, 0.33 mmol) and DIPEA (63 μL, 0.36 mmol). The reaction mixture was stirred for 12 hrs at room temperature. $H_2O$ (25 mL) was added to the reaction mixture and then extracted with EtOAc (50 mL). The organic extract was dried over anhydrous $MgSO_4$, filtered, and concentrated in vacuo. Purification by Prep-LC (Gilson) provided 83 mg (58%) of desired amine as solid.

$^1$H NMR (400 MHz, $CDCl_3$) δ 7.42-7.27 (m, 7H), 3.78 (s, 2H), 2.51-2.43 (m, 2H), 2.13 (s, 3H), 1.51 (s, 9H), 0.99 (t, J=6.8 Hz, 3H).
MH+ 518.

Example 291

2-tert-butyl-5-(5-(4-chlorophenyl)-1-(2,4-dichlorophenyl)-4-(piperidin-1-ylmethyl)-1H-pyrazol-3-yl)-1,3,4-oxadiazole $^1$H NMR (400 MHz, $CDCl_3$) δ 7.44-7.26 (m, 7H), 3.58 (s, 2H), 2.38 (br s, 4H), 1.60-1.45 (m, 15H).
MH+ 546.

Example 292

2-tert-butyl-5-(5-(4-chlorophenyl)-1-(2,4-dichlorophenyl)-4-(pyrrolidin-1-ylmethyl)-1H-pyrazol-3-yl)-1,3,4-oxadiazole $^1$H NMR (400 MHz, $CDCl_3$) δ 7.45-7.29 (m, 7H), 4.91 (s, 2H), 3.60-3.49 (m, 4H), 1.99-1.90 (m, 4H), 1.51 (s, 9H).
MH+ 532.

Example 293

4-((3-(5-tert-butyl-1,3,4-oxadiazol-2-yl)-5-(4-chlorophenyl)-1-(2,4-dichlorophenyl)-1H-pyrazol-4-yl)methyl)morpholine $^1$H NMR (400 MHz, $CDCl_3$) δ 7.43-7.41 (m, 1H), 7.38-7.27 (m, 4H), 6.98-6.81 (m, 2H), 4.92 (s, 2H), 3.77-3.51 (m, 8H), 2.51-2.39 (m, 8H), 1.50 (s, 9H).
MH+ 548.

Example 294

N-((3-(5-tert-butyl-1,3,4-oxadiazol-2-yl)-5-(4-chlorophenyl)-1-(2,4-dichlorophenyl)-1H-pyrazol-4-yl)methyl)-2-methylpropan-2-amine $^1$H NMR (400 MHz, $CDCl_3$) δ 7.47-7.28 (m, 7H), 4.01 (s, 2H), 3.03 (s, 1H), 1.51 (s, 9H), 1.10 (s, 9H).
MH+ 534.

Example 295

N-((3-(5-tert-butyl-1,3,4-oxadiazol-2-yl)-5-(4-chlorophenyl)-1-(2,4-dichlorophenyl)-1H-pyrazol-4-yl)methyl)propan-2-amine $^1$H NMR (400 MHz, $CDCl_3$) δ 7.43-7.31 (m, 7H), 3.95 (s, 2H), 3.20-3.07 (m, 1H), 1.51 (s, 9H), 1.05 (s, 6H).
MH+ 518.

Example 296

2-(4-((1H-1,2,4-triazol-1-yl)methyl)-5-(4-chlorophenyl)-1-(2,4-dichlorophenyl)-1H-pyrazol-3-yl)-5-tert-butyl-1,3,4-oxadiazole NaH (15 mg, 0.36 mmol, 60% dispersion in mineral oil) was added to the solution of 1,2,4-triazole (23 mg, 0.33 mmol) in THF (5 mL) at 0° C. The reaction mixture was stirred for 30 min at 0° C. The solution of bromide (33) (150 mg, 0.28 mmol) in THF (5 mL) was added to the reaction mixture. The reaction mixture was warmed up to room temperature and stirred for 12 hrs at room temperature. $H_2O$ (25 mL) was added to the reaction mixture and then extracted with EtOAc (50 mL). The organic extract was dried over anhydrous $MgSO_4$, filtered, and concentrated in vacuo. Purification by Prep-LC (Gilson) provided 70 mg (47%) of desired product as solid.

$^1$H NMR (400 MHz, $CDCl_3$) δ 8.79 (s, 1H), 7.99 (s, 1H), 7.49-7.44 (m, 3H), 7.49-7.29 (m, 4H), 5.59 (s, 2H), 1.48 (s, 9H).
MH+ 530.

Example 297

2-(4-((1H-imidazol-1-yl)methyl)-5-(4-chlorophenyl)-1-(2,4-dichlorophenyl)-1H-pyrazol-3-yl)-5-tert-butyl-1,3,4-oxadiazole $^1$H NMR (400 MHz, $CDCl_3$) δ 7.59 (s, 1H), 7.43-7.33 (m, 5H), 7.10-7.05 (m, 2H), 7.01 (t, J=6.8 Hz, 1H), 6.92 (t, J=1.2 Hz, 1H), 5.47 (s, 2H), 1.49 (s, 9H).
MH+ 527.

Example 298

2-(4-((1H-pyrazol-1-yl)methyl)-5-(4-chlorophenyl)-1-(2,4-dichlorophenyl)-1H-pyrazol-3-yl)-5-tert-butyl-1,3,4-oxadiazole $^1$H NMR (400 MHz, $CDCl_3$) δ 7.78 (d, J=2.0 Hz, 1H), 7.49-7.47 (m, 1H), 7.42-7.28 (m, 7H), 6.18 (t, J=2.0 Hz, 1H), 5.54 (s, 2H), 1.47 (s, 9H).
MH+ 527.

Example 299

2-(4-((1H-pyrrol-1-yl)methyl)-5-(4-chlorophenyl)-1-(2,4-dichlorophenyl)-1H-pyrazol-3-yl)-5-tert-butyl-1,3,4-oxadiazole $^1$H NMR (400 MHz, CDCl$_3$) δ 7.45-7.27 (m, 7H), 6.45-6.39 (m, 2H), 5.92-5.85 (m, 2H), 5.53 (s, 2H), 1.51 (s, 9H). MH+ 528.

Example 300

2-(4-((1H-tetrazol-1-yl)methyl)-5-(4-chlorophenyl)-1-(2,4-dichlorophenyl)-1H-pyrazol-3-yl)-5-tert-butyl-1,3,4-oxadiazole $^1$H NMR (400 MHz, CDCl$_3$) δ 8.43 (s, 1H), 7.44-7.43 (m, 1H), 7.36 (d, J=0.4 Hz, 1H), 7.33 (d, J=2.4 Hz, 1H), 7.31-7.27 (m, 2H), 7.16-7.13 (m, 2H), 6.07 (s, 2H), 1.47 (s, 9H). MH+ 531.

Example 301

2-(4-((1H-tetrazol-1-yl)methyl)-5-(4-chlorophenyl)-1-(2,4-dichlorophenyl)-1H-pyrazol-3-yl)-5-tert-butyl-1,3,4-oxadiazole $^1$H NMR (400 MHz, CDCl$_3$) δ 9.26 (s, 1H), 7.46-7.29 (m, 7H), 5.777 (s, 2H), 1.49 (s, 9H). MH+ 531.

Example 302

2-(4-((2H-tetrazol-2-yl)methyl)-5-(4-bromophenyl)-1-(2,4-dichlorophenyl)-1H-pyrazol-3-yl)-5-tert-butyl-1,3,4-oxadiazole $^1$H NMR (400 MHz, CDCl$_3$) δ 8.43 (s, 1H), 7.49-7.31 (m, 5H), 7.09-7.03 (m, 2H), 6.07 (s, 2H), 1.47 (s, 9H). MH+ 573.

Example 303

2-(4-((1H-tetrazol-1-yl)methyl)-5-(4-bromophenyl)-1-(2,4-dichlorophenyl)-1H-pyrazol-3-yl)-5-tert-butyl-1,3,4-oxadiazole $^1$H NMR (400 MHz, CDCl$_3$) δ 9.26 (s, 1H), 7.52-7.31 (m, 7H), 5.77 (s, 2H), 1.48 (s, 9H). MH+ 573.

Example 304

2-(4-((1H-1,2,3-triazol-1-yl)methyl)-5-(4-chlorophenyl)-1-(2,4-dichlorophenyl)-1H-pyrazol-3-yl)-5-tert-butyl-1,3,4-oxadiazole $^1$H NMR (400 MHz, CDCl$_3$) δ 8.21 (d, J=1.2 Hz, 1H), 7.66 (d, J=0.8 Hz, 1H), 7.44 (dd, J=1.6 Hz, 0.8 Hz, 1H), 7.42-7.29 (m, 6H), 5.76 (s, 2H), 1.48 (s, 9H). MH+ 530.

Example 305

1-((3-(5-tert-butyl-1,3,4-oxadiazol-2-yl)-5-(4-chlorophenyl)-1-(2,4-dichlorophenyl)-1H-pyrazol-4-yl)methyl)pyrrolidine-2,5-dione To the suspension of bromide (33) (150 mg, 0.28 mmol) in acetone (10 mL) was added succimide (35 mg, 0.33 mmol) and K$_2$CO$_3$ (60 mg, 0.42 mmol). The reaction mixture was refluxed for 12 hrs and cooled to room temperature. H$_2$O (25 mL) was added to the reaction mixture and then extracted with EtOAc (50 mL). The organic extract was dried over anhydrous MgSO$_4$, filtered, and concentrated in vacuo. Purification by Prep-LC (Gilson) provided 99 mg (64%) of desired product as solid.

$^1$H NMR (400 MHz, CDCl$_3$) δ 7.36-7.16 (m, 7H), 4.99 (s, 2H), 2.33 (s, 4H), 1.47 (s, 9H). MH+ 560.

Example 306

1-((3-(5-tert-butyl-1,3,4-oxadiazol-2-yl)-5-(4-chlorophenyl)-1-(2,4-dichlorophenyl)-1H-pyrazol-4-yl)methyl)pyrrolidin-2-one $^1$H NMR (400 MHz, CDCl$_3$) δ 7.42 (d, J=2.0 Hz, 1H), 7.36-7.27 (m, 4H), 7.13-7.09 (m, 2H), 4.87 (s, 2H), 3.26 (t, J=6.8 Hz, 2H), 2.12 (t, J=8.0 Hz, 2H), 1.68-1.65 (m, 2H), 1.50 (s, 9H). MH+ 544.

Example 307

3-((3-(5-tert-butyl-1,3,4-oxadiazol-2-yl)-5-(4-chlorophenyl)-1-(2,4-dichlorophenyl)-1H-pyrazol-4-yl)methyl)oxazolidin-2-one $^1$H NMR (400 MHz, CDCl$_3$) δ 7.45-7.41 (m, 1H), 7.37-7.28 (m, 4H), 7.18-7.15 (m, 2H), 4.75 (s, 2H), 4.13 (t, J=8.0 Hz, 2H), 3.62 (t, J=8.0 Hz, 2H), 1.50 (s, 9H). MH+ 546.

Example 308

S-(3-(5-tert-butyl-1,3,4-oxadiazol-2-yl)-5-(4-chlorophenyl)-1-(2,4-dichlorophenyl)-1H-pyrazol-4-yl)methyl ethanethioate To the solution of bromide (33) (150 mg, 0.28 mmol) in DMF (3 mL) was added KSAc (48 mg, 0.42 mmol). The reaction mixture was refluxed for 12 hrs at room temperature. The reaction mixture was diluted with EtOAc (25 mL) and washed with brine. The organic layer was dried over anhydrous MgSO$_4$, filtered, and concentrated in vacuo. Purification by Prep-LC (Gilson) provided 45 mg (30%) of desired thioacetate as solid.

$^1$H NMR (400 MHz, CDCl$_3$) δ 7.40 (d, J=2.4 Hz, 1H), 7.38-7.26 (m, 5H), 7.16-7.12 (m, 2H), 4.40 (s, 2H), 2.26 (s, 3H), 1.49 (s, 9H). MH+ 535.

Example 309

(3-(5-tert-butyl-1,3,4-oxadiazol-2-yl)-5-(4-chlorophenyl)-1-(2,4-dichlorophenyl)-1H-pyrazol-4-yl)methanethiol To the solution of thioacetate (47) (337 mg, 0.63 mmol) in H$_2$O/1,4-dioxane/THF (5 mL/5 mL/5 mL) was added NaOH (100 mg, 2.52 mmol). The reaction mixture was stirred for 12 hrs at room temperature. The reaction mixture was diluted with aq. saturated NH$_4$Cl solution and extracted with EtOAc. The organic layer was dried over anhydrous MgSO$_4$, filtered, and concentrated in vacuo. Purification by normal phase column chromatography (Biotage) provided 93 mg (30%) of desired thiol as solid.

$^1$H NMR (400 MHz, CDCl$_3$) δ 7.42-7.37 (m, 2H), 7.34-7.27 (m, 3H), 7.25-7.21 (m, 2H), 4.03 (s, 2H), 3.69 (s, 1H), 1.48 (s, 9H).

MH+ 493.

Example 310

2-(3-(5-tert-butyl-1,3,4-oxadiazol-2-yl)-5-(4-chlorophenyl)-1-(2,4-dichlorophenyl)-1H-pyrazol-4-yl)acetonitrile To the solution of bromide (33) (1.0 g, 1.85 mmol) in CH$_3$CN (20 mL) was added KCN (0.24 g, 3.70 mmol) and 18-crown-6 (0.20 g, 0.74 mmol). The reaction mixture was refluxed for 12 hrs. The reaction mixture was cooled to room temperature and diluted with brine. The aqueous layer was extracted with EtOAc. The organic layer was dried over anhydrous MgSO$_4$, filtered, and concentrated in vacuo. Purification by normal phase column chromatography (Biotage) provided 0.66 g (74%) of desired cyanide as solid.

$^1$H NMR (400 MHz, CDCl$_3$) δ 7.45-7.32 (m, 5H), 7.21-7.18 (m, 2H), 4.05 (s, 2H), 1.51 (s, 9H).

MH+ 488.

Example 311

2-tert-butyl-5-(1-(2,4-dichlorophenyl)-5-(4-(methylthio)phenyl)-4-(methylthiomethyl)-1H-pyrazol-3-yl)-1,3,4-oxadiazole To the solution of bromide (33) (150 mg, 0.28 mmol) in DMF (3 mL) was added NaSMe (28 mg, 0.36 mmol). The reaction mixture was heated for 12 hrs at 100° C. and then cooled to room temperature. The reaction mixture was diluted with EtOAc (25 mL) and washed with brine. The organic layer was dried over anhydrous MgSO$_4$, filtered, and concentrated in vacuo. Purification by Prep-LC (Gilson) provided 51 mg (35%) of desired disulfide as solid.

$^1$H NMR (400 MHz, CDCl$_3$) δ 7.34-7.26 (m, 5H), 7.19-7.16 (m, 1H), 7.15-7.10 (m, 1H), 4.03 (s, 2H), 2.47 (s, 3H), 2.08 (s, 3H), 1.49 (s, 9H).

MH+ 519.

Example 312

Step: 1 ethyl 4-((1H-1,2,4-triazol-1-yl)methyl)-5-(4-chlorophenyl)-1-(2,4-dichlorophenyl)-1H-pyrazole-3-carboxylate NaH (0.37 g, 9.21 mmol, 60% dispersion in mineral oil) was added to the solution of 1,2,4-triazole (0.51 g, 7.37 mmol) in THF (30 mL) at 0° C. The reaction mixture was stirred for 1 hr at 0° C. The solution of bromide (61) (3 g, 6.14 mmol) in THF (15 mL) was added to the reaction mixture. The reaction mixture was warmed up to room temperature, stirred for 1 hr at room temperature and for 12 hrs at 45° C. The reaction mixture was cooled to room temperature. H$_2$O (100 mL) was added to the reaction mixture and then extracted with EtOAc (150 mL). The organic extract was dried over anhydrous MgSO$_4$, filtered, and concentrated in vacuo. Purification by silica gel column chromatography (Biotage, Eluent: 12% EtOAc/Hexane→EtOAc (Gradient)) provided 1.35 g (46%) of desired triazole (62) as solid.

$^1$H NMR (400 MHz, CDCl$_3$) δ 8.76 (s, 1H), 8.09 (s, 1H), 7.41-7.27 (m, 7H), 5.48 (s, 2H), 4.44 (quartet, J=7.2 Hz, 2H), 1.398 (t, J=7.2 Hz, 3H).

MH+ 478.

Step 2: 4-((1H-1,2,4-triazol-1-yl)methyl)-5-(4-chlorophenyl)-1-(2,4-dichlorophenyl)-1H-pyrazole-3-carboxylic acid To the solution of bromide (62) (500 mg, 1.05 mmol) in THF (5 mL)/H$_2$O (15 mL) was added LiOH monohydrate (132 mg, 3.15 mmol). The reaction mixture was refluxed for 2 hrs and cooled to room temperature. The reaction mixture was acidified with aq. 1N HCl solution and extracted with 30% MeOH/CHCl$_3$. The organic extract was dried over anhydrous MgSO$_4$, filtered, concentrated and dried in vacuo to provide 470 mg (100%) of desired acid (63) as solid. The obtained acid was used without further purification.

Step 3: 4-((1H-1,2,4-triazol-1-yl)methyl)-5-(4-chlorophenyl)-1-(2,4-dichlorophenyl)-N'-pivaloyl-1H-pyrazole-3-carbohydrazide To the solution of acid (63) (330 mg, 0.74 mmol) in CH$_2$Cl$_2$ (10 mL) was added oxalyl chloride (77 μL, 0.88 mmol) and the catalytic amount of DMF. The reaction mixture was stirred for 1 hr and concentrated in vacuo. The residue (crude acyl chloride) was diluted with CH$_2$Cl$_2$ (10 mL) and pivalohydrazide (128 mg, 1.10 mmol) and triethylamine (0.31 mL, 2.21 mmol) was added. The reaction mixture was stirred for 2 hrs at room temperature. The reaction mixture was concentrated in vacuo and diluted with EtOAc (50 mL). The organic layer was washed with aq. 1N HCl and aq. sat'd NaHCO$_3$ solution, dried over anhydrous MgSO$_4$, filtered, and concentrated in vacuo. Purification by Prep-LC (Gilson) provided 244 mg (61%) of desired diamide as solid.

Step 4: 2-(4-((1H-1,2,4-triazol-1-yl)methyl)-5-(4-chlorophenyl)-1-(2,4-dichlorophenyl)-1H-pyrazol-3-yl)-5-tert-butyl-1,3,4-oxadiazole A solution of diamide (200 mg, 0.37 mmol) and Burgess reagent (217 mg, 0.91 mmol) in THF (3 mL) was irradiated in a microwave reactor (Biotage) for 1 hr at 160° C. Purification by Prep-LC (Gilson) provided 155 mg (79%) of desired oxadiazole as solid.

Example 313

2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopropyl)-1,3,4-oxadiazole $^1$H NMR (400 MHz, CDCl$_3$) δ 8.76 (s, 1H), 7.99 (s, 1H), 7.46-7.28 (m, 11H), 5.54 (s, 2H), 1.78 (m, 2H), 1.47 (m, 2H).

MH+ 624.

Example 314

2-(4-((1H-1,2,4-triazol-1-yl)methyl)-5-(4-chlorophenyl)-1-(2,4-dichlorophenyl)-1H-pyrazol-3-yl)-5-(1-(trifluoromethyl)cyclopropyl)-1,3,4-oxadiazole $^1$H NMR (400 MHz, DMSO-d$_6$) δ 8.43 (s, 1H), 7.88 (s, 1H), 7.85 (d, J=8.0 Hz, 1H), 7.80 (d, J=2.0 Hz, 1H), 7.60 (dd, J=8.4 Hz, 2.4 Hz, 1H), 7.50-7.39 (m, 4H), 5.52 (s, 2H), 1.66 (s, 4H).
MH+ 582.

Example 315

2-(4-((1H-1,2,4-triazol-1-yl)methyl)-5-(4-chlorophenyl)-1-(2,4-dichlorophenyl)-1H-pyrazol-3-yl)-5-cyclobutyl-1,3,4-oxadiazole $^1$H NMR (400 MHz, DMSO-d$_6$) δ 8.45 (s, 1H), 7.89 (s, 1H), 7.88-7.80 (m, 2H), 7.59 (dd, J=8.4 Hz, 2.4 Hz, 1H), 7.50-7.39 (m, 4H), 5.53 (s, 2H), 3.95-3.89 (m, 1H), 2.47-2.30 (m, 4H), 2.15-1.87 (m, 2H).
MH+ 528.

Example 316

2-(4-((1H-1,2,4-triazol-1-yl)methyl)-5-(4-chlorophenyl)-1-(2,4-dichlorophenyl)-1H-pyrazol-3-yl)-5-cyclohexyl-1,3,4-oxadiazole $^1$H NMR (400 MHz, DMSO-d$_6$) δ 8.45 (s, 1H), 7.89 (s, 1H), 7.85-7.78 (m, 2H), 7.59 (dd, J=8.4 Hz, 2.4 Hz, 1H), 7.51-7.38 (m, 4H), 5.52 (s, 2H), 3.08-2.99 (m, 1H), 2.07-1.97 (m, 2H), 1.79-1.69 (m, 2H), 1.68-1.33 (m, 6H).
MH+ 556.

Example 317

2-(4-((1H-1,2,4-triazol-1-yl)methyl)-5-(4-chlorophenyl)-1-(2,4-dichlorophenyl)-1H-pyrazol-3-yl)-5-(1-phenylcyclopropyl)-1,3,4-oxadiazole $^1$H NMR (400 MHz, DMSO-d$_6$) δ 8.38 (s, 1H), 7.94 (s, 1H), 7.89-7.78 (m, 2H), 7.60-7.55 (m, 1H), 7.48-7.26 (m, 8H), 5.52 (s, 2H), 1.69-1.64 (m, 2H), 1.55-1.47 (m, 2H).
MH+ 588.

Example 318

2-(4-((1H-1,2,4-triazol-1-yl)methyl)-5-(4-chlorophenyl)-1-(2,4-dichlorophenyl)-1H-pyrazol-3-yl)-5-(1-p-tolylcyclopropyl)-1,3,4-oxadiazole $^1$H NMR (400 MHz, DMSO-d$_6$) δ 8.37 (s, 1H), 7.88 (s, 1H), 7.84-7.76 (m, 2H), 7.57 (dd, J=8.4 Hz, 2.4 Hz, 1H), 7.48-7.43 (m, 2H), 7.43-7.36 (m, 8H), 7.30-7.24 (m, 2H), 7.18-7.12 (m, 2H), 5.52 (s, 2H), 2.26 (s, 3H), 1.65-1.59 (m, 2H), 1.48-1.41 (m, 2H).
MH+ 603.

Example 319

2-(4-((1H-1,2,4-triazol-1-yl)methyl)-5-(4-chlorophenyl)-1-(2,4-dichlorophenyl)-1H-pyrazol-3-yl)-5-(1-(4-methoxyphenyl)cyclopropyl)-1,3,4-oxadiazole $^1$H NMR (400 MHz, DMSO-d$_6$) δ 8.38 (s, 1H), 7.88 (s, 1H), 7.85-7.74 (m, 2H), 7.57 (dd, J=8.4 Hz, 2.4 Hz, 1H), 7.50-7.29 (m, 6H), 6.91-6.84 (m, 2H), 5.47 (s, 2H), 3.72 (s, 3H), 1.65-1.56 (m, 2H), 1.46-1.39 (m, 2H).
MH+ 619.

Example 320

2-(4-((1H-1,2,4-triazol-1-yl)methyl)-5-(4-chlorophenyl)-1-(2,4-dichlorophenyl)-1H-pyrazol-3-yl)-5-(1-(2,4-dichlorophenyl)cyclopropyl)-1,3,4-oxadiazole $^1$H NMR (400 MHz, DMSO-d$_6$) δ 8.37 (s, 1H), 7.87 (s, 1H), 7.82 (d, J=8.4 Hz, 1H), 7.77 (d, J=2.4 Hz, 1H), 7.65 (d, J=2.0 Hz, 1H), 7.60 (d, J=8.4 Hz, 1H), 7.57 (dd, J=8.4 Hz, 2.4 Hz, 1H), 7.49-7.25 (m, 5H), 5.46 (s, 2H), 1.83-1.74 (m, 2H), 1.60-1.51 (m, 2H).
MH+ 656.

Example 321

2-(4-((1H-1,2,4-triazol-1-yl)methyl)-5-(4-chlorophenyl)-1-(2,4-dichlorophenyl)-1H-pyrazol-3-yl)-5-(1-(trifluoromethyl)cyclobutyl)-1,3,4-oxadiazole $^1$H NMR (300 MHz, CDCl$_3$) δ 8.47 (s, 1H), 7.91 (s, 1H), 7.89-7.79 (m, 2H), 7.61 (dd, J=8.4 Hz, 2.4 Hz, 1H), 7.51-7.39 (m, 4H), 5.54 (s, 2H), 2.81-2.63 (m, 4H), 2.15-2.03 (m, 4H).
MH+ 594.

Example 322

2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclobutyl)-1,3,4-oxadiazole $^1$H NMR (300 MHz, CDCl$_3$) δ 8.42 (s, 1H), 7.89 (s, 1H), 7.86-7.75 (m, 2H), 7.58 (dd, J=8.7 Hz, 2.1 Hz, 1H), 7.50-7.31 (m, 8H), 5.49 (s, 2H), 3.01-2.83 (m, 2H), 2.76-2.62 (m, 2H), 2.15-1.85 (m, 2H).
MH+ 636.

Example 323

2-(4-((1H-1,2,4-triazol-1-yl)methyl)-5-(4-chlorophenyl)-1-(2,4-dichlorophenyl)-1H-pyrazol-3-yl)-5-(1-phenylcyclopentyl)-1,3,4-oxadiazole $^1$H NMR (300 MHz, CDCl$_3$) δ 8.41 (s, 1H), 7.88 (s, 1H), 7.85-7.76 (m, 2H), 7.57 (dd, J=8.7 Hz, 2.1 Hz, 1H), 7.50-7.31 (m, 9H), 5.48 (s, 2H), 2.73-2.65 (m, 2H), 2.21-2.11 (m, 2H), 1.80-1.65 (m, 4H).
MH+ 618.

Example 324

2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopentyl)-1,3,4-oxadiazole $^1$H NMR (300 MHz, CDCl$_3$) δ 8.42 (s, 1H), 7.88 (s, 1H), 7.86-7.77 (m, 2H), 7.58 (dd, J=8.7 Hz, 2.1 Hz, 1H), 7.52-7.31 (m, 8H), 5.48 (s, 2H), 2.74-2.63 (2H), 2.20-2.09 (m, 2H), 1.84-1.62 (m, 4H).
MH+ 650.

Example 325

2-(4-((1H-1,2,4-triazol-1-yl)methyl)-1-(2-chlorophenyl)-5-(4-chlorophenyl)-1H-pyrazol-3-yl)-5-tert-butyl-1,3,4-oxadiazole $^1$H NMR (400 MHz, CDCl$_3$) δ 8.88 (s, 1H), 8.05 (s, 1H), 7.49-7.32 (m, 8H), 5.64 (s, 2H), 1.51 (s, 9H), 1.45 (s, 9H).
MH+ 494.

Example 326

2-(4-((1H-1,2,4-triazol-1-yl)methyl)-5-(4-chlorophenyl)-1-(2,4-dichlorophenyl)-1H-pyrazol-3-yl)-5-(1-methylcyclopropyl)-1,3,4-oxadiazole $^1$H NMR (400 MHz, DMSO-d$_6$) δ 8.41 (s, 1H), 7.89 (s, 1H), 7.83 (d, J=8.8 Hz, 1H), 7.60 (d, J=2.4 Hz, 1H), 7.59 (dd, J=8.8 Hz, 2.4 Hz, 1H), 7.50-7.76 (m, 4H), 5.50 (s, 2H), 1.50 (s, 3H), 1.26-1.19 (m, 2H), 1.05-0.99 (m, 2H).
MH+ 528.

Example 327

2-(4-((1H-1,2,4-triazol-1-yl)methyl)-5-(4-bromophenyl)-1-(2,4-dichlorophenyl)-1H-pyrazol-3-yl)-5-(1-(trifluoromethyl)cyclopropyl)-1,3,4-oxadiazole $^1$H NMR (400 MHz, DMSO-d$_6$) δ 8.43 (s, 1H), 7.89 (s, 1H), 7.85 (d, J=8.8 Hz, 1H), 7.80 (d, J=2.4 Hz, 1H), 7.63-7.55 (m, 3H), 7.38-7.30 (m, 2H), 5.52 (s, 2H), 1.73 (s, 4H).
MH+ 624.

Example 328

2-(4-((1H-1,2,4-triazol-1-yl)methyl)-5-(4-bromophenyl)-1-(2,4-dichlorophenyl)-1H-pyrazol-3-yl)-5-(1-(4-chlorophenyl)cyclopropyl)-1,3,4-oxadiazole $^1$H NMR (400 MHz, DMSO-d$_6$) δ 8.39 (s, 1H), 7.88 (s, 1H), 7.81 (d, J=8.4 Hz, 1H), 7.77 (d, J=2.4 Hz, 1H), 7.63-7.43 (m, 3H), 7.47-7.39 (m, 4H), 7.35-7.29 (m, 2H), 5.48 (s, 2H), 1.70-1.63 (m, 2H), 1.53-1.46 (m, 2H).
MH+ 666.

Example 329

2-(4-((1H-1,2,4-triazol-1-yl)methyl)-5-(4-bromophenyl)-1-(2,4-dichlorophenyl)-1H-pyrazol-3-yl)-5-tert-butyl-1,3,4-oxadiazole $^1$H NMR (400 MHz, DMSO-d$_6$) δ 8.44 (s, 1H), 7.89 (s, 1H), 7.85 (d, J=8.8 Hz, 1H), 7.79 (d, J=2.0 Hz, 1H), 7.63-7.57 (m, 3H), 7.37-7.31 (m, 2H), 5.51 (s, 2H), 1.37 (s, 9H).
MH+ 572.

Example 330

2-(4-((1H-tetrazol-5-yl)methyl)-5-(4-chlorophenyl)-1-(2,4-dichlorophenyl)-1H-pyrazol-3-yl)-5-tert-butyl-1,3,4-oxadiazole To the solution of cyanide (200 mg, 0.41 mmol) in DMF (2 mL) was added NaN$_3$ (320 mg, 4.93 mmol) and NH$_4$Cl (264 mg, 4.93 mmol) and the reaction mixture was irradiated in a microwave reactor (Biotage) for 20 min at 180° C. The reaction mixture was cooled to room temperature and diluted with 30% MeOH/CHCl$_3$. The organic layer was washed with aq. saturated NaHCO$_3$ solution. The organic layer was dried over anhydrous MgSO$_4$, filtered, and concentrated in vacuo. Purification by Prep-LC (Gilson) provided 87 mg (40%) of desired tetrazole as solid.

$^1$H NMR (400 MHz, CDCl$_3$) δ 7.46-7.28 (m, 7H), 4.34 (s, 2H), 2.91 (d, J=29.2 Hz, 1H), 1.54 (s, 9H).
MH+ 529.

Example 331

2-tert-butyl-5-(5-(4-chlorophenyl)-1-(2,4-dichlorophenyl)-4-((2-methyl-2H-tetrazol-5-yl)methyl)-1H-pyrazol-3-yl)-1,3,4-oxadiazole $^1$H NMR (400 MHz, CDCl$_3$) δ 7.47-7.42 (m, 3H), 7.35-7.29 (m, 4H), 4.32 (s, 2H), 4.25 (s, 3H), 1.45 (s, 9H).
MH+ 543.

Example 332

2-tert-butyl-5-(5-(4-chlorophenyl)-1-(2,4-dichlorophenyl)-4-((1-methyl-1H-tetrazol-5-yl)methyl)-1H-pyrazol-3-yl)-1,3,4-oxadiazole $^1$H NMR (400 MHz, CDCl$_3$) δ 7.42-7.37 (m, 2H), 7.31-7.23 (m, 3H), 7.18-7.14 (m, 2H), 4.48 (s, 2H), 4.22 (s, 3H), 1.45 (s, 9H).
MH+ 543.

Example 333

2-(4-chloro-5-(4-chlorophenyl)-1-(2,4-dichlorophenyl)-1H-pyrazol-3-yl)-5-cyclobutyl-1,3,4-oxadiazole Step 1: Ethyl 4-chloro-5-(4-chlorophenyl)-1-(2,4-dichlorophenyl)-1H-pyrazole-3-carboxylate To a solution of ethyl 5-(4-chlorophenyl)-1-(2,4-dichlorophenyl)-1H-pyrazole-3-carboxylate (3.0 g, 7.6 mmol) in acetic acid (30 ml) at room temperature was bubbled chlorine gas for 10 minutes. The reaction mixture was stirred at room temperature for 2 hours and the resulting solution was quenched with water (100 ml). The organic solution was extracted with diethyl ether (100 ml×2). With saturated sodium bicarbonate solution, remained acetic acid was removed and organic phase was evaporated with reduced pressure. The crude residue was purified with silica gel column (hexane/ethyl acetate=5/1) to produce title compound (3.1 g, 95% yield) as white solid.

$^1$H NMR (400 MHz, CDCl$_3$) δ 7.41 (d, J=2.0 Hz, 1H), 7.38 (d, J=8.4 Hz, 1H), 7.35-7.32 (m, 3H), 7.20-7.18 (m, 2H), 4.48 (q, J=7.2 Hz, 2H), 1.44 (t, J=7.2 Hz, 3H).
MH+ 430.

Step 2: 4-chloro-5-(4-chlorophenyl)-1-(2,4-dichlorophenyl)-1H-pyrazole-3-carbohydrazide A solution of ethyl 4-chloro-5-(4-chlorophenyl)-1-(2,4-dichlorophenyl)-1H-pyrazole-3-carboxylate (3.1 g, 7.2 mmol) in ethyl alcohol (30 ml) was added hydrazine (5 ml, 64% solution in water) in one portion. The reaction mixture was refluxed 100° C. for 6 hours, and then cooled down to room temperature. After volatile solvent was removed in reduced pressure, the residue was purified with silica gel column (5% methanol in methylene chloride) to obtained title compound (3 g, quantitatively) as slightly yellow solid.
MH+ 415.

Step 3: 2-(4-chloro-5-(4-chlorophenyl)-1-(2,4-dichlorophenyl)-1H-pyrazol-3-yl)-5-cyclobutyl-1,3,4-oxadiazole $^1$H NMR (400 MHz, CDCl$_3$) δ 7.44-7.38 (m, 1H), 7.40-7.33 (m, 4H), 7.25-7.22 (m, 2H), 4.06-4.02 (m, 1H), 2.61-2.57 (m, 2H), 2.54-2.48 (m, 2H), 2.18-2.07 (m, 2H).
MH+ 481.

Example 334

2-(4-chloro-5-(4-chlorophenyl)-1-(2,4-dichlorophenyl)-1H-pyrazol-3-yl)-5-tert-pentyl-1,3,4-oxadiazole $^1$H NMR (400 MHz, CDCl$_3$) δ 7.45-7.44 (m, 1H), 7.38-7.33 (m, 4H), 7.26-7.22 (m, 2H), 1.86 (q, J=7.2 Hz, 2H), 1.56 (s, 3H), 1.50 (s, 3H), 0.89 (t, J=7.2 Hz, 3H).
MH+ 497.

Example 335

2-(4-chloro-5-(4-chlorophenyl)-1-(2,4-dichlorophenyl)-1H-pyrazol-3-yl)-5-cyclohexyl-1,3,4-oxadiazole $^1$H NMR (400 MHz, CDCl$_3$) δ 7.45-7.40 (m, 2H), 7.38-7.33 (m, 3H), 7.26-7.22 (m, 2H), 3.26-3.24 (m, 1H), 2.20-1.86 (m, 4H), 1.58-1.44 (m, 6H).
MH+ 509.

Example 336

2-sec-butyl-5-(4-chloro-5-(4-chlorophenyl)-1-(2,4-dichlorophenyl)-1H-pyrazol-3-yl)-1,3,4-oxadiazole $^1$H NMR (400 MHz, CDCl$_3$) δ 7.45-7.41 (m, 2H), 7.38-7.26 (m, 3H), 7.25-7.22 (m, 2H), 3.39-3.34 (m, 1H), 1.87-1.75 (m, 2H), 1.46 (d, J=6.8 Hz, 3H), 0.99 (t, J=7.2 Hz).
MH+ 483.

Example 337

2-tert-butyl-5-(4-chloro-5-(4-chlorophenyl)-1-(2,4-dichlorophenyl)-1H-pyrazol-3-yl)-1,3,4-oxadiazole $^1$H NMR (400 MHz, CDCl$_3$) δ 7.48-7.41 (m, 2H), 7.39-7.24 (m, 3H), 7.23-7.19 (m, 2H), 1.57 (s, 9H).
MH+ 483.

Example 338

2-(4-bromo-5-(4-chlorophenyl)-1-(2,4-dichlorophenyl)-1H-pyrazol-3-yl)-5-tert-butyl-1,3,4-oxadiazole Step 1: 4-bromo-5-(4-chlorophenyl)-1-(2,4-dichlorophenyl)-1H-pyrazole-3-carboxylic acid To a solution of ethyl 4-bromo-5-(4-chlorophenyl)-1-(2,4-dichlorophenyl)-1H-pyrazole-3-carboxylate (3.5 g, 7.37 mmol) in methanol (50 ml) at room temperature was added potassium hydroxide (830 mg, 14.8 mmol) in one portion. The reaction mixture was warmed to 100° C. and then stirred for 5 hours. The resulting solution was cooled down to room temperature and then evaporated the volatile solvent. The residue was acidified with 10% hydrochloric acid and then filtered using water and hexane. The filtrated solid was dried under vacuum to obtain the title compound (3.2 g, 97%) as pale yellow solid.
MH+ 446.

Step 2: 2-(4-bromo-5-(4-chlorophenyl)-1-(2,4-dichlorophenyl)-1H-pyrazol-3-yl)-5-tert-butyl-1,3,4-oxadiazole $^1$H NMR (400 MHz, CDCl$_3$) δ 7.50-7.41 (m, 2H), 7.37-7.24 (m, 3H), 7.23-7.19 (m, 2H), 1.57 (s, 9H).
MH+ 527.

Example 339

2-(4-bromo-5-(4-chlorophenyl)-1-(2,4-dichlorophenyl)-1H-pyrazol-3-yl)-5-sec-butyl-1,3,4-oxadiazole $^1$H NMR (400 MHz, CDCl$_3$) δ 7.43-7.42 (m, 1H), 7.40-7.37 (m, 1H), 7.35-7.32 (m, 3H), 7.25-7.21 (m, 2H), 3.14-3.10 (m, 1H), 1.96-1.90 (m, 1H), 1.79-1.71 (m, 1H), 1.43 (dd, J=2.8, 7.2 Hz, 3H), 0.91 (m, 3H).
MH+ 527.

Example 340

2-(4-bromo-5-(4-chlorophenyl)-1-(2,4-dichlorophenyl)-1H-pyrazol-3-yl)-5-cyclobutyl-1,3,4-oxadiazole $^1$H NMR (400 MHz, CDCl$_3$) δ 7.43 (d, J=2.0 Hz, 1H), 7.38 (d, J=8.8 Hz, 1H), 7.35-7.32 (m, 3H), 7.25-7.21 (m, 2H), 3.87-3.78 (m, 1H), 2.60-2.42 (m, 4H), 2.17-2.05 (m, 2H).
MH+ 525.

Example 341

2-(4-bromo-5-(4-chlorophenyl)-1-(2,4-dichlorophenyl)-1H-pyrazol-3-yl)-5-cyclohexyl-1,3,4-oxadiazole $^1$H NMR (400 MHz, CDCl$_3$) δ 7.42 (dd, J=2.0, 3.6 Hz, 1H), 7.38 (dd, J=3.2, 8.4 Hz, 1H), 7.36-7.32 (m, 3H), 7.26-7.21 (m, 2H), 3.04-2.98 (m, 1H), 2.16-2.12 (m, 2H), 1.86-1.76 (m, 2H), 1.73-1.67 (m, 3H), 1.45-1.33 (m, 3H).
MH+ 553.

Example 342

2-(4-bromo-5-(4-chlorophenyl)-1-(2,4-dichlorophenyl)-1H-pyrazol-3-yl)-5-tert-pentyl-1,3,4-oxadiazole $^1$H NMR (400 MHz, CDCl$_3$) δ 7.43-7.39 (m, 2H), 7.35-7.32 (m, 3H), 7.23-7.21 (m, 2H), 1.58-1.68 (dq, J=7.6, 49.2 Hz, 2H), 1.46 (s, 3H), 1.36 (s, 3H), 0.90-0.78 (dt, J=7.6, 31.6 Hz, 3H).
MH+ 541.

Example 343

2-(4-bromo-5-(4-chlorophenyl)-1-(2,4-dichlorophenyl)-1H-pyrazol-3-yl)-5-(2-(4-chlorophenyl)propan-2-yl)-1,3,4-oxadiazole $^1$H NMR (400 MHz, CDCl$_3$) δ 7.42-7.37 (m, 1H), 7.35-7.10 (m, 4H), 7.29-7.27 (m, 3H), 7.24-7.18 (m, 2H), 7.12-7.09 (m, 1H), 1.88 (s, 3H), 1.72 (s, 3H)
MH+ 623.

Example 344

2-(4-bromo-5-(4-chlorophenyl)-1-(2,4-dichlorophenyl)-1H-pyrazol-3-yl)-5-(1-(4-chlorophenyl)cyclopropyl)-1,3,4-oxadiazole $^1$H NMR (400 MHz, CDCl$_3$) δ 7.44-7.41 (m, 1H), 7.37-7.32 (m, 4H), 7.27-7.24 (m, 3H), 7.21-7.18 (m, 2H), 7.12-7.08 (m, 1H), 1.96 (dd, J=9.2, 6.7 Hz, 2H), 1.45 (dd, J=9.2, 6.7 Hz, 2H)

MH+ 621.

Preparation of 1,3,4-thiadiazole (Formula (Ib))

Example 345

2-(5-(4-chlorophenyl)-1-(2,4-dichlorophenyl)-4-methyl-1H-pyrazol-3-yl)-5-cyclobutyl-1,3,4-thiadiazole N-cyclobutanoyl-N'-[5-(4-Chlorophenyl)-1-(2,4-dichlorophenyl)-4-methyl-1H-pyrazole-3-carbonyl]-hydrazine (0.14 g, 0.29 mmol) was added to a microwave reactor containing Lawesson's reagent (0.18 g, 0.44 mmol) in 1,4-dioxane (3 mL). The capped reactor was placed into a microwave reactor and the mixture was heated at 180° C. for 15 min, and the process was repeated one more time. The reaction mixture was then purified by preparative HPLC to provide the title compound (60 mg, 0.16 mmol, 43%) as yellow solid.

$^1$H NMR (400 MHz, CDCl$_3$) δ 7.43 (d, J=2.3 Hz, 1H), 7.34-7.28 (m, 4H), 7.13-7.09 (m, 2H), 4.01 (m, 1H), 2.62-2.52 (m, 2H), 2.49 (s, 3H), 2.47-2.39 (m, 2H), 2.20-2.00 (m, 2H).

MH+ 475.

The following compounds of Examples 346 to 547 were obtained by using corresponding starting materials and repeating the procedure of Example 345.

Example 346

2-(5-(4-chlorophenyl)-1-(2,4-dichlorophenyl)-4-methyl-1H-pyrazol-3-yl)-5-cyclopentyl-1,3,4-thiadiazole $^1$H NMR (400 MHz, CDCl$_3$) δ 7.42 (d, J=1.84 Hz, 1H), 7.34-7.28 (m, 4H), 7.11 (dt, J=2.28, 8.24 Hz, 2H), 3.60 (m, 1H), 2.49 (s, 3H), 2.26 (m, 2H), 1.94-1.81 (m, 4H), 1.74 (m, 2H).

MH+ 489.

Example 347

2-(5-(4-chlorophenyl)-1-(2,4-dichlorophenyl)-4-methyl-1H-pyrazol-3-yl)-5-cyclohexyl-1,3,4-thiadiazole $^1$H NMR (400 MHz, CDCl$_3$) δ 7.41 (d, J=1.84 Hz, 1H), 7.37-7.29 (m, 4H), 7.11 (dt, J=2.28, 8.24 Hz, 2H), 2.99 (m, 1H), 2.44 (s, 3H), 2.16-2.12 (m, 2H), 1.87-1.81 (m, 2H), 1.78-1.65 (m, 3H), 1.44-1.28 (m, 3H).

MH+ 487.

Example 348

2-(5-(4-chlorophenyl)-1-(2,4-dichlorophenyl)-4-methyl-1H-pyrazol-3-yl)-5-cyclopropyl-1,3,4-thiadiazole

MH+ 461.

Example 349

2-(5-(4-chlorophenyl)-1-(2,4-dichlorophenyl)-4-methyl-1H-pyrazol-3-yl)-5-(furan-2-yl)-1,3,4-thiadiazole

MH+ 486.

Example 350

2-(5-(4-chlorophenyl)-1-(2,4-dichlorophenyl)-4-methyl-1H-pyrazol-3-yl)-5-(pyrazin-2-yl)-1,3,4-thiadiazole $^1$H-NMR (400 MHz, CDCl$_3$) δ 9.64 (d, J=1.40 Hz, 1H), 8.67 (d, J=2.28 Hz, 1H), 8.64 (dd, J=1.40, 2.32 Hz, 1H), 7.44 (d, J=1.84 Hz, 1H), 7.36-7.29 (m, 4H), 7.15-7.11 (m, 2H), 2.56 (s, 3H).

MH+ 499.

Example 351

2-(5-(4-chlorophenyl)-1-(2,4-dichlorophenyl)-4-methyl-1H-pyrazol-3-yl)-5-(thiophen-2-yl)-1,3,4-thiadiazole $^1$H-NMR (400 MHz, CDCl$_3$) δ 7.58 (dd, J=0.92, 3.68 Hz, 1H), 7.50 (dd, J=1.36, 5.04 Hz, 1H), 7.44 (d, J=1.84 Hz, 1H), 7.36-7.29 (m, 4H), 7.15-7.11 (m, 3H), 2.52 (s, 3H).

MH+ 503.

Example 352

2-(5-(4-chlorophenyl)-1-(2,4-dichlorophenyl)-4-methyl-1H-pyrazol-3-yl)-5-(pyridin-2-ylmethyl)-1,3,4-thiadiazole $^1$H-NMR (400 MHz, CDCl$_3$) δ 8.59 (d, J=5.04 Hz, 1H), 7.66 (dt, J=1.84, 7.76 Hz, 1H), 7.41 (d, J=1.84 Hz, 1H), 7.36 (d, J=7.76 Hz, 1H), 7.33-7.28 (m, 4H), 7.20 (dd, J=5.04, 7.32 Hz, 1H), 7.13-7.09 (m, 2H), 4.66 (s, 2H), 2.48 (s, 3H).

MH+ 512.

Example 353

2-(5-(4-chlorophenyl)-1-(2,4-dichlorophenyl)-4-methyl-1H-pyrazol-3-yl)-5-isopropyl-1,3,4-thiadiazole $^1$H-NMR (400 MHz, CDCl$_3$) δ 7.42 (d, J=1.84 Hz, 1H), 7.33-7.28 (m, 3H), 7.13-7.09 (m, 2H), 3.50 (m, 1H), 2.49 (s, 3H), 1.47 (d, J=6.88 Hz, 6H).

MH+ 463.

Example 354

2-benzyl-5-(5-(4-chlorophenyl)-1-(2,4-dichlorophenyl)-4-methyl-1H-pyrazol-3-yl)-1,3,4-thiadiazole $^1$H-NMR (400 MHz, CDCl$_3$) δ 7.40 (br s, 1H), 7.34-7.28 (m, 9H), 7.16-7.12 (m, 2H), 4.45 (s, 2H), 2.48 (s, 3H).
MH+ 511.

Example 355

2-Butyl-5-(5-(4-chlorophenyl)-1-(2,4-dichlorophenyl)-4-methyl-1H-pyrazol-3-yl)-1,3,4-thiadiazole $^1$H-NMR (400 MHz, CDCl$_3$) δ 7.43-7.42 (m, 1H), 7.34-7.29 (m, 4H), 7.13-7.10 (m, 2H), 3.14 (t, J=7.8 Hz, 2H), 2.49 (s, 3H), 1.85-1.79 (m, 2H), 1.52-1.42 (m, 2H), 0.97 (t, J=7.3 Hz, 3H).
MH+ 477.

Example 356

2-(5-(4-Chlorophenyl)-1-(2,4-dichlorophenyl)-4-methyl-1H-pyrazol-3-yl)-5-phenyl-1,3,4-thiadiazole $^1$H-NMR (300 MHz, CDCl$_3$) δ 8.05-8.01 (m, 2H), 7.51-7.48 (m, 3H), 7.45-7.44 (m, 1H), 7.35-7.31 (m, 4H), 7.16-7.12 (m, 2H), 2.55 (s, 3H).
MH+ 497.

Example 357

2-(5-(4-Chlorophenyl)-1-(2,4-dichlorophenyl)-4-methyl-1H-pyrazol-3-yl)-5-(cyclopentylmethyl)-1,3,4-thiadiazole $^1$H-NMR (300 MHz, CDCl$_3$) δ 7.43-7.42 (m, 1H), 7.35-7.28 (m, 4H), 7.13-7.10 (m, 2H), 3.14 (d, J=7.5, 2H), 2.50 (s, 3H), 2.36-2.26 (m, 1H), 1.88-1.84 (m, 2H), 1.71-1.54 (m, 4H), 1.37-1.25 (m, 2H).
MH+ 503.

Example 358

2-(5-(4-Chlorophenyl)-1-(2,4-dichlorophenyl)-4-methyl-1H-pyrazol-3-yl)-5-(tetrahydro-2H-pyran-4-yl)-1,3,4-thiadiazole $^1$H-NMR (300 MHz, CDCl$_3$) δ 7.43-7.42 (m, 1H), 7.35-7.30 (m, 4H), 7.14-7.10 (m, 2H), 4.11-4.07 (m, 2H), 3.63-3.55 (m, 2H), 3.50-3.40 (m, 1H), 2.50 (s, 3H), 2.14-2.11 (m, 2H), 2.05-1.92 (m, 2H).
MH+ 505.

Example 359

2-(5-(4-Chlorophenyl)-1-(2,4-dichlorophenyl)-4-methyl-1H-pyrazol-3-yl)-5-(tetrahydrofuran-2-yl)-1,3,4-thiadiazole $^1$H-NMR (300 MHz, CDCl$_3$) δ 7.43-7.42 (m, 1H), 7.35-7.30 (m, 4H), 7.13-7.10 (m, 2H), 5.43-5.39 (m, 1H), 4.11-4.04 (m, 1H), 4.00-3.93 (m, 1H), 2.52-2.47 (m, 1H), 2.49 (s, 3H), 2.37-2.28 (m, 1H), 2.09-2.03 (m, 2H).
MH+ 491.

Example 360

2-(5-(4-chlorophenyl)-1-(2,4-dichlorophenyl)-4-methyl-1H-pyrazol-3-yl)-5-methyl-1,3,4-thiadiazole $^1$H-NMR (400 MHz, CDCl$_3$) δ 7.42 (d, J=1.84 Hz, 1H), 7.35-7.29 (m, 4H), 7.13-7.10 (m, 2H), 2.82 (s, 3H), 2.48 (s, 3H).
MH+ 435.

Example 361

2-(5-(4-Chlorophenyl)-1-(2,4-dichlorophenyl)-4-methyl-1H-pyrazol-3-yl)-5-pentyl-1,3,4-thiadiazole $^1$H-NMR (400 MHz, CDCl$_3$) δ 7.43-7.42 (m, 1H), 7.34-7.29 (m, 4H), 7.13-7.10 (m, 2H), 3.14 (t, J=7.8 Hz, 2H), 2.49 (s, 3H), 1.88-1.81 (m, 2H), 1.43-1.38 (m, 4H), 0.91 (t, J=7.3 Hz, 3H).
MH+ 491.

Example 362

2-(5-(4-Chlorophenyl)-1-(2,4-dichlorophenyl)-4-methyl-1H-pyrazol-3-yl)-5-cycloheptyl-1,3,4-thiadiazole $^1$H-NMR (400 MHz, CDCl$_3$) δ 7.43-7.42 (m, 1H), 7.34-7.31 (m, 4H), 7.13-7.10 (m, 2H), 3.47-3.43 (m, 1H), 2.47 (s, 3H), 2.22-2.17 (m, 4H), 1.87-1.79 (m, 4H), 1.70-1.59 (m, 4H).
MH+ 517.

Example 363

2-(5-(4-Chlorophenyl)-1-(2,4-dichlorophenyl)-4-methyl-1H-pyrazol-3-yl)-5-(2,4-dichlorophenyl)-1,3,4-thiadiazole $^1$H-NMR (400 MHz, CDCl$_3$) δ 8.40 (d, J=8.4 Hz, 1H), 7.57 (d, J=2.2 Hz, 1H), 7.44 (d, J=1.8 Hz, 1H), 7.42 (d, J=2.2 Hz, 1H), 7.37-7.31 (m, 4H), 7.16-7.12 (m, 2H), 2.55 (s, 3H).
MH+ 564.

Example 364

2-(5-(4-Bromophenyl)-1-(2,4-dichlorophenyl)-4-methyl-1H-pyrazol-3-yl)-5-cyclobutyl-1,3,4-thiadiazole $^1$H-NMR (400 MHz, CDCl$_3$) δ 7.50-7.45 (m, 2H), 7.43-7.42 (m, 1H), 7.34-7.28 (m, 2H), 7.07-7.02 (m, 2H), 4.06-3.96 (m, 1H), 2.61-2.52 (m, 2H), 2.50 (s, 3H), 2.46-2.38 (m, 2H), 2.18-1.99 (m, 2H).
MH+ 519.

Example 365

2-(5-(4-Chlorophenyl)-1-(2,4-dichlorophenyl)-4-methyl-1H-pyrazol-3-yl)-5-(cyclohexylmethyl)-1,3,4-thiadiazole $^1$H-NMR (400 MHz, CDCl$_3$) δ 7.42 (bs, 1H), 7.34-7.29 (m, 4H), 7.12-7.10 (m, 2H), 3.02 (d, J=6.4 Hz, 2H), 2.50 (s, 3H), 1.82-1.64 (m, 5H), 1.30-1.02 (m, 6H).
MH+ 517.

Example 366

2-(5-(4-Bromophenyl)-1-(2,4-dichlorophenyl)-4-methyl-1H-pyrazol-3-yl)-5-cyclopentyl-1,3,4-thiadiazole $^1$H-NMR (400 MHz, CDCl$_3$) δ 7.49-7.45 (m, 2H), 7.43-7.42 (m, 1H), 7.34-7.28 (m, 2H), 7.07-7.03 (m, 2H), 3.64-3.57 (m, 1H), 2.49 (s, 3H), 2.29-2.21 (m, 2H), 1.94-1.82 (m, 4H), 1.79-1.69 (m, 2H).
MH+ 533.

Example 367

2-sec-Butyl-5-(5-(4-chlorophenyl)-1-(2,4-dichlorophenyl)-4-methyl-1H-pyrazol-3-yl)-1,3,4-thiadiazole $^1$H-NMR (400 MHz, CDCl$_3$) δ 7.43-7.42 (m, 1H), 7.40-7.28 (m, 4H), 7.13-7.10 (m, 2H), 3.36-3.27 (m, 1H), 2.50 (s, 3H), 1.91-1.73 (m, 2H), 1.44 (d, J=6.9 Hz, 3H), 0.98 (t, J=7.3 Hz, 3H).
MH+ 477.

Example 368

2-(5-(4-Chlorophenyl)-1-(2,4-dichlorophenyl)-4-methyl-1H-pyrazol-3-yl)-5-(pentan-2-yl)-1,3,4-thiadiazole $^1$H-NMR (400 MHz, CDCl$_3$) δ 7.43-7.42 (m, 1H), 7.34-7.28 (m, 4H), 7.13-7.10 (m, 2H), 3.45-3.37 (m, 1H), 2.49 (s, 3H), 1.84-1.67 (m, 2H), 1.44 (d, J=6.9 Hz, 3H), 1.41-1.33 (m, 2H), 0.92 (t, J=7.3 Hz, 3H).
MH+ 491.

Example 369

2-(5-(4-Bromophenyl)-1-(2,4-dichlorophenyl)-4-methyl-1H-pyrazol-3-yl)-5-tert-butyl-1,3,4-thiadiazole $^1$H-NMR (400 MHz, CDCl$_3$) δ 7.49-7.45 (m, 2H), 7.43-7.42 (m, 1H), 7.33-7.28 (m, 2H), 7.07-7.04 (m, 2H), 2.49 (s, 3H), 1.53 (s, 9H).
MH+ 521.

Example 370

2-(5-(4-Chlorophenyl)-1-(2,4-dichlorophenyl)-4-methyl-1H-pyrazol-3-yl)-5-(cyclopropylmethyl)-1,3,4-thiadiazole $^1$H-NMR (400 MHz, CDCl$_3$) δ 7.43-7.42 (m, 1H), 7.34-7.29 (m, 4H), 7.14-7.10 (m, 2H), 3.03 (d, J=7.3 Hz, 2H), 2.50 (s, 3H), 1.25-1.14 (m, 1H), 0.69-0.64 (m, 2H), 0.40-0.35 (m, 2H).
MH+ 475.

Example 371

2-(4-tert-Butylcyclohexyl)-5-(5-(4-chlorophenyl)-1-(2,4-dichlorophenyl)-4-methyl-1H-pyrazol-3-yl)-1,3,4-thiadiazole $^1$H-NMR (400 MHz, CDCl$_3$) δ 7.43-7.42 (m, 1H), 7.37-7.28 (m, 4H), 7.13-7.10 (m, 2H), 3.14-3.08 (m, 1H), 2.49 (s, 3H), 2.31-2.28 (m, 2H), 1.95-1.92 (m, 2H), 1.66-1.52 (m, 4H), 1.25-1.04 (m, 1H), 0.89 (s, 9H).
MH+ 559.

Example 372

2-tert-Butyl-5-(5-(4-chlorophenyl)-1-(2,4-dichlorophenyl)-4-methyl-1H-pyrazol-3-yl)-1,3,4-thiadiazole $^1$H-NMR (400 MHz, CDCl$_3$) δ 7.43-7.42 (m, 1H), 7.38-7.28 (m, 4H), 7.14-7.10 (m, 2H), 2.50 (s, 3H), 1.53 (s, 9H).
MH+ 477.

Example 373

2-(5-(4-Bromophenyl)-1-(2,4-dichlorophenyl)-4-methyl-1H-pyrazol-3-yl)-5-cyclohexyl-1,3,4-thiadiazole $^1$H-NMR (400 MHz, CDCl$_3$) δ 7.50-7.45 (m, 2H), 7.43-7.42 (m, 1H), 7.34-7.28 (m, 2H), 7.07-7.03 (m, 2H), 3.22-3.16 (m, 1H), 2.49 (s, 3H), 2.22-2.17 (m, 2H), 1.90-1.84 (m, 2H), 1.78-1.28 (m, 6H).
MH+ 547.

Example 374

2-(5-(4-Bromophenyl)-1-(2,4-dichlorophenyl)-4-ethyl-1H-pyrazol-3-yl)-5-cyclohexyl-1,3,4-thiadiazole $^1$H-NMR (400 MHz, CDCl$_3$) δ 7.49-7.45 (m, 2H), 7.42-7.41 (m, 1H), 7.33 (d, J=8.3 Hz, 1H), 7.30-7.28 (m, 1H), 7.09-7.05 (m, 2H), 3.21-3.15 (m, 1H), 2.95-2.89 (m, 2H), 2.23-2.18 (m, 2H), 1.90-1.84 (m, 2H), 1.78-1.28 (m, 6H), 1.26-1.22 (m, 3H).
MH+ 561.

Example 375

2-(5-(4-Bromophenyl)-1-(2,4-dichlorophenyl)-4-ethyl-1H-pyrazol-3-yl)-5-cyclobutyl-1,3,4-thiadiazole $^1$H-NMR (400 MHz, CDCl$_3$) δ 7.49-7.45 (m, 2H), 7.42-7.41 (m, 1H), 7.34-7.28 (m, 2H), 7.08-7.05 (m, 2H), 4.05-3.96 (m, 1H), 2.95-2.89 (m, 2H), 2.60-2.52 (m, 2H), 2.49-2.39 (m, 2H), 2.18-2.00 (m, 2H), 1.30-1.22 (m, 3H).
MH+ 533.

Example 376

2-(5-(4-Bromophenyl)-1-(2,4-dichlorophenyl)-4-ethyl-1H-pyrazol-3-yl)-5-cyclopentyl-1,3,4-thiadiazole $^1$H-NMR (400 MHz, CDCl$_3$) δ 7.49-7.45 (m, 2H), 7.42-7.41 (m, 1H), 7.34-7.28 (m, 2H), 7.08-7.05 (m, 2H), 3.64-3.56 (m, 1H), 2.95-2.89 (m, 2H), 2.29-2.22 (m, 2H), 1.95-1.82 (m, 4H), 1.79-1.70 (m, 2H), 1.26-1.22 (m, 3H).
MH+ 547.

Example 377

2-(5-(4-Bromophenyl)-1-(2,4-dichlorophenyl)-4-ethyl-1H-pyrazol-3-yl)-5-tert-butyl-1,3,4-thiadiazole $^1$H-NMR (400 MHz, CDCl$_3$) δ 7.49-7.45 (m, 2H), 7.42-7.41 (m, 1H), 7.34-7.28 (m, 2H), 7.08-7.05 (m, 2H), 2.95-2.89 (m, 2H), 1.56 (s, 9H), 1.28-1.24 (m, 3H).
MH+ 535.

Example 378

2-(5-(4-Bromophenyl)-1-(2,4-dichlorophenyl)-4-methyl-1H-pyrazol-3-yl)-5-cycloheptyl-1,3,4-thiadiazole $^1$H-NMR (300 MHz, CDCl$_3$) δ 7.49-7.46 (m, 2H), 7.43-7.42 (m, 1H), 7.35-7.28 (m, 2H), 7.06-7.04 (m, 2H), 3.47-3.37 (m, 1H), 2.49 (s, 3H), 2.24-2.18 (m, 2H), 1.87-1.60 (m, 10H).
MH+ 561.

Example 379

2-(5-(4-Chlorophenyl)-1-(2,4-dichlorophenyl)-4-methyl-1H-pyrazol-3-yl)-5-(hexan-2-yl)-1,3,4-thiadiazole $^1$H-NMR (300 MHz, CDCl$_3$) δ 7.43-7.42 (m, 1H), 7.35-7.28 (m, 4H), 7.13-7.10 (m, 2H), 3.42-3.35 (m, 1H), 2.50 (s, 3H), 1.78-1.73 (m, 2H), 1.44 (d, J=6.7 Hz, 3H), 1.34-1.32 (m, 4H), 0.90-0.85 (m, 3H).
MH+ 505.

Example 380

2-(5-(4-Bromophenyl)-1-(2,4-dichlorophenyl)-4-methyl-1H-pyrazol-3-yl)-5-(hexan-2-yl)-1,3,4-thiadiazole $^1$H-NMR (300 MHz, CDCl$_3$) δ 7.49-7.45 (m, 2H), 7.43-7.42 (m, 1H), 7.35-7.28 (m, 2H), 7.07-7.03 (m, 2H), 3.44-3.35 (m, 1H), 2.50 (s, 3H), 1.85-1.69 (m, 2H), 4.44 (d, J=6.7 Hz, 3H), 1.36-1.25 (m, 4H), 0.90-0.85 (m, 3H).
MH+ 549.

Example 381

2-(5-(4-chlorophenyl)-1-(2,4-dichlorophenyl)-4-methyl-1H-pyrazol-3-yl)-5-(1-phenylethyl)-1,3,4-thiadiazole $^1$H NMR (400 MHz, CDCl$_3$) δ 7.40-7.23 (m, 10H), 7.12-7.08 (m, 2H), 4.64 (m, 1H), 2.48 (s, 3H), 1.87 (d, J=7.4 Hz, 3H).
MH+ 525.

Example 382

5-(5-(4-chlorophenyl)-1-(2,4-dichlorophenyl)-4-methyl-1H-pyrazol-3-yl)-N-cyclohexyl-1,3,4-thiadiazol-2-amine

MH+ 518.

Example 383

2-(5-(4-chlorophenyl)-1-(2,4-dichlorophenyl)-4-methyl-1H-pyrazol-3-yl)-5-(cyclohex-3-enyl)-1,3,4-thiadiazole

MH+ 501.

Example 384

2-(5-(4-chlorophenyl)-1-(2,4-dichlorophenyl)-4-methyl-1H-pyrazol-3-yl)-5-(cyclopent-3-enyl)-1,3,4-thiadiazole $^1$H NMR (400 MHz, CDCl$_3$) δ 7.42 (d, J=1.8 Hz), 7.34-7.28 (m, 4H), 7.15-7.10 (m, 2), 5.80 (s, 2H), 4.05 (m, 1H), 4.06 (m, 2H), 4.05 (m, 2H), 2.49 (s, 3H).
MH+ 487.

Example 385

2-(5-(4-chlorophenyl)-1-(2,4-dichlorophenyl)-4-methyl-1H-pyrazol-3-yl)-5-(1-phenylpropan-2-yl)-1,3,4-thiadiazole $^1$H NMR (300 MHz, CDCl$_3$) δ 7.43 (d, J=2.34 Hz, 2H), 7.38-7.24 (m, 5H), 7.24-7.19 (m, 3H), 7.12-7.10 (m, 2H), 3.48-3.43 (m, 1H), 3.37-3.30 (m, 1H), 2.95-2.88 (m, 1H), 2.50 (s, 3H), 1.46 (d, J=6.78 Hz, 3H).
MH+ 541.

Example 386

2-(5-(4-bromophenyl)-1-(2,4-dichlorophenyl)-4-ethyl-1H-pyrazol-3-yl)-5-(cyclohexylmethyl)-1,3,4-thiadiazole $^1$H NMR (300 MHz, CDCl$_3$) δ 7.49-7.46 (m, 2H), 7.42-7.41 (m, 1H), 7.36-7.27 (m, 2H), 7.08-7.05 (m, 2H), 3.02 (d, J=6.6 Hz, 2H), 2.96-2.88 (m, 2H), 1.85-1.65 (m, 7H), 1.27-1.04 (m, 7H).
MH+ 576.

Example 387

2-(5-(4-bromophenyl)-1-(2,4-dichlorophenyl)-4-methyl-1H-pyrazol-3-yl)-5-(cyclohexylmethyl)-1,3,4-thiadiazole $^1$H NMR (300 MHz, CDCl$_3$) δ 7.50-7.45 (m, 2H), 7.43-7.42 (m, 1H), 7.36-7.28 (m, 2H), 7.06-7.03 (m, 2H), 3.03 (d, J=6.6 Hz, 2H), 2.49 (s, 3H), 1.88-1.62 (m, 7H), 1.23-1.02 (m, 4H).
MH+ 561.

Example 388

2-(5-(4-bromophenyl)-1-(2,4-dichlorophenyl)-4-ethyl-1H-pyrazol-3-yl)-5-(hexan-2-yl)-1,3,4-thiadiazole $^1$H NMR (300 MHz, CDCl$_3$) δ 7.49-7.46 (m, 2H), 7.42-7.41 (m, 1H), 7.35-7.27 (m, 2H), 7.09-7.05 (m, 2H), 3.41-3.34 (m, 1H), 2.96-2.88 (m, 2H), 1.83-1.73 (m, 2H), 1.44 (d, J=6.9 Hz, 3H), 1.36-1.23 (m, 7H), 0.90-0.86 (m, 3H).
MH+ 563.

Example 389

2-tert-butyl-5-(5-(4-chlorophenyl)-1-(2,4-dichlorophenyl)-4-ethyl-1H-pyrazol-3-yl)-1,3,4-thiadiazole $^1$H NMR (300 MHz, CDCl$_3$) δ 7.42-7.41 (m, 1H), 7.35-7.27 (m, 4H), 7.15-7.12 (m, 2H), 2.95-2.88 (m, 2H), 1.53 (s, 9H), 1.26 (t, J=7.3 Hz, 3H).
MH+ 491.

Example 390

2-(5-(4-chlorophenyl)-1-(2,4-dichlorophenyl)-4-ethyl-1H-pyrazol-3-yl)-5-cyclohexyl-1,3,4-thiadiazole

MH+ 517.

Example 391

2-(5-(4-chlorophenyl)-1-(2,4-dichlorophenyl)-4-methyl-1H-pyrazol-3-yl)-5-(1-cyclopentylethyl)-1,3,4-thiadiazole $^1$H NMR (300 MHz, CDCl$_3$) δ 7.42-7.11 (m, 5H), 7.15-7.11 (m, 2H), 3.12-3.10 (m, 1H), 2.44 (s, 3H), 1.90-1.73 (m, 1H), 1.70-1.50 (m, 4H), 1.44-1.40 (m, 4H), 1.41 (d, J=7.0 Hz, 3H).
MH+ 519.

Example 392

2-(5-(4-chlorophenyl)-1-(2,4-dichlorophenyl)-4-methyl-1H-pyrazol-3-yl)-5-(1-cyclohexylethyl)-1,3,4-thiadiazole $^1$H NMR (300 MHz, CDCl$_3$) δ 7.42-7.11 (m, 5H), 7.09-7.02 (m, 2H), 3.22-3.19 (m, 1H), 2.42 (s, 3H), 1.91-1.72 (m, 2H), 1.69-1.50 (m, 5H), 1.44-1.40 (m, 4H), 1.44 (d, J=7.33 Hz, 3H).
MH+ 531.

Example 393

2-(5-(4-chlorophenyl)-1-(2,4-dichlorophenyl)-4-methyl-1H-pyrazol-3-yl)-5-(2-cyclopentylpropan-2-yl)-1,3,4-thiadiazole $^1$H NMR (300 MHz, CDCl$_3$) δ 7.56-7.53 (m, 2H), 7.39-7.33 (m, 2H), 7.25-7.20 (m, 2H), 7.11-7.08 (m, 1H), 2.50 (s, 3H), 1.90-1.88 (m, 1H), 1.74-1.50 (m, 4H), 1.45 (s, 6H), 1.43-1.40 (m, 4H).
MH+ 531.

Example 394

2-(5-(4-chlorophenyl)-1-(2,4-dichlorophenyl)-4-methyl-1H-pyrazol-3-yl)-5-(2-cyclohexylpropan-2-yl)-1,3,4-thiadiazole $^1$H NMR (300 MHz, CDCl$_3$) δ 7.56-7.53 (m, 2H), 7.38-7.34 (m, 2H), 7.26-7.20 (m, 2H), 7.15-7.12 (m, 1H), 2.54 (s, 3H), 1.97-1.87 (m, 1H), 1.74-1.50 (m, 6H), 1.44 (s, 6H), 1.43-1.40 (m, 3H).
MH+ 547.

Example 395

2-(5-(4-chlorophenyl)-1-(2,4-dichlorophenyl)-4-ethyl-1H-pyrazol-3-yl)-5-cyclobutyl-1,3,4-thiadiazole $^1$H NMR (400 MHz, CDCl$_3$) δ 7.42-7.41 (m, 1H), 7.35-7.28 (m, 4H), 7.15-7.12 (m, 2H), 4.03-3.98 (m, 1H), 2.94-2.89 (m, 2H), 2.60-2.52 (m, 2H), 2.49-2.39 (m, 2H), 2.16-2.01 (m, 2H), 1.25 (t, J=7.2 Hz, 3H).
MH+ 489.

Example 396

2-(5-(4-chlorophenyl)-1-(2,4-dichlorophenyl)-4-ethyl-1H-pyrazol-3-yl)-5-cyclopentyl-1,3,4-thiadiazole $^1$H NMR (400 MHz, CDCl$_3$) δ 7.42-7.41 (m, 1H), 7.34-7.28 (m, 4H), 7.14-7.12 (m, 2H), 3.62-3.58 (m, 1H), 2.94-2.89 (m, 2H), 2.30-2.23 (m, 2H), 1.95-1.70 (m, 6H), 1.25 (t, J=7.2 Hz, 3H).
MH+ 503.

Example 397

2-(5-(4-chlorophenyl)-1-(2,4-dichlorophenyl)-4-ethyl-1H-pyrazol-3-yl)-5-cycloheptyl-1,3,4-thiadiazole $^1$H NMR (400 MHz, CDCl$_3$) δ 7.42-7.41 (m, 1H), 7.34-7.27 (m, 4H), 7.15-7.11 (m, 2H), 3.43-3.38 (m, 1H), 2.94-2.89 (m, 2H), 2.24-2.18 (m, 2H), 1.90-1.79 (m, 4H), 1.70-1.57 (m, 6H), 1.24 (t, J=7.3 Hz, 3H).
MH+ 531.

Example 398

2-sec-butyl-5-(5-(4-chlorophenyl)-1-(2,4-dichlorophenyl)-4-ethyl-1H-pyrazol-3-yl)-1,3,4-thiadiazole $^1$H NMR (400 MHz, CDCl$_3$) δ 7.42-7.41 (m, 1H), 7.34-7.27 (m, 4H), 7.15-7.10 (m, 2H), 3.35-3.26 (m, 1H), 2.95-2.89 (m, 2H), 1.92-1.73 (m, 2H), 1.45 (d, J=6.88 Hz, 3H), 1.25 (t, J=7.32 Hz, 3H), 0.98 (t, J=7.36 Hz, 3H).
MH+ 491.

Example 399

2-(5-(4-bromophenyl)-1-(2,4-dichlorophenyl)-4-ethyl-1H-pyrazol-3-yl)-5-sec-butyl-1,3,4-thiadiazole $^1$H NMR (400 MHz, CDCl$_3$) δ 7.49-7.45 (m, 2H), 7.42 (d, J=1.84 Hz, 1H), 7.33 (d, J=8.28 Hz, 1H), 7.29 (dd, J=8.24, 1.81 Hz, 1H), 7.08-7.05 (m, 2H), 3.34-3.28 (m, 1H), 2.95-2.89 (m, 2H), 1.90-1.75 (m, 2H), 1.45 (d, J=6.88 Hz, 3H), 1.25 (t, J=7.32 Hz, 3H), 1.98 (t, J=7.32 Hz, 3H).
MH+ 535.

Example 400

2-(5-(4-bromophenyl)-1-(2,4-dichlorophenyl)-4-ethyl-1H-pyrazol-3-yl)-5-cycloheptyl-1,3,4-thiadiazole $^1$H NMR (400 MHz, CDCl$_3$) δ 7.49-7.46 (m, 2H), 7.41 (d, J=1.84 Hz, 1H), 7.33 (d, J=8.24 Hz, 1H), 7.29 (dd, J=8.24, 1.84 Hz, 1H), 7.10-7.05 (m, 2H), 3.43-3.37 (m, 1H), 2.95-2.89 (m, 2H), 2.25-2.19 (m, 2H), 1.90-1.79 (m, 4H), 1.70-1.57 (m, 6H), 1.24 (t, J=7.32 Hz, 3H).

MH+ 575.

Example 401

2-(5-(4-chlorophenyl)-1-(2,4-dichlorophenyl)-4-methyl-1H-pyrazol-3-yl)-5-(2-phenylpropan-2-yl)-1,3,4-thiadiazole $^1$H NMR (400 MHz, CDCl$_3$) δ 7.42-7.38 (m, 1H), 7.36-7.27 (m, 7H), 7.26-7.21 (m, 1H), 7.11-7.01 (m, 2H), 2.50 (s, 3H), 1.95 (s, 6H).

MH+ 539.

Example 402

2-(5-(4-chlorophenyl)-1-(2,4-dichlorophenyl)-4-methyl-1H-pyrazol-3-yl)-5-(2-(4-chlorophenyl)propan-2-yl)-1,3,4-thiadiazole $^1$H NMR (400 MHz, CDCl$_3$) δ 7.41-7.38 (m, 1H), 7.35-7.27 (m, 6H), 7.26-7.21 (m, 1H), 7.11-7.09 (m, 2H), 2.50 (s, 3H), 1.91 (s, 6H).

MH+ 575.

Example 403

2-(5-(4-bromophenyl)-1-(2,4-dichlorophenyl)-4-methyl-1H-pyrazol-3-yl)-5-sec-butyl-1,3,4-thiadiazole $^1$H NMR (400 MHz, CDCl$_3$) δ 7.48-7.46 (m, 2H), 7.42 (bs, 1H), 7.34-7.29 (m, 2H), 7.06-7.04 (m, 2H), 3.34-3.29 (m, 1H), 2.50 (s, 3H), 1.87-1.76 (m, 2H), 1.44 (d, J=6.8 Hz, 3H), 0.98 (t, J=7.6 Hz, 3H).

MH+ 522.

Example 404

2-(5-(4-bromophenyl)-1-(2,4-dichlorophenyl)-4-ethyl-1H-pyrazol-3-yl)-5-(2-phenylpropan-2-yl)-1,3,4-thiadiazole $^1$H NMR (400 MHz, CDCl$_3$) δ 7.48-7.46 (m, 2H), 7.42-7.38 (m, 3H), 7.34-7.30 (m, 2H), 7.27-7.22 (m, 3H), 7.06-7.04 (m, 2H), 2.92-2.90 (m, 2H), 1.94 (s, 6H), 1.27 (t, J=7.6 Hz, 3H).

MH+ 598.

Example 405

2-tert-butyl-5-(1-(2-chlorophenyl)-5-(4-chlorophenyl)-4-methyl-1H-pyrazol-3-yl)-1,3,4-thiadiazole $^1$H NMR (400 MHz, CDCl$_3$) δ 7.44-7.24 (m, 6H), 7.18-7.12 (m, 2H), 2.51 (s, 3H), 1.53 (s, 9H).

MH+ 443.

Example 406

2-(5-(4-chlorophenyl)-1-(2,4-dichlorophenyl)-4-methyl-1H-pyrazol-3-yl)-5-(2-methylhexan-2-yl)-1,3,4-thiadiazole $^1$H NMR (400 MHz, CDCl$_3$) δ 7.42 (m, 1H), 7.35-7.30 (m, 4H), 7.34-7.30 (m, 2H), 2.50 (s, 3H), 1.77 (m, 2H), 1.50 (s, 6H), 1.26 (m, 4H), 0.86 (t, J=6.8 Hz, 3H).

MH+ 519.

Example 407

2-sec-butyl-5-(1-(2-chlorophenyl)-5-(4-chlorophenyl)-4-methyl-1H-pyrazol-3-yl)-1,3,4-thiadiazole $^1$H NMR (400 MHz, CDCl$_3$) δ 7.42-7.26 (m, 6H), 7.14-7.09 (m, 2H), 3.31 (sextet, J=6.8 Hz, 1H), 2.50 (s, 3H), 1.80-1.72 (m, 2H), 1.44 (d, J=7.2 Hz, 3H), 0.97 (t, J=7.6 Hz, 3H).

MH+ 443.

Example 408

2-(1-(2-chlorophenyl)-5-(4-chlorophenyl)-4-methyl-1H-pyrazol-3-yl)-5-cyclohexyl-1,3,4-thiadiazole $^1$H NMR (400 MHz, CDCl$_3$) δ 7.43-7.26 (m, 6H), 7.15-7.05 (m, 2H), 3.25-3.17 (m, 1H), 2.51 (s, 3H), 2.26-2.17 (m, 2H), 1.93-1.80 (m, 2H), 1.80-1.72 (m, 1H), 1.68-1.53 (m, 2H), 1.52-1.38 (m, 2H), 1.38-1.26 (m, 1H).

MH+ 469.

Example 409

2-(1-(2-chlorophenyl)-5-(4-chlorophenyl)-4-methyl-1H-pyrazol-3-yl)-5-cyclobutyl-1,3,4-thiadiazole $^1$H NMR (400 MHz, CDCl$_3$) δ 7.43-7.27 (m, 6H), 7.15-7.07 (m, 2H), 4.01 (quintet, J=8.8 Hz, 1H), 2.61-2.38 (m, 7H), 2.19-2.01 (m, 2H).

MH+ 441.

Example 410

2-(1-(2-chlorophenyl)-5-(4-chlorophenyl)-4-methyl-1H-pyrazol-3-yl)-5-tert-pentyl-1,3,4-thiadiazole $^1$H NMR (400 MHz, CDCl$_3$) δ 7.43-7.26 (m, 6H), 7.16-7.10 (m, 2H), 2.52 (s, 3H), 1.83 (quartet, J=7.6 Hz, 2H), 1.46 (s, 6H), 0.87 (t, J=7.6 Hz, 3H).

MH+ 457.

Example 411

2-(1-(2-chlorophenyl)-5-(4-chlorophenyl)-4-methyl-1H-pyrazol-3-yl)-5-(hexan-2-yl)-1,3,4-thiadiazole $^1$H NMR (400 MHz, CDCl$_3$) δ 7.42-7.27 (m, 6H), 7.18-7.12 (m, 2H), 3.39 (sextet, J=6.8 Hz, 1H), 2.51 (s, 3H), 1.85-1.69 (m, 3H), 1.44 (d, J=7.2 Hz, 2H), 1.42-1.25 (m, 4H), 0.89 (t, J=6.8 Hz, 3H).

MH+ 471.

Example 412

2-(5-(4-chlorophenyl)-1-(2,4-dichlorophenyl)-4-ethyl-1H-pyrazol-3-yl)-5-(pentan-2-yl)-1,3,4-thiadiazole $^1$H NMR (400 MHz, CDCl$_3$) δ 7.42-7.41 (m, 2H), 7.34-7.30 (m, 4H), 7.15-7.12 (m, 2H), 3.43-3.38 (m, 1H), 2.95-2.90 (m, 2H), 1.84-1.67 (m, 4H), 1.46-1.44 (m, 2H), 1.25 (t, J=7.2 Hz, 3H), 0.93 (t, J=7.6 Hz, 3H).
MH+ 505.

Example 413

2-(5-(4-bromophenyl)-1-(2,4-dichlorophenyl)-4-methyl-1H-pyrazol-3-yl)-5-(pentan-2-yl)-1,3,4-thiadiazole $^1$H NMR (400 MHz, CDCl$_3$) δ 7.49-7.46 (m, 2H), 7.43-7.42 (m, 1H), 7.34-7.31 (m, 2H), 7.06-7.04 (m, 2H), 3.44-3.38 (m, 1H), 2.49 (s, 3H), 1.84-1.66 (m, 4H), 1.44 (d, J=6.8 Hz, 3H), 1.41-1.36 (m, 2H), 0.93 (t, J=7.2 Hz, 3H).
MH+ 536.

Example 414

2-(5-(4-bromophenyl)-1-(2,4-dichlorophenyl)-4-ethyl-1H-pyrazol-3-yl)-5-(pentan-2-yl)-1,3,4-thiadiazole $^1$H NMR (400 MHz, CDCl$_3$) δ 7.48-7.46 (m, 2H), 7.42-7.41 (m, 1H), 7.34-7.28 (m, 2H), 7.08-7.06 (m, 2H), 3.43-3.37 (m, 1H), 2.95-2.89 (m, 2H), 1.83-1.67 (m, 4H), 1.45-1.43 (d, J=6.8 Hz, 3H), 1.41-1.34 (m, 2H), 1.25 (t, J=7.2 Hz, 3H), 0.93 (t, J=7.2 Hz, 3H).
MH+ 549.

Example 415

2-(1-(2-chlorophenyl)-5-(4-chlorophenyl)-4-methyl-1H-pyrazol-3-yl)-5-(2-methylhexan-2-yl)-1,3,4-thiadiazole $^1$H NMR (400 MHz, CDCl$_3$) δ 7.46-7.27 (m, 6H), 7.30-7.11 (m, 2H), 2.45 (s, 3H), 1.83-1.74 (m, 2H), 1.47 (s, 6H), 1.33-1.18 (m, 4H), 0.88 (t, J=6.8 Hz, 3H).
MH+ 485.

Example 416

2-(1-(2-chlorophenyl)-5-(4-chlorophenyl)-4-methyl-1H-pyrazol-3-yl)-5-(2-phenylpropan-2-yl)-1,3,4-thiadiazole $^1$H NMR (400 MHz, CDCl$_3$) δ 7.43-7.21 (m, 11H), 7.19-7.09 (m, 2H), 2.51 (s, 3H), 1.94 (s, 6H).
MH+ 505.

Example 417

2-(5-(4-bromophenyl)-1-(4-chlorophenyl)-4-methyl-1H-pyrazol-3-yl)-5-tert-pentyl-1,3,4-thiadiazole $^1$H NMR (400 MHz, CDCl$_3$) δ 7.55 (d, J=8.8 Hz, 2H), 7.31 (d, J=6.4 Hz, 2H), 7.20 (d, J=6.4 Hz, 2H), 7.08 (d, J=8.8 Hz, 2H), 2.47 (s, 3H), 1.85 (q, J=7.2 Hz, 2H), 1.50 (s, 6H), 0.90 (t, J=7.2 Hz, 3H).
MH+ 503.

Example 418

2-(5-(4-bromophenyl)-1-(4-chlorophenyl)-4-methyl-1H-pyrazol-3-yl)-5-sec-butyl-1,3,4-thiadiazole $^1$H NMR (400 MHz, CDCl$_3$) δ 7.55-7.53 (m, 2H), 7.35-7.30 (m, 2H), 7.26-7.20 (m, 2H), 7.09-7.06 (m, 2H), 3.35-3.23 (m, 1H), 2.46 (s, 3H), 1.97-1.91 (m, 2H), 1.71-1.40 (m, 2H), 1.42 (d, J=6.8 Hz, 3H), 0.96 (t, J=7.2 Hz, 3H).
MH+ 489.

Example 419

2-(5-(4-chlorophenyl)-1-(2,4-dichlorophenyl)-4-methyl-1H-pyrazol-3-yl)-5-(2-methoxypropan-2-yl)-1,3,4-thiadiazole $^1$H NMR (400 MHz, CDCl$_3$) δ 7.44 (m, 1H), 7.36-7.32 (m, 4H), 7.16-7.12 (m, 2H), 7.28 (s, 3H), 2.51 (s, 3H), 1.74 (s, 6H).
MH+ 493.

Example 420

2-(1-(2,4-dichlorophenyl)-4-methyl-5-phenyl-1H-pyrazol-3-yl)-5-tert-pentyl-1,3,4-thiadiazole $^1$H NMR (400 MHz, CDCl$_3$) δ 7.41 (d, J=2.0 Hz, 1H), 7.35-7.32 (m, 3H), 7.31 (s, 1H), 7.28 (d, J=2.0 Hz, 1H), 7.21-7.17 (m, 2H), 2.52 (s, 3H), 1.84 (q, J=8.0 Hz, 2H), 1.49 (s, 6H), 0.88 (t, J=7.2 Hz, 3H).
MH+ 457.

Example 421

2-tert-butyl-5-(1-(2,4-dichlorophenyl)-4-methyl-5-phenyl-1H-pyrazol-3-yl)-1,3,4-thiadiazole $^1$H NMR (400 MHz, CDCl$_3$) δ 7.41 (d, J=2.4 Hz, 1H), 7.35-7.32 (m, 3H), 7.31 (s, 1H), 7.28 (d, J=2.0 Hz, 1H), 7.21-7.17 (m, 2H), 2.51 (s, 3H), 1.53 (s, 9H).
MH+ 443.

Example 422

2-sec-butyl-5-(1-(2,4-dichlorophenyl)-4-methyl-5-phenyl-1H-pyrazol-3-yl)-1,3,4-thiadiazole $^1$H NMR (400 MHz, CDCl$_3$) δ 7.41 (d, J=2.0 Hz, 1H), 7.35-7.32 (m, 3H), 7.31 (s, 1H), 7.28 (d, J=2.0 Hz, 1H), 7.21-7.17 (m, 2H), 3.39-3.28 (m, 1H), 2.52 (s, 3H), 1.89-1.75 (m, 2H), 1.45 (d, J=6.8 Hz, 3H), 0.98 (t, J=7.2 Hz, 3H).
MH+ 443.

Example 423

2-cyclobutyl-5-(1-(2,4-dichlorophenyl)-4-methyl-5-phenyl-1H-pyrazol-3-yl)-1,3,4-thiadiazole $^1$H NMR (400 MHz, CDCl$_3$) δ 7.41 (d, J=2.4 Hz, 1H), 7.35-7.32 (m, 3H), 7.31 (s, 1H), 7.28 (d, J=2.0 Hz, 1H), 7.20-7.17 (m, 2H), 4.05-3.97 (m, 1H), 2.61-2.38 (m, 7H), 2.16-2.03 (m, 2H).
MH+ 441.

Example 424

2-(5-(4-bromophenyl)-1-(4-chlorophenyl)-4-methyl-1H-pyrazol-3-yl)-5-cyclobutyl-1,3,4-thiadiazole $^1$H NMR (400 MHz, CDCl$_3$) δ 7.55-7.54 (m, 2H), 7.32-7.31 (m, 2H), 7.26-7.20 (m, 2H), 7.08-7.06 (m, 2H), 3.81-3.79 (m, 1H), 2.57-2.53 (m, 2H), 2.49-2.45 (m, 2H), 2.42 (s, 3H), 2.17-2.04 (m, 2H).
MH+ 487.

Example 425

2-(5-(4-bromophenyl)-1-(2-chlorophenyl)-4-methyl-1H-pyrazol-3-yl)-5-tert-butyl-1,3,4-thiadiazole $^1$H NMR (400 MHz, CDCl$_3$) δ 7.46-7.43 (m, 3H), 7.41-7.38 (m, 1H), 7.36-7.31 (m, 2H), 7.07-7.04 (m, 2H), 2.5 (s, 3H), 1.50 (s, 9H).
MH+ 487.

Example 426

2-(5-(4-bromophenyl)-1-(2-chlorophenyl)-4-methyl-1H-pyrazol-3-yl)-5-cyclohexyl-1,3,4-thiadiazole $^1$H NMR (400 MHz, CDCl$_3$) δ 7.45-7.41 (m, 3H), 7.40-7.38 (m, 1H), 7.37-7.32 (m, 2H), 7.07-7.05 (m, 2H), 3.22-3.15 (m, 1H), 2.50 (s, 3H), 2.21-2.18 (m, 2H), 1.89-1.84 (m, 2H), 1.77-1.65 (m, 1H), 1.64-1.55 (m, 2H), 1.50-1.40 (m, 2H), 1.35-1.29 (m, 1H).
MH+ 513.

Example 427

2-(5-(4-bromophenyl)-1-(2-chlorophenyl)-4-methyl-1H-pyrazol-3-yl)-5-cyclobutyl-1,3,4-thiadiazole $^1$H NMR (400 MHz, CDCl$_3$) δ 7.45-7.31 (m, 6H), 7.07-7.05 (m, 2H), 4.03-3.98 (m, 1H), 2.59-2.52 (m, 2H), 2.51 (s, 3H), 2.50-2.40 (m, 2H), 2.16-2.02 (m, 2H).
MH+ 485.

Example 428

2-(5-(4-bromophenyl)-1-(2-chlorophenyl)-4-methyl-1H-pyrazol-3-yl)-5-sec-butyl-1,3,4-thiadiazole $^1$H NMR (400 MHz, CDCl$_3$) δ 7.46-7.29 (m, 6H), 7.08-7.05 (m, 2H), 3.34-3.29 (m, 1H), 2.50 (s, 3H), 1.89-1.76 (m, 1H), 1.44 (d, J=6.8 Hz, 3H), 0.98 (t, J=7.6 Hz, 3H).
MH+ 487.

Example 429

2-(5-(4-bromophenyl)-1-(2-chlorophenyl)-4-methyl-1H-pyrazol-3-yl)-5-tert-pentyl-1,3,4-thiadiazole $^1$H NMR (400 MHz, CDCl$_3$) δ 7.46-7.29 (m, 6H), 7.08-7.05 (m, 2H), 2.51 (s, 3H), 1.83 (q, J=7.6 Hz, 2H), 1.49 (s, 6H), 0.88 (t, J=7.6 Hz, 3H).
MH+ 501.

Example 430

2-(5-(4-chlorophenyl)-1-(2,4-dichlorophenyl)-4-methyl-1H-pyrazol-3-yl)-5-(1-(4-chlorophenyl)cyclopropyl)-1,3,4-thiadiazole $^1$H NMR (400 MHz, CDCl$_3$) δ 7.44-5.28 (m, 9H), 7.15-7.08 (m, 2H), 2.46 (s, 3H), 1.94 (m, 2H), 1.50 (m, 2H).
MH+ 571.

Example 431

2-(5-(4-chlorophenyl)-1-(2,4-dichlorophenyl)-4-methyl-1H-pyrazol-3-yl)-5-(1-(4-chlorophenyl)cyclobutyl)-1,3,4-thiadiazole $^1$H NMR (400 MHz, CDCl$_3$) δ 7.40 (m, 1H), 7.35-7.25 (m, 8H), 7.12-7.08 (m, 2H), 3.08 (m, 2H), 2.85 (m, 2H), 2.49 (s, 3H), 2.38 (m, 1H), 2.02 (m, 1H).
MH+ 585.

Example 432

2-(5-(4-bromophenyl)-1-(2,4-dichlorophenyl)-4-ethyl-1H-pyrazol-3-yl)-5-(1-(4-chlorophenyl)cyclopropyl)-1,3,4-thiadiazole $^1$H NMR (400 MHz, CDCl$_3$) δ 7.48-7.31 (m, 9H), 7.06-7.02 (m, 2H), 2.87 (q, J=7.2 Hz, 2H), 1.95 (dd, J=7.2, 4.8 Hz, 2H), 1.50 (dd, J=7.2, 4.8 Hz, 2H), 1.23 (t, J=7.2 Hz, 3H).
MH+ 629.

Example 433

2-(1-(2-chlorophenyl)-5-(4-chlorophenyl)-4-methyl-1H-pyrazol-3-yl)-5-(1-(4-chlorophenyl)cyclopropyl)-1,3,4-thiadiazole $^1$H NMR (400 MHz, CDCl$_3$) δ 7.46-7.26 (m, 10H), 7.14-7.08 (m, 2H), 2.47 (s, 3H), 1.98-1.92 (m, 2H), 1.54-1.48 (m, 2H).
MH+ 536.

Example 434

2-tert-butyl-5-(5-(3-chlorophenyl)-1-(2,4-dichlorophenyl)-4-methyl-1H-pyrazol-3-yl)-1,3,4-thiadiazole $^1$H NMR (400 MHz, CDCl$_3$) δ 7.43 (dd, J=2.4 Hz, 1.8 Hz, 1H), 7.35-7.31 (m, 3H), 7.30-7.24 (m, 2H), 7.22-7.21 (m, 1H), 7.05 (dt, J=8.0 Hz, 1.2 Hz, 1H), 2.51 (s, 3H), 1.53 (s, 9H).
MH+ 477.

Example 435

2-sec-butyl-5-(5-(3-chlorophenyl)-1-(2,4-dichlorophenyl)-4-methyl-1H-pyrazol-3-yl)-1,3,4-thiadiazole $^1$H NMR (400 MHz, CDCl$_3$) δ 7.43 (dd, J=2.4 Hz, 1.8 Hz, 1H), 7.35-7.31 (m, 3H), 7.30-7.26 (m, 2H), 7.22-7.21 (m, 1H), 7.03 (dt, J=7.6 Hz, 1.6 Hz, 1H), 3.34-3.29 (m, 1H), 2.50 (s, 3H), 1.87-1.76 (m, 1H), 1.44 (d, 3H), 0.98 (t, 3H).
MH+ 477.

Example 436

2-(5-(3-chlorophenyl)-1-(2,4-dichlorophenyl)-4-methyl-1H-pyrazol-3-yl)-5-cyclobutyl-1,3,4-thiadiazole $^1$H NMR (400 MHz, CDCl$_3$) δ 7.43 (dd, J=2.0 Hz, 0.4 Hz, 1H), 7.35-7.31 (m, 3H), 7.30-7.24 (m, 2H), 7.22-7.21 (m, 1H), 7.04 (dt, J=7.6 Hz, 1.2 Hz, 1H), 4.01 (m, 1H), 2.60-2.52 (m, 2H), 2.50 (s, 3H), 2.46-2.41 (m, 2H), 2.41-2.03 (m, 2H).
MH+ 475.

Example 437

2-(5-(4-chlorophenyl)-1-(2,4-dichlorophenyl)-4-methyl-1H-pyrazol-3-yl)-5-(2-ethoxypropan-2-yl)-1,3,4-thiadiazole $^1$H NMR (400 MHz, CDCl$_3$) δ 7.42 (br d, J=2.0 Hz, 1H), 7.36-7.29 (m, 4H), 7.14-7.10 (m, 2H), 3.45 (q, J=7.2 Hz, 2H), 2.50 (s, 3H), 1.74 (s, 6H), 1.19 (t, J=7.2 Hz, 3H).
MH+ 507.

Example 438

2-(5-(3-Chlorophenyl)-1-(2,4-dichlorophenyl)-4-methyl-1H-pyrazol-3-yl)-5-cyclohexyl-1,3,4-thiadiazole $^1$H NMR (400 MHz, CDCl$_3$) δ 7.43 (dd, 1H, J=2.0 Hz, 0.4 Hz), 7.35-7.31 (m, 3H), 7.30-7.24 (m, 2H), 7.22-7.21 (m, 1H), 7.04 (dt, 1H, J=7.6 Hz, 1.6 Hz), 3.24-3.16 (m, 1H), 2.51 (s, 3H), 2.22-2.02 (m, 2H), 1.90-1.75 (m, 3H), 1.66-1.56 (m, 2H), 1.51-1.26 (m, 3H).
MH+ 502.

Example 439

2-(5-(3-Chlorophenyl)-1-(2,4-dichlorophenyl)-4-methyl-1H-pyrazol-3-yl)-5-tert-pentyl-1,3,4-thiadiazole $^1$H NMR (400 MHz, CDCl$_3$) δ 7.43 (dd, 1H, J=2.0 Hz, 0.4 Hz), 7.34-7.31 (m, 3H), 7.29-7.24 (m, 2H), 7.22-7.21 (m, 1H), 7.04 (dt, 1H, J=7.6 Hz, 1.2 Hz), δ 2.50 (s, 3H), 1.83 (q, 2H, J=7.6 Hz), 1.49 (s, 6H), 0.88 (t, 3H, J=7.2 Hz).
MH+ 491.

Example 440

2-(5-(4-chlorophenyl)-4-cyclopropyl-1-(2,4-dichlorophenyl)-1H-pyrazol-3-yl)-5-cyclohexyl-1,3,4-thiadiazole $^1$H NMR (400 MHz, CDCl$_3$) δ 7.55-7.49 (m, 2H), 7.36-7.31 (m, 2H), 7.21-7.16 (m, 1H), 7.11-7.01 (m, 2H), 3.14-3.10 (m, 1H), 2.14-2.12 (m, 2H), 1.91-1.87 (m, 2H), 1.78-1.70 (m, 2H), 1.44-1.20 (m, 4H), 0.62-0.60 (m, 2H), 0.37-0.34 (m, 2H).
MH+ 531.

Example 441

2-tert-butyl-5-(5-(4-chlorophenyl)-4-cyclopropyl-1-(2,4-dichlorophenyl)-1H-pyrazol-3-yl)-1,3,4-thiadiazole $^1$H NMR (400 MHz, CDCl$_3$) δ 7.56-7.51 (m, 2H), 7.34-7.31 (m, 2H), 7.20-7.17 (m, 1H), 7.15-7.11 (m, 2H), 1.44 (m, 1H), 1.32 (s, 9H), 0.61-0.59 (m, 2H), 0.37-0.34 (m, 2H).
MH+ 505.

Example 442

2-(5-(4-chlorophenyl)-4-cyclopropyl-1-(2,4-dichlorophenyl)-1H-pyrazol-3-yl)-5-cyclobutyl-1,3,4-thiadiazole $^1$H NMR (400 MHz, CDCl$_3$) δ 7.54-7.51 (m, 2H), 7.33-7.31 (m, 2H), 7.22-7.18 (m, 1H), 7.14-7.11 (m, 2H), 3.25-2.22 (m, 1H), 1.50-1.47 (m, 1H), 1.45-1.44 (m, 4H), 1.37-1.30 (m, 2H), 0.60-0.57 (m, 2H), 0.37-0.35 (m, 2H).
MH+ 503.

Example 443

2-(1,5-bis(4-chlorophenyl)-4-methyl-1H-pyrazol-3-yl)-5-tert-butyl-1,3,4-thiadiazole $^1$H NMR (400 MHz, CDCl$_3$) δ 7.38 (d, J=8.8 Hz, 2H), 7.30 (d, J=8.8 Hz, 2H), 7.19 (d, J=9.2 Hz, 2H), 7.15 (d, J=8.8 Hz, 2H), 2.46 (s, 3H), 1.54 (s, 9H).
MH+ 443.

Example 444

2-(1,5-bis(4-chlorophenyl)-4-methyl-1H-pyrazol-3-yl)-5-sec-butyl-1,3,4-thiadiazole $^1$H NMR (400 MHz, CDCl$_3$) δ 7.38 (d, J=8.4 Hz, 2H), 7.30 (d, J=8.8 Hz, 2H), 7.19 (d, J=158.8 Hz, 2H), 7.15 (d, J=8.4 Hz, 2H), 3.37-3.28 (m, 1H), 2.46 (s, 3H), 1.91-1.76 (m, 2H), 1.46 (d, J=7.2 Hz, 3H), 0.99 (t, J=7.2 Hz, 3H).
MH+ 443.

Example 445

2-(1,5-bis(4-chlorophenyl)-4-methyl-1H-pyrazol-3-yl)-5-cyclobutyl-1,3,4-thiadiazole $^1$H NMR (400 MHz, CDCl$_3$) δ 7.39 (d, J=8.4 Hz, 2H), 7.30 (d, J=8.8 Hz, 2H), 7.19 (d, J=8.8 Hz, 2H), 7.15 (d, J=8.4 Hz, 2H), 4.06-3.08 (m, 1H), 2.62-2.54 (m, 2H), 2.52-2.42 (m, 5H), 2.20-2.02 (m, 2H).
MH+ 441.

Example 446

2-(1,5-bis(4-chlorophenyl)-4-methyl-1H-pyrazol-3-yl)-5-cyclohexyl-1,3,4-thiadiazole $^1$H NMR (400 MHz, CDCl$_3$) δ 7.38 (d, J=8.8 Hz, 2H), 7.30 (d, J=8.4 Hz, 2H), 7.19 (d, J=8.8 Hz, 2H), 7.15 (d, J=8.4 Hz, 2H), 3.24-3.16 (m, 1H), 2.46 (s, 3H), 2.24-2.20 (m, 2H), 1.91-1.86 (m, 2H), 1.79-1.74 (m, 1H), 1.67-1.57 (m, 2H), 1.52-1.26 (m, 3H).
MH+ 469.

Example 447

2-(1,5-bis(4-chlorophenyl)-4-methyl-1H-pyrazol-3-yl)-5-(1-(4-chlorophenyl)cyclopropyl)-1,3,4-thiadiazole $^1$H NMR (400 MHz, CDCl$_3$) δ 7.45 (d, J=8.8 Hz, 2H), 7.39-7.34 (m, 4H), 7.28-7.24 (m, 2H), 7.14-7.11 (m, 4H), 2.42 (s, 3H), 1.96-1.94 (m, 2H), 1.53-1.50 (m, 2H).
MH+ 537.

Example 448

2-(1,5-bis(4-chlorophenyl)-4-methyl-1H-pyrazol-3-yl)-5-tert-pentyl-1,3,4-thiadiazole $^1$H NMR (400 MHz, CDCl$_3$) δ 7.38 (d, J=8.8 Hz, 2H), 7.29 (d, J=11.6 Hz, 2H), 7.19 (d, J=8.8 Hz, 2H), 7.15 (d, J=8.4 Hz, 2H), 2.46 (s, 3H), 1.84 (q, J=7.2 Hz, 2H), 1.50 (s, 6H), 0.89 (t, J=0.90 Hz, 3H).
MH+ 457.

Example 449

2-(5-(4-chlorophenyl)-1-(2,4-dichlorophenyl)-4-methyl-1H-pyrazol-3-yl)-5-(2-propoxypropan-2-yl)-1,3,4-thiadiazole $^1$H NMR (400 MHz, CDCl$_3$) δ 7.42 (br d, J=2.0 Hz, 1H), 7.36-7.29 (m, 4H), 7.14-7.10 (m, 2H), 3.35 (t, J=6.8 Hz, 2H), 2.50 (s, 3H), 1.73 (s, 6H), 1.57 (m, 2H), 0.90 (t, J=7.2 Hz, 3H).
MH+ 521.

Example 450

2-(5-(4-bromophenyl)-1-(2,4-dichlorophenyl)-4-ethyl-1H-pyrazol-3-yl)-5-(1-phenylcyclopropyl)-1,3,4-thiadiazole $^1$H NMR (400 MHz, CDCl$_3$) δ 7.51-7.42 (m, 4H), 7.37-7.27 (m, 6H), 7.05-7.02 (m, 2H), 2.87 (quartet, J=7.6 Hz, 2H), 1.95 (m, 2H), 1.53 (m, 2H), 1.10 (t, J=7.6 Hz, 3H).
MH+ 596.

Example 451

2-(5-(4-bromophenyl)-1-(2,4-dichlorophenyl)-4-ethyl-1H-pyrazol-3-yl)-5-tert-pentyl-1,3,4-thiadiazole $^1$H NMR (400 MHz, CDCl$_3$) δ 7.49-7.45 (m, 2H), 7.42-7.40 (m, 1H), 7.32-7.26 (m, 2H), 7.08-7.03 (m, 2H), 2.91 (quartet, J=7.2 Hz, 2H), 1.82 (quartet, J=8.0 Hz, 2H), 1.48 (s, 6H), 1.25 (t, J=7.2 Hz, 3H), 0.88 (t, J=7.2 Hz, 3H).
MH+ 550.

Example 452

2-(bicyclo[2.2.1]heptan-2-yl)-5-(5-(4-bromophenyl)-1-(2,4-dichlorophenyl)-4-ethyl-1H-pyrazol-3-yl)-1,3,4-thiadiazole $^1$H NMR (400 MHz, CDCl$_3$) δ 7.49-7.44 (m, 2H), 7.42-7.39 (m, 1H), 7.33-7.26 (m, 2H), 7.08-7.04 (m, 2H), 3.35-3.31 (m, 1H), 2.90 (quartet, J=7.6 Hz, 2H), 2.56 (br d, J=3.6 Hz, 1H), 2.49-2.37 (m, 1H), 2.20-2.02 (m, 1H), 1.95-1.85 (m, 1H), 1.70-1.18 (m, 9H).
MH+ 574.

Example 453

2-(5-(4-bromophenyl)-1-(2,4-dichlorophenyl)-4-ethyl-1H-pyrazol-3-yl)-5-isopropyl-1,3,4-thiadiazole $^1$H NMR (400 MHz, CDCl$_3$) δ 7.48-7.44 (m, 2H), 7.42-7.39 (m, 1H), 7.33-7.26 (m, 2H), 7.08-7.04 (m, 2H), 3.48 (quintet, J=7.2 Hz, 1H), 2.91 (quartet, J=7.2 Hz, 2H), 1.48 (d, J=6.8 Hz, 6H), 1.24 (t, J=7.2 Hz, 3H).
MH+ 522.

Example 454

2-(5-(4-bromophenyl)-1-(2,4-dichlorophenyl)-4-ethyl-1H-pyrazol-3-yl)-5-(pentan-3-yl)-1,3,4-thiadiazole $^1$H NMR (400 MHz, CDCl$_3$) δ 7.48-7.45 (m, 2H), 7.41-7.40 (m, 1H), 7.33-7.26 (m, 2H), 7.08-7.04 (m, 2H), 3.03-3.01 (m, 1H), 2.92 (quartet, J=7.6 Hz, 2H), 1.80-1.45 (m, 4H), 1.24 (t, J=7.6 Hz, 3H), 0.92 (t, J=7.6 Hz, 3H).
MH+ 550.

Example 455

2-(5-(4-bromophenyl)-1-(2,4-dichlorophenyl)-4-ethyl-1H-pyrazol-3-yl)-5-(1-methylcyclohexyl)-1,3,4-thiadiazole $^1$H NMR (400 MHz, CDCl$_3$) δ 7.48-7.44 (m, 2H), 7.41-7.40 (m, 1H), 7.33-7.269 (m, 2H), 7.09-7.04 (m, 2H), 2.91 (quartet, J=7.6 Hz, 2H), 2.28-2.18 (m, 2H), 1.75-1.45 (m, 8H), 1.41 (s, 3H), 1.26 (t, J=7.2 Hz, 3H).
MH+ 577.

Example 456

2-(2-(allyloxy)propan-2-yl)-5-(5-(4-chlorophenyl)-1-(2,4-dichlorophenyl)-4-methyl-1H-pyrazol-3-yl)-1,3,4-thiadiazole $^1$H NMR (400 MHz, CDCl$_3$) δ 7.42-7.30 (m, 5H), 7.14-7.10 (m, 2H), 5.90 (m, 1H), 5.30 (br d, J=17.2 Hz, 1H), 5.14 (br d, J=10.4 Hz, 1H), 3.95 (dt, J=5.2, 1.6 Hz, 2H), 2.50 (s, 3H), 1.77 (s, 6H).
MH+ 519.

Example 457

2-(2-butoxypropan-2-yl)-5-(5-(4-chlorophenyl)-1-(2,4-dichlorophenyl)-4-methyl-1H-pyrazol-3-yl)-1,3,4-thiadiazole $^1$H NMR (400 MHz, CDCl$_3$) δ 7.42 (br d, J=2.0 Hz), 7.37-7.29 (m, 4H), 7.13-7.09 (m, 2H), 3.39 (t, J=6.8 Hz, 2H), 2.50 (s, 3H), 1.73 (s, 6H), 1.54 (m, 2H), 1.36 (m, 2H), 0.89 (t, J=7.2 Hz, 3H).
MH+ 535.

Example 458

2-(5-(4-chlorophenyl)-1-(2,4-dichlorophenyl)-4-methyl-1H-pyrazol-3-yl)-5-(1-(4-methoxyphenyl)cyclopropyl)-1,3,4-thiadiazole $^1$H NMR (400 MHz, CDCl$_3$) δ 7.42-7.37 (m, 3H), 7.31-7.24 (m, 4H), 7.07 (m, 2H), 6.87 (m, 2H), 3.79 (s, 3H), 2.45 (s, 3H), 1.92 (dd, J=7.2, 4.4 Hz, 2H), 1.48 (dd, J=7.2, 4.4 Hz, 2H).
MH+ 567.

Example 459

2-(5-(4-chlorophenyl)-1-(2,4-dichlorophenyl)-4-methyl-1H-pyrazol-3-yl)-5-(1-(2,4-dichlorophenyl)cyclopropyl)-1,3,4-thiadiazole $^1$H NMR (400 MHz, CDCl$_3$) δ 7.44-7.42 (m, 2H), 7.38 (t, J=1.2 Hz, 1H), 7.31-7.25 (m, 5H), 7.08 (m, 2H), 2.45 (s, 3H), 2.01 (dd, J=7.6, 5.2 Hz, 2H), 1.54 (dd, J=7.6, 5.2 Hz, 2H).
MH+ 605.

Example 460

2-(5-(4-chlorophenyl)-1-(2,4-dichlorophenyl)-4-methyl-1H-pyrazol-3-yl)-5-(1-p-tolylcyclopropyl)-1,3,4-thiadiazole $^1$H NMR (400 MHz, CDCl$_3$) δ 7.38-7.25 (m, 7H), 7.14 (m, 2H), 7.08 (m, 2H), 2.46 (s, 3H), 2.33 (s, 3H), 1.94 (dd, J=7.2, 4.4 Hz, 2H), 1.50 (dd, J=7.2, 4.4 Hz, 2H).
MH+ 551.

Example 461

2-(5-(4-chlorophenyl)-1-(2,4-dichlorophenyl)-4-methyl-1H-pyrazol-3-yl)-5-(2-(pentyloxy)propan-2-yl)-1,3,4-thiadiazole $^1$H NMR (400 MHz, CDCl$_3$) δ 7.42 (dd, J=2.0, 0.4 Hz, 1H), 7.34-7.28 (m, 4H), 7.11 (m, 2H), 3.36 (t, J=6.4 Hz, 2H), 2.49 (s, 3H), 1.72 (s, 6H), 1.50 (m, 2H), 1.27 (m, 4H), 0.87 (t, J=5.2 Hz, 3H).
MH+ 549.

Example 462

2-(5-(4-chlorophenyl)-1-(2,4-dichlorophenyl)-4-methyl-1H-pyrazol-3-yl)-5-(1-(trifluoro methyl)cyclopropyl)-1,3,4-thiadiazole $^1$H NMR (400 MHz, CDCl$_3$) δ 7.42 (dd, J=1.6, 0.8 Hz, 1H), 7.33-7.29 (m, 4H), 7.10 (m, 2H), 2.48 (s, 3H), 1.72 (m, 2H), 1.64 (m, 2H).
MH+ 529.

Example 463

2-(5-(4-chlorophenyl)-1-(2,4-dichlorophenyl)-4-ethyl-1H-pyrazol-3-yl)-5-(1-(4-chlorophenyl)cyclopropyl)-1,3,4-thiadiazole $^1$H NMR (400 MHz, CDCl$_3$) δ 7.44-7.40 (m, 2H), 7.38-7.36 (m, 1H), 7.34-7.27 (m, 4H), 7.26-7.23 (m, 2H), 7.12-7.08 (m, 2H), 2.87 (quartet, J=7.6 Hz, 2H), 1.93 (m, 2H), 1.50 (m, 2H), 1.23 (t, J=7.6 Hz, 3H).
MH+ 587.

Example 464

2-(5-(4-bromophenyl)-1-(2-chlorophenyl)-4-ethyl-1H-pyrazol-3-yl)-5-(1-(4-chlorophenyl)cyclopropyl)-1,3,4-thiadiazole $^1$H NMR (400 MHz, CDCl$_3$) δ 7.45-7.41 (m, 4H), 7.37-7.35 (m, 2H), 7.34-7.31 (m, 2H), 7.29-7.24 (m, 2H), 7.05 (d, J=8.8 Hz, 2H), 2.88 (q, J=7.2 Hz, 2H), 1.96-1.93 (m, 2H), 1.52-1.49 (m, JAB=7.2 Hz, 2H), 1.24 (t, J=7.2 Hz, 3H).
MH+ 597.

Example 465

2-(5-(4-chlorophenyl)-1-(2,4-dichlorophenyl)-4-methyl-1H-pyrazol-3-yl)-5-(1-(trifluoro methyl)cyclobutyl)-1,3,4-thiadiazole $^1$H NMR (400 MHz, CDCl$_3$) δ 7.42 (m, 1H), 7.34-7.30 (m, 4H), 7.11 (m, 2H), 2.83 (m, 4H), 2.51 (s, 3H), 2.17 (m, 2H).
MH+ 543.

Example 466

2-(5-(4-chlorophenyl)-1-(2,4-dichlorophenyl)-4-methyl-1H-pyrazol-3-yl)-5-(2,2,2-trifluoroethyl)-1,3,4-thiadiazole $^1$H NMR (400 MHz, CDCl$_3$) δ 7.42 (dd, J=1.6, 0.4 Hz, 1H), 7.34-7.30 (m, 4H), 7.11 (m, 2H), 4.01 (q, J=10.0 Hz, 2H), 2.50 (s, 3H).
+503.

Example 467

2-(1-benzylcyclopropyl)-5-(5-(4-chlorophenyl)-1-(2,4-dichlorophenyl)-4-methyl-1H-pyrazol-3-yl)-1,3,4-thiadiazole $^1$H NMR (400 MHz, CDCl$_3$) δ 7.42-7.41 (m, 1H), 7.35-7.26 (m, 6H), 7.21-7.17 (m, 3H), 7.10-7.08 (m, 2H), 3.30 (s, 2H), 2.45 (s, 3H), 1.50-1.47 (m, 2H), 1.19-1.16 (m, 2H).
MH+ 595.

Example 468

2-(1-benzylcyclopropyl)-5-(5-(4-bromophenyl)-1-(2,4-dichlorophenyl)-4-ethyl-1H-pyrazol-3-yl)-1,3,4-thiadiazole $^1$H NMR (400 MHz, CDCl$_3$) δ 7.46-7.44 (m, 2H), 7.39 (d, J=1.2 Hz, 1H), 7.30-7.23 (m, 6H), 7.21-7.18 (m, 1H), 7.05-7.03 (m, 2H), 3.30 (s, 2H), 2.87 (q, J=7.6 Hz, 2H), 1.51-1.48 (m, 2H), 1.23 (t, J=7.6 Hz, 3H), 1.19-1.16 (m, 2H).
MH+ 611.

Example 469

2-(5-(4-chlorophenyl)-1-(2,4-dichlorophenyl)-4-methyl-1H-pyrazol-3-yl)-5-(1-methylcyclopropyl)-1,3,4-thiadiazole $^1$H NMR (400 MHz, CDCl$_3$) δ 7.41 (dd, J=0.8, 2 Hz, 2H), 7.33-7.28 (m, 4H), 7.14-7.09 (m, 2H), 2.47 (s, 3H), 1.64 (s, 3H), 1.42-1.40 (m, 2H), 1.08-1.05 (m, 2H).
MH+ 475.

Example 470

2-(5-(4-bromophenyl)-1-(2,4-dichlorophenyl)-4-ethyl-1H-pyrazol-3-yl)-5-(1-methylcyclopropyl)-1,3,4-thiadiazole $^1$H NMR (400 MHz, CDCl$_3$) δ 7.47-7.45 (m, 2H), 7.40 (d, J=2 Hz, 1H), 7.32-7.26 (m, 2H), 7.07-7.05 (m, 2H), 2.90 (q, J=7.2 Hz, 2H), 1.64 (s, 3H), 1.46-1.40 (m, 2H), 1.23 (t, J=7.2 Hz, 3H), 1.08-1.06 (m, 2H).
MH+ 535.

Example 471

2-(1-(4-chlorobenzyl)cyclopropyl)-5-(5-(4-chlorophenyl)-1-(2,4-dichlorophenyl)-4-methyl-1H-pyrazol-3-yl)-1,3,4-thiadiazole $^1$H NMR (400 MHz, CDCl$_3$) δ 7.42-7.41 (m, 1H), 7.32-7.28 (m, 4H), 7.23-7.20 (m, 3H), 7.11-7.07 (m, 2H), 3.25 (s, 2H), 2.45 (s, 3H), 1.47 (dd, J=4.8, 6.8 Hz, 2H), 1.72 (dd, J=4.8, 6.8 Hz, 2H).
MH+ 587.

Example 472

2-(1-(4-chlorobenzyl)cyclopropyl)-5-(5-(4-bromophenyl)-1-(2,4-dichlorophenyl)-4-ethyl-1H-pyrazol-3-yl)-1,3,4-thiadiazole $^1$H NMR (400 MHz, CDCl$_3$) δ 7.48-7.44 (m, 2H), 7.40-7.39 (m, 1H), 7.32-7.26 (m, 3H), 7.23-7.20 (m, 3H), 7.06-7.02 (m, 2H), 3.25 (s, 2H), 2.86 (q, J=7.5 Hz, 2H), 1.49-1.46 (m, 2H), 1.36-1.27 (m, 5H).
MH+ 645.

Example 473

2-(5-(4-bromophenyl)-1-(2,4-dichlorophenyl)-4-ethyl-1H-pyrazol-3-yl)-5-(1-(4-methoxyphenyl)cyclopropyl)-1,3,4-thiadiazole $^1$H NMR (400 MHz, CDCl$_3$) δ 7.46-7.39 (m, 4H), 7.37 (dd, J=1.6, 1.2 Hz, 1H), 7.25 (m, 2H), 7.04-7.00 (m, 2H), 6.89-6.85 (m, 2H), 3.80 (s, 3H), 2.87 (q, J=7.6 Hz, 2H), 1.94 (dd, J=7.2, 4.8 Hz, 2H), 1.49 (dd, J=7.2, 4.8 Hz, 2H), 1.21 (t, J=7.6 Hz, 3H).
MH+ 625.

Example 474

2-(5-(4-bromophenyl)-1-(2,4-dichlorophenyl)-4-ethyl-1H-pyrazol-3-yl)-5-(1-p-tolylcyclopropyl)-1,3,4-thiadiazole $^1$H NMR (400 MHz, CDCl$_3$) δ 7.46-7.39 (m, 2H), 7.38-7.36 (m, 3H), 7.24 (m, 2H), 7.17-7.14 (m, 2H), 7.06-7.02 (m, 2H), 2.87 (q, J=7.6 Hz, 2H), 1.96 (dd, J=7.2, 4.8 Hz, 2H), 1.52 (dd, J=7.2, 4.8 Hz, 2H), 1.24 (t, J=7.6 Hz, 3H).
MH+ 609.

Example 475

2-(5-(4-bromophenyl)-1-(2,4-dichlorophenyl)-4-ethyl-1H-pyrazol-3-yl)-5-(1-phenylcyclopropyl)-1,3,4-thiadiazole $^1$H NMR (400 MHz, CDCl$_3$) δ 7.50-7.43 (m, 2H), 7.36-7.29 (m, 4H), 7.24 (m, 2H), 7.04-7.02 (m, 2H), 2.87 (q, J=7.6 Hz, 2H), 1.96 (dd, J=7.2, 4.8 Hz, 2H), 1.54 (dd, J=7.2, 4.8 Hz, 2H), 1.22 (t, J=7.6 Hz, 3H).
MH+ 595.

Example 476

2-(5-(4-bromophenyl)-1-(2,4-dichlorophenyl)-4-ethyl-1H-pyrazol-3-yl)-5-(1-(4-chlorophenyl)cyclobutyl)-1,3,4-thiadiazole $^1$H NMR (400 MHz, CDCl$_3$) δ 7.47-7.43 (m, 2H), 7.38 (t, J=1.2 Hz, 1H), 7.30-7.24 (m, 6H), 7.04-7.02 (m, 2H), 3.09 (m, 2H), 2.90 (q, J=7.6 Hz, 2H), 2.56 (m, 2H), 2.36 (m, 1H), 2.02 (m, 1H), 1.24 (t, J=7.6 Hz, 3H).
MH+ 643.

Example 477

2-(5-(4-bromophenyl)-1-(2,4-dichlorophenyl)-4-ethyl-1H-pyrazol-3-yl)-5-(1-(4-chlorophenyl)cyclopropyl)-1,3,4-thiadiazole $^1$H NMR (400 MHz, CDCl$_3$) δ 7.46-7.40 (m, 4H), 7.38 (m, 1H), 7.34-7.30 (m, 2H), 7.24 (m, 2H), 7.04-7.02 (m, 2H), 2.87 (q, J=7.6 Hz, 2H), 1.94 (dd, J=7.2, 4.8 Hz, 2H), 1.50 (dd, J=7.2, 4.8 Hz, 2H), 1.22 (t, J=7.6 Hz, 3H).
MH+ 629.

Example 478

2-(5-(4-bromophenyl)-1-(2,4-dichlorophenyl)-4-ethyl-1H-pyrazol-3-yl)-5-(1-(2,4-dichlorophenyl)cyclopropyl)-1,3,4-thiadiazole $^1$H NMR (400 MHz, CDCl$_3$) δ 7.46-7.40 (m, 4H), 7.38 (m, 1H), 7.28-7.24 (m, 3H), 7.04-7.02 (m, 2H), 2.87 (q, J=7.6 Hz, 2H), 2.05 (dd, J=7.2, 4.8 Hz, 2H), 1.54 (dd, J=7.2, 4.8 Hz, 2H), 1.24 (t, J=7.6 Hz, 3H).
MH+ 663.

Example 479

2-(5-(4-chlorophenyl)-1-(2,4-dichlorophenyl)-4-ethyl-1H-pyrazol-3-yl)-5-(1-phenylcyclopropyl)-1,3,4-thiadiazole $^1$H NMR (300 MHz, CDCl$_3$) δ 7.50 (d, J=5.5 Hz, 2H), 7.38-7.25 (m, 8H), 7.11 (d, J=8.5 Hz, 2H), 2.88 (q, J=7.4 Hz, 2H), 1.99-1.96 (m, 2H), 1.56-1.53 (m, 2H), 1.23 (t, J=7.4 Hz, 3H).
MH+ 553.

Example 480

2-(5-(4-chlorophenyl)-1-(2,4-dichlorophenyl)-4-ethyl-1H-pyrazol-3-yl)-5-(1-p-tolylcyclopropyl)-1,3,4-thiadiazole $^1$H NMR (300 MHz, CDCl$_3$) δ 7.39-7.37 (m, 2H), 7.31-7.25 (m, 5H), 7.17-7.14 (m, 2H), 7.11 (d, J=8.6 Hz, 2H), 2.88 (q, J=7.4 Hz, 2H), 2.34 (s, 3H), 1.96-1.93 (m, 2H), 1.53-1.49 (m, 2H), 1.23 (t, J=7.4 Hz, 3H).
MH+ 567.

Example 481

2-(5-(4-chlorophenyl)-1-(2,4-dichlorophenyl)-4-ethyl-1H-pyrazol-3-yl)-5-(1-(4-methoxyphenyl)cyclopropyl)-1,3,4-thiadiazole $^1$H NMR (300 MHz, CDCl$_3$) δ 7.43-7.37 (m, 3H), 7.31-7.25 (m, 4H), 7.11 (d, J=8.4 Hz, 2H), 6.87 (d, J=8.6 Hz, 2H), 3.80 (s, 3H), 2.88 (q, J=7.4 Hz, 2H), 1.95-1.92 (m, 2H), 1.51-1.48 (m, 2H), 1.23 (t, J=7.4 Hz, 3H).
MH+ 583.

Example 482

2-(5-(4-chlorophenyl)-1-(2,4-dichlorophenyl)-4-ethyl-1H-pyrazol-3-yl)-5-(1-(2,4-dichlorophenyl)cyclopropyl)-1,3,4-thiadiazole $^1$H NMR (300 MHz, CDCl$_3$) δ 7.47-7.38 (m, 3H), 7.31-7.25 (m, 5H), 7.11 (d, J=8.6 Hz, 2H), 2.88 (q, J=7.4 Hz, 2H), 2.08-2.04 (m, 2H), 1.57-1.53 (m, 2H), 1.23 (t, J=7.3 Hz, 3H).
MH+ 621.

Example 483

2-(5-(4-chlorophenyl)-1-(2,4-dichlorophenyl)-4-ethyl-1H-pyrazol-3-yl)-5-(1-(4-chlorophenyl)cyclobutyl)-1,3,4-thiadiazole $^1$H NMR (300 MHz, CDCl$_3$) δ 7.41-7.40 (m, 1H), 7.35-7.28 (m, 8H), 7.13 (d, J=8.4 Hz, 2H), 3.13-3.05 (m, 2H), 2.92 (q, J=7.4 Hz, 2H), 2.88-2.78 (m, 2H), 2.40-2.30 (m, 1H), 2.06-1.95 (m, 1H), 1.27 (t, J=7.4 Hz, 3H).
MH+ 601.

Example 484

2-(5-(4-chlorophenyl)-1-(2,4-dichlorophenyl)-4-ethyl-1H-pyrazol-3-yl)-5-(1-methylcyclopropyl)-1,3,4-thiadiazole $^1$H NMR (400 MHz, CDCl$_3$) δ 7.39 (d, J=1.6 Hz, 1H), 7.33-7.27 (m, 4H), 7.15-7.10 (m, 2H), 2.90 (q, J=7.2 Hz, 2H), 1.64 (s, 3H), 1.44 (dd, J=4.4, 6.8 Hz, 2H), 1.24 (t, J=7.6 Hz, 3H), 1.09 (dd, J=4.4, 6.8 Hz, 2H).
MH+ 489.

Example 485

2-(5-(4-bromophenyl)-1-(2,4-dichlorophenyl)-4-ethyl-1H-pyrazol-3-yl)-5-(1-phenylcyclopentyl)-1,3,4-thiadiazole $^1$H NMR (400 MHz, CDCl$_3$) δ 7.46-7.41 (m, 4H), 7.37 (m, 1H), 7.32-7.24 (m, 4H), 7.23-7.19 (m, 1H), 7.04-7.01 (m, 2H), 2.90 (q, J=7.6 Hz, 2H), 2.83 (m, 2H), 2.31 (m, 2H), 1.85 (m, 4H), 1.23 (t, J=7.6 Hz, 3H).
MH+ 623.

Example 486

2-(5-(4-bromophenyl)-1-(2,4-dichlorophenyl)-4-ethyl-1H-pyrazol-3-yl)-5-(1-(4-chlorophenyl)cyclopentyl)-1,3,4-thiadiazole $^1$H NMR (400 MHz, CDCl$_3$) δ 7.46-7.43 (m, 2H), 7.38-7.35 (m, 3H), 7.28-7.25 (m, 4H), 7.05-7.02 (m, 2H), 2.89 (t, J=7.6 Hz, 2H), 2.82 (m, 2H), 2.27 (m, 2H), 1.86 (m, 4H), 1.23 (t, J=7.6 Hz, 3H).
MH+ 657.

Example 487

2-(5-(4-chlorophenyl)-1-(2,4-dichlorophenyl)-4-methyl-1H-pyrazol-3-yl)-5-(1-phenylcyclopropyl)-1,3,4-thiadiazole $^1$H NMR (400 MHz, CDCl$_3$) δ 7.50-7.47 (m, 2H), 7.38-7.27 (m, 6H), 7.25-7.24 (m, 2H), 7.10-7.04 (m, 2H), 2.45 (s, 3H), 1.98 (d, J=7.2, 3.6 Hz, 2H), 1.55 (dd, J=7.2, 3.6 Hz, 2H).
MH+ 537.

Example 488

2-(5-(4-chlorophenyl)-1-(2,4-dichlorophenyl)-4-methyl-1H-pyrazol-3-yl)-5-(1-ethylcyclopropyl)-1,3,4-thiadiazole $^1$H NMR (400 MHz, CDCl$_3$) δ 7.43-7.42 (m, 1H), 7.34-7.30 (m, 4H), 7.14-7.10 (m, 2H), 2.48 (s, 3H), 1.89 (q, J=9.7 Hz, 2H), 1.37 (dd, J=9.3, 6.2 Hz, 2H), 1.11 (t, J=9.7 Hz, 3H), 1.06 (dd, J=9.3, 6.2 Hz).
MH+ 489.

Example 489

2-(5-(4-chlorophenyl)-1-(2,4-dichlorophenyl)-4-ethyl-1H-pyrazol-3-yl)-5-(1-ethylcyclopropyl)-1,3,4-thiadiazole $^1$H NMR (400 MHz, CDCl$_3$) δ 7.44-7.42 (m, 1H), 7.34-7.30 (m, 4H), 7.16-7.11 (m, 2H), 2.87 (q, J=9.4 Hz, 2H), 1.93 (q, J=9.7 Hz, 2H), 1.38 (dd, J=9.3, 6.2 Hz, 2H), 1.27 (t, J=9.4 Hz, 3H), 1.03 (t, J=9.7 Hz, 3H), 1.00 (dd, J=9.3, 6.2 Hz).
MH+ 504.

Example 490

2-(5-(4-bromophenyl)-1-(2,4-dichlorophenyl)-4-ethyl-1H-pyrazol-3-yl)-5-(1-ethylcyclopropyl)-1,3,4-thiadiazole $^1$H NMR (400 MHz, CDCl$_3$) δ 7.49-7.45 (m, 2H), 7.42-7.41 (m, 1H), 7.34-7.29 (m, 2H), 7.10-7.05 (m, 2H), 2.90 (q, J=9.8 Hz, 2H), 1.90 (q, J=9.8 Hz, 2H), 1.38 (dd, J=9.2, 6.2 Hz, 2H), 1.27 (t, J=9.8 Hz, 3H), 1.10 (t, J=9.8 Hz, 3H), 1.03 (dd, J=9.2, 6.2 Hz).
MH+ 547.

Example 491

1-(5-(5-(4-chlorophenyl)-1-(2,4-dichlorophenyl)-4-ethyl-1H-pyrazol-3-yl)-1,3,4-thiadiazol-2-yl)cyclopropanecarbonitrile $^1$H NMR (400 MHz, CDCl$_3$) δ 7.43-7.42 (m, 1H), 7.34-7.30 (m, 4H), 7.14-7.11 (m, 2H), 2.88 (q, J=10.0 Hz, 2H), 2.11-2.05 (m, 2H), 1.99-1.94 (m, 2H), 1.24 (t, J=10.0 Hz, 3H).
MH+ 501.

Example 492

2-(5-(4-bromophenyl)-1-(2,4-dichlorophenyl)-4-ethyl-1H-pyrazol-3-yl)-5-(1-(4-fluorophenyl)cyclopropyl)-1,3,4-thiadiazole $^1$H NMR (400 MHz, CDCl$_3$) δ 7.45-7.42 (m, 1H), 7.35-7.30 (m, 6H), 7.20-7.13 (m, 4H), 2.79 (q, J=9.8 Hz, 2H), 2.19 (dd, J=9.4, 6.1, 2H), 2.02 (dd, J=9.4, 6.1, 2H), 1.21 (t, J=9.8 Hz, 3H).
MH+ 613.

Example 493

2-(5-(4-chlorophenyl)-1-(2,4-dichlorophenyl)-4-methyl-1H-pyrazol-3-yl)-5-(1-(3-chlorophenyl)cyclopropyl)-1,3,4-thiadiazole $^1$H NMR (400 MHz, CDCl$_3$) δ 7.47-7.44 (m, 2H), 7.39-7.37 (m, 1H), 7.36-7.34 (m, 1H), 7.33-7.32 (m, 1H), 7.29-7.25 (m, 4H), 7.04-7.02 (m, 2H), 2.45 (s, 3H), 1.95 (dd, J=7.2, 4.4 Hz, 2H), 1.53 (dd, J=7.2, 4.4 Hz, 2H).
MH+ 571.

Example 494

2-(5-(4-chlorophenyl)-1-(2,4-dichlorophenyl)-4-ethyl-1H-pyrazol-3-yl)-5-(1-(3-chlorophenyl)cyclopropyl)-1,3,4-thiadiazole $^1$H NMR (400 MHz, CDCl$_3$) δ 7.47-7.44 (m, 2H), 7.39 (d, J=2.0 Hz, 1H), 7.36-7.32 (m, 2H), 7.30-7.29 (m, 1H), 7.27-7.25 (m, 4H), 7.04-7.02 (m, 2H), 2.78 (q, J=7.6 Hz, 2H), 1.79 (dd, J=7.2, 4.8 Hz, 2H), 1.47 (dd, J=7.2, 4.8 Hz, 2H), 1.17 (t, J=7.6 Hz, 3H).
MH+ 586.

Example 495

2-(5-(4-bromophenyl)-1-(2,4-dichlorophenyl)-4-ethyl-1H-pyrazol-3-yl)-5-(1-(3-chlorophenyl)cyclopropyl)-1,3,4-thiadiazole $^1$H NMR (400 MHz, CDCl$_3$) δ 7.48-7.43 (m, 3H), 7.39-7.36 (m, 2H), 7.29-7.22 (m, 4H), 7.05-7.03 (m, 2H), 2.88 (q, J=7.2 Hz, 2H), 1.94 (dd, J=7.2, 4.0 Hz, 2H), 1.52 (dd, J=7.2, 4.0 Hz, 2H), 1.23 (t, J=7.2 Hz, 3H).
MH+ 629.

Example 496

2-(5-(4-chlorophenyl)-1-(2,4-dichlorophenyl)-4-methyl-1H-pyrazol-3-yl)-5-(1-(4-fluorophenyl)cyclopropyl)-1,3,4-thiadiazole $^1$H NMR (400 MHz, CDCl$_3$) δ 7.47-7.44 (m, 3H), 7.38-7.35 (m, 2H), 7.29-7.22 (m, 4H), 7.04-7.01 (m, 2H), 2.27 (s, 3H), 1.90 (dd, J=8.3, 6.7 Hz, 2H), 1.44 (dd, J=8.3, 6.7 Hz, 2H).
MH+ 555.

Example 497

2-(5-(4-chlorophenyl)-1-(2,4-dichlorophenyl)-4-isopropyl-1H-pyrazol-3-yl)-5-(1-(4-chlorophenyl)cyclopropyl)-1,3,4-thiadiazole $^1$H NMR (400 MHz, CDCl$_3$) δ 7.36 (d, J=8.4 Hz, 2H), 7.30-7.19 (m, 5H), 7.14-7.12 (m, 2H), 7.07 (d, J=8.4 Hz, 2H), 3.51-3.43 (m, 1H), 1.90-1.88 (m, 2H), 1.45-1.43 (m, 2H), 1.21 (d, J=7.2 Hz, 6H).
MH+ 601.

Example 498

2-(5-(4-chlorophenyl)-1-(2,4-dichlorophenyl)-4-isopropyl-1H-pyrazol-3-yl)-5-(1-(trifluoromethyl)cyclopropyl)-1,3,4-thiadiazole $^1$H NMR (400 MHz, CDCl$_3$) δ 7.40 (s, 1H), 7.31-7.24 (m, 4H), 7.15 (d, J=8.4 Hz, 2H), 3.59-3.51 (m, 1H), 1.76-1.73 (m, 2H), 1.63-1.60 (m, 2H), 1.28 (d, J=6.8 Hz, 6H).
MH+ 559.

Example 499

2-(5-(4-chlorophenyl)-1-(2,4-dichlorophenyl)-4-propyl-1H-pyrazol-3-yl)-5-(1-(trifluoromethyl)cyclopropyl)-1,3,4-thiadiazole $^1$H NMR (400 MHz, CDCl$_3$) δ 7.41 (s, 1H), 7.32-7.27 (m, 4H), 7.12 (d, J=8.4 Hz, 2H), 2.87-2.83 (m, 2H), 1.69-1.57 (m, 6H), 0.88 (t, J=7.6 Hz, 2H).
MH+ 559.

Example 500

2-(5-(4-chlorophenyl)-1-(2,4-dichlorophenyl)-4-ethyl-1H-pyrazol-3-yl)-5-(1-(trifluoromethyl)cyclopropyl)-1,3,4-thiadiazole $^1$H NMR (400 MHz, CDCl$_3$) δ 7.42 (s, 1H), 7.32-7.29 (m, 4H), 7.13 (d, J=8.8 Hz, 2H), 2.90 (q, J=7.6 Hz, 2H), 1.78-1.72 (m, 2H), 1.64-1.61 (m, 2H), 1.25 (t, J=7.6 Hz, 3H).
MH+ 545.

Example 501

2-(5-(4-chlorophenyl)-1-(2,4-dichlorophenyl)-4-ethyl-1H-pyrazol-3-yl)-5-(1-(2-fluorophenyl)cyclopropyl)-1,3,4-thiadiazole $^1$H NMR (400 MHz, CDCl$_3$) δ 7.51-7.44 (m, 1H), 7.37-7.22 (m, 6H), 7.15-7.05 (m, 4H), 2.87 (q, J=7.2 Hz, 2H), 2.05-1.99 (m, 2H), 1.55-1.52 (m, 2H), 1.22 (t, J=7.6 Hz, 3H).
MH+ 571.

Example 502

2-(4-((1H-1,2,4-triazol-1-yl)methyl)-5-(4-chlorophenyl)-1-(2,4-dichlorophenyl)-1H-pyrazol-3-yl)-5-tert-butyl-1,3,4-thiadiazole $^1$H NMR (400 MHz, CDCl$_3$) δ 8.79 (s, 1H), 7.99 (s, 1H), 7.45-7.42 (m, 3H), 7.39-7.34 (m, 4H), 5.64 (s, 2H), 1.52 (s, 9H).
MH+ 544.

Example 503

2-(4-((1H-1,2,4-triazol-1-yl)methyl)-5-(4-bromophenyl)-1-(2,4-dichlorophenyl)-1H-pyrazol-3-yl)-5-tert-butyl-1,3,4-thiadiazole $^1$H NMR (400 MHz, CDCl$_3$) δ 8.77 (s, 1H), 7.96 (s, 1H), 7.53-7.50 (m, 2H), 7.45-7.44 (m, 1H), 7.39-7.36 (m, 2H), 7.35-7.30 (m, 2H), 5.63 (s, 2H), 1.52 (s, 9H).
MH+ 588.

Example 504

2-(4-((1H-1,2,4-triazol-1-yl)methyl)-5-(4-chlorophenyl)-1-(2,4-dichlorophenyl)-1H-pyrazol-3-yl)-5-cyclobutyl-1,3,4-thiadiazole $^1$H NMR 400 MHz, CDCl$_3$) δ 8.82 (s, 1H), 7.96 (s, 1H), 7.50-7.23 (m, 7H), 5.65 (s, 2H), 4.08-3.93 (m, 1H), 2.63-2.51 (m, 2H), 2.50-2.37 (m, 2H), 2.20-2.01 (m, 2H).
MH+ 542.

Example 505

2-(4-((1H-1,2,4-triazol-1-yl)methyl)-5-(4-chlorophenyl)-1-(2,4-dichlorophenyl)-1H-pyrazol-3-yl)-5-cyclohexyl-1,3,4-thiadiazole $^1$H NMR (400 MHz, CDCl$_3$) δ 9.16 (s, 1H), 8.16 (s, 1H), 7.49-7.31 (m, 7H), 5.69 (s, 2H), 3.23-3.12 (m, 1H), 2.24-2.15 (m, 2H), 1.98-1.91 (m, 2H), 1.65-1.21 (m, 6H).
MH+ 570.

Example 506

2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopropyl)-1,3,4-thiadiazole $^1$H NMR (400 MHz, CDCl$_3$) δ 9.07 (s, 1H), 8.13 (s, 1H), 7.44-7.24 (m, 11H), 5.29 (s, 2H), 1.99-1.88 (m, 2H), 1.59-1.51 (m, 2H).
MH+ 638.

Example 507

2-(4-((1H-1,2,4-triazol-1-yl)methyl)-5-(4-chlorophenyl)-1-(2,4-dichlorophenyl)-1H-pyrazol-3-yl)-5-(1-phenylcyclopropyl)-1,3,4-thiadiazole $^1$H NMR (400 MHz, CDCl$_3$) δ 8.91 (s, 1H), 8.05 (s, 1H), 7.50-7.46 (m, 2H), 7.42-7.21 (m, 10H), 5.63 (s, 2H), 1.98-1.90 (m, 2H), 1.61-1.53 (m, 2H).
MH+ 604.

Example 508

2-(4-((1H-1,2,4-triazol-1-yl)methyl)-5-(4-chlorophenyl)-1-(2,4-dichlorophenyl)-1H-pyrazol-3-yl)-5-(1-p-tolylcyclopropyl)-1,3,4-thiadiazole $^1$H NMR (400 MHz, CDCl$_3$) δ 8.89 (s, 1H), 8.04 (s, 1H), 7.47-7.22 (m, 9H), 7.18-7.10 (m, 2H), 5.62 (s, 2H), 2.33 (s, 3H), 1.95-1.88 (m, 2H), 1.56-1.49 (m, 2H).
MH+ 618.

Example 509

2-(4-((1H-1,2,4-triazol-1-yl)methyl)-5-(4-chlorophenyl)-1-(2,4-dichlorophenyl)-1H-pyrazol-3-yl)-5-(1-(4-methoxyphenyl)cyclopropyl)-1,3,4-thiadiazole $^1$H NMR (400 MHz, CDCl$_3$) δ 9.03 (s, 1H), 8.07 (s, 1H), 7.49-7.21 (m, 9H), 6.92-6.83 (m, 2H), 5.64 (s, 2H), 3.78 (s, 3H), 1.98-1.87 (m, 2H), 1.65-1.49 (m, 2H).
MH+ 634.

Example 510

2-(4-((1H-1,2,4-triazol-1-yl)methyl)-5-(4-chlorophenyl)-1-(2,4-dichlorophenyl)-1H-pyrazol-3-yl)-5-(1-(2,4-dichlorophenyl)cyclopropyl)-1,3,4-thiadiazole $^1$H NMR (400 MHz, CDCl$_3$) δ 9.03 (s, 1H), 8.11 (s, 1H), 7.48-7.22 (m, 9H), 5.64 (s, 2H), 2.09-1.99 (m, 2H), 1.65-1.53 (m, 2H).
MH+ 672.

Example 511

2-(4-((1H-1,2,4-triazol-1-yl)methyl)-5-(4-chlorophenyl)-1-(2,4-dichlorophenyl)-1H-pyrazol-3-yl)-5-(1-(trifluoromethyl)cyclopropyl)-1,3,4-thiadiazole $^1$H NMR (400 MHz, CDCl$_3$) δ 8.94 (s, 1H), 8.01 (s, 1H), 7.48-7.28 (m, 7H), 5.65 (s, 2H), 1.83-1.61 (m, 4H).
MH+ 596.

Example 512

2-(4-((1H-1,2,4-triazol-1-yl)methyl)-5-(4-chlorophenyl)-1-(2,4-dichlorophenyl)-1H-pyrazol-3-yl)-5-(1-(trifluoromethyl)cyclobutyl)-1,3,4-thiadiazole $^1$H NMR (400 MHz, CDCl$_3$) δ 9.41 (s, 1H), 8.28 (s, 1H), 7.47-7.45 (m, 1H), 7.43-7.31 (m, 6H), 5.72 (s, 2H), 2.84 (d, J=8.0 Hz, 4H), 2.20 (m, 2H).
MH+ 610.

Example 513

2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclobutyl)-1,3,4-thiadiazole $^1$H NMR (400 MHz, CDCl$_3$) δ 9.41 (s, 1H), 8.28 (s, 1H), 7.43-7.23 (m, 11H), 5.70 (s, 2H), 3.10-3.01 (m, 2H), 2.89-2.78 (m, 2H), 2.42-2.31 (m, 1H), 2.10-1.98 (m, 1H).
MH+ 652.

Example 514

2-(4-((1H-1,2,4-triazol-1-yl)methyl)-5-(4-chlorophenyl)-1-(2,4-dichlorophenyl)-1H-pyrazol-3-yl)-5-(1-phenylcyclopentyl)-1,3,4-thiadiazole $^1$H NMR (400 MHz, CDCl$_3$) δ 9.56 (s, 1H), 8.34 (s, 1H), 7.45-7.25 (m, 12H), 5.69 (s, 2H), 2.84-2.75 (m, 2H), 2.41-2.32 (m, 2H), 1.95-1.80 (m, 4H).
MH+ 632.

Example 515

2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopentyl)-1,3,4-thiadiazole $^1$H NMR (400 MHz, CDCl$_3$) δ 9.46 (s, 1H), 8.29 (s, 1H), 7.43-7.24 (m, 11H), 5.68 (s, 2H), 2.82-2.73 (m, 2H), 2.37-2.26 (m, 2H), 1.92-1.80 (m, 4H).
MH+ 666.

Example 516

2-(4-((1H-1,2,4-triazol-1-yl)methyl)-5-(4-chlorophenyl)-1-(2,4-dichlorophenyl)-1H-pyrazol-3-yl)-5-(1-methylcyclopropyl)-1,3,4-thiadiazole $^1$H NMR (400 MHz, CDCl$_3$) δ 9.13 (s, 1H), 8.16 (s, 1H), 7.48-7.29 (m, 7H), 5.68 (s, 2H), 1.65 (s, 3H), 1.45-1.39 (m, 2H), 1.16-1.10 (m, 2H).
MH+ 543.

Example 517

2-(4-((1H-1,2,4-triazol-1-yl)methyl)-5-(4-bromophenyl)-1-(2,4-dichlorophenyl)-1H-pyrazol-3-yl)-5-(1-(trifluoromethyl)cyclopropyl)-1,3,4-thiadiazole $^1$H NMR (400 MHz, CDCl$_3$) δ 9.30 (s, 1H), 8.25 (s, 1H), 7.58-7.54 (m, 2H), 7.47 (d, J=1.6 Hz, 1H), 7.39-7.31 (m, 4H), 5.69 (s, 2H), 1.77-1.65 (m, 4H).
MH+ 640.

Example 518

2-(4-((1H-1,2,4-triazol-1-yl)methyl)-5-(4-bromophenyl)-1-(2,4-dichlorophenyl)-1H-pyrazol-3-yl)-5-(1-(4-chlorophenyl)cyclopropyl)-1,3,4-thiadiazole $^1$H NMR (400 MHz, CDCl$_3$) δ 9.15 (s, 1H), 8.18 (s, 1H), 7.53 (d, J=8.4 Hz, 1H), 7.46-7.40 (m, 2H), 7.38-7.24 (m, 8H), 5.67 (s, 2H), 2.05-1.93 (m, 2H), 1.59-1.52 (m, 2H).
MH+ 682.

Example 519

2-(4-((1H-1,2,4-triazol-1-yl)methyl)-1-(2-chlorophenyl)-5-(4-chlorophenyl)-1H-pyrazol-3-yl)-5-tert-butyl-1,3,4-thiadiazole $^1$H NMR (400 MHz, CDCl$_3$) δ 9.16 (s, 1H), 8.18 (s, 1H), 7.47-7.31 (m, 8H), 5.71 (s, 2H), 1.54 (s, 9H).
MH+ 510.

Example 520

(5-(4-bromophenyl)-3-(5-tert-butyl-1,3,4-thiadiazol-2-yl)-1-(2,4-dichlorophenyl)-1H-pyrazol-4-yl)methyl acetate $^1$H NMR (400 MHz, CDCl$_3$) δ 7.49-7.45 (m, 2H), 7.44-7.43 (m, 1H), 7.32-7.31 (m, 2H), 7.09-7.06 (m, 2H), 5.39 (s, 2H), 2.00 (s, 3H), 1.51 (s, 9H).
MH+ 579.

Example 521

(3-(5-tert-butyl-1,3,4-thiadiazol-2-yl)-5-(4-chlorophenyl)-1-(2,4-dichlorophenyl)-1H-pyrazol-4-yl)methyl acetate $^1$H NMR (400 MHz, CDCl$_3$) δ 7.44-7.43 (m, 1H), 7.34-7.29 (m, 4H), 7.15-7.12 (m, 2H), 5.40 (s, 2H), 2.00 (s, 3H), 1.52 (s, 9H).
MH+ 535.

Example 522

(5-(4-bromophenyl)-3-(5-tert-butyl-1,3,4-thiadiazol-2-yl)-1-(2,4-dichlorophenyl)-1H-pyrazol-4-yl)methanol $^1$H NMR (400 MHz, CDCl$_3$) δ 7.48-7.45 (m, 2H), 7.44-7.43 (m, 1H), 7.30-7.29 (m, 2H), 7.09-7.07 (m, 2H), 4.70 (s, 2H), 1.52 (s, 9H).
MH+ 537.

Example 523

(3-(5-tert-butyl-1,3,4-thiadiazol-2-yl)-5-(4-chlorophenyl)-1-(2,4-dichlorophenyl)-1H-pyrazol-4-yl)methanol $^1$H NMR (400 MHz, CDCl$_3$) δ 7.44-7.43 (m 1H), 7.33-7.29 (m, 4H), 7.24-7.12 (m, 2H), 4.70 (s, 2H), 1.54 (2, 9H).
MH+ 493.

Example 524

2-(5-(4-bromophenyl)-1-(2,4-dichlorophenyl)-4-(methoxymethyl)-1H-pyrazol-3-yl)-5-tert-butyl-1,3,4-thiadiazole $^1$H NMR (400 MHz, CDCl$_3$) δ 7.48-7.46 (m, 2H), 7.45-7.44 (m, 1H), 7.30-7.29 (m, 2H), 7.19-7.17 (m, 2H), 4.73 (s, 2H), 3.47 (s, 3H), 1.52 (s, 9H).
MH+ 551.

Example 525

2-(5-(4-bromophenyl)-1-(2,4-dichlorophenyl)-4-(fluoromethyl)-1H-pyrazol-3-yl)-5-tert-butyl-1,3,4-thiadiazole $^1$H NMR (400 MHz, CDCl$_3$) δ 7.51-7.45 (m, 3H), 7.33-7.32 (m, 2H), 7.17-7.14 (m, 2H), 5.74 (d, J=48.4 Hz, 2H), 1.53 (s, 9H).
MH+ 539.

Example 526

2-(5-(4-bromophenyl)-1-(2,4-dichlorophenyl)-4-((5-(trifluoromethyl)pyridin-2-yloxy)methyl)-1H-pyrazol-3-yl)-5-tert-butyl-1,3,4-thiadiazole $^1$H NMR (400 MHz, CDCl$_3$) δ 8.00-7.99 (m, 1H), 7.43-7.40 (m, 3H), 7.34-7.27 (m, 3H), 7.01-6.99 (m, 2H), 6.42-6.40 (m, 1H), 5.48 (s, 2H), 1.52 (s, 9H).
MH+ 682.

Example 527

5-(4-bromophenyl)-3-(5-tert-butyl-1,3,4-thiadiazol-2-yl)-1-(2,4-dichlorophenyl)-1H-pyrazole-4-carbaldehyde $^1$H NMR (400 MHz, CDCl$_3$) δ 10.80 (s, 1H), 7.48-7.42 (m, 3H), 7.34-7.26 (m, 2H), 7.20-7.07 (m, 2H), 1.53 (s, 9H). MH+ 535.

Example 528

1-(5-(4-bromophenyl)-3-(5-tert-butyl-1,3,4-thiadiazol-2-yl)-1-(2,4-dichlorophenyl)-1H-pyrazol-4-yl)ethanol $^1$H NMR (400 MHz, CDCl$_3$) δ 7.49-7.46 (m, 2H), 7.42-7.41 (m, 1H), 7.30-7.26 (m, 2H), 7.07-7.04 (m, 2H), 4.83-4.78 (m, 1H), 1.59 (d, J=6.8 Hz, 3H), 1.52 (s, 9H).
MH+ 551.

Example 529

1-(3-(5-tert-butyl-1,3,4-thiadiazol-2-yl)-5-(4-chlorophenyl)-1-(2,4-dichlorophenyl)-1H-pyrazol-4-yl)ethanol

MH+ 507.

Example 530

2-(5-(4-bromophenyl)-1-(2,4-dichlorophenyl)-4-(1-fluoroethyl)-1H-pyrazol-3-yl)-5-tert-butyl-1,3,4-thiadiazole

MH+ 553.

Example 531

2-(5-(4-bromophenyl)-1-(2,4-dichlorophenyl)-4-vinyl-1H-pyrazol-3-yl)-5-tert-butyl-1,3,4-thiadiazole $^1$H NMR (400 MHz, CDCl$_3$) δ 7.48-7.44 (m, 2H), 7.42-7.40 (m, 1H), 7.29-7.21 (m, 3H), 7.15-7.11 (m, 2H), 5.43 (dd, J=18, 1.6 Hz, 1H), 5.22 (dd, J=11.6, 1.6 Hz, 1H), 1.51 (s, 9H).
MH+ 533.

Example 532

Methyl 1-(5-(4-bromophenyl)-3-(5-tert-butyl-1,3,4-thiadiazol-2-yl)-1-(2,4-dichlorophenyl)-1H-pyrazol-4-yl)ethylcarbamate $^1$H NMR (400 MHz, CDCl$_3$) δ 7.51-7.41 (m, 3H), 7.27-7.22 (m, 4H), 5.02 (bs, 1H), 3.62 (s, 3H), 1.53 (s, 9H), 1.48 (d, J=7.2 Hz, 3H).
MH+ 609.

Example 533

1-(5-(4-bromophenyl)-3-(5-tert-butyl-1,3,4-thiadiazol-2-yl)-1-(2,4-dichlorophenyl)-1H-pyrazol-4-yl)ethanone $^1$H NMR (400 MHz, CDCl$_3$) δ 7.46-7.43 (m, 3H), 7.30-7.29 (m, 2H), 7.15-7.12 (m, 2H), 2.53 (s, 3H), 1.52 (s, 9H).
MH+ 549.

Example 534

2-(5-(4-bromophenyl)-3-(5-tert-butyl-1,3,4-thiadiazol-2-yl)-1-(2,4-dichlorophenyl)-1H-pyrazol-4-yl)propan-2-ol

MH+ 565.

Example 535

2-(5-(4-bromophenyl)-1-(2,4-dichlorophenyl)-4-(prop-1-en-2-yl)-1H-pyrazol-3-yl)-5-tert-butyl-1,3,4-thiadiazole $^1$H NMR (400 MHz, CDCl$_3$) δ 7.43-7.39 (m, 3H), 7.34 (d, J=8.4 Hz, 1H), 7.31-7.28 (m, 1H), 7.07-7.03 (m, 2H), 5.29-5.24 (m, 1H), 4.97-4.96 (m, 1H), 2.10 (s, 3H), 1.51 (s, 9H).
MH+ 547.

Example 536

2-(4-chloro-5-(4-chlorophenyl)-1-(2,4-dichlorophenyl)-1H-pyrazol-3-yl)-5-cyclobutyl-1,3,4-thiadiazole $^1$H NMR (400 MHz, CDCl$_3$) δ 7.45-7.38 (m, 1H), 7.41-7.34 (m, 4H), 7.25-7.23 (m, 2H), 4.07-4.02 (m, 1H), 2.60-2.56 (m, 2H), 2.54-2.48 (m, 2H), 2.18-2.05 (m, 2H).
MH+ 497.

Example 537

2-(4-chloro-5-(4-chlorophenyl)-1-(2,4-dichlorophenyl)-1H-pyrazol-3-yl)-5-tert-pentyl-1,3,4-thiadiazole $^1$H NMR (400 MHz, CDCl$_3$) δ 7.45-7.44 (m, 1H), 7.38-7.33 (m, 4H), 7.26-7.22 (m, 2H), 1.86 (q, J=7.6 Hz, 2H), 1.52 (s, 3H), 1.50 (s, 3H), 0.89 (t, J=7.6 Hz, 3H).
MH+ 514.

Example 538

2-(4-chloro-5-(4-chlorophenyl)-1-(2,4-dichlorophenyl)-1H-pyrazol-3-yl)-5-cyclohexyl-1,3,4-thiadiazole $^1$H NMR (400 MHz, CDCl$_3$) δ 7.46-7.40 (m, 2H), 7.37-7.32 (m, 3H), 7.26-7.22 (m, 2H), 3.26-3.24 (m, 1H), 2.22-1.86 (m, 4H), 1.56-1.44 (m, 6H).
MH+ 525.

Example 539

2-sec-butyl-5-(4-chloro-5-(4-chlorophenyl)-1-(2,4-dichlorophenyl)-1H-pyrazol-3-yl)-1,3,4-thiadiazole $^1$H NMR (400 MHz, CDCl$_3$) δ 7.46-7.41 (m, 2H), 7.39-7.26 (m, 3H), 7.24-7.20 (m, 2H), 3.36-3.32 (m, 1H), 1.87-1.75 (m, 2H), 1.48 (d, J=6.9 Hz, 3H), 0.99 (t, J=7.2 Hz).
MH+ 499

Example 540

2-tert-butyl-5-(4-chloro-5-(4-chlorophenyl)-1-(2,4-dichlorophenyl)-1H-pyrazol-3-yl)-1,3,4-thiadiazole $^1$H NMR (400 MHz, CDCl$_3$) δ 7.49-7.41 (m, 2H), 7.38-7.24 (m, 3H), 7.23-7.19 (m, 2H), 1.59 (s, 9H).
MH+ 499.

Example 541

2-(4-bromo-5-(4-chlorophenyl)-1-(2,4-dichlorophenyl)-1H-pyrazol-3-yl)-5-tert-butyl-1,3,4-thiadiazole $^1$H NMR (400 MHz, CDCl$_3$) δ 7.51-7.48 (m, 2H), 7.38-7.27 (m, 3H), 7.23-7.19 (m, 2H), 1.55 (s, 9H).
MH+ 544.

Example 542

2-(4-bromo-5-(4-chlorophenyl)-1-(2,4-dichlorophenyl)-1H-pyrazol-3-yl)-5-sec-butyl-1,3,4-thiadiazole $^1$H NMR (400 MHz, CDCl$_3$) δ 7.44-7.42 (m, 1H), 7.40-7.37 (m, 1H), 7.35-7.32 (m, 3H), 7.25-7.21 (m, 2H), 3.37-3.32 (m, 1H), 1.87-1.76 (m, 2H), 1.45 (d, J=6.8 Hz, 3H), 0.91 (t, J=7.2, 3H).
MH+ 543.

Example 543

2-(4-bromo-5-(4-chlorophenyl)-1-(2,4-dichlorophenyl)-1H-pyrazol-3-yl)-5-cyclobutyl-1,3,4-thiadiazole $^1$H NMR (400 MHz, CDCl$_3$) δ 7.44-7.42 (m, 1H), 7.37-7.31 (m, 4H), 7.25-7.22 (m, 2H), 4.12-4.01 (m, 1H), 2.61-2.57 (m, 2H), 2.53-2.39 (m, 2H), 2.19-2.05 (m, 2H).
MH+ 541.

Example 544

2-(4-bromo-5-(4-chlorophenyl)-1-(2,4-dichlorophenyl)-1H-pyrazol-3-yl)-5-cyclohexyl-1,3,4-thiadiazole $^1$H NMR (400 MHz, CDCl$_3$) δ 7.43-7.37 (m, 2H), 7.34-7.31 (m, 3H), 7.25-7.21 (m, 2H), 3.02-2.97 (m, 1H), 2.16-2.11 (m, 2H), 1.87-1.76 (m, 2H), 1.73-1.68 (m, 3H), 1.44-1.33 (m, 3H).
MH+ 569.

Example 545

2-(4-bromo-5-(4-chlorophenyl)-1-(2,4-dichlorophenyl)-1H-pyrazol-3-yl)-5-tert-pentyl-1,3,4-thiadiazole $^1$H NMR (400 MHz, CDCl$_3$) δ 7.44-7.43 (m, 2H), 7.38-7.33 (m, 3H), 6.99-6.95 (m, 2H), 1.66 (dq, J=28.8, 7.2 Hz, 2H), 1.49 (s, 3H), 1.42 (s, 3H), 0.83 (t, J=18.8, 7.2 Hz, 3H).
MH+ 557.

Example 546

2-(4-bromo-5-(4-chlorophenyl)-1-(2,4-dichlorophenyl)-1H-pyrazol-3-yl)-5-(2-(4-chlorophenyl)propan-2-yl)-1,3,4-thiadiazole $^1$H NMR (400 MHz, CDCl$_3$) δ 7.45-7.41 (m, 1H), 7.38-7.33 (m, 4H), 7.27-7.24 (m, 3H), 7.22-7.18 (m, 2H), 7.12-7.08 (m, 1H), 1.92 (s, 3H), 1.81 (s, 3H).
MH+ 639.

Example 547

2-(4-bromo-5-(4-chlorophenyl)-1-(2,4-dichlorophenyl)-1H-pyrazol-3-yl)-5-(1-(4-chlorophenyl)cyclopropyl)-1,3,4-thiadiazole $^1$H NMR (400 MHz, CDCl$_3$) δ 7.46-7.42 (m, 1H), 7.39-7.36 (m, 4H), 7.27-7.24 (m, 3H), 7.21-7.18 (m, 2H), 7.12-7.08 (m, 1H), 2.01 (dd, J=9.1, 6.7 Hz, 2H), 1.49 (dd, J=9.1, 6.7 Hz, 2H).
MH+ 635.

Preparation of 1,2,4-oxadiazole

Example 548

3-(5-(4-chlorophenyl)-1-(2,4-dichlorophenyl)-4-methyl-1H-pyrazol-3-yl)-5-cyclohexyl-1,2,4-oxadiazole Step 1: 5-(4-Chlorophenyl)-1-(2,4-dichlorophenyl)-4-methyl-1H-pyrazole-3-carboxamide Thionyl chloride (1.3 ml, 22.0 mmol) was added to a solution of 5-(4-chlorophenyl)-1-(2,4-dichlorophenyl)-4-methyl-1H-pyrazole-3-carboxylic acid (2.09 g, 5.5 mmol) in toluene (50 ml) maintained at room temperature. The mixture was refluxed at 110° C. for 2 hours and then cooled to room temperature. The resulting solution was evaporated and dried under a vacuum to produce crude 5-(4-chlorophenyl)-1-(2,4-dichlorophenyl)-4-methyl-1H-pyrazole-3-carbonyl chloride, which are not further purified. 27% aqueous ammonia (2 ml) was added to the solution of crude 5-(4-chlorophenyl)-1-(2,4-dichlorophenyl)-4-methyl-1H-pyrazole-3-carbonyl chloride in methylene chloride (10 ml) at 0° C. After stirring 3 hours at room temperature, the resulting solution was quenched with saturated ammonium chloride which was extracted twice with 50 ml portions of ethyl acetate. After concentrating the extract by evaporation, the crude residue was purified using a silica gel column (hexane/ethyl acetate=1/1), to obtain the title compound (2.07 g, 99%) as white solid.

Step 2: 5-(4-Chlorophenyl)-1-(2,4-dichlorophenyl)-4-methyl-1H-pyrazole-3-carbonitrile Added dropwise to a solution of 5-(4-chlorophenyl)-1-(2,4-dichlorophenyl)-4-methyl-1H-pyrazole-3-carboxamide (1.57 g, 4.1 mmol) obtained in Step 1 dissolved in dimethylformamide (10 ml) at 0° C., was phosphoryl chloride (0.72 ml, 8.2 mmol). The resulting mixture was stirred for 20 minutes at 0° C. and then stirred for 1 hour at room temperature. The reaction mixture was quenched with water at 0° C., and an mixture was extracted with ethyl acetate (30 ml twice). After removing the solvent, 5-(4-chloro phenyl)-1-(2,4- dichlorophenyl)-4-methyl-1H-pyrazole-3-carbonitrile was obtained by column chromatography as white solid (1.47 g, quantativly).

¹H NMR (400 MHz, CDCl₃) δ 7.40 (br s, 1H), 7.31-7.27 (m, 4H), 7.08-7.03 (m, 2H), 2.33 (s, 3H), 2.31 (t, J=7.8 Hz, 2H), 1.72 (m, 1H), 0.97 (t, J=7.3 Hz, 3H).

MH+ 463.

Step 3: 5-(4-chlorophenyl)-1-(2,4-dichlorophenyl)-N-hydroxy-4-methyl-1H-pyrazole-3-carboximidamide Potassium carbonate (0.58 g, 4.14 mmol) was added to a sealed tube containing a solution of 5-(4-chlorophenyl)-1-(2,4-dichlorophenyl)-4-methyl-1H-pyrazole-3-carbonitrile (1.0 g, 2.76 mmol) obtained in Step 2, hydroxylamine hydrochloride (0.39 g, 5.52 mmol) dissolved in MeOH (16 mL). The mixture was stirred vigorously and heated at 100° C. for 16 hr. The white precipitate formed was filtered and washed twice with cold water. It was further dried under a high vacuum. The filtrate was extracted with chloroform (30 mL×2), dried over MgSO₄, filtered and evaporated under a vacuum, to obtain the title product in a compound amount of 1.04 g (2.63 mmol, 95%).

¹H NMR (400 MHz, DMSO-d₆) δ 9.77 (s, 1H), 8.27 (s, 1H), 7.69 (d, J=2.2 Hz, 1H), 7.63 (d, J=8.4 Hz, 1H), 7.51 (dd, J=2.2, 8.4 Hz, 1H), 7.41 (br d, J=8.6 Hz, 2H), 7.19 (br d, J=8.6 Hz, 2H), 5.49 (br s, 1H), 2.20 (s, 3H).

MH+ 395.

Step 4: 3-(5-(4-chlorophenyl)-1-(2,4-dichlorophenyl)-4-methyl-1H-pyrazol-3-yl)-5-cyclohexyl-1,2,4-oxadiazole NMM (0.42 mL, 3.77 mmol) was added to a solution of 5-(4-chlorophenyl)-1-(2,4-dichlorophenyl)-N-hydroxy-4-methyl-1H-pyrazole-3-carboxamid amide (0.30 g, 0.75 mmol) obtained in Step 3, cyclohexylcarboxylic acid (97 mg, 0.75 mmol), HOBt (194 mg, 1.43 mmol) and EDCI (220 mg, 1.13 mmol) dissolved in DCM (7 mL). The mixture was stirred overnight at room temperature. After adding thereto EtOAc (30 mL), the mixture was successively washed with water, saturated NaHCO₃ solution (20 mL) and brine (20 mL). The organic layer was isolated, dried over MgSO₄, filtered, and concentrated under a vacuum, to obtain 5-(4-chlorophenyl)-N-(cyclohexanecarbonyloxy)-1-(2,4-dichlorophenyl)-4-methyl-1H-pyrazole-3-carboximidamide as a white solid, which was used in the next step without further purification. The crude material was dissolved in pyridine (4 mL), and was subjected to microwave irradiation at 180° C. for 20 min., to remove volatile components under a vacuum. The residue was further purified by reverse phase preparative HPLC, to obtain the title compound as white solid (67 mg, 0.137 mmol, 18% via two steps).

¹H NMR (300 MHz, CDCl₃) δ 7.42-7.38 (m, 2H), 7.34-7.28 (m, 3H), 7.14-7.09 (m, 2H), 3.06 (m, 1H), 2.39 (s, 3H), 2.14 (m, 2H), 1.88-1.81 (m, 2H), 1.80-1.68 (m, 2H), 1.48-1.25 (m, 4H).

(M+Na)+ 509.

The following compounds of Examples 549 to 564 were obtained by using corresponding starting materials and repeating the procedure of Example 548.

Example 549

3-(5-(4-chlorophenyl)-1-(2,4-dichlorophenyl)-4-methyl-1H-pyrazol-3-yl)-5-cyclopentyl-1,2,4-oxadiazole ¹H NMR (300 MHz, CDCl₃) δ 7.42-7.38 (m, 2H), 7.34-7.28 (m, 3H), 7.14-7.09 (m, 2H), 3.45 (m, 1H), 2.39 (s, 3H), 2.20 (m, 2H), 2.06 (m, 2H), 1.86 (m, 2H), 1.72 (m, 2H).

(M+Na)+ 495.

Example 550

3-(5-(4-chlorophenyl)-1-(2,4-dichlorophenyl)-4-methyl-1H-pyrazol-3-yl)-5-(pentan-3-yl)-1,2,4-oxadiazole ¹H NMR (300 MHz, CDCl₃) δ 7.42-7.38 (m, 2H), 7.34-7.28 (m, 3H), 7.14-7.09 (m, 2H), 3.01 (m, 1H), 2.40 (s, 3H), 1.99-1.75 (m, 4H), 0.92 (t, J=7.5 Hz, 3H).

(M+Na)+ 497.

Example 551

5-benzyl-3-(5-(4-chlorophenyl)-1-(2,4-dichlorophenyl)-4-methyl-1H-pyrazol-3-yl)-1,2,4-oxadiazole ¹H NMR (300 MHz, CDCl₃) δ 7.41-7.27 (m, 10H), 7.13-7.09 (m, 2H), 4.33 (s, 2H), 2.38 (s, 3H), 2.67-2.42 (m, 4H), 2.39 (s, 3H), 2.24-2.02 (m, 2H).

(M+Na)+ 517.

Example 552

3-(5-(4-chlorophenyl)-1-(2,4-dichlorophenyl)-4-methyl-1H-pyrazol-3-yl)-5-cyclobutyl-1,2,4-oxadiazole ¹H NMR (300 MHz, CDCl₃) δ 7.42-7.38 (m, 2H), 7.34-7.28 (m, 3H), 7.14-7.10 (m, 2H), 3.86 (m, 1H), 2.67-2.42 (m, 4H), 2.39 (s, 3H), 2.24-2.02 (m, 2H).

(M+Na)+ 481.

Example 553

3-(5-(4-chlorophenyl)-1-(2,4-dichlorophenyl)-4-methyl-1H-pyrazol-3-yl)-5-cycloheptyl-1,2,4-oxadiazole ¹H NMR (300 MHz, CDCl₃) δ 7.42-7.37 (m, 2H), 7.32-7.27 (m, 3H), 7.13-7.10 (m, 2H), 3.25 (m, 1H), 2.39 (s, 3H), 2.24-2.15 (m, 2H), 2.01-1.81 (m, 4H), 1.65-1.60 (m, 6H).

(M+Na)+523.

Example 554

3-(5-(4-chlorophenyl)-1-(2,4-dichlorophenyl)-4-methyl-1H-pyrazol-3-yl)-5-(cyclopropyl methyl)-1,2,4-oxadiazole ¹H NMR (400 MHz, CDCl₃) δ 7.41-7.37 (m, 2H), 7.32-7.27 (m, 3H), 7.13-7.10 (m, 2H), 2.89 (d, J=6.88 Hz, 2H), 2.40 (s, 3H), 1.26 (m, 1H), 0.64 (m, 2H), 0.35 (AB q, J=5.04 Hz, 2H).

MH+ 459.

Example 555

3-(5-(4-chlorophenyl)-1-(2,4-dichlorophenyl)-4-methyl-1H-pyrazol-3-yl)-5-(cyclopentyl methyl)-1,2,4-oxadiazole $^1$H NMR (400 MHz, CDCl$_3$) δ 7.41-7.37 (m, 2H), 7.32-7.27 (m, 3H), 7.13-7.10 (m, 2H), 2.98 (d, J=7.80 Hz, 2H), 2.46 (m, 1H), 2.40 (s, 3H), 1.98 (m, 1H), 1.91-1.82 (m, 2H), 1.72-1.52 (m, 4H), 1.36-1.25 (m, 2H).
MH+ 487.

Example 556

3-(5-(4-chlorophenyl)-1-(2,4-dichlorophenyl)-4-methyl-1H-pyrazol-3-yl)-5-(cyclohexylmethyl)-1,2,4-oxadiazole $^1$H NMR (400 MHz, CDCl$_3$) δ 7.41-7.37 (m, 2H), 7.32-7.27 (m, 3H), 7.13-7.10 (m, 2H), 2.86 (d, J=7.36 Hz, 2H), 2.40 (s, 3H), 1.98 (m, 1H), 1.80-1.62 (m, 5H), 1.33-1.10 (m, 5H).
MH+ 501.

Example 557

3-(5-(4-chlorophenyl)-1-(2,4-dichlorophenyl)-4-methyl-1H-pyrazol-3-yl)-5-isopropyl-1,2,4-oxadiazole

MH+ 447.

Example 558

3-(5-(4-chlorophenyl)-1'-(2,4-dichlorophenyl)-4-methyl-1H-pyrazol-3-yl)-5-cyclopropyl-1,2,4-oxadiazole

MH+ 445.

Example 559

5-sec-butyl-3-(5-(4-chlorophenyl)-1-(2,4-dichlorophenyl)-4-methyl-1H-pyrazol-3-yl)-1,2,4-oxadiazole $^1$H NMR (400 MHz, CDCl$_3$) δ 7.42-7.37 (m, 2H), 7.33-7.28 (m, 3H), 7.14-7.11 (m, 2H), 3.14 (m, 1H), 2.40 (s, 3H), 2.95 (m, 1H), 1.78 (m, 1H), 1.45 (d, J=6.9 Hz, 3H), 0.97 (t, J=7.6 Hz, 3H).
MH+ 461.

Example 560

3-(5-(4-chlorophenyl)-1-(2,4-dichlorophenyl)-4-methyl-1H-pyrazol-3-yl)-5-(pentan-2-yl)-1,2,4-oxadiazole $^1$H NMR (400 MHz, CDCl$_3$) δ 7.40-7.35 (m, 2H), 7.32-7.27 (m, 3H), 7.14-7.11 (m, 2H), 3.25 (m, 1H), 2.39 (s, 3H), 1.91 (m, 1H), 1.70 (m, 1H), 1.43 (d, J=7.3 Hz), 1.36 (m, 1H), 0.92 (t, J=7.3 Hz, 3H).
MH+ 475.

Example 561

3-(5-(4-chlorophenyl)-1-(2,4-dichlorophenyl)-4-methyl-1H-pyrazol-3-yl)-5-(hexan-2-yl)-1,2,4-oxadiazole $^1$H NMR (400 MHz, CDCl$_3$) δ 7.43-7.37 (m, 2H), 7.33-7.28 (m, 3H), 7.14-7.11 (m, 2H), 3.23 (m, 1H), 2.40 (s, 3H), 1.98-1.88 (m, 1H), 1.77-1.67 (m, 1H), 1.44 (d, J=6.5 Hz, 3H), 1.39-1.23 (m, 4H), 0.89 (t, J=7.1 Hz, 3H).
MH+ 489.

Example 562

3-(5-(4-chlorophenyl)-1'-(2,4-dichlorophenyl)-4-methyl-1H-pyrazol-3-yl)-5-(cyclopent-3-enyl)-1,2,4-oxadiazole $^1$H NMR (400 MHz, CDCl$_3$) δ 7.41-7.37 (m, 2H), 7.34-7.27 (m, 3H), 7.14-7.10 (m, 2H), 5.76 (s, 2H), 3.83 (m, 1H), 2.92 (d, J=8.24 Hz, 4H), 2.39 (s, 3H).
MH+ 471.

Example 563

3-(5-(4-chlorophenyl)-1-(2,4-dichlorophenyl)-4-methyl-1H-pyrazol-3-yl)-5-(2-methylcyclopropyl)-1,2,4-oxadiazole $^1$H NMR (400 MHz, CDCl$_3$) δ 7.40-7.36 (m, 2H), 7.33-7.27 (m, 3H), 7.12-7.09 (m 2H), 2.37 (s, 3H), 1.99 (m, 1H), 1.73 (m, 1H), 1.54 (m, 1H), 1.23 (d, J=6.0 Hz, 3H), 1.04 (m, 1H).
MH+ 459.

Example 564

3-benzyl-5-(5-(4-chlorophenyl)-1-(2,4-dichlorophenyl)-4-methyl-1H-pyrazol-3-yl)-1,2,4-oxadiazole

MH+ 495.

Preparation of Tetrazoles (Formula (Ie) and (If))

Example 565

5-(5-(4-Chlorophenyl)-1-(2,4-dichlorophenyl)-4-methyl-1H-pyrazol-3-yl)-1-propyl-1H-tetrazole Step 1: 5-(5-(4-Chlorophenyl)-1-(2,4-dichlorophenyl)-4-methyl-1H-pyrazol-3-yl)-1H-tetrazole A mixture of 5-(4-chlorophenyl)-1-(2,4-dichlorophenyl)-4-methyl-1H-pyrazole-3-carbonitrile (500 mg, 1.39 mmol), sodium azide (1.08 g, 16.6 mmol) and ammonium chloride (890 mg, 16.6 mmol) dissolved in dimethylformamide (3 ml) was placed in a microwave synthesizer tube, and subjected to microwave irradiation in a Biotage® Initiator was set at 180° C. After 20 minutes, the mixture was quenched with water and extracted with ethyl acetate. The solvent of the extracted organic layer was evaporated off and the residue was purified by reverse phase preparative HPLC, to obtain 5-(5-(4-chlorophenyl)-1-(2,4-dichlorophenyl)-4-methyl-1H-pyrazol-3-yl)-1H-tetrazole (550 mg, 98%) as white solid.
MH+ 404.

Step 2: 5-(5-(4-Chlorophenyl)-1-(2,4-dichlorophenyl)-4-methyl-1H-pyrazol-3-yl)-1-propyl-1H-tetrazole 5-(5-(4-chlorophenyl)-1-(2,4-dichlorophenyl)-4-methyl-1H-pyrazol-3-yl)-1H-tetrazole (150 mg, 0.37 mmol) obtained in Step 1 was dissolved in dimethylformamide (1 ml), and potassium carbonate (250 mg, 1.85 mmol) and 1-iodopropane (0.07 ml, 1.1 mmol) were added thereto at room temperature. After stirring for 5 hours, the resulting solution was quenched with water (1 ml) and the mixture was three time extracted with 5 ml portion of ethyl acetate. The solvent of the extracted organic layer was evaporated under a reduced pressure and the residue was subjected to silica gel column chromatography (hexane/ethyl acetate=1/7 to hexane/ethyl acetate=1/5), to obtain two compounds, one of which was the title compound (61 mg, 37%) in the form of white solid.
$^1$H NMR (400 MHz, CDCl$_3$) δ 7.51 (d, J=2.28 Hz, 1H), 7.36-7.32 (m, 2H), 7.29 (dd, J=8.72, 2.28 Mz, 1H), 7.18 (d, J=8.68 Hz, 1H), 7.14-7.10 (m, 2H), 4.78 (t, J=7.32 Hz, 2H), 2.46 (s, 3H), 2.03-1.93 (m, 20.94 (t, J=7.32 Hz, 3H).
MH+ 447.

Example 566

5-(5-(4-Chlorophenyl)-1-(2,4-dichlorophenyl)-4-methyl-1H-pyrazol-3-yl)-2-propyl-2H-tetrazole The title compound (62 mg, 37%) was the other compound obtained as white solid in Example 565, which was relatively more polar than the compound of Example 565.
$^1$H NMR (400 MHz, CDCl$_3$) δ 7.41-7.38 (m, 2H), 7.33-7.28 (m, 3H), 7.15-7.12 (m, 2H), 4.66 (t, J=5.16, 2H), 2.46 (s, 3H), 2.17-2.07 (m, 2H), 1.01 (t, J=5.52 Hz, 3H).
MH+ 447.

The following compounds of Examples 567 to 592 were obtained by using corresponding starting materials and repeating the procedure of Example 565 and 566.

Example 567

5-(5-(4-Chlorophenyl)-1-(2,4-dichlorophenyl)-4-methyl-1H-pyrazol-3-yl)-1-methyl-1H-tetrazole $^1$H NMR (400 MHz, CDCl$_3$) δ 7.49 (d, J=2.32 Hz, 1H), 7.35-7.22 (m, 4H), 7.14-7.10 (m, 2H), 4.39 (s, 3H), 2.47 (s, 3H).
MH+ 419.

Example 568

5-(5-(4-Chlorophenyl)-1-(2,4-dichlorophenyl)-4-methyl-1H-pyrazol-3-yl)-2-methyl-2H-tetrazole $^1$H NMR (400 MHz, CDCl$_3$) δ 7.40-7.38 (m, 2H), 7.33-7.27 (m, 3H), 7.14-7.12 (m, 2H), 4.44 (s, 3H), 2.46 (s, 3H).
MH+ 421.

Example 569

5-(5-(4-Chlorophenyl)-1-(2,4-dichlorophenyl)-4-methyl-1H-pyrazol-3-yl)-1-ethyl-1H-tetrazole $^1$H NMR (400 MHz, CDCl$_3$) δ 7.49 (d, J=1.71 Hz, 1H), 7.36-7.28 (m, 3H), 7.20 (d, J=6.51 Hz, 1H), 7.14-7.10 (m, 2H), 4.86 (q, J=5.52 Hz, 2H), 2.47 (s, 3H), 1.56 (t, J=5.52 Hz, 3H).
MH+ 433.

Example 570

5-(5-(4-Chlorophenyl)-1-(2,4-dichlorophenyl)-4-methyl-1H-pyrazol-3-yl)-2-ethyl-2H-tetrazole $^1$H NMR (400 MHz, CDCl$_3$) δ 7.41-7.38 (m, 2H), 7.33-7.27 (m, 3H), 7.15-7.12 (m, 2H), 4.75 (q, J=7.36 Hz, 2H), 2.46 (s, 3H), 1.71 (t, J=7.36 Hz, 3H).
MH+ 433.

Example 571

1-Butyl-5-(5-(4-chlorophenyl)-1-(2,4-dichlorophenyl)-4-methyl-1H-pyrazol-3-yl)-1H-tetrazole $^1$H NMR (400 MHz, CDCl$_3$) δ 7.49 (d, J=2.32 Hz, 1H), 7.35-7.27 (m, 3H), 7.19 (d, J=8.72 Hz, 1H), 7.14-7.10 (m, 2H), 4.82 (t, J=7.32 Hz, 2H), 2.46 (s, 3H), 1.97-1.89 (m, 2H), 1.55-1.33 (m, 2H), 0.91 (t, J=7.36 Hz, 3H).
MH+ 460.

Example 572

2-Butyl-5-(5-(4-chlorophenyl)-1-(2,4-dichlorophenyl)-4-methyl-1H-pyrazol-3-yl)-2H-tetrazole $^1$H NMR (400 MHz, CDCl$_3$) δ 7.41-7.38 (m, 2H), 7.33-7.27 (m, 3H), 7.15-7.12 (m, 2H), 4.70 (t, J=7.32 Hz, 2H), 2.46 (s, 3H), 2.10-2.03 (m, 2H), 1.44-1.38 (m, 2H), 0.98 (t, J=7.32 Hz, 3H).
MH+ 459.

Example 573

5-(5-(4-Chlorophenyl)-1-(2,4-dichlorophenyl)-4-methyl-1H-pyrazol-3-yl)-1-pentyl-1H-tetrazole $^1$H NMR (300 MHz, CDCl$_3$) δ 7.50 (d, J=2.22 Hz, 1H), 7.36-7.27 (m, 3H), 7.19 (d, J=11.24 Hz, 1H), 7.14-7.10 (m, 2H), 4.81 (t, J=9.76 Hz, 2H), 2.46 (s, 3H), 1.97-1.83 (m, 2H), 1.32-1.25 (m, 4H), 0.86-81 (m, 3H).
MH+ 475.

Example 574

5-(5-(4-Chlorophenyl)-1-(2,4-dichlorophenyl)-4-methyl-1H-pyrazol-3-yl)-2-pentyl-2H-tetrazole $^1$H NMR (300 MHz, CDCl$_3$) δ 7.42-7.39 (m, 2H), 7.34-7.27 (m, 3H), 7.15-7.12 (m, 2H), 4.69 (t, J=7.14 Hz, 2H), 2.46 (s, 3H), 2.11-2.09 (m, 2H), 1.37-1.36 (m, 4H), 0.92-0.88 (m, 3H).
MH+ 477.

Example 575

5-(5-(4-Chlorophenyl)-1-(2,4-dichlorophenyl)-4-methyl-1H-pyrazol-3-yl)-1-isopropyl-1H-tetrazole $^1$H NMR (300 MHz, CDCl$_3$) δ 7.49 (d, J=2.19 Hz, 1H), 7.36-7.27 (m, 3H), 7.20 (d, J=8.61 Hz, 1H), 7.14-7.10 (m, 2H), 5.68-5.61 (m, 1H), 2.44 (s, 3H), 1.66 (s, 3H), 1.63 (s, 3H).
MH+ 449.

Example 576

5-(5-(4-Chlorophenyl)-1-(2,4-dichlorophenyl)-4-methyl-1H-pyrazol-3-yl)-2-isopropyl-2H-tetrazole $^1$H NMR (300 MHz, CDCl$_3$) δ 7.42-7.38 (m, 2H), 7.33-7.27 (m, 3H), 7.15-7.12 (m, 2H), 5.22-5.12 (m, 1H), 2.46 (s, 3H), 1.74 (s, 3H), 1.72 (s, 3H).
MH+ 447.

Example 577

5-(5-(4-Chlorophenyl)-1-(2,4-dichlorophenyl)-4-methyl-1H-pyrazol-3-yl)-1-cyclopentyl-1H-tetrazole $^1$H NMR (400 MHz, CDCl$_3$) δ 7.49 (d, J=2.28 Hz, 1H), 7.35-7.27 (m, 3H), 7.20 (d, J=8.72 Hz, 1H), 7.14-7.09 (m, 2H), 5.75-5.67 (m, 1H), 2.44 (s, 3H), 2.24-2.16 (m, 4H), 2.04-1.98 (m, 2H), 1.78-1.68 (m, 2H).
MH+ 473.

Example 578

5-(5-(4-Chlorophenyl)-1-(2,4-dichlorophenyl)-4-methyl-1H-pyrazol-3-yl)-2-cyclopentyl-2H-tetrazole $^1$H NMR (400 MHz, CDCl$_3$) δ 7.41-7.36 (m, 2H), 7.33-7.27 (m, 3H), 7.15-7.11 (m, 2H), 5.34-5.27 (m, 1H), 2.44 (s, 3H), 2.37-2.24 (m, 4H), 2.04-1.94 (m, 2H), 1.84-1.73 (m, 2H).
MH+ 473.

Example 579

5-(5-(4-Chlorophenyl)-1-(2,4-dichlorophenyl)-4-methyl-1H-pyrazol-3-yl)-1-cyclohexyl-1H-tetrazole $^1$H NMR (400 MHz, CDCl$_3$) δ 7.52 (d, J=2.28 Hz, 1H), 7.36-7.26 (m, 3H), 7.16-7.10 (m, 3H), 5.25-5.17 (m, 1H), 2.42 (s, 3H), 2.19-1.30 (m, 10H).
MH+ 487.

Example 580

5-(5-(4-Chlorophenyl)-1-(2,4-dichlorophenyl)-4-methyl-1H-pyrazol-3-yl)-2-cyclohexyl-2H-tetrazole $^1$H NMR (400 MHz, CDCl$_3$) δ 7.41-7.38 (m, 2H), 7.35-7.27 (m, 3H), 7.15-7.10 (m, 2H), 4.84-4.76 (m, 1H), 2.45 (s, 3H), 2.31-1.31 (m, 10H).
MH+ 487.

Example 581

1-Benzyl-5-(5-(4-chlorophenyl)-1-(2,4-dichlorophenyl)-4-methyl-1H-pyrazol-3-yl)-1H-tetrazole $^1$H NMR (400 MHz, CDCl$_3$) δ 7.49 (d, J=2.28 Hz, 1H), 7.37-7.26 (m, 8H), 7.19 (d, J=8.24 Hz, 1H), 7.11-7.07 (m, 2H), 6.05 (s, 2H), 2.44 (s, 3H).
MH+ 496.

Example 582

2-Benzyl-5-(5-(4-chlorophenyl)-1-(2,4-dichlorophenyl)-4-methyl-1H-pyrazol-3-yl)-2H-tetrazole $^1$H NMR (400 MHz, CDCl$_3$) δ 7.45-7.43 (m, 2H), 7.39-7.27 (m, 8H), 7.13-7.10 (m, 2H), 5.85 (s, 2H), 2.43 (s, 3H).
MH+ 497.

Example 583

2-((5-(5-(4-Chlorophenyl)-1-(2,4-dichlorophenyl)-4-methyl-1H-pyrazol-3-yl)-1H-tetrazol-1-yl)methyl)pyridine $^1$H NMR (400 MHz, CDCl$_3$) δ 8.52 (d, J=4.53, 1H), 7.61-7.57 (m, 1H), 7.42 (d, J=2.32 Hz, 1H), 7.33-7.30 (m, 2H), 7.27-7.24 (m, 2H), 7.20-7.17 (m, 2H), 7.11-7.05 (m, 3H), 7.00 (d, J=7.80 Hz, 1H), 6.21 (s, 2H), 2.48 (s, 3H).
MH+ 496.

Example 584

2-((5-(5-(4-Chlorophenyl)-1-(2,4-dichlorophenyl)-4-methyl-1H-pyrazol-3-yl)-2H-tetrazol-2-yl)methyl)pyridine $^1$H NMR (400 MHz, CDCl$_3$) δ 8.61-8.59 (m, 1H), 7.71-7.66 (m, 1H), 7.40-7.37 (dd, J=5.04, 2.72 Hz, 2H), 7.33-7.26 (m, 4H), 7.18 (d, J=8.24 Hz, 1H), 7.14-7.11 (m, 2H), 6.03 (s, 2H), 2.45 (s, 3H).
MH+ 498.

Example 585

3-((5-(5-(4-Chlorophenyl)-1-(2,4-dichlorophenyl)-4-methyl-1H-pyrazol-3-yl)-1H-tetrazol-1-yl)methyl)pyridine $^1$H NMR (400 MHz, CDCl$_3$) δ 8.65 (d, J=1.84, 1H), 8.54 (dd, J=4.56, 1.36 Hz, 1H), 7.23-7.70 (m, 1H), 7.50 (d, J=2.32 Hz, 1H), 7.35-7.31 (m, 3H), 7.26-7.20 (m, 2H), 7.11-7.08 (m, 2H), 6.09 (s, 2H), 2.46 (s, 3H).
MH+ 496.

Example 586

3-((5-(5-(4-Chlorophenyl)-1-(2,4-dichlorophenyl)-4-methyl-1H-pyrazol-3-yl)-2H-tetrazol-2-yl)methyl)pyridine $^1$H NMR (400 MHz, CDCl$_3$) δ 8.76 (d, J=1.84 Hz, 1H), 8.62 (dd, J=5.04, 1.84 Hz, 1H), 7.79-7.76 (m, 1H), 7.39-7.36 (m, 2H), 7.33-7.27 (m, 4H), 7.13-7.10 (m, 2H), 5.88 (s, 2H), 2.43 (s, 3H).
MH+ 498.

Example 587

4-((5-(5-(4-Chlorophenyl)-1-(2,4-dichlorophenyl)-4-methyl-1H-pyrazol-3-yl)-1H-tetrazol-1-yl)methyl)pyridine $^1$H NMR (400 MHz, CDCl$_3$) δ 8.54-8.52 (m, 2H), 7.48 (d, J=2.28 Hz, 1H), 7.34-7.28 (m, 3H), 7.14-7.07 (m, 5H), 6.07 (s, 2H), 2.47 (s, 3H).
MH+ 496.

Example 588

4-((5-(5-(4-Chlorophenyl)-1-(2,4-dichlorophenyl)-4-methyl-1H-pyrazol-3-yl)-2H-tetrazol-2-yl)methyl)pyridine $^1$H NMR (400 MHz, CDCl$_3$) δ 8.64-8.62 (m, 2H), 7.40-7.13 (m, 7H), 7.14-7.11 (m, 2H), 5.87 (s, 2H), 2.45 (s, 3H). MH+ 496.

Example 589

5-(5-(4-Chlorophenyl)-1-(2,4-dichlorophenyl)-4-methyl-1H-pyrazol-3-yl)-1-(cyclohexylmethyl)-1H-tetrazole $^1$H NMR (300 MHz, CDCl$_3$) δ 7.51 (d, J=2.4 Hz, 1H), 7.36-7.26 (m, 3H), 7.18-7.09 (m, 3H), 4.68 (d, J=7.32 Hz, 2H), 2.46 (s, 3H), 2.04-2.00 (m, 1H), 1.68-0.90 (m, 10H). MH+ 501.

Example 590

5-(5-(4-Chlorophenyl)-1-(2,4-dichlorophenyl)-4-methyl-1H-pyrazol-3-yl)-2-(cyclohexylmethyl)-2H-tetrazole $^1$H NMR (300 MHz, MeOH-d$_4$) δ 7.58-7.55 (m, 2H), 7.47-7.44 (m, 1H), 7.41-7.37 (m, 2H), 7.27-7.23 (m, 2H), 4.60 (d, J=7.14 Hz, 2H), 2.39 (s, 3H), 2.18-2.02 (m, 1H), 1.77-0.86 (m, 10H).
MH+ 501.

Example 591

5-(5-(4-Chlorophenyl)-1-(2,4-dichlorophenyl)-4-methyl-1H-pyrazol-3-yl)-1-phenethyl-1H-tetrazole $^1$H NMR (300 MHz, CDCl$_3$) δ 7.52 (d, J=2.37 Hz, 1H), 7.36-7.07 (m, 11H), 5.04 (t, J=7.68 Hz, 2H), 3.24 (t, J=7.86 Hz, 2H), 2.39 (s, 3H).
MH+ 508.

Example 592

5-(5-(4-Chlorophenyl)-1-(2,4-dichlorophenyl)-4-methyl-1H-pyrazol-3-yl)-2-phenethyl-2H-tetrazole $^1$H NMR (300 MHz, CDCl$_3$) δ 7.42-7.39 (m, 2H), 7.34-7.26 (m, 6H), 7.25-7.19 (m, 2H), 7.16-7.11 (m, 2H), 4.92 (t, J=7.68 Hz, 2H), 3.41 (t, J=7.89 Hz, 2H), 2.45 (2, 3H).
MH+ 509.

Example 593

5-(5-(4-Chlorophenyl)-1-(2,4-dichlorophenyl)-4-methyl-1H-pyrazol-3-yl)-1-(furan-2-ylmethyl)-1H-tetrazole A mixture of 5-(5-(4-chlorophenyl)-1-(2,4-dichlorophenyl)-4-methyl-1H-pyrazol-3-yl)-1H-tetrazole (113 mg, 0.28 mmol) obtained in Step 1 of Example 52, furfuryl alcohol (0.05 ml, 0.56 mmol) and triphenylphosphine (146 mg, 0.56 mmol) was dissolved in tetrahydronfuran (3 ml) and cooled down to 0° C. Then, diisopropyl azodicarboxylate (0.11 ml, 0.56 mmol) was slowly added thereto at 0° C. After stirring for 2 hours at room temperature, the resulting solution was quenched with saturated ammonium chloride solution (1 ml). The mixture was extracted with ethyl acetate, and then the solvent of the organic layer was removed under a reduced pressure. The residue contained two regioisomers were separated by silica gel column chromatography (hexane/ethyl acetate=1/5), and repurified by reverse phase preparative HPLC, to obtain two compound, one of which was the title compound (22 mg, 16%).

$^1$H NMR (400 MHz, CDCl$_3$) δ 7.50-7.47 (m, 1H), 7.35-7.23 (m, 6H), 7.14-7.10 (m, 3H), 6.07 (s, 2H), 2.46 (s, 3H).
MH+ 484.

Example 594

5-(5-(4-Chlorophenyl)-1-(2,4-dichlorophenyl)-4-methyl-1H-pyrazol-3-yl)-2-(furan-2-ylmethyl)-2H-tetrazole The title compound (24 mg, 18%) was the other regioisomer obtained as white solid in Example 593, which is relatively more polar than the compound of Example 593.

$^1$H NMR (400 MHz, CDCl$_3$) δ 7.48-7.27 (m, 7H), 7.14-7.10 (m, 3H), 5.86 (s, 2H), 2.43 (s, 3H).
MH+ 485.

The following compounds of Examples 595 to 598 were obtained by using corresponding starting materials and repeating the procedure of Example 593 and 594.

Example 595

5-(5-(4-Chlorophenyl)-1-(2,4-dichlorophenyl)-4-methyl-1H-pyrazol-3-yl)-1-(furan-3-ylmethyl)-1H-tetrazole $^1$H NMR (400 MHz, CDCl$_3$) δ 7.50-7.51 (m 1H), 7.46 (s, 1H), 7.36-7.31 (m, 4H), 7.25-7.23 (m, 1H), 7.14-7.10 (m, 2H), 6.46 (s, 1H), 5.91 (s, 2H), 2.47 (s, 3H).
MH+ 484.

Example 596

5-(5-(4-Chlorophenyl)-1-(2,4-dichlorophenyl)-4-methyl-1H-pyrazol-3-yl)-2-(furan-3-ylmethyl)-2H-tetrazole $^1$H NMR (400 MHz, CDCl$_3$) δ 7.61 (s, 1H), 7.41-7.37 (m, 3H), 7.32-7.27 (m, 3H), 7.14-7.10 (m, 2H), 6.52 (m, 2H), 5.73 (s, 2H), 2.44 (s, 3H).
MH+ 484.

Example 597

5-(5-(4-Chlorophenyl)-1-(2,4-dichlorophenyl)-4-methyl-1H-pyrazol-3-yl)-1-(thiophen-3-ylmethyl)-1H-tetrazole $^1$H NMR (300 MHz, CDCl$_3$) δ 7.51 (d, J=2.19 Hz, 1H), 7.35-7.30 (m, 4H), 7.26-7.21 (m, 2H), 7.13-7.09 (m, 3H), 6.06 (s, 2H), 2.45 (s, 3H).
MH+ 501.

Example 598

5-(5-(4-Chlorophenyl)-1-(2,4-dichlorophenyl)-4-methyl-1H-pyrazol-3-yl)-2-(thiophen-3-ylmethyl)-2H-tetrazole $^{1}$H NMR (300 MHz, CDCl$_3$) δ 7.43-7.41 (m, 1H), 7.40-737 (m, 2H), 7.33-7.27 (m, 4H), 7.18 (dd, J=4.95, 1.29 Hz, 1H), 7.14-7.10 (m, 2H), 5.87 (s, 2H), 2.44 (s, 3H).
MH+ 501.

Example 599

5-(5-(4-Chlorophenyl)-1-(2,4-dichlorophenyl)-4-methyl-1H-pyrazol-3-yl)-1-cyclopropyl-1H-tetrazole Crude 5-(4-chlorophenyl)-1-(2,4-dichlorophenyl)-4-methyl-1H-pyrazole-3-carbonyl chloride (150 mg, 0.37 mmol) was dissolved in methylene chloride (3 ml) at 0° C., and triethyl amine (0.05 ml, 1.11 mmol) and cyclopropyl amine (0.03 ml, 0.56 mmol) were slowly added thereto. The resulting solution was stirred at room temperature for 3 hours, quenched with saturated ammonium chloride solution, extracted with ethyl acetate and filtrated with magnesium sulfate. The crude solution was evaporated and dried under a reduced pressure, to obtain 5-(4-chlorophenyl)-N-cyclopropyl-1-(2,4-dichlorophenyl)-4-methyl-1H-pyrazole-3-carboxamide, which are not further purified. The resulting product was dissolved in benzene (3 ml), and phosphorus pentachloride (85 mg, 0.41 mmol) was added thereto at room temperature. The solution was stirred for 20 minutes, hydroazoic acid (1.0 ml, 2.0 M solution in benzene) was added thereto and maintained room temperature for overnight. For completion of the reaction, reaction solution was refluxed for 10 minutes and purified by reverse phase preparative HPLC, to obtain the title compound (83 mg, 50%) as white solid.

$^{1}$H NMR (300 MHz, CDCl$_3$) δ 7.49-7.47 (m, 1H0, 7.34-7.22 (4H), 7.14-7.11 (m, 2H), 4.44 (m, 1H), 2.44 (s, 3H), 1.46-1.40 (m, 2H), 1.24-1.18 (m, 2H).
MH+ 445.

The following compounds of Examples 600 to 610 were obtained by using corresponding starting material and repeating the procedure of Example 599.

Example 600

5-(5-(4-Chlorophenyl)-1-(2,4-dichlorophenyl)-4-methyl-1H-pyrazol-3-yl)-1-cyclobutyl-1H-tetrazole $^{1}$H NMR (400 MHz, CDCl$_3$) δ 7.50 (d, J=2.32 Hz, 1H), 7.35-7.29 (m, 3H), 7.22 (d, J=8.24 Hz, 1H), 7.13-7.09 (m, 2H), 5.75-5.67 (m, 1H), 2.86-2.75 (m, 2H), 2.62-2.53 (m, 2H), 2.43 (s, 3H), 2.03-1.85 (m, 2H).
MH+ 459.

Example 601

5-(5-(4-Chlorophenyl)-1-(2,4-dichlorophenyl)-4-methyl-1H-pyrazol-3-yl)-1-cycloheptyl-1H-tetrazole $^{1}$H NMR (300 MHz, CDCl$_3$) δ 7.42 (m, 1H), 7.36-7.26 (m, 3H), 7.07-7.04 (m, 2H), 6.91-6.88 (m, 1H), 4.13 (m, 1H), 2.37 (s, 3H), 2.08-2.02 (m, 2H), 1.75-1.52 (m, 8H), 1.27-1.22 (m, 3H), 0.93-0.82 (m, 3H).
MH+ 500.

Example 602

1-tert-Butyl-5-(5-(4-chlorophenyl)-1-(2,4-dichlorophenyl)-4-methyl-1H-pyrazol-3-yl)-1H-tetrazole $^{1}$H NMR (300 MHz, CDCl$_3$) δ 7.44-7.43 (m, 1H), 7.34-7.26 (m, 4H), 7.07-7.03 (m, 2H), 2.25 (s, 3H), 1.58 (s, 9H).
MH+ 460.

Example 603

5-(5-(4-Chlorophenyl)-1-(2,4-dichlorophenyl)-4-methyl-1H-pyrazol-3-yl)-1-hexyl-1H-tetrazole $^{1}$H NMR (300 MHz, CDCl$_3$) δ 7.43-7.42 (m, 1H), 7.32-7.23 (m, 2H), 7.07-7.04 (m, 2H), 6.94 (m, 1H), 3.41 (q, J=6.96 Hz, 2H), 2.38 (s, 3H), 1.63-1.25 (m, 7H), 0.91-0.85 (m, 4H).
MH+ 489.

Example 604

5-(5-(4-Chlorophenyl)-1-(2,4-dichlorophenyl)-4-methyl-1H-pyrazol-3-yl)-1-octyl-1H-tetrazole $^{1}$H NMR (300 MHz, CDCl$_3$) δ 7.43-7.41 (m, 1H), 7.31-7.24 (m, 3H), 7.10-7.03 (m, 2H), 6.94-6.92 (m, 1H), 3.41 (q, J=7.14 Hz, 2H), 2.38 (s, 3H), 1.62-0.85 (m, 15H).
MH+ 516.

Example 605

1-Adamantyl-5-(5-(4-chlorophenyl)-1-(2,4-dichlorophenyl)-4-methyl-1H-pyrazol-3-yl)-1H-tetrazole $^{1}$H NMR (300 MHz, CDCl$_3$) δ 7.47 (d, J=2.22 Hz, 1H), 7.34-7.28 (m, 4H), 7.15-7.12 (m, 2H), 2.42 (s, 6H), 2.20 (br, 3H), 2.12 (s, 3H), 1.76 (m, 6H).
MH+ 541.

Example 606

5-(5-(4-bromophenyl)-1-(2,4-dichlorophenyl)-4-methyl-1H-pyrazol-3-yl)-1-cyclopentyl-1H-tetrazole $^{1}$H NMR (400 MHz, CDCl$_3$) δ 7.50-7.47 (m, 3H), 7.31-7.28 (m, 1H), 7.20 (d, J=8.8 Hz, 1H), 7.06-7.03 (m, 2H), 5.73-5.69 (m, 1H), 2.43 (s, 3H), 2.27-2.16 (m, 4H), 2.06-1.96 (m, 2H), 1.77-1.67 (m, 2H).
MH+ 517.

Example 607

5-(5-(4-bromophenyl)-1-(2,4-dichlorophenyl)-4-methyl-1H-pyrazol-3-yl)-1-cyclohexyl-1H-tetrazole $^{1}$H NMR (400 MHz, CDCl$_3$) δ 7.52-7.48 (m, 3H), 7.29-7.26 (m, 1H), 7.15 (d, J=8.4 Hz, 1H), 7.06-7.04 (m, 2H), 5.23-5.18 (m, 1H), 2.42 (s, 3H), 2.18-2.15 (m, 2H), 2.03-2.00 (m, 2H), 1.93-1.90 (m, 2H), 1.41-1.34 (m, 4H).
MH+ 531.

Example 608

5-(5-(4-bromophenyl)-1-(2,4-dichlorophenyl)-4-methyl-1H-pyrazol-3-yl)-1-cycloheptyl-1H-tetrazole $^{1}$H NMR (400 MHz, CDCl$_3$) δ 7.51-7.47 (m, 3H), 7.27 (dd, J=8.4 Hz, J=2.4 Hz, 1H), 7.15 (d, J=8.4 Hz, 1H), 7.05-7.03

(m, 2H), 5.43-5.41 (m, 1H), 2.41 (s, 3H), 2.21-2.15 (m, 4H), 1.86-1.82 (m, 2H), 1.66-1.63 (m, 4H), 1.51-1.49 (m, 2H).
MH+ 545.

Example 609

5-(5-(4-bromophenyl)-1-(2,4-dichlorophenyl)-4-ethyl-1H-pyrazol-3-yl)-1-cyclopentyl-1H-tetrazole $^1$H NMR (400 MHz, CDCl$_3$) δ 7.50-7.46 (m, 3H), 7.29-7.26 (m, 1H), 7.20 (d, J=8.8 Hz, 1H), 7.08-7.04 (m, 2H), 5.72-5.65 (m, 1H), 2.88-2.82 (m, 2H), 2.22-2.16 (m, 4H), 2.02-1.96 (m, 2H), 1.74-1.67 (m, 2H), 1.16 (t, J=7.6 Hz, 3H).
MH+ 531.

Example 610

5-(5-(4-chlorophenyl)-1-(2,4-dichlorophenyl)-4-ethyl-1H-pyrazol-3-yl)-1-cyclopentyl-1H-tetrazole $^1$H NMR (400 MHz, CDCl$_3$) δ 7.47-7.46 (m, 1H), 7.34-7.30 (m, 2H), 7.28-7.26 (m, 1H), 7.20 (d, J=8.4 Hz, 1H), 7.14-7.11 (m, 2H), 5.71-5.67 (m, 1H), 2.85 (q, J=7.6 Hz, 2H), 2.22-2.16 (m, 4H), 2.02-1.97 (m, 2H), 1.73-1.69 (m, 2H), 1.16 (t, J=7.6 Hz, 3H).
MH+ 487.

Preparation of Triazole (Formula (Id))

Example 611

3-(5-(4-Chlorophenyl)-1-(2,4-dichlorophenyl)-4-methyl-1H-pyrazol-3-yl)-5-cyclopentyl-1H-1,2,4-triazole A solution of 5-(4-chlorophenyl)-1-(2,4-dichlorophenyl)-4-methyl-1H-pyrazole-3-carbonitrile (300 mg, 0.83 mmol), cyclopentanecarbohydrazide (116 mg, 0.90 mmol) and potassium carbonate (57 mg, 0.41 mmol) dissolved in 1-butanol (2 ml) was placed in a sealed tube, stirred at room temperature for 10 minutes and then refluxed at 150° C. for 1 day. The mixture was cooled down to room temperature and methanol (4 ml) was added thereto, followed by filtering. The filtrate was purified by reverse phase preparative HPLC, to obtain the title compound as white solid.

$^1$H NMR (400 MHz, CDCl$_3$) δ 7.43 (d, J=2.32 Hz, 1H), 7.35-7.27 (m, 3H), 7.07-7.03 (m, 2H), 3.32-3.23 (m, 1H), 2.25 (s, 3H), 2.17-2.08 (m, 2H), 1.98-1.78 (m, 4H), 1.74-1.67 (m, 2H).
MH+ 472.

The following compounds of Examples 612 to 636 were obtained by using corresponding starting materials and repeating the procedure of Example 611.

Example 612

3-(5-(4-Chlorophenyl)-1-(2,4-dichlorophenyl)-4-methyl-1H-pyrazol-3-yl)-5-cyclohexyl-1H-1,2,4-triazole $^1$H NMR (400 MHz, CDCl$_3$) δ 7.39-7.35 (m, 2H), 7.32-7.27 (m, 3H), 7.12-7.09 (m, 2H), 2.91-2.84 (m, 1H), 2.43 (s, 3H), 2.17-2.10 (m, 2H), 1.87-1.83 (m, 2H), 1.75-1.73 (m, 1H), 1.67-1.58 (m, 3H), 1.46-1.28 (m, 2H).
MH+ 486.

Example 613

3-(5-(4-Chlorophenyl)-1-(2,4-dichlorophenyl)-4-methyl-1H-pyrazol-3-yl)-5-phenyl-1H-1,2,4-triazole $^1$H NMR (400 MHz, CDCl$_3$) δ 8.21-8.18 (m, 2H), 7.47-7.42 (m, 4H), 7.35-7.29 (m, 4H), 7.14-7.12 (m, 2H), 2.54 (s, 3H).
MH+ 480.

Example 614

3-(5-(4-Chlorophenyl)-1-(2,4-dichlorophenyl)-4-methyl-1H-pyrazol-3-yl)-5-(thiophen-2-yl)-1H-1,2,4-triazole $^1$H NMR (400 MHz, CDCl$_3$) δ 7.44-7.43 (m, 1H), 7.35-7.81 (m, 4H), 7.31-7.29 (m, 1H), 7.14-7.11 (m, 2H), 7.07-7.03 (m, 2H), 2.25 (s, 3H).
MH+ 486.

Example 615

3-(5-(4-chlorophenyl)-1-(2,4-dichlorophenyl)-4-methyl-1H-pyrazol-3-yl)-5-cycloheptyl-1H-1,2,4-triazole $^1$H NMR (400 MHz, CDCl$_3$) δ 7.40-7.35 (m, 2H), 7.32-7.27 (m, 3H), 7.12-7.09 (m 2H), 3.11-3.04 (m, 1H), 2.43 (s, 3H), 2.18-2.12 (m, 2H), 1.89-1.80 (m, 4H), 1.70-1.55 (m, 6H).
MH+ 502.

Example 616

3-(5-(4-chlorophenyl)-1-(2,4-dichlorophenyl)-4-methyl-1H-pyrazol-3-yl)-5-(furan-2-yl)-1H-1,2,4-triazole $^1$H NMR (400 MHz, CDCl$_3$) δ 7.43 (m, 1H), 7.34-7.27 (m, 5H), 7.14-7.10 (m, 2H), 7.07-7.04 (m, 2H), 2.25 (s, 3H).
MH+Na 493.

Example 617

3-(5-(4-chlorophenyl)-1-(2,4-dichlorophenyl)-4-methyl-1H-pyrazol-3-yl)-5-propyl-1H-1,2,4-triazole $^1$H NMR (400 MHz, CDCl$_3$) δ 7.41-7.32 (m, 2H), 7.34-7.27 (m, 3H), 7.08-7.05 (m, 2H), 2.57-2.50 (m, 2H), 2.15 (s, 3H), 1.70-1.65 (m, 2H), 1.01-0.98 (m, 3H).
MH+ 445.

Example 618

3-(5-(4-chlorophenyl)-1-(2,4-dichlorophenyl)-4-methyl-1H-pyrazol-3-yl)-5-isopropyl-1H-1,2,4-triazole $^1$H NMR (400 MHz, CDCl$_3$) δ 7.40-7.26 (m, 5H), 7.12-7.09 (m 2H), 3.23-3.18 (m, 1H), 2.44 (s, 3H), 1.43 (s, 3H), 1.41 (s, 3H).
MH+ 447.

Example 619

3-(5-(4-chlorophenyl)-1-(2,4-dichlorophenyl)-4-methyl-1H-pyrazol-3-yl)-5-cyclopropyl-1H-1,2,4-triazole $^1$H NMR (400 MHz, CDCl$_3$) δ 7.40-7.27 (m, 5H), 7.12-7.09 (m, 2H), 2.41 (s, 3H), 2.10-2.04 (m, 1H), 1.34-1.10 (m, 2H), 1.04-0.99 (m, 2H).
MH+ 445.

Example 620

3-(5-(4-chlorophenyl)-1-(2,4-dichlorophenyl)-4-methyl-1H-pyrazol-3-yl)-5-(cyclopropylmethyl)-1H-1,2,4-triazole $^1$H NMR (400 MHz, CDCl$_3$) δ 7.42-7.26 (m, 5H), 7.14-7.08 (m, 2H), 2.97-2.80 (m, 2H), 1.58-1.48 (m, 1H), 1.33-1.09 (m, 2H), 1.04-1.00 (m, 2H).
MH+ 458.

Example 621

3-(5-(4-chlorophenyl)-1-(2,4-dichlorophenyl)-4-methyl-1H-pyrazol-3-yl)-5-cyclobutyl-1H-1,2,4-triazole $^1$H NMR (400 MHz, CDCl$_3$) δ 7.46-7.43 (m, 2H), 7.34-7.27 (m, 3H), 7.07-7.04 (m, 2H), 3.51-3.47 (m, 1H), 2.57-2.52 (m, 2H), 2.38-2.29 (m, 2H), 2.25 (s, 3H), 2.25-1.93 (m, 2H).
MH+ 459.

Example 622

5-sec-butyl-3-(5-(4-chlorophenyl)-1-(2,4-dichlorophenyl)-4-methyl-1H-pyrazol-3-yl)-1H-1,2,4-triazole $^1$H NMR (400 MHz, CDCl$_3$) δ 7.40-7.27 (m, 5H), 7.13-7.09 (m, 2H), 3.10-2.93 (m, 1H), 2.44 (s, 3H), 1.93-1.83 (m, 1H), 1.76-1.67 (m, 1H), 1.39 (d, J=6.9 Hz, 3H), 0.93 (t, J=7.3 Hz, 3H).
MH+ 460.

Example 623

3-(5-(4-chlorophenyl)-1-(2,4-dichlorophenyl)-4-methyl-1H-pyrazol-3-yl)-5-cyclopentyl-1-methyl-1H-1,2,4-triazole A solution of 3-(5-(4-Chlorophenyl)-1-(2,4-dichlorophenyl)-4-methyl-1H-pyrazol-3-yl)-5-cyclopentyl-1H-1,2,4-triazole (400 mg, 0.82 mmol), iodomethane (0.19 ml, 2.5 mmol) and potassium hydroxide (138 mg, 2.5 mmol) dissolved in methanol (3 ml) was placed in a round bottom flask, stirred at room temperature for 1 day. After evaporation of the volatile solvent, the crude residue was purified by column chromatography to obtain the title compound (330 mg, 80%) as white solid.

$^1$H NMR (400 MHz, CDCl$_3$) δ 7.46-7.45 (m, 1H), 7.33-7.27 (m, 3H), 7.22-7.20 (d, J=8.7 Hz, 1H), 7.11-7.08 (m, 2H), 4.11 (s, 3H), 3.28-3.20 (m, 1H), 2.35 (s, 3H), 2.12-2.06 (m, 2H), 1.97-1.78 (m, 2H), 1.73-1.63 (m, 2H).
MH+ 486.

Example 624

3-(5-(4-chlorophenyl)-1-(2,4-dichlorophenyl)-4-methyl-1H-pyrazol-3-yl)-5-cyclohexyl-1-methyl-1H-1,2,4-triazole $^1$H NMR (400 MHz, CDCl$_3$) δ 7.46-7.45 (d, J=2.32 Hz, 1H), 7.33-7.27 (m, 3H), 7.22-7.20 (d, J=8.2 Hz, 1H), 7.11-7.08 (m, 2H), 4.12 (s, 3H), 2.83-2.77 (m, 1H), 2.35 (s, 3H), 2.11-2.06 (m, 2H), 1.87-1.82 (m, 2H), 1.74-1.67 (m, 2H), 1.67-1.57 (m, 2H), 1.46-1.28 (m, 4H).
MH+ 500.

Example 625

3-(5-(4-chlorophenyl)-1-(2,4-dichlorophenyl)-4-methyl-1H-pyrazol-3-yl)-5-cyclohexyl-1-ethyl-1H-1,2,4-triazole $^1$H NMR (400 MHz, CDCl$_3$) δ 7.47-7.46 (d, J=2.3 Hz, 1H), 7.33-7.27 (m, 3H), 7.20-7.18 (d, J=8.2 Hz, 1H), 7.11-7.07 (m, 2H), 4.55-4.50 (q, J=6.9 Hz, 3H), 2.83-2.77 (m, 1H), 2.35 (s, 3H), 2.11-2.05 (m, 2H), 1.87-1.82 (m, 2H), 1.75-1.67 (m, 2H), 1.67-1.57 (m, 2H), 1.47-1.44 (t, J=7.4 Hz, 3H), 1.44-1.28 (m, 4H).
MH+ 515.

Example 626

3-(5-(4-chlorophenyl)-1-(2,4-dichlorophenyl)-4-methyl-1H-pyrazol-3-yl)-5-cyclohexyl-1-isopropyl-1H-1,2,4-triazole $^1$H NMR (400 MHz, CDCl$_3$) δ 7.46-7.45 (d, J=2.3 Hz, 1H), 7.33-7.25 (m, 3H), 7.21-7.19 (d, J=8.2 Hz, 1H), 7.11-7.07 (m, 2H), 5.28-5.22 (m, 1H), 2.85-2.79 (m, 1H), 2.31 (s, 3H), 2.07-2.03 (m, 2H), 1.89-1.81 (m, 2H), 1.73-1.62 (m, 2H), 1.51-1.49 (d, J=6.4 Hz, 6H), 1.49-1.25 (m, 5H).
MH+ 530.

Example 627

3-(5-(4-chlorophenyl)-1-(2,4-dichlorophenyl)-4-methyl-1H-pyrazol-3-yl)-5-cyclohexyl-1-isopropyl-1H-1,2,4-triazole $^1$H NMR (400 MHz, CDCl$_3$) δ 7.46-7.45 (d, J=2.3 Hz, 1H), 7.33-7.25 (m, 3H), 7.21-7.19 (d, J=8.2 Hz, 1H), 7.11-7.07 (m, 2H), 5.28-5.22 (m, 1H), 2.85-2.79 (m, 1H), 2.31 (s, 3H), 2.07-2.03 (m, 2H), 1.89-1.81 (m, 2H), 1.73-1.62 (m, 2H), 1.51-1.49 (d, J=6.4 Hz, 6H), 1.49-1.25 (m, 5H).
MH+ 530.

Example 628

3-(5-(4-chlorophenyl)-1-(2,4-dichlorophenyl)-4-methyl-1H-pyrazol-3-yl)-5-cyclopropyl-1-methyl-1H-1,2,4-triazole $^1$H NMR (400 MHz, CDCl$_3$) δ 7.47-7.46 (d, J=2.3 Hz, 1H), 7.34-7.25 (m, 3H), 7.20-7.17 (d, J=8.1 Hz, 1H), 7.10-7.08 (m, 2H), 4.1 (s, 3H), 2.32 (s, 3H), 2.12-2.07 (m, 1H), 1.55-1.04 (m, 2H), 1.00-0.96 (m, 2H).
MH+ 459.

Example 629

3-(5-(4-chlorophenyl)-1-(2,4-dichlorophenyl)-4-methyl-1H-pyrazol-3-yl)-5-cyclopropyl-1-ethyl-1H-1,2,4-triazole $^1$H NMR (400 MHz, CDCl$_3$) δ 7.47-7.46 (d, J=2.3 Hz, 1H), 7.33-7.25 (m, 3H), 7.20-7.17 (d, J=8.2 Hz, 1H), 7.10-7.08 (m, 2H), 4.53-4.78 (q, J=7.3 Hz, 2H), 2.32 (s, 3H), 2.12-2.07 (m, 1H), 1.47-1.44 (t, J=7.4 Hz, 3H), 1.54-1.03 (m, 2H), 1.00-0.96 (m, 2H).
MH+ 473.

Example 630

3-(5-(4-chlorophenyl)-1-(2,4-dichlorophenyl)-4-methyl-1H-pyrazol-3-yl)-5-cyclopropyl-1-isopropyl-1H-1,2,4-triazole $^1$H NMR (400 MHz, CDCl$_3$) δ 7.46-7.45 (d, J=2.3 Hz, 1H), 7.33-7.25 (m, 3H), 7.20-7.18 (d, J=8.2 Hz, 1H), 7.10-7.08 (m, 2H), 5.28-5.24 (m, 1H) 2.23 (s, 3H), 2.14-2.10 (m, 1H), 1.51-1.49 (d, J=6.4 Hz, 6H), 1.07-1.30 (m, 2H), 0.99-0.95 (m, 2H).
MH+ 487.

Example 631

5-sec-butyl-3-(5-(4-chlorophenyl)-1-(2,4-dichlorophenyl)-4-methyl-1H-pyrazol-3-yl)-1-methyl-1H-1,2,4-triazole $^1$H NMR (400 MHz, CDCl$_3$) δ 7.47-7.44 (d, J=2.3 Hz, 1H), 7.32-7.24 (m, 3H), 7.20-7.18 (d, J=8.6 Hz, 1H), 7.11-7.08 (m, 2H), 4.15 (s, 3H), 2.92-2.87 (m, 1H), 2.34 (s. 3H), 1.91-1.83 (m, 1H), 1.71-1.64 (m, 1H), 1.37-1.36 (d, J=7.3 Hz), 0.94 (t, J=7.3 Hz, 3H).
MH+ 475.

Example 632

5-sec-butyl-3-(5-(4-chlorophenyl)-1-(2,4-dichlorophenyl)-4-methyl-1H-pyrazol-3-yl)-1-ethyl-1H-1,2,4-triazole $^1$H NMR (400 MHz, CDCl$_3$) δ 7.47-7.46 (d, J=2.3 Hz, 1H), 7.33-7.24 (m, 3H), 7.20-7.18 (d, J=8.7 Hz, 1H), 7.11-7.08 (m, 2H), 4.55-4.50 (q, J=6.9 Hz, 2H), 2.92-2.87 (m, 1H), 2.34 (s. 3H), 1.91-1.83 (m, 1H), 1.71-1.64 (m, 1H), 1.47-1.44 (t, J=6.8 Hz, 3H), 1.37-1.35 (d, J=7.4 Hz), 0.95-0.91 (t, J=7.3 Hz, 3H).
MH+ 489.

Example 633

5-sec-butyl-3-(5-(4-chlorophenyl)-1-(2,4-dichlorophenyl)-4-methyl-1H-pyrazol-3-yl)-1-isopropyl-1H-1,2,4-triazole $^1$H NMR (400 MHz, CDCl$_3$) δ 7.46 (d, J=1.8 Hz, 1H), 7.34-7.22 (m, 3H), 7.21-7.19 (d, J=8.2 Hz, 1H), 7.10-7.08 (m, 2H), 5.26-5.22 (m, 1H), 2.91-2.88 (m, 1H), 2.30 (s. 3H), 1.89-1.82 (m, 1H), 1.70-1.64 (m, 1H), 1.51-1.49 (d, 6.4 Hz, 6H), 1.36-1.34 (d, J=7.3 Hz), 0.93-0.90 (t, J=7.3 Hz, 3H).
MH+ 503.

Example 634

3-(5-(4-chlorophenyl)-1-(2,4-dichlorophenyl)-4-methyl-1H-pyrazol-3-yl)-5-isopropyl-1-methyl-1H-1,2,4-triazole $^1$H NMR (400 MHz, CDCl$_3$) δ 7.47-7.50 (d, J=2.3 Hz, 1H), 7.33-7.23 (m, 3H), 7.22-7.20 (m, 1H), 7.11-7.08 (m, 2H), 4.12 (s, 3H), 3.14-3.08 (m, 1H), 2.37 (s. 3H), 1.40-1.38 (d, J=6.9 Hz, 6H).
MH+ 461.

Example 635

3-(5-(4-chlorophenyl)-1-(2,4-dichlorophenyl)-4-methyl-1H-pyrazol-3-yl)-5-isopropyl-1-ethyl-1H-1,2,4-triazole $^1$H NMR (400 MHz, CDCl$_3$) δ 7.48-7.47 (d, J=2.3 Hz, 1H), 7.33-7.23 (m, 3H), 7.22-7.20 (d, J=8.7 Hz, 1H), 7.11-7.08 (m, 2H), 4.54-4.49 (q, J=7.4 Hz, 2H), 3.20-3.15 (m, 1H), 2.32 (s. 3H), 1.49-1.45 (t, J=7.3 Hz, 3H), 1.41-1.39 (d, J=6.9 Hz, 6H).
MH+ 475.

Example 636

3-(5-(4-chlorophenyl)-1-(2,4-dichlorophenyl)-4-methyl-1H-pyrazol-3-yl)-1,5-diisopropyl-1H-1,2,4-triazole $^1$H NMR (400 MHz, CDCl$_3$) δ 7.46-7.45 (d, J=2.3 Hz, 1H), 7.33-7.23 (m, 3H), 7.21-7.19 (d, J=8.2 Hz, 1H), 7.11-7.08 (m, 2H), 5.26-5.23 (m, 1H), 3.17-3.10 (m, 1H), 2.31 (s. 3H), 1.51-1.49 (d, J=6.9 Hz, 6H), 1.39-1.37 (d, J=7.3 Hz, 6H).
MH+ 488.

Preparation of Pyrazole (Formula (89))

Example 637

5'-tert-butyl-5-(4-chlorophenyl)-1-(2,4-dichlorophenyl)-4-methyl-1H,1'H-3,3'-bipyrazole Step 1: (Z)-1-(5-(4-chlorophenyl)-1-(2,4-dichlorophenyl)-4-methyl-1H-pyrazol-3-yl)-3-hydroxyl-4,4-dimethylpent-2-en-1-one (87)

To a solution of sodium amide (215 mg, 5.5 mmol) in THF (5 mL) was added pinacolone (1.0 M THF solution, 5 mL, 5.0 mmol). The reaction mixture was refluxed at 80° C. for 30 min and then ethyl 5-(4-chlorophenyl)-1-(2,4-dichlorophenyl)-4-methyl-1H-pyrazole-3-carboxylate (4) (2.05 g, 5.0 mmol) in THF (15 mL) was added. The resulting solution was stirred and refluxed at 80° C. overnight. HCl aqueous solution (11.0M, 50 mL) was added and extracted organic layer with ethyl acetate (50 mL twice). The combined organic phase was evaporated under vacuum. The crude residue was further purified by prep HPLC to provide 0.862 g (1.86 mmol, 37%) of the title compound.

$^1$H NMR (400 MHz, CDCl$_3$) δ 7.44-41 (m, 1H), 7.35-7.21 (m, 4H), 7.08-7.03 (m, 2H), 6.54 (s, 1H), 2.36 (s, 3H), 1.24 (s, 9H).
MH+ 463.

Step 2: 5'-tert-butyl-5-(4-chlorophenyl)-1-(2,4-dichlorophenyl)-4-methyl-1H,1'H-3,3'-bipyrazole (89)

To a suspension of 1-(5-(4-chlorophenyl)-1-(2,4-dichlorophenyl)-4-methyl-1H-pyrazol-3-yl)-4,4-dimethylpentane-1,3-dione (555 mg, 1.20 mmol) (B) in EtOH (5.5 mL) was added hydrazine monohydrate (0.12 g, 2.4 mmol). The reaction mixture was refluxed at 90° C. for 6 hours. After cooled down to room temperature, the resulting suspension was dissolved by addition of THF (15 mL) and further purified by prep HPLC to provide 350 mg (0.761 mmol, 63%) of the title compound.

$^1$H NMR (400 MHz, CDCl$_3$) δ 7.40 (d, J=2.8 Hz, 1H), 7.35-7.25 (m, 4H), 7.11 (d, J=11.2 Hz, 2H), 6.54 (br s, 1H), 2.33 (s, 3H), 1.38 (s, 9H).

MH+ 459.

Preparation of Oxazole (Formula 1g))

Example 638

2-(5-(4-chlorophenyl)-1-(2,4-dichlorophenyl)-4-methyl-1H-pyrazol-3-yl)-5-cyclohexyloxazole

Step 1: tert-Butyl 2-(methoxy(methyl)amino)-2-oxoethylcarbamate

To a 2-(tert-butoxycarbonylamino)acetic acid (800 mg, 4.57 mmol), N,O-dimethylhydroxylamine hydrochloride (535 mg, 5.48 mmol), EDCI (1.05 g, 5.48 mmol), HOBt (740 mg, 5.48 mmol) in DCM (25 mL) was added NMM (2.77 g, 27.42 mmol) at rt. The reaction mixture was stirred overnight. After the reaction was completed, DCM was evaporated in vacuo. The residue was dissolved in MeOH, filtered through a syringe filter, and then purified by reverse-phase prep HPLC to provide the desired product (705 mg, 71%) as white solid

Step 2: tert-Butyl 2-cyclohexyl-2-oxoethylcarbamate

To a tert-butyl 2-(methoxy(methyl)amino)-2-oxoethylcarbamate (400 mg, 1.83 mmol) in THF (10 mL) was added cyclohexylmagnesium chloride (4.12 mL, 8.24 mmol) portionwise at room temperature under N$_2$ atmosphere. As addition of the Grignard reagent was completed, the reaction mixture was stirred and heated to reflux for an hour. Then the mixture was allowed to cool down to room temperature. The reaction was quenched by adding water (10 mL) slowly. 1N HCl solution (30 mL) was added to the mixture, and extracted with EtOAc (20 mL×3). The combined organic layers were collected and evaporated in vacuo. The crude material was purified by column chromatography (hexane:EtOAc=10:1 to 5:1) to yield the desired product (110 mg, 25%).

Step 3: 5-(4-chlorophenyl)-N-(2-cyclohexyl-2-oxoethyl)-1-(2,4-dichlorophenyl)-4-methyl-1H-pyrazole-3-carboxamide To a tert-butyl 2-cyclohexyl-2-oxoethylcarbamate (228 mg, 0.946 mmol) in DCM (5 mL) was added 4M HCl in 1,4-dioxane (5 mL) at room temperature. The reaction continued for an hour at room temperature. The volatiles were removed under vacuum. To the residue (2-amino-1-cyclohexylethanone hydrochloric acid), 5-(4-chlorophenyl)-1-(2,4-dichlorophenyl)-4-methyl-1H-pyrazole-3-carboxylic acid (361 mg, 0.946 mmol), EDCI (272 mg, 1.429 mmol), HOBt (192 mg, 1.429 mmol) in DMF (9 mL) was added NMM (1.0 mL, 9.46 mmol) at room temperature. The reaction mixture was stirred at room temperature overnight. The residue was purified by reverse-phase prep HPLC to afford the title compound (232 mg, 49%).

Step 4: 2-(5-(4-chlorophenyl)-1-(2,4-dichlorophenyl)-4-methyl-1H-pyrazol-3-yl)-5-cyclohexyloxazole 5-(4-chlorophenyl)-N-(2-cyclohexyl-2-oxoethyl)-1-(2,4-dichlorophenyl)-4-methyl-1H-pyrazole-3-carboxamide (116 mg, 0.23 mmol) obtained in Step 3 was added to a microwave reactor containing Burgess reagent (165 mg, 0.689 mmol) in THF (2 mL). The capped reactor was placed in a microwave reactor and the mixture was irradiated at 160° C. for 20 min. The reaction product was purified by reverse-phase prep HPLC to provide the title compound (62 mg, 55%) as white solid.

$^1$H NMR (400 MHz, CDCl$_3$) δ 7.40-7.26 (m, 5H), 7.13-7.09 (m, 2H), 6.86 (d, J=0.93 Hz, 1H), 2.78 (m, 1H), 2.42 (s, 3H), 2.10 (m, 2H), 1.83-1.68 (m, 3H), 1.51-1.25 (m, 5H).

MH+ 486.

The following compounds of Examples 639 to 644 were obtained by using corresponding starting materials and repeating the procedure of Example 638.

Example 639

5-butyl-2-(5-(4-chlorophenyl)-1-(2,4-dichlorophenyl)-4-methyl-1H-pyrazol-3-yl)oxazole $^1$H NMR (300 MHz, CDCl$_3$) δ 7.40-7.28 (m, 5H), 7.14-7.09 (m, 2H), 6.91 (t, J=1.0 Hz, 1H), 2.74 (t, J=7.6 Hz, 2H), 2.42 (s, 3H), 1.70 (m, 2H), 1.40 (m, 2H), 0.94 (t, J=7.3 Hz, 3H).

MH+ 460.

Example 640

2-(5-(4-chlorophenyl)-1-(2,4-dichlorophenyl)-4-methyl-1H-pyrazol-3-yl)-5-ethyloxazole $^1$H NMR (400 MHz, CDCl$_3$) δ 7.40-7.28 (m, 5H), 7.13-7.09 (m, 2H), 6.91 (t, J=1.2 Hz, 1H), 2.78 (q, J=7.5 Hz, 2H), 2.43 (s, 3H), 1.31 (t, J=7.5 Hz, 3H).

MH+ 432.

Example 641

2-(5-(4-chlorophenyl)-1-(2,4-dichlorophenyl)-4-methyl-1H-pyrazol-3-yl)-5-isobutyloxazole $^1$H NMR (400 MHz, CDCl$_3$) δ 7.40-7.28 (m, 5H), 7.13-7.09 (m, 2H), 6.92 (br s, 1H), 2.61 (d, J=6.7 Hz, 2H), 2.43 (s, 3H), 2.05 (m, 1H), 0.97 (d, J=6.6 Hz, 6H).

MH+ 460.

Example 642

2-(5-(4-chlorophenyl)-1-(2,4-dichlorophenyl)-4-methyl-1H-pyrazol-3-yl)-4,5,6,7-tetrahydrobenzo[d]oxazole $^1$H NMR (400 MHz, CDCl$_3$) δ 7.40-7.27 (m, 5H), 7.14-7.10 (m, 2H), 2.71 (m, 2H), 2.64 (m, 2H), 2.43 (s, 3H), 1.87-1.80 (m, 4H).

MH+ 458.

Example 643

2-(5-(4-chlorophenyl)-1-(2,4-dichlorophenyl)-4-methyl-1H-pyrazol-3-yl)-5-cyclopentyloxazole $^1$H NMR (400 MHz, CDCl$_3$) δ 7.40-7.37 (m, 2H), 7.34-7.28 (m, 3H), 7.14-7.08 (m, 2H), 6.89 (s, 1H), 3.21 (m, 1H), 2.42 (s, 3H), 2.07 (m, 2H), 1.80-1.60 (m, 6H).
MH+ 472.

Example 644

5-tert-butyl-2-(5-(4-chlorophenyl)-1-(2,4-dichlorophenyl)-4-methyl-1H-pyrazol-3-yl)oxazole $^1$H NMR (400 MHz, CDCl$_3$) δ 7.42-7.38 (m, 2H), 7.33-7.26 (m, 3H), 7.12-7.08 (m, 2H), 6.85 (d, J=0.4 Hz, 1H), 2.41 (s, 3H), 1.37 (s, 9H).
MH+ 460.

Preparation of Thiazole (Formula (1h))

Example 645

2-(5-(4-chlorophenyl)-1-(2,4-dichlorophenyl)-4-methyl-1H-pyrazol-3-yl)-5-cyclohexylthiazole 5-(4-chlorophenyl)-N-(2-cyclohexyl-2-oxoethyl)-1-(2,4-dichlorophenyl)-4-methyl-1H-pyrazole-3-carboxamide (116 mg, 0.23 mmol) obtained in Step 3 of preparation of oxazole was added to a microwave reactor containing Lawesson's reagent (186 mg, 0.46 mmol) in THF (2 mL). The capped reactor was placed in a microwave reactor and the mixture was irradiated at 1860° C. for 30 min. The reaction product was purified by reverse-phase prep HPLC to provide the title compound (88 mg, 76%) as white solid.

$^1$H NMR (400 MHz, CDCl$_3$) δ 7.59 (br d, J=0.8 Hz, 1H), 7.40 (d, J=2.0 Hz, 1H), 7.37-7.27 (m, 4H), 7.13-7.08 (m, 2H), 2.89 (m, 1H), 2.43 (s, 3H), 2.07 (m, 2H), 1.85-1.71 (m, 3H), 1.53-1.34 (m, 5H).
MH+ 502.

The following compounds of Examples 646 to 649 were obtained by using corresponding starting materials and repeating the procedure of Example 645.

Example 646

2-(5-(4-chlorophenyl)-1-(2,4-dichlorophenyl)-4-methyl-1H-pyrazol-3-yl)-5-isobutylthiazole $^1$H NMR (400 MHz, CDCl$_3$) δ 7.56 (s, 1H), 7.40-7.26 (m, 5H), 7.12-7.09 (m, 2H), 2.73 (d, J=7.0 Hz, 2H), 2.44 (s, 3H), 1.90 (m, 1H), 0.97 (d, J=6.8 Hz, 6H).
MH+ 476.

Example 647

2-(5-(4-chlorophenyl)-1-(2,4-dichlorophenyl)-4-methyl-1H-pyrazol-3-yl)-4,5,6,7-tetrahydrobenzo[d]thiazole $^1$H NMR (400 MHz, CDCl$_3$) δ 7.41-7.37 (m, 2H), 7.34-7.25 (m, 3H), 7.12-7.08 (m, 2H), 2.84 (d, J=18.8 Hz, 4H), 2.41 (s, 3H), 1.90 (m, 4H).
MH+ 474.

Example 648

2-(5-(4-chlorophenyl)-1-(2,4-dichlorophenyl)-4-methyl-1H-pyrazol-3-yl)-5-cyclopentylthiazole $^1$H NMR (400 MHz, CDCl$_3$) δ 7.60 (s, 1H), 7.42-7.26 (m, 5H), 7.14-7.09 (m, 2H), 3.31 (m, 1H), 2.44 (s, 3H), 2.16 (m, 2H), 1.90-1.60 (m, 6H).
MH+ 488.

Example 649

5-tert-butyl-2-(5-(4-chlorophenyl)-1-(2,4-dichlorophenyl)-4-methyl-1H-pyrazol-3-yl)thiazole $^1$H NMR (400 MHz, CDCl$_3$) δ 7.59 (d, J=0.4 Hz, 1H), 7.42-7.27 (m, 5H), 7.14-7.10 (m, 2H), 2.44 (s, 3H), 1.43 (s, 9H).
MH+ 476.

Preparation of Isoxazole (Formula (90) and (91))

A solution of diketone (87) (200 mg, 0.43 mmol) and hydroxylamine hydrochloride (60 mg, 0.86 mmol) in EtOH (5 mL) was irradiated in a microwave reactor (Biotage) for 20 min. at 140° C. Purification by Prep-LC (Gilson) provided 67 mg (34%) of 5-t-butylisoxazole and 28 mg (14%) of 3-t-butylisoxazole as solid.

Example 650

5-tert-butyl-3-(5-(4-chlorophenyl)-1-(2,4-dichlorophenyl)-4-methyl-1H-pyrazol-3-yl)isoxazole (90)

$^1$H NMR (400 MHz, CDCl$_3$) δ 7.41 (d, J=2.4 Hz, 1H), 7.31-7.29 (m, 4H), 7.10 (d, J=9.6 Hz, 2H), 6.47 (s, 1H), 2.38 (s, 3H), 1.38 (s, 9H).
MH+ 460.

Example 651

3-tert-butyl-5-(5-(4-chlorophenyl)-1-(2,4-dichlorophenyl)-4-methyl-1H-pyrazol-3-yl)isoxazole (91)

$^1$H NMR (400 MHz, CDCl$_3$) δ 7.41 (d, J=1.6 Hz, 1H), 7.32-7.29 (m, 4H), 7.09 (d, J=4.4 Hz, 2H), 6.62 (s, 1H), 2.36 (s, 3H), 1.38 (s, 9H).
MH+ 460.

Preparation of Isothiazole

Example 652

5-tert-butyl-3-(5-(4-chlorophenyl)-1-(2,4-dichlorophenyl)-4-methyl-1H-pyrazol-3-yl)isothiazole A solution of diketone (20 mg, 0.043 mmol), hydroxylamine hydrochloride (9 mg, 0.13 mmol) and Lawesson reagent (52 mg, 0.13 mmol) in 1,4-dioxane (4 mL) was irradiated in a microwave reactor (Biotage) for 20 min. at 140° C. Purification by Prep-LC (Gilson) provided 1 mg (5%) of desired isothiazole as solid.

$^1$H NMR (400 MHz, CDCl$_3$) δ 7.52 (s, 1H), 7.40 (d, J=2.0 Hz, 1H), 7.35-7.28 (m, 4H), 7.09 (d, J=6.4 Hz, 2H), 2.28 (s, 3H), 1.41 (s, 9H).
MH+ 476.

Experiment 1

Pharmacological Test

In Vitro Activity Analysis

The compounds of the present invention were analyzed for their binding characteristics for $CB_1$ and $CB_2$ and the pharmacological activity thereof in accordance with the method disclosed in [Devane W A, Dysarz F A $3^{rd}$, Johnson M R, Melvin L S and Howlett A C, Determination and characterization of a cannabinoid receptor in rat brain, *Mol. Pharmacol.*, 34(5): 605-13 (1998)]. The analysis was performed using [$^3$H]CP-55940 which is a selectively radioactivity-labeled 5-(1,1-dimethyheptyl)-2[5-hydroxy-2-(3-hydroxypropyl)-cyclohexyl]-phenol, purchased from PerkinElmer Life Sciences, Inc. (Boston, Mass., U.S.A.), through a rat CB-1 receptor binding protocol as follows.

The tissue obtained from the brain of SD rats was homogenized with a Dounce homogenate system in TME (50 mM Tris, 3 mM $MgCl_2$ and 1 mM EDTA, pH 7.4) at 4° C., and the homogenate was centrifuged at 48,000 g for 30 min. at 4° C. The pellet was resuspended in 5 ml of TME and the suspension was divided into aliquots and stored at −70° C. until its use in the following assay.

2 ml of the test compound was diluted in dimethylsulphoxide and was added to a deep well of a polypropylene plate, to which 50 μl of [$^3$H]CP-55940 diluted in a ligand buffer solution (0.1% bovine serum albumin(BAS)+TME) was added. The tissue concentrations were determined by Bradford protein analysis, and 148 μl of brain tissue of the required concentration was added to the plate. The plate was covered and placed in a 30° C. incubator for 60 min, and then transformed on GF/B filtermat pretreated in polyethylenimine (PEI) using a cell harvester. Each filter was washed five times and dried at 60° C. for 1 hr. Then, the degree of radioactivity retained by the filter was measured using Wallac Microbeta™ (PerkinElmer Life Sciences, Inc., Massachusetts, U.S.A.) and the activity of the compound for inhibiting $CB_1$ receptor was determined therefrom.

The examples of the present invention were tested in the cannabinoid-1 receptor (CB1R) binding affinity assay (Table 1). All of the preferred examples were shown to have binding affinities in the range of CB1R $IC_{50}$<1.0 uM. Among them, more than twenty and less than thirty examples of the present invention were shown to have binding affinities in the range of $IC_{50}$<3.0 nM, while rimonabant (SR141716) showed binding affinity in the range of $IC_{50}$=5.0 nM.

TABLE 1

Cannabinoid-1 receptor (CB1R) binding affinity assay

| Example | $IC_{50}$(nM) |
|---|---|
| 2 | 563 |
| 8 | 112 |
| 10 | 196 |
| 11 | 96.6 |
| 18 | 333 |
| 22 | 35.7 |
| 23 | 163 |
| 24 | 22.7 |
| 25 | 60.0 |
| 52 | 12.7 |
| 54 | 11.2 |
| 55 | 10.3 |
| 56 | 37.6 |
| 61 | 22.2 |
| 62 | 51.7 |
| 63 | 19.1 |
| 64 | 15.2 |
| 65 | 12.4 |
| 67 | 8.61 |
| 71 | 11.0 |
| 80 | 36.1 |
| 97 | 15.7 |
| 98 | 33.7 |
| 110 | 13.0 |
| 111 | 3.96 |
| 112 | 7.40 |
| 116 | 23.9 |
| 119 | 550 |
| 129 | 9.46 |
| 130 | 8.14 |
| 131 | 7.26 |
| 132 | 8.53 |
| 133 | 5.47 |
| 135 | 16.3 |
| 136 | 74.2 |
| 137 | 141 |
| 138 | 10.0 |
| 144 | 2.16 |
| 147 | 5.75 |
| 150 | 6.05 |
| 151 | 7.05 |
| 152 | 5.62 |
| 153 | 5.83 |
| 154 | 7.42 |
| 159 | 7.51 |
| 161 | 52.6 |
| 162 | 59.2 |
| 167 | 41.9 |
| 168 | 200 |
| 172 | 17.9 |
| 174 | 6.97 |
| 175 | 5.71 |
| 176 | 4.47 |
| 177 | 3.01 |
| 181 | 9.72 |
| 182 | 22.5 |
| 186 | 12.1 |
| 187 | 11.1 |
| 188 | 15.5 |
| 190 | 15.0 |
| 191 | 15.0 |
| 195 | 12.1 |
| 196 | 22.4 |
| 197 | 7.07 |
| 198 | 68.8 |
| 199 | 14.6 |
| 200 | 6.35 |
| 201 | 4.02 |
| 202 | 36.2 |
| 203 | 18.8 |
| 204 | 5.39 |
| 205 | 15.4 |
| 206 | 113 |
| 207 | 10.1 |
| 208 | 6.72 |
| 209 | 5.77 |
| 210 | 14.1 |
| 211 | 12.1 |
| 212 | 4.97 |
| 213 | 49.4 |
| 214 | 11.9 |
| 215 | 10.8 |
| 216 | 57.3 |
| 217 | 22.6 |
| 218 | 17.1 |
| 219 | 4.83 |
| 220 | 8.26 |
| 221 | 14.7 |
| 222 | 7.99 |
| 223 | 7.89 |

TABLE 1-continued

Cannabinoid-1 receptor (CB1R) binding affinity assay

| Example | IC$_{50}$(nM) |
|---|---|
| 224 | 36.1 |
| 225 | 12.1 |
| 226 | 62.7 |
| 227 | 16.9 |
| 228 | 16.6 |
| 229 | 14.1 |
| 230 | 9.01 |
| 231 | 4.06 |
| 232 | 15.6 |
| 233 | 28.9 |
| 234 | 24.4 |
| 235 | 42.0 |
| 236 | 177 |
| 237 | 17.3 |
| 238 | 18.4 |
| 239 | 4.48 |
| 240 | 13.7 |
| 241 | 73.4 |
| 242 | 67.3 |
| 243 | 9.78 |
| 244 | 15.1 |
| 245 | 9.41 |
| 248 | 25.1 |
| 249 | 11.1 |
| 251 | 12.8 |
| 252 | 54.5 |
| 253 | 97.9 |
| 254 | 492 |
| 257 | 11.3 |
| 258 | 8.72 |
| 259 | 9.57 |
| 260 | 10.6 |
| 261 | 15.4 |
| 266 | 15.5 |
| 267 | 95.3 |
| 268 | 83.8 |
| 269 | 19.9 |
| 270 | 15.0 |
| 271 | 5.88 |
| 272 | 5.80 |
| 273 | 2.32 |
| 274 | 12.3 |
| 275 | 14.7 |
| 276 | 13.0 |
| 277 | 12.6 |
| 278 | 17.1 |
| 279 | 12.8 |
| 280 | 11.7 |
| 281 | 6.21 |
| 282 | 4.08 |
| 283 | 11.0 |
| 286 | 9.36 |
| 287 | 34.9 |
| 288 | 60.2 |
| 290 | 227 |
| 291 | 45.7 |
| 293 | 135 |
| 295 | 41.5 |
| 296 | 2.36 |
| 297 | 18.7 |
| 298 | 20.5 |
| 299 | 38.4 |
| 300 | 3.37 |
| 301 | 7.64 |
| 302 | 6.44 |
| 303 | 12.0 |
| 304 | 12.8 |
| 305 | 287 |
| 306 | 93.9 |
| 307 | 125 |
| 308 | 20.7 |
| 310 | 6.12 |
| 311 | 25.8 |
| 313 | 2.21 |
| 315 | 3.42 |
| 316 | 3.42 |
| 318 | 1.09 |
| 319 | 2.89 |
| 321 | 1.73 |
| 322 | 3.41 |
| 323 | 5.29 |
| 324 | 4.66 |
| 325 | 2.26 |
| 329 | 2.75 |
| 330 | 897 |
| 332 | 14.8 |
| 333 | 150 |
| 334 | 51.0 |
| 335 | 512 |
| 336 | 207 |
| 337 | 105 |
| 338 | 30.4 |
| 339 | 21.3 |
| 340 | 35.5 |
| 341 | 81.4 |
| 342 | 27.8 |
| 343 | 22.2 |
| 344 | 11.6 |
| 345 | 4.08 |
| 346 | 8.8 |
| 347 | 51.3 |
| 351 | 63.3 |
| 352 | 41.2 |
| 353 | 21.5 |
| 354 | 26.0 |
| 355 | 46.0 |
| 356 | 231 |
| 357 | 30.9 |
| 358 | 54.3 |
| 359 | 27.6 |
| 360 | 97.2 |
| 361 | 69.2 |
| 362 | 36.1 |
| 364 | 34.4 |
| 365 | 20.4 |
| 366 | 18.1 |
| 367 | 24.8 |
| 368 | 13.4 |
| 369 | 12.5 |
| 370 | 67.7 |
| 372 | 25.2 |
| 373 | 20.5 |
| 374 | 30.5 |
| 375 | 18.5 |
| 376 | 18.7 |
| 377 | 9.57 |
| 378 | 31.0 |
| 379 | 16.9 |
| 380 | 11.5 |
| 381 | 11.2 |
| 382 | 60.3 |
| 383 | 85.3 |
| 384 | 20.2 |
| 385 | 33.6 |
| 386 | 13.2 |
| 387 | 24.3 |
| 388 | 7.01 |
| 389 | 11.1 |
| 390 | 18.2 |
| 391 | 14.3 |
| 392 | 46.7 |
| 393 | 19.5 |
| 394 | 13.9 |
| 395 | 21.8 |
| 396 | 9.94 |
| 397 | 9.42 |
| 398 | 7.99 |
| 399 | 7.63 |
| 400 | 5.26 |
| 401 | 6.90 |

TABLE 1-continued

Cannabinoid-1 receptor (CB1R) binding affinity assay

| Example | IC$_{50}$(nM) |
|---|---|
| 402 | 5.34 |
| 403 | 10.7 |
| 404 | 5.15 |
| 405 | 14.7 |
| 406 | 27.4 |
| 407 | 18.4 |
| 408 | 61.0 |
| 409 | 58.1 |
| 410 | 11.7 |
| 411 | 13.5 |
| 412 | 11.0 |
| 413 | 14.6 |
| 414 | 9.18 |
| 415 | 8.02 |
| 416 | 9.27 |
| 417 | 134 |
| 418 | 465 |
| 419 | 62.1 |
| 420 | 112 |
| 421 | 160 |
| 422 | 226 |
| 423 | 168 |
| 424 | 966 |
| 425 | 11.2 |
| 427 | 29.6 |
| 428 | 15.7 |
| 429 | 8.67 |
| 430 | 13.9 |
| 431 | 7.50 |
| 432 | 7.98 |
| 433 | 7.53 |
| 434 | 172 |
| 435 | 277 |
| 436 | 893 |
| 437 | 53.6 |
| 439 | 263 |
| 440 | 11.0 |
| 441 | 29.8 |
| 442 | 18.0 |
| 444 | 292 |
| 447 | 453 |
| 448 | 199 |
| 449 | 61.3 |
| 450 | 7.42 |
| 451 | 19.7 |
| 452 | 54.1 |
| 453 | 27.1 |
| 454 | 23.1 |
| 455 | 14.5 |
| 456 | 61 |
| 457 | 16.9 |
| 458 | 25.8 |
| 459 | 10.8 |
| 460 | 20.1 |
| 461 | 13.7 |
| 462 | 36.5 |
| 463 | 3.95 |
| 464 | 4.41 |
| 465 | 33.9 |
| 466 | 102 |
| 467 | 14.8 |
| 468 | 5.94 |
| 469 | 36.3 |
| 470 | 11.8 |
| 471 | 27.2 |
| 472 | 6.66 |
| 473 | 4.53 |
| 474 | 18.8 |
| 475 | 8.75 |
| 477 | 4.10 |
| 478 | 6.49 |
| 479 | 6.56 |
| 480 | 5.08 |
| 481 | 7.60 |
| 482 | 3.94 |
| 483 | 2.32 |
| 484 | 31.5 |
| 485 | 32.8 |
| 486 | 23.0 |
| 487 | 9.60 |
| 488 | 106 |
| 489 | 19.8 |
| 490 | 19.8 |
| 491 | 143 |
| 492 | 2.24 |
| 494 | 6.43 |
| 495 | 6.23 |
| 496 | 48.9 |
| 498 | 11.4 |
| 499 | 21.0 |
| 500 | 23.3 |
| 501 | 6.81 |
| 504 | 2.18 |
| 506 | 2.49 |
| 507 | 1.79 |
| 508 | 5.74 |
| 509 | 2.07 |
| 510 | 11.3 |
| 511 | 2.29 |
| 512 | 2.89 |
| 513 | 2.34 |
| 514 | 2.88 |
| 515 | 1.91 |
| 519 | 1.93 |
| 520 | 9.01 |
| 521 | 16.7 |
| 522 | 4.61 |
| 523 | 6.88 |
| 524 | 8.31 |
| 525 | 8.93 |
| 526 | 31.3 |
| 527 | 10.1 |
| 528 | 6.47 |
| 530 | 11.8 |
| 531 | 20.6 |
| 532 | 8.75 |
| 533 | 6.03 |
| 535 | 12.0 |
| 536 | 199 |
| 537 | 127 |
| 538 | 653 |
| 539 | 102 |
| 540 | 98.1 |
| 541 | 23.1 |
| 542 | 51.9 |
| 543 | 70.3 |
| 544 | 91.2 |
| 545 | 23.3 |
| 546 | 29.5 |
| 547 | 12.9 |
| 565 | 68.9 |
| 566 | 62.1 |
| 569 | 202 |
| 571 | 87.8 |
| 572 | 87.7 |
| 573 | 184 |
| 574 | 122 |
| 575 | 166 |
| 576 | 101 |
| 577 | 26.5 |
| 578 | 67.9 |
| 580 | 75.8 |
| 581 | 94.3 |
| 582 | 105 |
| 583 | 105 |
| 584 | 93 |
| 585 | 103 |
| 586 | 100 |
| 587 | 88.2 |
| 588 | 135 |

TABLE 1-continued

Cannabinoid-1 receptor (CB1R) binding affinity assay

| Example | IC$_{50}$(nM) |
|---|---|
| 590 | 85.3 |
| 591 | 135 |
| 592 | 122 |
| 593 | 53.8 |
| 594 | 93.8 |
| 595 | 105 |
| 596 | 195 |
| 597 | 39.8 |
| 598 | 77.6 |
| 599 | 181 |
| 600 | 42.3 |
| 601 | 26.7 |
| 602 | 361 |
| 603 | 50.6 |
| 604 | 47.3 |
| 605 | 128 |
| 606 | 11.6 |
| 608 | 16.5 |
| 609 | 14.2 |
| 610 | 22.6 |
| 611 | 699 |
| 612 | 227 |
| 613 | 476 |
| 614 | 389 |
| 615 | 625 |
| 616 | 534 |
| 617 | 523 |
| 618 | 142 |
| 619 | 128 |
| 620 | 720 |
| 621 | 348 |
| 622 | 840 |
| 623 | 368 |
| 624 | 388 |
| 628 | 904 |
| 629 | 301 |
| 630 | 573 |
| 632 | 834 |
| 633 | 60.9 |
| 634 | 289 |
| 635 | 712 |
| 636 | 851 |
| 638 | 93.9 |
| 639 | 57.2 |
| 640 | 51.4 |
| 641 | 40.6 |
| 642 | 44.2 |
| 643 | 65.5 |
| 644 | 14.2 |
| 646 | 112 |
| 648 | 69.4 |
| 649 | 12.7 |
| 650 | 84.1 |
| 651 | 95.2 |

Experiment 2

Measurements of In Vivo Activity Analysis

Male C57BL/6J mice weighing over 38 g were housed 1 per cage on a 12-/12-h light/dark cycle, had free access to food (rodent sterilizable diet) and water, and were experimentally native before testing. Mice were allowed at least 7 days to habituate to the experimental room prior to testing, and testing was conducted during the light period. Mice were maintained and experiments were conducted in accordance with the Institutional Animal Care.

The reference (rimonabant) and the inventive compounds of Examples 132, 155 and 502 were prepared fresh daily by dissolving it in deionized water containing 10% DMSO. By oral administration, animals received at a volume of 10 ml/kg for 14 days. All control animals received 10% DMSO dissolved in deionized water.

The vehicles 10% DMSO treated group were comprised of 5 mice in oral test. There were 6 mice in each of the other experimental groups (n=6 in each group). By oral administration, the losing weight was checked everyday for the drug treated group and the control group.

FIG. 1 shows chronic effects of compounds of Examples 132, 155, 502 and rimonabant in DIO mice. Body weight change from day 0 was observed on all days at 10 mg/kg of Example 132 compound, at 10 mg/kg of Example 155 compound, at 10 mg/kg of Example 502 compound, and at 10 mg/kg of rimonabant.

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I) or a pharmaceutically acceptable salt thereof:

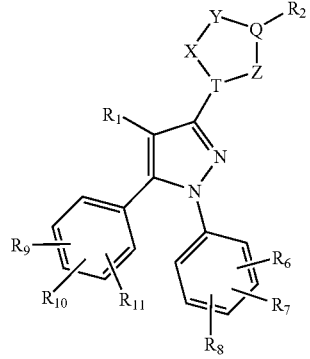

wherein:
$R_1$ is, $C_{1-5}$ alkyl, substituted with triazole, pyrrole, pyrazole, imidazole, or tetrazole;
$R_2$ is hydrogen, $NR_3R_4$, carbocycle, substituted carbocycle, aryl, substituted aryl, heteroaryl, substituted heteroaryl, heterocycle, substituted heterocycle, $C_{1-8}$ alkyl optionally substituted with hydroxy, acyloxy, $C_{1-6}$ alkoxy, substituted $C_{1-6}$ alkoxy; $C_{3-5}$ alkenyloxy, substituted $C_{3-5}$ alkenyloxy; $C_{3-5}$ alkynyloxy, substituted $C_{3-5}$ alkynyloxy; aryloxy, substituted aryloxy; heteroaryloxy, substituted heteroaryloxy or halogen, $C_{2-6}$ alkenyl optionally substituted with alkoxy or halogen, $C_{2-6}$ alkynyl optionally substituted with alkoxy or halogen, —(CH$_2$)$_m$—C$_{3-6}$ carbocycle optionally substituted with alkoxy or halogen, or —(CH$_2$)$_m$—R$_5$, m being 1 or 2;
$R_3$ and $R_4$ are each independently hydrogen, $C_{1-6}$ alkyl, substituted $C_{1-6}$ alkyl, $C_{3-7}$ cycloalkyl, substituted $C_{3-7}$ cycloalkyl, aryl, substituted aryl, heteroaryl, substituted heteroaryl, heterocycloalkyl, substituted heterocycloalkyl; or
$R_3$ and $R_4$, together with the nitrogen atom to which they are bonded, form a 4- to 10-membered saturated or unsaturated heterocyclic ring which is optionally substituted with one or more $C_{1-3}$ alkyl, benzyl, phenyl, $C_{1-3}$ alkoxy or halogen;
$R_5$ is phenyl, furanyl, benzofuranyl, thienyl, benzothienyl, pyridinyl, pyrimidinyl, pyrazinyl, pyridizinyl, tetrahydrofuranyl, tetrahydropyranyl, dioxanyl, 1,4-benzodioxanyl or benzo[1,3]dioxolyl, each being optionally substituted with one or more halogen, $C_{1-3}$ alkyl and $C_{1-2}$ alkoxy, each optionally having one to three fluorine substitutes;

$R_6$, $R_7$, $R_8$, $R_9$, $R_{10}$ and $R_{11}$ are each independently hydrogen, halogen, $C_{1-3}$ alkyl, $C_{1-3}$ alkoxy or trifluoromethyl;

X, Y and Z are each independently selected from the group consisting of —C($R_{12}$)=, —O—, —N=, —N($R_{13}$)— and —S— to form an aromatic heterocycle together with Q and T;

$R_{12}$ and $R_{13}$ are each independently hydrogen, $NR_3R_4$, carbocycle, substituted carbcycle, aryl, substituted aryl, heteroaryl, substituted heteroaryl, heterocycle, substituted heterocycle, $C_{1-8}$ alkyl optionally substituted with alkoxy or halogen, $C_{2-6}$ alkenyl optionally substituted with alkoxy or halogen, $C_{2-6}$ alkynyl optionally substituted with alkoxy or halogen, —(CH$_2$)$_m$—$C_{3-6}$ carbocycle optionally substituted with alkoxy or halogen, or —(CH$_2$)$_m$—$R_5$, m being 1 or 2, and $R_3$, $R_4$, and $R_5$ having the same meaning as defined above; or $R_2$ and $R_{12}$ are bonded together to form a 4- to 10-membered saturated or unsaturated carbocyclic or heterocyclic ring which is optionally substituted with one or more $C_{1-3}$ alkyl, benzyl, phenyl, $C_{1-3}$ alkoxy or halogen, Q and T are each independently

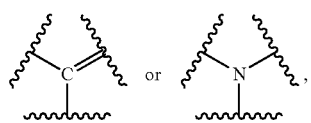

with the proviso that
i) both Q and T can not be simultaneously

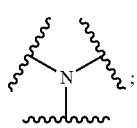

ii) Z cannot be —NH— when both Q and T are

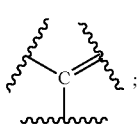

iii) $R_1$ cannot be unsubstituted $C_{1-5}$ alkyl when both X and Y are —N=,
Z is —O—, and
$R_2$ is $C_{1-7}$ alkyl substituted with halogen, $C_{1-4}$ alkoxy, trifluoromethoxy or phenoxy; $C_{3-12}$ carbocycle optionally substituted with $C_{1-4}$ alkyl; or phenyl optionally substituted with halogen, $C_{1-4}$ alkyl, $C_{1-4}$ alkoxy, $CF_3$ or trifluoromethoxy; and iv) X, Y and Z cannot be simultaneously N.

2. The compound of claim 1, which is a compound of formula (Ib), (Ia), (Ig) or (Ih):

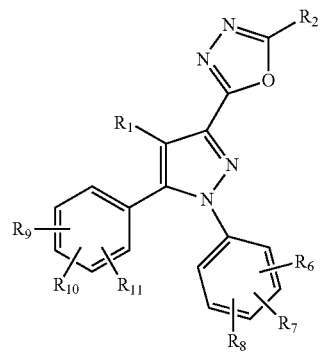

(Ia)

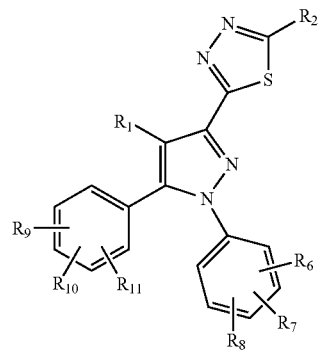

(Ib)

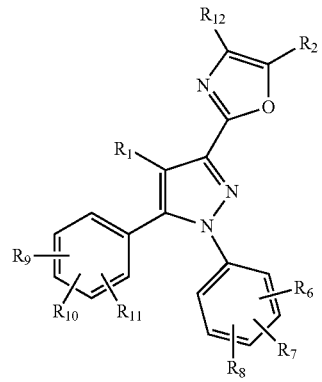

(Ig)

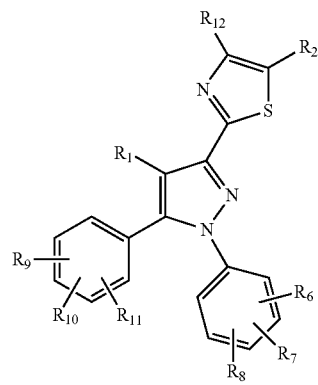

(Ih)

wherein $R_1$, $R_2$, $R_6$, $R_7$, $R_8$, $R_9$, $R_{10}$, $R_{11}$ and $R_{12}$ have the same meanings as defined in claim 1.

3. A compound according to claim 1, selected from the group consisting of:
- 2-(4-((1H-1,2,3-triazol-1-yl)methyl)-5-(4-chlorophenyl)-1-(2,4-dichlorophenyl)-1H-pyrazol-3-yl)-5-tert-butyl-1,3,4-oxadiazole,
- 2-(4-((1H-1,2,4-triazol-1-yl)methyl)-1-(2-chlorophenyl)-5-(4-chlorophenyl)-1H-pyrazol-3-yl)-5-tert-butyl-1,3,4-oxadiazole,
- 2-(4-((1H-1,2,4-triazol-1-yl)methyl)-1-(2-chlorophenyl)-5-(4-chlorophenyl)-1H-pyrazol-3-yl)-5-tert-butyl-1,3,4-thiadiazole,
- 2-(4-((1H-1,2,4-triazol-1-yl)methyl)-5-(4-bromophenyl)-1-(2,4-dichlorophenyl)-1H-pyrazol-3-yl)-5-tert-butyl-1,3,4-thiadiazole,
- 2-(4-((1H-1,2,4-triazol-1-yl)methyl)-5-(4-bromophenyl)-1-(2,4-dichlorophenyl)-1H-pyrazol-3-yl)-5-tert-butyl-1,3,4-oxadiazole,
- 2-(4-((1H-1,2,4-triazol-1-yl)methyl)-5-(4-bromophenyl)-1-(2,4-dichlorophenyl)-1H-pyrazol-3-yl)-5-(1-(trifluoromethyl)cyclopropyl)-1,3,4-oxadiazole,
- 2-(4-((1H-1,2,4-triazol-1-yl)methyl)-5-(4-bromophenyl)-1-(2,4-dichlorophenyl)-1H-pyrazol-3-yl)-5-(1-(4-chlorophenyl)cyclopropyl)-1,3,4-oxadiazole,
- 2-(4-((1H-1,2,4-triazol-1-yl)methyl)-5-(4-bromophenyl)-1-(2,4-dichlorophenyl)-1H-pyrazol-3-yl)-5-(1-(trifluoromethyl)cyclopropyl)-1,3,4-thiadiazole,
- 2-(4-((1H-1,2,4-triazol-1-yl)methyl)-5-(4-bromophenyl)-1-(2,4-dichlorophenyl)-1H-pyrazol-3-yl)-5-(1-(4-chlorophenyl)cyclopropyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-tert-butyl-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-tert-butyl-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopropyl)-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-cyclobutyl-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-cyclohexyl-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-(1-phenylcyclopropyl)-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-(1-p-tolylcyclopropyl)-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-(1-(4-methoxyphenyl)cyclopropyl)-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-(1-(2,4-dichlorophenyl)cyclopropyl)-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-cyclobutyl-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-cyclohexyl-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopropyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-phenylcyclopropyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-p-tolylcyclopropyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-(4-methoxyphenyl)cyclopropyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-(2,4-dichlorophenyl)cyclopropyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-(trifluoromethyl)cyclopropyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-(trifluoromethyl)cyclobutyl)-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclobutyl)-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-(1-phenylcyclopentyl)-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopentyl)-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-(1-(trifluoromethyl)cyclobutyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclobutyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-phenylcyclopentyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-(4-chlorophenyl)cyclopentyl)-1,3,4-thiadiazole,
- 2-(4-((1H-1,2,4-triazol-1-yl)methyl)-5-(4-chlorophenyl)-1-(2,4-dichlorophenyl)-1H-pyrazol-3-yl)-5-(1-methylcyclopropyl)-1,3,4-oxadiazole,
- 2-(4-((1H-1,2,4-triazol-1-yl)methyl)-5-(4-chlorophenyl)-1-(2,4-dichlorophenyl)-1H-pyrazol-3-yl)-5-(1-methylcyclopropyl)-1,3,4-thiadiazole,
- 2-(4-((1H-imidazol-1-yl)methyl)-5-(4-chlorophenyl)-1-(2,4-dichlorophenyl)-1H-pyrazol-3-yl)-5-tert-butyl-1,3,4-oxadiazole,
- 2-(4-((1H-pyrazol-1-yl)methyl)-5-(4-chlorophenyl)-1-(2,4-dichlorophenyl)-1H-pyrazol-3-yl)-5-tert-butyl-1,3,4-oxadiazole,
- 2-(4-((1H-pyrrol-1-yl)methyl)-5-(4-chlorophenyl)-1-(2,4-dichlorophenyl)-1H-pyrazol-3-yl)-5-tert-butyl-1,3,4-oxadiazole,
- 2-(4-((1H-tetrazol-1-yl)methyl)-5-(4-bromophenyl)-1-(2,4-dichlorophenyl)-1H-pyrazol-3-yl)-5-tert-butyl-1,3,4-oxadiazole,
- 2-(4-((1H-tetrazol-1-yl)methyl)-5-(4-chlorophenyl)-1-(2,4-dichlorophenyl)-1H-pyrazol-3-yl)-5-tert-butyl-1,3,4-oxadiazole,
- 2-(4-((1H-tetrazol-5-yl)methyl)-5-(4-chlorophenyl)-1-(2,4-dichlorophenyl)-1H-pyrazol-3-yl)-5-tert-butyl-1,3,4-oxadiazole, 2-(4-((2H-tetrazol-2-yl)methyl)-5-(4-bromophenyl)-1-(2,4-dichlorophenyl)-1H-pyrazol-3-yl)-5-tert-butyl-1,3,4-oxadiazole, and a pharmaceutically acceptable salt thereof.

4. A method for preparing the compound of formula (Ia), which comprises (i) reacting a carboxylic acid derivative of formula (5) with a hydrazide compound of formula (7) or a semicarbazide compound of formula (12) in the presence of a coupling reagent in a solvent, or reacting a hydrazide derivative of formula (A) with a carboxylic acid derivative in the presence of a coupling reagent, and (ii) cyclizing the resulting product using a dehydrating agent:

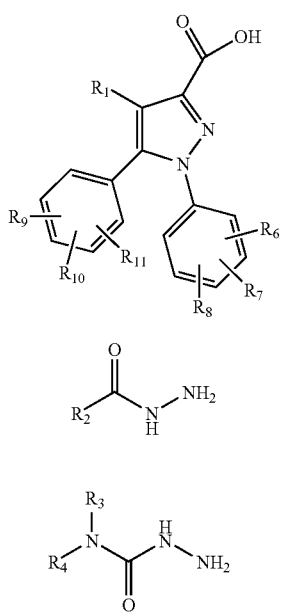

(5)

(7)

(12)

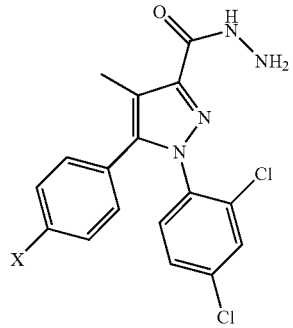

(A)

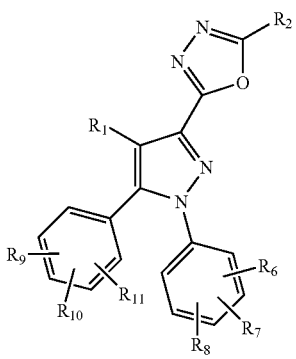

(Ia)

wherein $R_1$, $R_2$, $R_3$, $R_4$, $R_6$, $R_7$, $R_8$, $R_9$, $R_{10}$ and $R_{11}$ have the same meanings as defined in claim 1.

5. A pharmaceutical composition comprising the compound of formula (I) of claim 1, as an active ingredient and a pharmaceutically acceptable carrier.

6. A compound of formula (I) of claim 1, for treating obesity or an obesity-related metabolic disorders in a mammal.

* * * * *